United States Patent
Xie et al.

(10) Patent No.: US 12,139,514 B2
(45) Date of Patent: *Nov. 12, 2024

(54) CHIMERIC PAPILLOMA VIRUS L1 PROTEIN

(71) Applicant: SinoCellTech Ltd., Beijing (CN)

(72) Inventors: Liangzhi Xie, Beijing (CN); Chunxia Luo, Beijing (CN); Wei Zhang, Beijing (CN); Xiaoyan Suo, Beijing (CN); Lin Pang, Beijing (CN); Ping Hu, Beijing (CN)

(73) Assignee: SINOCELLTECH LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,447

(22) Filed: Jan. 19, 2022

(65) Prior Publication Data

US 2022/0281925 A1 Sep. 8, 2022

Related U.S. Application Data

(63) Continuation of application No. PCT/CN2020/102603, filed on Jul. 17, 2020.

(30) Foreign Application Priority Data

Jul. 19, 2019 (CN) .......................... 201910656278.7

(51) Int. Cl.
*C07K 14/025* (2006.01)
*A61K 39/12* (2006.01)
(Continued)

(52) U.S. Cl.
CPC ............ *C07K 14/025* (2013.01); *A61K 39/12* (2013.01); *A61P 31/20* (2018.01); *C12N 7/00* (2013.01);
(Continued)

(58) Field of Classification Search
None
See application file for complete search history.

(56) References Cited

U.S. PATENT DOCUMENTS 6,066,324 A    5/2000  Gissmann
2004/0224305 A1  11/2004  Wilson
(Continued)

FOREIGN PATENT DOCUMENTS

CN    106831961 A    6/2017
CN    109251235 A    1/2019
(Continued)

OTHER PUBLICATIONS

Li et al. (Nature Communications. 2018; 9 (1): 2360).*
(Continued)

*Primary Examiner* — Shanon A. Foley

(57) ABSTRACT

The present invention relates to chimeric papilloma virus L1 proteins and polynucleotides encoding thereof, and also to HPV virus-like particles and the preparation methods thereof. Said chimeric papilloma virus L1 protein comprises an N-terminal fragment derived from L1 protein of the first papilloma virus type, said N-terminal fragment maintains the immunogenicity of the L1 protein of the corresponding type of HPV; and a C-terminal fragment derived from L1 protein of the second papilloma virus type, said L1 protein of the second papilloma virus type has a better expression level and a better solubility compared to the L1 proteins of other HPV types; wherein said chimeric papilloma virus L1 proteins have the immunogenicity of the L1 proteins of the corresponding HPV types. Said chimeric papilloma virus L proteins have better expression amount and solubility for mass production of vaccines.

8 Claims, 19 Drawing Sheets

Specification includes a Sequence Listing.

(51) Int. Cl.
*A61P 31/20* (2006.01)
*C12N 7/00* (2006.01)
*A61K 39/00* (2006.01)

(52) U.S. Cl.
CPC ............... *A61K 2039/5258* (2013.01); *C12N 2710/20022* (2013.01); *C12N 2710/20023* (2013.01); *C12N 2710/20034* (2013.01)

(56) References Cited

U.S. PATENT DOCUMENTS

| | | | |
|---|---|---|---|
| 2008/0233141 | A1* | 9/2008 | Garcea ................. C07K 14/005 435/193 |
| 2022/0281925 | A1* | 9/2022 | Xie ........................ A61K 39/12 |

FOREIGN PATENT DOCUMENTS

| | | |
|---|---|---|
| EA | 001092 B1 | 10/2000 |
| KR | 10-2009-0100998 A | 9/2009 |
| RU | 2173170 C2 | 9/2001 |
| RU | 2206608 C2 | 6/2003 |
| WO | 96/11274 A1 | 4/1996 |
| WO | WO 01/97840 * | 12/2001 |
| WO | 2017157172 A1 | 9/2017 |
| WO | 2017157173 A1 | 9/2017 |

OTHER PUBLICATIONS

Ma et al. (Frontiers in Bioengineering and Biotechnology. Jan. 1-13, 2023).*
Yang et al. (Genomics, Proteomics & Bioinformatics 2006; 4 (1): 34-41).*
Zhou et al. (Virology. 1991; 185: 625-632).*
Sequence alignment of SEQ ID No. 2 with geneseq database accession No. BEH13803 2017 of Liu et al.*
Sequence alignment of SEQ ID 1 with geneseq db access No. BCQ70642 of Chen et al. 2016.*
A Notice for Eligibility of Grant issued by the Intellectual Property Office of Singapore on Sep. 5, 2022 in connection with corresponding Singaporean application No. 11202200503S.
First Office Action, Directorate General of Intellectual Property, Application No. P00202201345, Mar. 13, 2023,3 pages, Jakarta Selatan, Indonesia.
Second Office Action, Directorate General of Intellectual Property,Application No. P00202201345, Sep. 12, 2023,4 pages, Jakarta Selatan, Indonesia.
Beiss BK, Heimer E, Felix A, Burk RD, Ritter DB, Mallon RG, Kadish AS. Type-specific and cross-reactive epitopes in human papillomavirus type 16 capsid proteins. Virology. Sep. 1991;184(1):460-4. doi: 10.1016/0042-6822(91)90870-h. PMID: 1714667.
First Office Action, Patent Application No. MX/a/2022/000778, Jan. 16, 2023, Mexican Institute of Industrial Property Office, Jan. 16, 2023, 9 pages, Mexico, D.F., C.P.
Second Office Action, Patent Application No. MX/a/2022/000778, Sep. 27, 2023, Mexican Institute of Industrial Property Office, Sep. 27, 2023, 8 pages, Mexico, D.F., C.P.
First Office Action, Australian Intellectual Property Office, Patent Application No. 2020318114, Oct. 30, 2023, 4 Pages, Australia.
First Office Action, Chinese Intellectual Property Office, Jun. 3, 2023, 6 Pages, China.
International Search Report and Written Opinion dated Oct. 13, 2020 in connection with International Application No. PCT/CN2020/102603, 11 pages.
An Examination Report issued by the Canadian Intellectual Property Office on Feb. 17, 2023 in connection with Canadian Patent Application No. 3147850.
A First Office Action issued by the China National Intellectual Property Administration on Jun. 3, 2023 in connection with Chinese Patent Application No. 202080051690.7.
An extended European search report issued by the European Patent Office on Aug. 28, 2023 in connection with European Patent Application No. 20843433.2.
A First Office Action issued by the Japanese Patent Office on Feb. 6, 2023 in connection with Japanese Patent Application No. 2022-503542.
A Decision of Refusal issued by the Japanese Patent Office on Jun. 15, 2023 in connection with Japanese Patent Application No. 2022-503542.
A Notice of Preliminary Rejection issued by the Korean Intellectual Property Office on May 16, 2023 in connection with Korean Patent Application No. 10-2022-7005645.
A First Office Action issued by the Russian patent Office on Dec. 1, 2022 in connection with Russian Patent Application No. 100,181.
A First Office Action issued by the Russian patent Office on Dec. 1, 2022 in connection with Russian Patent Application No. 2022102875.
A Second Office Action issued by the Russian patent Office on May 17, 2023 in connection with Russian Patent Application No. 2022102875.

* cited by examiner

CHIMERIC PAPILLOMA VIRUS L1 PROTEIN

CROSS-REFERENCE SECTION

This application is a continuation of and claims priority to PCT Application No. PCT/CN2020/102603 filed Jul. 17, 2020, which itself claims priority to Chinese Patent Application No. 201910656278.7 filed Jul. 19, 2019. The contents from all of the above are hereby incorporated in their entirety by reference.

FIELD OF THE INVENTION

The present invention relates to the papilloma virus (HPV) L1 protein and the polynucleotide encoding the same, and also to HPV virus-like particles and the preparation methods thereof.

BACKGROUND OF THE INVENTION

Papilloma virus (PV) belongs to the Papillomaviridae Family and causes papillomas in humans, cattle, dogs, and rabbits. One of its member, human papilloma virus (HPV), is a non-enveloped DNA virus. The genome of this virus is a double-stranded closed circular DNA, about 7.2-8 kb in size, with 8 open reading frames, which can be divided into three regions according to their functions: (1) early region (E), about 4.5 kb, encoding E1, E2, E4-E7, a total of 6 non-structural proteins related to viral replication, transcription and transformation; (2) late region (L), about 2.5 kb, encoding the major capsid protein L1 and the minor capsid protein L2; (3) long regulatory region (LCR), which is located between the end of the L region and the beginning of the E region, is about 800-900 bp long and does not encode any protein, serving as DNA replication and expression regulatory elements.

The L1 proteins and the L2 proteins are synthesized late in the HPV infection cycle. The L1 protein is the major capsid protein and has a molecular weight of 55-60 kDa. The L2 protein is the minor capsid protein. 72 L1 protein-pentamers form the outer shell of the icosahedral HPV particle (45-55 nm in diameter), which encloses closed circular double-stranded DNA. The L2 protein is located on the inner side of the L1 protein (Structure of Small Virus-like Particles Assembled from the L1 Protein of Human Papillomavirus 16 Chen, X. S., R. L. Garcea, Mol. Cell. 5(3):557-567, 2000).

The ORF of the L1 protein, the most conserved gene in the PV genome, can be used to identify new PV types. A new PV type is identified if its complete genome is cloned and its L1 ORF DNA sequence differs from the closest known PV type by more than 10%. Homologies with differences between 2% and 10% are defined as different subtypes, and differences of less than 2% are defined as different variants of the same subtype (E.-M. de Villiers et al./Virology 324 (2004) 17-27).

At late stages of HPV infection, newly synthesized L1 proteins in the cytoplasm are transported to the nucleus of terminally differentiated keratin where, together with L2 proteins, package the replicated HPV genomic DNA to form infectious viruses (Nelson, L. M, et al. 2002. Nuclear import strategies of high risk HPV16 L1 major capsid protein. J. Biol. Chem. 277: 23958-23964). This suggests that nuclear import of the L1 protein plays a very important role in HPV infection and production. The ability of the virus to enter the nucleus is determined by the nuclear localization signal (NLS) at the C-terminus of the HPV L1 protein, the NLS is characterized by its abundance of basic amino acids (Garcia-Bustos, J., et al. 1991. Nuclear protein localization. Biochimica et Biophysica Acta 1071: 83-101).

15 high-risk (HR) HPV types can lead to cancers of cervix, anus, penis, vagina, vulva and oropharynx, among which HPV-16 and HPV-18 are by far the most common causes of cancers, accounting for approximately 70% of cervical cancers, and the other HR-HPV types (Types 31, 33, 35, 39, 45, 51, 52, 56, 58, 59, 68, 73, and 82) cause the rest. HPV-16 accounts for approximately 95% of HPV-positive oropharyngeal cancers (OPCs). The persistent low-risk genotypes HPV-6 and HPV-11 cause most anogenital warts and respiratory papillomas, but are rarely associated with cancers (Human Papillomavirus in Cervical Cancer and Oropharyngeal Cancer: One Cause, Two Diseases Tara A. Bermanand John T. Schiller, PhD2 Cancer 2017; 123:2219-29).

The L1 protein can be recombinantly expressed by pox-virus, baculovirus, or yeast systems and then self-assembles to form virus-like particles (VLP) containing approximately 72 L1 proteins, similar to the virus capsid. VLP has no indication. VLP induces neutralizing antibodies in inoculated animals and protects experimental animals from subsequent attack by infectious viruses. Thus, VLP appears to be an excellent candidate for papilloma virus vaccines (Structure of Small Virus-like Particles Assembled from the L1 Protein of Human Papillomavirus 16 Chen, X. S., R. L. Garcea, Mol. Cell. 5(3):557-567, 2000).

Glaxo's CERVARIX®, a bivalent recombinant HPV vaccine, contains HPV Type 16 recombinant L1 protein and HPV Type 18 recombinant L1 protein. The L1 protein is obtained by expression of a recombinant baculovirus expression vector system in insect cells of the nocturnal moth (*Trichoplusia ni*). The L1 protein self-assembles into virus-like particles for the prevention of cervical cancer, Grade 2 or 3 cervical intraepithelial neoplasia and adenocarcinoma in situ caused by HPV Types 16 and 18, and Grade 1 cervical intraepithelial neoplasia (oncogenic) in women aged 9-25 years.

GARDASIL® is a human papilloma virus quadrivalent (Types 6, 11, 16 and 18) recombinant vaccine from Merck for the prevention of cervical cancer, genital warts (condyloma *acuminata*) and precancerous or proliferative abnormal lesions caused by HPV Types 6, 11, 16 and 18 in girls and women aged 9-26 years; and for the prevention of anal cancer, genital warts (condyloma *acuminatum*) and precancerous or abnormal developmental lesions caused by HPV Types 6, 11, 16, and 18 in boys and men aged 9-26.

GARDASIL®9 is a nine-valent recombinant human papilloma virus vaccine from Merck that contains virus-like particles of L1 proteins of HPV Types 6, 11, 16, 18, 31, 33, 45, 52 and 58, the L1 protein is produced by fermentation of *Saccharomyces cerevisiae* and self-assembles into VLP. It is used in girls and women aged 9-45 years for the prevention of cervical cancer, vulvar cancer, vaginal cancer and anal cancer caused by HPV Types 16, 18, 31, 33, 45, 52 and 58, genital warts (condyloma *acuminata*) caused by HPV Types 6 and 11, and precancerous or proliferative abnormalities caused by HPV Types 6, 11, 16, 18, 31, 33, 45, 52 and 58; and in boys and men aged 9-45 years for the prevention of anal cancer caused by HPV Types 16, 18, 31, 33, 45, 52 and 58, genital warts (*Condyloma acuminatum*) caused by HPV Types 6 and 11 and pre-cancerous or developmentally abnormal lesions caused by HPV Types 6, 11, 16, 18, 31, 33, 45, 52 and 58.

The instruction for GARDASIL®9 announced that HPV Types 16 and 18 are the cause of about 70% of cervical cancers, with the remaining 20% of cases attributed to Types 31, 33, 45, 52 and 58, therefor GARDASIL®9 prevents 90% of cervical cancers.

Industrial production of virus-like particles is critical to HPV vaccine development. The common systems for producing virus-like particles are mainly classified into the eukaryotic expression system and the prokaryotic expression system.

Commonly used eukaryotic expression systems include poxvirus expression systems, insect baculovirus expression systems, and yeast expression systems. The HPV L1 protein expressed in eukaryotic expression systems can be spontaneously assembled to virus-like particles as its natural conformation is less disrupted, but the yield thereof is low. The HPV L1 protein expressed in prokaryotic expression systems, mainly E. coli expression systems, is of high yields but mostly in the form of inclusion bodies, this form of protein cannot be easily purified thus makes the production process complicated.

Therefore, there is still a need to obtain high yields of HPV virus-like particles.

SUMMARY OF THE INVENTION

In one aspect, the present invention provides a chimeric papilloma virus L1 protein comprising, from its N-terminus to C-terminus orientation, a. an N-terminal fragment derived from L1 protein of the first papilloma virus type, said N-terminal fragment maintains the immunogenicity of the L1 protein of the corresponding human papilloma virus type; and b. a C-terminal fragment derived from L1 protein of the second papilloma virus type, said L1 protein of the second papilloma virus type has a better expression level and solubility compared to the L1 proteins of other types; wherein said chimeric papilloma virus L1 protein has the immunogenicity of the L1 protein of the first papilloma virus type.

In another aspect, the present invention provides a papilloma virus-like particle comprising a chimeric papilloma virus L1 protein.

In another aspect, the present invention provides an immunogenic composition for the prevention of papilloma virus-associated diseases or infections, comprising papilloma virus-like particles and adjuvants as previously described.

In another aspect, the present invention provides an isolated polynucleotide encoding a chimeric papilloma virus L1 protein.

In a further aspect, the present invention provides a vector comprising a polynucleotide encoding a chimeric papilloma virus L1 protein.

In a further aspect, the present invention provides a baculovirus comprising a polynucleotide encoding a chimeric papilloma virus L1 protein.

In another aspect, the present invention provides a host cell comprising said polynucleotides, said vectors, or said baculovirus as previously described.

In another aspect, the present invention provides a method of preparing a papilloma virus-like particle, comprising culturing host cells as previously described to express said chimeric papilloma virus L1 proteins and to assemble into virus-like particles; and purifying said papilloma virus-like particles.

SPECIFIC EMBODIMENTS

Figure 1A:
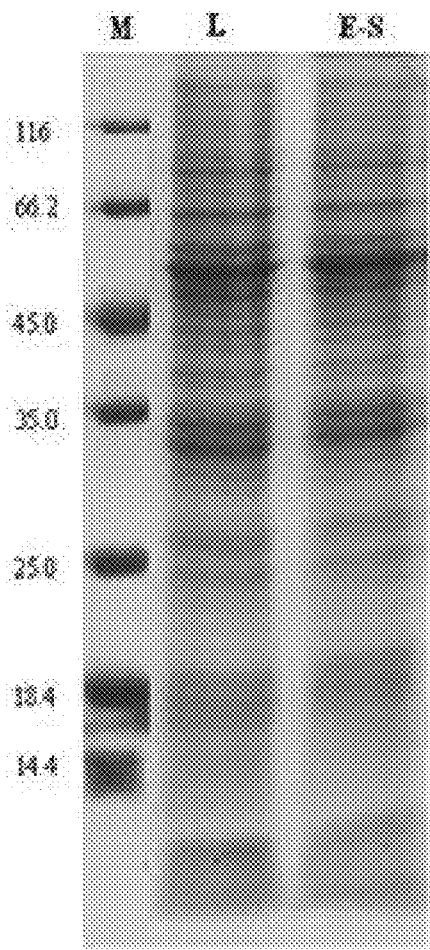
FIG. 1A: Expression of L1 protein of HPV 6 L1: 33C. M: Marker; L: cell lysate; E-S: supernatant collected after centrifugation of the lysate.

In one aspect, the present invention provides a chimeric papilloma virus L1 protein comprising, from its N-terminus to C-terminus orientation: a. an N-terminal fragment derived from L1 protein of the corresponding human papilloma virus type, said N-terminal fragment maintains the immunogenicity of the L1 protein of the corresponding type of HPV; and b. a C-terminal fragment derived from L1 protein of the second papilloma virus type, said L1 protein of the second papilloma virus type has a better expression level and solubility compared to L1 proteins of other types; wherein said chimeric papilloma virus L1 protein has the immunogenicity of L1 protein of the first papilloma virus type.

In one embodiment, said N-terminal fragment is a fragment obtained by truncating the C-terminus of the natural sequence of said L1 protein of the first papilloma virus type at any amino acid position within its α5 region, and a fragment having at least 98% identity therewith; said C-terminal fragment is a fragment obtained by truncating the N-terminus of the natural sequence of L1 protein of the second papilloma virus type at any amino acid position within its α5 region and functional variants resulting from further mutations, deletions and/or additions to the fragment.

In another embodiment, said N-terminal fragment has at least 98.5%, 99%, 99.5% or 100% identity to a fragment obtained by truncating the C-terminus of the natural sequence of said L1 protein of the first papilloma virus type at any amino acid position within its α5 region.

In one embodiment, said C-terminal fragment comprises one or plurality of nuclear localization sequences.

In one embodiment, said papilloma virus L1 protein is an HPV L1 protein.

In one embodiment, said L1 protein of the second papilloma virus type is selected from L1 proteins of HPV Types 1, 2, 3, 4, 6, 7, 10, 11, 13, 16, 18, 22, 26, 28, 31, 32, 33, 35, 39, 42, 44, 45, 51, 52, 53, 56, 58, 59, 60, 63, 66, 68, 73 or 82.

Preferably, said L1 protein of the second papilloma virus type is selected from L1 proteins of HPV Types 16, 28, 33, 59, or 68.

More preferably, said L1 protein of the second papilloma virus type is selected from L1 protein of HPV Type 33 or HPV Type 59.

In one embodiment, said L1 protein of the second papilloma virus type is an HPV Type 33 L1 protein, said C-terminal fragment is SEQ ID No: 2; or a fragment having a length of m1 amino acids, preferably a fragment covering amino acids 1-m1 position of SEQ ID No: 2; wherein m1 is an integer of 8-26; or said C-terminal fragment is SEQ ID No: 132; or a fragment having a length of m2 amino acids, preferably a fragment covering amino acids 1-m2 position of SEQ ID No: 132; wherein m2 is an integer of 13-31.

In one embodiment, the C-terminal fragment of the HPV Type 33 L1 protein has a nuclear localization sequence. In another embodiment, the C-terminal fragment of the HPV Type 33 L1 protein has two nuclear localization sequences. In some embodiments, the chimeric papilloma virus L1 protein comprises one or plurality of C-terminal fragments of the HPV Type 33 L1 protein. Said plurality of C-terminal fragments of the HPV Type 33 L1 protein may be the same or different. In one embodiment, the amino acid sequences with amino acid No: 7-8 (KR) and the amino acid sequences amino with amino acid No: 20-23 (KRKK) of SEQ ID No: 2 are nuclear localization sequences of the C-terminal fragments of the HPV Type 33 L1 protein.

In another embodiment, said L1 protein of the second papilloma virus type is the HPV Type 59 L1 protein, said C-terminal fragment is SEQ ID No: 13; or a fragment having a length of n amino acids, preferably covering amino acids 1-n position of SEQ ID No: 13; wherein n is an integer of 16-38.

In one embodiment, the C-terminal fragment of the HPV Type 59 L1 protein has a nuclear localization sequence. In another embodiment, the C-terminal fragment of the HPV Type 59 L1 protein has two nuclear localization sequences. In some embodiments, the chimeric papilloma virus L1 protein comprises one or plurality of C-terminal fragments of the HPV Type 59 L1 protein. Said plurality of C-terminal fragments of the HPV Type 59 L1 protein may be the same or different.

In one embodiment, said L1 protein of the first papilloma virus type is selected from L1 proteins of HPV Types 6, 11, 16, 18, 31, 35, 39, 45, 51, 52, 56 or 58.

In one embodiment, the C-terminus of said N-terminal fragment is connected to the N-terminus of said C-terminal fragment directly or via a linker.

The linker does not affect the immunogenicity of said N-terminal fragment and does not affect the expression level or solubility of the protein. In one embodiment, said N-terminal fragment and said C-terminal fragment are connected via a linker comprising 1, 2, 3, 4, 5, 6, 7, 8, 9 or 10 amino acids. In one embodiment, the linker is an artificial sequence. In another embodiment, the linker is a naturally occurring sequence in the HPV L1 protein. In another embodiment, the linker may be a partial sequence of the HPV Type 33 L1 protein. In another embodiment, the linker may be a partial sequence of the HPV Type 59 L1 protein.

In one embodiment, within the range of plus or minus 4 amino acid positions of the connection point when the C-terminus of said N-terminal fragment is connected to the N-terminus of said C-terminal fragment, there presents the following continuous amino acid sequence: RKFL (SEQ ID NO: 157); preferably, within the range of plus or minus 6 amino acid positions of the connection point, there presents the following continuous amino acid sequence: LGRKFL (SEQ ID NO: 158).

In one aspect, the present invention provides a papilloma virus-like particle, comprising a chimeric papilloma virus L1 protein as previously described. In one embodiment, the papilloma virus-like particle is the HPV virus-like particle, and in one embodiment, the HPV virus-like particle is the icosahedron comprising 72 pentamers of said chimeric HPV L1 protein. In one embodiment, the HPV virus-like particle has correctly formed disulfide bonds and thus has a good natural conformation. In one embodiment, the HPV virus-like particles self-assemble in an in vivo expression system.

In one aspect, the present invention provides an immunogenic composition for the prevention of papilloma virus-related disease or infections, comprising papilloma virus-like particles and adjuvants as previously described. Said prevention may be considered as a treatment and they can be used interchangeably.

In one aspect, the above-described immunogenic composition is administered to a subject. In one embodiment, the subject is a human. In one embodiment, the subject is a rabbit. In one embodiment, the subject is a dog.

In one aspect, the present invention provides an isolated polynucleotide encoding a chimeric papilloma virus L1 protein as previously described. In one embodiment, the polynucleotide is a codon-optimized polynucleotide for varieties of expression systems. In one embodiment, the polynucleotide is a codon-optimized polynucleotide for an insect baculovirus expression system.

In one aspect, the present invention provides a vector, comprising a polynucleotide as previously described. In one embodiment, the vector is a baculovirus vector. In one embodiment, the vector may be a transfer vector for a baculovirus expression system. In another embodiment, the vector may be an expression vector for a baculovirus expression system. In another embodiment, the vector may be a recombinant vector for the baculovirus expression system.

In one aspect, the present invention provides a baculovirus, comprising a polynucleotide as previously described.

In one aspect, the present invention provides a host cell, comprising the polynucleotide, the vector, or the baculovirus as previously described. In one embodiment, the host cell is an insect cell, preferably, said insect cell is selected from Sf9 cells, Sf21 cells, Hi5 cells and S2 cells.

In one aspect, the present invention provides a method for preparing papilloma virus-like particles as previously described, comprising: culturing the host cells as previously described to express said chimeric papilloma virus L1 proteins which is assembled into virus-like particles; and purifying said papilloma virus-like particles.

In one embodiment, the host cells are insect cells. In one embodiment, the host cells are Hi5 cells. In one embodiment, the chimeric papilloma L1 proteins are chimeric HPV L1 proteins that self-assemble into HPV virus-like particles in host cells. In one embodiment, the chimeric HPV L1 proteins self-assemble into HPV virus-like particles in host cells having an icosahedron comprising 72 pentamers of said chimeric HPV L1 proteins. In one embodiment, the HPV virus-like particles have correctly formed disulfide bonds and thus have a good natural conformation.

In one embodiment, the purification is carried out using cation exchange chromatography. In one embodiment, the purification is carried out using strong cation exchange chromatography. In another embodiment, the purification is carried out using weak cation exchange chromatography. In one embodiment, the purification is carried out using a combination of multiple cation exchange chromatography. In one embodiment, the purification is carried out using HS strong cation exchange chromatography. In another embodiment, the purification is carried out using MMA ion exchange chromatography. In another embodiment, purification is performed using HS-MMA two-step chromatography.

Papillomavirus L1 proteins expressed by eukaryotic expression systems can spontaneously assemble to virus-like particles, but the low expression level make them not suitable for mass production.

The sequences of the L1 proteins of each HPV type can be easily obtained from UniProt. For a given HPV type, the L1 protein can be derived from different strains, thus the amino acid sequence thereof may have multiple versions, any version of the natural sequence can be used in the present invention. It is possible that the sequence of the HPV L1 protein of a given type used during the conception and design of the present invention may differ from the sequence used in the following examples, but such differences do not affect the decisions and conclusions of the inventors.

It is generally accepted by those of skill in the art that the C-terminus of the L1 protein does not contain major neutralizing antigenic epitope and therefore attempts have been made to increase expression by truncating the C-terminus of the HPV L1 protein, for example Glaxo's U.S. Pat. No. 6,361,778 B1, in which the C-terminus of the HPV16 L1 protein is truncated by 1-34 amino acids, preferably 26 amino acids, states that the yield of VLP is increased by many-fold, preferably at least by 10 folds, and in particular by about 10 to 100 folds. Inspired by this, the inventors attempted to truncate the C-terminus of HPV 16 L1 protein by 31 amino acids and named the truncated protein as HPV 16 L1 (1-474). The protein is in high expression level but poor solubility, and is difficult to be extract and purified (see Comparative Example).

The poor solubility of the protein due to this truncation may be due to the deletion of the nuclear localization sequence located at the C-terminus, but the present invention is not binding to this speculation. During research and production, the inventor discovered that HPV Type 16 L1 protein, HPV Type 28 L1 protein, HPV Type 33 L1 protein, HPV Type 59 L1 protein and HPV Type 68 L1 protein have better expression levels and solubility than other HPV types L1 proteins. Inspired by the discovery, the inventors replaced the C-terminus of specific HPV types L1 proteins that are less extractable or less soluble with the C-terminus of specific HPV types L1 protein having better expression levels and solubility. That is, the inventors have constructed a chimeric protein: comprising, in the N-terminus to C-terminus orientation, an N-terminal fragment derived from L1 protein of the first papilloma virus type (e.g. HPV L1 protein), which provides the immunogenicity of the first papilloma virus type (e.g. HPV), and a C-terminal fragment derived from L1 protein of the second papilloma virus type (e.g. HPV L1 protein), which provides the features of better expression levels and solubility. These two fragments can be connected directly or via a linker.

The length of the N-terminal fragment of the HPV L1 protein appropriate for maintaining the immunogenicity of the L1 protein of the first HPV type and ensuring the formation of VLP is determined. The following reports relate to epitope studies of common HPV types.

Sunanda Baidya et al. reported that the epitopes of the L1 protein 48EEYDLQFIFQLCKITLTA65 (SEQ ID NO: 159), 45RHGEEYDLQFIFQLCKITLTA65 (SEQ ID NO: 160), 63LPDPNKF69 (SEQ ID NO: 161), 79PETQRLVWAC88 (SEQ ID NO: 162), 36PVPGQYDA43 (SEQ ID NO: 163), 77YNPETQRLVWAC88 (SEQ ID NO: 164), 188DTGYG-AMD195 (SEQ ID NO: 165), 36PVPGQYDATK45 (SEQ ID NO: 166), 45KQDIPKVSAYQYRVFRV61 (SEQ ID NO: 167), 130RDNVSVDYKQTQLCI144 (SEQ ID NO: 168) and 49YSRHVEEYDLQFIF62 (SEQ ID NO: 169) can be used as tools for designing HPV 16 and 18 vaccines (see Epitope design of L1 protein for vaccine production against Human Papilloma Virus types 16 and 18, Bioinformation 13(3): 86-93 March 2017, incorporated herein by reference in its entirety).

Katharina Slupetzky et al. reported that the regions near aa 282-286 and 351-355 of HPV-16 contribute to the neutralization epitopes and that the latter is the immunodominant site (see Chimeric papilloma virus-like particles expressing a foreign epitope on capsid surface loops, Journal of General Virology (2001), 82, 2799-2804, incorporated herein by reference in its entirety).

Brooke Bishop et al. prepared the following three variants of the HPV 11, 16, 18 and 35 L1 proteins: deletion of 9 amino acids at its N terminus, deletion of α4 (corresponding to amino acid residues 404-436 of HPV 16), and deletion of 31 amino acids at its C terminus respectively, and reported that the former two could not be assembled into VLP, but this phenomenon has not been reported in the latter one (Crystal Structures of Four Types of Human Papillomavirus L1 Capsid Proteins UNDERSTANDING THE SPECIFICITY OF NEUTRALIZING MONOCLONAL ANTIBODIES, The Journal of Biological Chemistry, 282, 31803-31811. incorporated herein by reference in its entirety). Each the α-helix, β-fold sheets and Loop Region of each type of HPV L1 protein can be conveniently determined by sequence analysis software commonly used in the field. Wherein the α-helix regions contains the α1 Region, α2 Region, α3 Region, α4 Region and α5 Region.
(The sequences in the following sequence alignment correspond with SEQ ID NOS: 170-173, respectively)

L1 Capsid Proteins UNDERSTANDING THE SPECIFICITY OF NEUTRALIZING MONOCLONAL ANTIBODIES, The Journal of Biological Chemistry, 282,31803-31811), the results of which are shown below, where the part between the downward-pointing arrows corresponds to the

```
                    ↓    ↓                    β-B1       β-B2        BC-loop         β-C
HPV16-L1   msiWlpseaTVYiPP-vpVskVVsTDeYVaiTsIyYHAgtSRLLaVGhPYfpikkpnnhKilyPKVSglQYRVFrihLPDPNKFgfPDTS   89
HPV35-L1   msiWrsneaTVYiPP-vsVskVVsTDeYVtiTsIyYHAgsSRLLaVGhPYyaikkqdshKiayPKVSglQYRVFryKLPDPNKFgfPDTS   89
HPV11-L1   --mWrpsdsTVYvPPpnpVskVVaTDaYVkiTsIfYHAssSRLLaVGhPYysikkvn-sKtvyPKVSgyQYRVFkyvLPDPNKFa1PDSS    86
HPV18-L1   malWrpsdnTVYipp-psVarVVnTDdYVypTsIfYHAgsSRLLtVGnPYfrvpagggnKqdiPKVSayQYRVFryqLPDPNKFg1PDTS   89
                    β-D              DE-loop                     β-E         EF-
HPV16-L1   fynPdtQRLVWACvGyEyGRGQPLGVGiSGHPliNKlDDtEnasayaaNagvDnReciymDYKQTQLCliGCkPpiGEHWgKGspCtnva  179
HPV35-L1   fydPasQRLVWACtGyEyGRGQPLGVGiSGHPliNKlDDtEnsnkyvgNsgtDnReciymDYKQTQLCliGCrPpiGEHWgKGtpCnanq  179
HPV11-L1   lfdPttQRLVWACtGleyGRGQPLGVGvSGHPliNKyDDvEnsggyggNpsqDnRvnvgmDYKQTQLCmvGCaPplGEHWgKGtqCsnts  176
HPV18-L1   iynPetQRLVWACaGyEiGRGQPLGVGlSGHPfyNKlDDtEsshaatsNvseDvRdnvsvDYKQTQLCilGCaPaiGEHWaKGtaCksrp  179
           loop                                              α1         β-F         FG-
HPV16-L1   snpGdCPPLELintVigDGDMVDTGFGAMdFttLQaNKseVPLDICtsiCKYPDYIkMvsePYGDslFFyLRsEQmFvRHlfNRAGayGs  269
HPV35-11   ykaGeCPPLELlntVlgDGDMVDTGFGAMdFttLQaNKsdVPLDICssiCKYPDYLkMvsePYGDmiFFyLRsEQmFvRHlfNRAGtyGs  269
HPV11-L1   yqnGdCPPLELitsVigDGDMVDTGFGAMnFadLQtNKsdVPLDICgtvCKYPDYLqMaadPYGDriFFyLRkEQmFaRHffNRAGtyGs  266
HPV18-L1   lsqGdCPPLELkntVleDGDMVDTGYGAMdFssLQdTKceVPLDICqsiCKYPDYLqMsadPYGDsmFFcLRsEQlFaRHfwNRAGtmGd  269
           loop                           G1       G2         β-H1      β-H2     H1-loop
HPV16-L1   nVPddLyiKGsgstanlaSsnYfpsPSGSmVsSdaQiFNKPYWLqrAQGHNNGiCWgNqLFVTVVDTTsSTNmslCaaistse-ttYknt  358
HPV35-L1   tVPadLyiKG--ttgtlpStsYfpsPSGSmVsSdaQiFNKPYWLqrAQGHNNGiCWsNqLFVTVVDTTsSTNmsvCsavsssd-stYkhd  356
HPV11-L1   pVPddLlvKGgnnrssvaSsiYvhsPSGSlVsSeaQlFNKPYWLqkAQGHNNGiCWgNhLFVTVVDTTsSTNmtlCasvsks--atYths  354
HPV18-L1   tVPqsLyiKGtgmpaspgScvYspsPSGSiVsSdsQlFNKPYWLhkAQGHNNGvCWhNqLFVTVVDTTpSTNltiCastqspvPgqYdat  359
             ___   β-I         α2       α3   ↓         α4            ↓           ____
HPV16-L1   niKsYlRHgEEyDLQFIFQLCkITLtAdVMtYIHsMNstiLEDWNFGiqPPPggtLsDTYRfvtSqAiaCQKhtppapkeDPlikytFWs  448
HPV35-L1   niKsYlRHgEEyDLQFIFQLCkITLtAdVMtYIHsMNpsiLEDWNFGitPPPsgtLsDTYRyVtSqAviCQKpsapkpkdDPlknytFWs  446
HPV11-L1   dyKsYmRHvEEfDLQFIFQLCsITLsAeVMaYIHtMNpsvLEDWNFGisPPPngtLsDTYRyVqSqAitCQKptpekekqDPykdmsFWs  444
HPV18-L1   ksKqYsRHvEEyDLQFIFQLCtITLtAdVMsYIHsMNssiLEDWNFGvpPPPttsLvDTYRfVqSvAitCQKdaapaenkDPydklkFWn  449
           β-J         α5                  ↓                      ↓
HPV16-L1   VnLKEKFSadLDQfPLGRKFLiQsGikakpkftlgks-katpttsststtakRkkrkl   505
HPV35-L1   VdLKEKFSadLDQfPLGRKFLiQsGikarpnfrlgks-aapastskkssstkrRkvks   502
HPV11-L1   VnLKEKFSseLDQfPLGRKFLiQsGyrgrtsartgik-rpavskpstapkrkRtktkk   501
HPV18-L1   VdLKEKFSldLDQyPLGRKFLyQsGirrkptigprkisapsattsskpakrvRvrark  507
```

The inventors performed sequence alignments of L1 proteins of 14 HPV types (Types 6, 11, 16, 18, 31, 33, 35, 39, 45, 51, 52, 56, 58, and 59) and then performed secondary structure prediction according to the literature cited above (Crystal Structures of Four Types of Human Papillomavirus regions which had been deleted for preparing the variants in that literature. (The sequences in the following sequence alignments correspond with SEQ ID NOS: 174, 172, 175-178, 170-171, 179-182, 173, 183, respectively)

```
                  ▼      ▼                    β-B1        β-B2         BC-
HPV6-L1    --MWRPSDSTVYVPPPNPVSKVVATDAYVTRTNIFYHASSSRLLAVGHPYFSIKRA----        54
HPV11-L1   --MWRPSDSTVYVPPPNPVSKVVATDAYVKRINIFYHASSSRLLAVGHPYYSIKKV----        54
HPV52-L1   MSVWRPSEATVYLP-PVPVSKVVSTDEYVSRTSIYYYAGSSRLLTVGHPYFSIKNTSSGN        59
HPV58-L1   MSVWRPSEATVYLP-PVPVSKVVSTDEYVSRTSIYYYAGSSRLLAVGNPYFSIKSP--NN        57
HPV33-L1   MSVWRPSEATVYLP-PVPVSKVVSTDEYVSRTSIYYYAGSSRLLAVGHPYFSIKNP--TN        57
HPV31-L1   MSLWRPSEATVYLP-PVPVSKVVSTDEYVTRTNIYYHAGSARLLTVGHPYYSIPKS--DN        57
HPV16-L1   MSLWLPSEATVYLP-PVPVSKVVSTDEYVARTNIYYHAGTSRLLAVGHPYFPIKKP--NN        57
HPV35-L1   MSLWRSNEATVYLP-PVSVSKVVSTDEYVTRTNIYYHAGSSRLLAVGHPYAIKKQ--DS        57
HPV51-L1   MALWRTNDSKVYLP-PAPVSRIVNTEEYITRTGIYYAGSSRLITLGHPYFPIPK----T        55
HPV56-L1   MATWRPSENKVYLP-PTPVSKVVATDSYVKRTSIFYHAGSSRLLAVGHPYYSVTK----D        55
HPV39-L1   MAMWRSSDSMVYLP-PPSVAKVVNTDDYVTRTGIYYAGSSRLLTVGHPYFKV-GM--NG        56
HPV59-L1   MALWRSSDNKVYLP-PPSVAKVVSTDEYVTRTSIFYHAGSSRLLTVGHPYFKV-PK--GG        56
HPV18-L1   MALWRPSDNTVYLP-PPSVARVVNTDDYVTRTSIFYHAGSSRLLTVGNPYFRV-PA--GG        56
HPV45-L1   MALWRPSDSTVYLP-PPSVARVVNTDDYVSRTSIFYHAGSSRLLTVGNPYFRVVPS--GA        57 loop            β-C                     β-D
HPV6-L1    -NKTVVPKVSGYQYRVFKVVLPDPNKFALPDSSLFDPTTQRLVWACTGLEVGRGQPLGVG        113
HPV11-L1   -NKTVVPKVSGYQYRVFKVVLPDPNKFALPDSSLFDPTTQRLVWACTGLEVGRGQPLGVG        113
HPV52-L1   GKKVLVPKVSGLQYRVFRIKLPDPNKFGFPDTSFYNPETQRLVWACTGLEIGRGQPLGVG        119
HPV58-L1   NKKVLVPKVSGLQYRVFRVRLPDPNKFGFPDTSFYNPDTQRLVWACVGLEIGRGQPLGVG        117
HPV33-L1   AKKLLVPKVSGLQYRVFRVRLPDPNKFGFPDTSFYNPDTQRLVWACVGLEIGRGQPLGVG        117
HPV31-L1   PKKIVVPKVSGLQYRVFRVRLPDPNKFGFPDTSFYNPETQRLVWACVGLEVGRGQPLGVG        117
HPV16-L1   -NKILVPKVSGLQYRVFRIHLPDPNKFGFPDTSFYNPDTQRLVWACVGVEVGRGQPLGVG        116
HPV35-L1   -NKIAVPKVSGLQYRVFRVKLPDPNKFGFPDTSFYDPASQRLVWACTGVEVGRGQPLGVG        116
HPV51-L1   STRAAIPKVSAFQYRVFRVQLPDPNKFGLPDPNLYNPDTDRLVWGCVGVEVGRGQPLGVG        115
HPV56-L1   NTKTNIPKVSAYQYRVFRVRLPDPNKFGLPDTNIYNPDQERLVWACVGLEVGRGQPLGAG        115
HPV39-L1   GRKQDIPKVSAYQYRVFRVTLPDPNKFSIPDASLYNPETQRLVWACVGVEVGRGQPLGVG        116
HPV59-L1   NGRQDVPKVSAYQYRVFRVKLPDPNKFGLPDNTVYDPNSQRLVWACVGVEIGRGQPLGVG        116
HPV18-L1   GNKQDIPKVSAYQYRVFRVQLPDPNKFGLPDTSIYNPETQRLVWACAGVEIGRGQPLGVG        116
HPV45-L1   GNKQAVPKVSAYQYRVERVALPDPNKFGLPDSTIYNPETQRLVWACVGMEIGRGQPLGIG        117

DE-loop                           β-E            EF-
HPV6-L1    VSGHPFLNKYDDVENSG-SGGNPGQDNRVNVGMDYKQTQLCMVGCAPPLGEHWGKGKQCT        172
HPV11-L1   VSGHPLLNKYDDVENSGGYGGNPGQDNRVNVGMDYKQTQLCMVGCAPPLGEHWGKGTQCS        173
HPV52-L1   ISGHPLLNKFDDTETSNKYAGKPGIDNRECLSMDYKQTQLCILGCKPPIGEHWGKGTPCN        179
HPV58-L1   VSGHPYLNKFDDTETSNRYPAQPGSDNRECLSMDYKQTQLCLIGCKPPTGEHWGKGVACN        177
HPV33-L1   ISGHPLLNKFDDTETGNKYPGQPGADNRECLSMDYKQTQLCLLGCKPPTGEHWGKGVACT        177
HPV31-L1   ISGHPLLNKFDDTENSNRYAGGPGTDNRECISMDYKQTQLCLLGCKPPIGEHWGKGSPCS        177
HPV16-L1   ISGHPLLNKLDDTENASAYAANAGVDNRECISMDYKQTQLCLIGCKPPIGEHWGKGSPCT        176
HPV35-L1   ISGHPLLNKLDDTENSNKYVGNSGTDNRECISMDYKQTQLCLIGCRPPIGEHWGKGTPCN        176
HPV51-L1   LSGHPLFNKYDDTENSRIANGNAQQDVRDNTSVDNKQTQLCIIGCAPPIGEHWGIGTTCK        175
HPV56-L1   LSGHPLFNRLDDTESSNLANNNVIEDSRDNISVDGKQTQLCIVGCTPAMGEHWTKGAVCK        175
HPV39-L1   ISGHPLYNRQDDTENSPFS-STTNKDSRDNVSVDYKQTQLCIGCKPÅIGEHWGKGKACK        175
HPV59-L1   LSGHPYNKLDDTENSHVASAVDTKDTRDNVSVDYKQTQLCIIGCVPAIGEHWTKGTACK        176
HPV18-L1   LSGHPFYNKLDDTESSHAATSNVSEDVRDNVSVDYKQTQLCILGCAPAIGEHWAKGTACK        176
HPV45-L1   LSGHPFYNKLDDTESAHAATAVITQDVRDNVSVDYKQTQLCILGCVPAIGEHWAKGTLCK        177 loop                                              _
HPV6-L1    NTPVQAGDCPPLELITSVIQDGDMVDTGFGAMNFADLQTNKSDVPIDICGTTCKYPDYLQ        232
HPV11-L1   NTSVQNGDCPPLELITSVIQDGDMVDTGFGAMNFADLQTNKSDVPLDICGTVCKYPDYLQ        233
HPV52-L1   NNSGNPGDCPPLQLINSVIQDGDMVDTGFGCMDFNTLQASKSDVPIDICSSVCKYPDYLQ        239
HPV58-L1   NNA-AATDCPPLELFNSIIEDGDMVDTGFGCMDFGTLQANKSDVPIDICNSTCKYPDYLK        236
HPV33-L1   NAA-PANDCPPLELINTIIEDGDMVDTGFGCMDFKTLQANKSDVPIDICGSTCKYPDYLK        236
HPV31-L1   NNAITPGDCPPLELKNSVIQDGDMVDTGFGAMDFTALQDTKSNVPLDICNSICKYPDYLK        237
HPV16-L1   NVAVNPGDCPPLELINTVVQDGDMVDTGFGAMDFTTLQANKSEVPLDICTSICKYPDYIK        236
HPV35-L1   ANQVKAGECPPLELLNTVLQDGDMVDTGFGAMDFTTLQANKSDVPLDICSSICKYPDYLK        236
HPV51-L1   NTPVPPGDCPPLELVSSVIQDGDMIDTGFGAMDFAALQATKSDVPLDISQSVCKYPDYLK        235
HPV56-L1   STQVTTGDCPPLALINTPIEDGDMIDTGFGAMDFKVLQESKAEVPLDIVQSTCKYPDYLK        235
HPV39-L1   PNNVSTGDCPPLELVNTPIEDGDMIDTGYGAMDFGALQETKSEVPLDICQSICKYPDYLQ        235
HPV59-L1   PTTVVQGDCPPLELINTPIEDGDMVDTGYGAMDFKLLQDNKSEVPLDICQSICKYPDYLQ        236
HPV18-L1   SRPLSQGDCPPLELKNTVLEDGDMVDTGYGAMDFSTLQDTKCEVPLDICQSICKYPDYLQ        236
HPV45-L1   PAQLQPGDCPPLELKNTIIEDGDMVDTGYGAMDFSTLQDTKCEVPLDICQSICKYPDYLQ        237

α1    β-F                               FG-loop
HPV6-L1    MAADPYGDRLFFFLRKEQMFARHFFNRAGEVGEPVPDTLIIKGS--GNRTSVGSSIYVNT        290
HPV11-L1   MAADPYGDRLFYLRKEQMFARHFFNRAGTVGEPVPDDLLVKGG--NNRSSVASSIYVHT        291
HPV52-L1   MASEPYGDSLFFFLRREQMFVRHFFNRAGTLGDPVPGDLYIQGSNSGNTATVQSSAFFPT        299
HPV58-L1   MASEPYGDSLFFFLRREQMFVRHFFNRAGKLGEAVPDDLYIKGS--GNTAVIQSSAFFPT        294
HPV33-L1   MTSEPYGDSLFFFLRREQMFVRHFFNRAGTLGEAVPDDLYIKGS--GTTASIQSSAFFPT        294
HPV31-L1   MVAEPYGDTLFYFLRREQMFVRHFFNRSGTVGESVPTDLYIKGS--GSTATLANSTYFPT        295
HPV16-L1   MVSEPYGDSLFFYLRREQMFVRHLFNRAGAVGENVPDDLYIKGS--GSTANLÅSSNYFPT        294
HPV35-L1   MVSEPYGDMLFFYLRREQMFVRHLFNRAGTVGETVPADLYIKGT--T--GTLPSTSYFPT        292
HPV51-L1   MSADTYGNSMFPHLRREQIFARHYYNKLVGVGEDIPNDYIKGSG-NGRDPIESYIYSAT        294
HPV56-L1   MSADAYGDSMWFYLRREQMLFARHFYNRAGKVGETIPAELYLKGS--NGREPPSSVYVAT        293
HPV39-L1   MSADVYGDSMFFCLRREQLFARHFWNRGGMVGDAIPAQLYIKGT--DIRANPGSSVYCPS        293
HPV59-L1   MSADAYGDSMFFCLRREQVFARHFWNRSGTMGDQLPESLYIKGT--DIRANPGSYLYSPS        294
HPV18-L1   MSADPYGDSMFFCLRREQLFARHFWNRAGTMGDTVPQSLYIKGT--GMRASPGSCVYSPS        294
HPV45-L1   MSADPYGDSMFFCLRREQLFARHFWNRAGVMGDTVPTDLYIKGTSANMRETPGSCVYSPS        297
```

-continued

```
                   β1              β2           3.0.          8-H2    H1-
HPV6-L1    PSGSLVSSEAQLFNKPYWLQKAQGHNNGICWGNQLFVTVVDTTRSTNMTLCASVT--TSS    348
HPV11-L1   PSGSLVSSEAQLFNKPYWLQKAQGHNNGICWGNHLFVTVVDTTRSTNMTLCASVS--KSA    349
HPV52-L1   PSGSMVTSESQLFNKPYWLQRAQGHNNGICWGNQLFVTVVDTTRSTNMTLCAEVK--KES    357
HPV58-L1   PSGSIVTSESQLFNKPYWLQRAQGHNNGICWGNQLFVTVVDTTRSTNMTLCTEVT--KEG    352
HPV33-L1   PSGSMVTSESQLFNKPYWLQRAQGHNNGICWGNQVFVTVVDTTRSTNMTLCTQVT--SDS    352
HPV31-L1   PSGSMVTSDAQIFNKPYWMQRAQGHNNGICWGNQLFVTVVDTTRSTNMSVCAAIAN-SDT    354
HPV16-L1   PSGSMVTSDAQIFNKPYWLQRAQGHNNGICWGNQLFVTVVDTTRSTNMSLCAAIST-SET    353
HPV35-L1   PSGSMVTSDAQIFNKPYWLQRAQGHNNGICWSNQLFVTVVDTTRSTNMSVCSAVSS-SDS    351
HPV51-L1   PSGSMITSDSQIFNKPYWLHRAQGHNNGICWNNQLFITCVDTTRSTNLTISTATAA-VSP    353
HPV56-L1   PSGSMITSEAQLFNKPYWLQKAQGHNNGICWGNQLFVTVVDTTRSTNMTISTATE--QLS    351
HPV39-L1   PSGSMVTSDSQLFNKPYWLHKAQGHNNGICWHNQLFLTVVDTTRSTNFTLSTSIESSIPS    353
HPV59-L1   PSGSVVTSDSQLFNKPYWLHKAQGLNNGICWHNQLFLTVVDTTRSTNLSVCASTTSSIPN    354
HPV18-L1   PSGSIVTSDSQLFNKPYWLHKAQGHNNGVCWHNQLFVTVVDTTRSTNLTICASTQSPVPG    354
HPV45-L1   PSGSITTSDSQLFNKPYWLHKAQGHNNGICWHNQLFVTVVDTTRSTNLTLCASTQNPVPN    357 loop              β3              β5             β7          ▼
HPV6-L1    TYTNSDYKEYMRHVEEYDLQFIFQLCSITLSAEVMAYIHTMNPSVLEDWNFGLSPPPNGT    408
HPV11-L1   TYTNSDYKEYMRHVEEFDLQFIFQLCSITLSAEVMAYIHTMNPSVLEDWNFGLSPPPNGT    409
HPV52-L1   TYKNENFKEYLRHGEEFDLQFIFQLCKITLTADVMTYIHKMDATILEDWQFGLTPPPSAS    417
HPV58-L1   TYKNDNFKEYVRHVEEYDLQFVFQLCKITLTAEIMTYIHTMDSNILEDWQFGLTPPPSAS    412
HPV33-L1   TYKNENFKEYIRHVEEYDLQFVFQLCKVTLTAEVMTYIHAMNPDILEDWQFGLTPPPSAS    412
HPV31-L1   TFKSSNFKEYLRHGEEFDLQFIFQLCKITLSADIMTYIHSMNPAILEDWNFGLTTPPSGS    414
HPV16-L1   TYKNTNFKEYLRHGEEYDLQFIFQLCKITLTADVMTYIHSMNSTILEDWNFGLQPPPGGT    413
HPV35-L1   TYKNDNFKEYLRHGEEYDLQFIFQLCKITLTADVMTYIHSMNPSILEDWNFGLTPPPSGT    411
HPV51-L1   TFTPSNFKQYIRHGEEYELQFIFQLCKITLTTEVMAYLHTMDPTILEQWNFGLTLPPSAS    413
HPV56-L1   KYDARKINQYLRHVEEYELQFVFQLCKITLSAEVMAYLHNMNANLLEDWNIGLSPPVATS    411
HPV39-L1   TYDPSKFKEYTRHVEEYDLQFIFQLCTVTLTTDVMSYIHTMNSSILDNWNFAVAPPPSAS    413
HPV59-L1   VYTPTSFKEYARHVEEFDLQFIFQLCKITLTTEVMSYIHNMNTTILEDWNFGVTPPPTAS    414
HPV18-L1   QYDATKFKQYSRHVEEYDLQFIFQLCTITLTADVMSYIHSMNSSILEDWNFGVPPPPTTS    414
HPV45-L1   TYDPTKFKHYSRHVEEYDLQFIFQLCTITLTAEVMSYIHSMNSSILENWNFGVPPPPTTS    417

α4                     ▼          β-X                α5
HPV6-L1    LEDTYRYVQSQAITCQKPTPEKEKPDPYKNLSFWEVNLKEKFSSELDQYPLGRKFLLQSG    468
HPV11-L1   LEDTYRYVQSQAITCQKPTPEKEKQDPYKDMSFWEVNLKEKFSSELDQFPLGRKFLLQSG    469
HPV52-L1   LEDTYRFVTSTAITCQKNTPPKGKEDPLKDYMFWEVNLKEKFSADLDQFPLGRKFLLQAG    477
HPV58-L1   LQDTYRFVTSQAITCQKTAPPKEKEDPLNKYTFWEVNLKEKFSADLDQFPLGRKFLLQSG    472
HPV33-L1   LQDTYRFVTSQAITCQKTVPPKEKEDPLGKYTFWEVDLKEKFSADLDQFPLGRKFLLQAG    472
HPV31-L1   LEDTYRFVTSQAITCQKSAPQKPKEDPFKDYVFWEVNLKEKFSADLDQFPLGRKFLLQAG    474
HPV16-L1   LEDTYRFVTSQAIACQKHTPPAPKEDPLKKYTFWEVNLKEKFSADLDQFPLGRKFLLQAG    473
HPV35-L1   LEDTYRYVTSQAVTCQKPSAPKPKDDPLKNYTFWEVDLKEKFSADLDQFPLGRKFLLQAG    471
HPV51-L1   LEDAYRFVRNAATSCQKDTPPQAKPDDPLAKYKFWDVDLKERFSLDLDQFALGRKFLLQVG    473
HPV56-L1   LEDKYRYVRSTAITCQREQPPTEKQDPLAKYKFWDVNLQDSFSTDLDQFPLGRKFLMQLG    471
HPV39-L1   LVDTYRYLQSAAITCQKDAPAPEKKDPYDGLKFWNVDLREKFSLELDQFPLGRKFLLQAR    473
HPV59-L1   LYDTYRFVQSAAVTCQKDTAPPVKQDPYDKLKFWPVDLKERFSADLDQFPLGRKFLLQLG    474
HPV18-L1   LVDTYRFVQSVAITCQKDAAPAENKDPYDKLKFWNVDLKEKFSLDLDQYPLGRKFLVQAG    474
HPV45-L1   LVDTYRFVQSVAVTCQKDTTPPEKQDPYDKLKFWTVDLKEKFSSDLDQYPLGRKFLVQAG    477

▼                               ▼
HPV6-L1    YRGRSSIRTGVKRPAVSKASAAPKRKRAKTKR--                              500
HPV11-L1   YRGRTSARTGIKRPAVSKPSTAPKRKRTKTKK--                              501
HPV52-L1   LQARPKLKRPASSAPRTST----KKK-KVKR---                              503
HPV58-L1   LKAKPRLKRSAPTTRAP-ST---KRK-KVKK---                              498
HPV33-L1   LKAKPKLKRAAPTSTRTSSA---KRK-KVKK---                              499
HPV31-L1   YRARPKFKAGKRSAPSASTTTPAKRKKTKK----                              504
HPV16-L1   LKAKPKFTLGKRKATPTTSSTSTTAKRKKRKL--                              505
HPV35-L1   LKARPNFRLGKRAAPASTSKKSSTKRRKVKS---                              502
HPV51-L1   VQRKPRPGLKRPASSASSSSSSAKRKRVKK---                               504
HPV56-L1   TRSKPAVATSKKRSAPTSTS-TPAKRKRR-----                              499
HPV39-L1   VRRRPTIGPRKRPAASTSSSSATKHKRKRVSK--                              505
HPV59-L1   ARPKPTIGPRKRAAPAPTSTPSPKRVKRRKSSRK                              508
HPV18-L1   LRRKPTIGPRKRSAPSATTSSKPAKRVRVRARK-                              507
HPV45-L1   LRRRPTIGPRKRPAASTSTASRPAKRVRIRSKK-                              510
```

In addition to the methods used by the inventors for sequence alignments, protein secondary structure prediction software that can be used for prediction includes, but is not limited to:

1. JPred
2. ProtPredicct
3. PsiPred
4. SCRATCH-1D
5. Nnpredict
6. Predictprotein
7. SSPRED In one embodiment of the present invention, the inventors determine the length of the N-terminal fragment of the HPV L1 protein derived from the first type in the following manner: the natural sequence of the L1 protein is truncated within its α5 region and nearby regions thereof, with the sequence from its N-terminus to the newly generated C-terminus within the α5 region retained. Such a truncated sequence ensures that it has the immunogenicity of the first type and is capable of forming VLP.

The N-terminal fragment of the HPV L1 protein derived from the first type can be further modified as long as it retains the immunogenicity of the first type and is capable of forming VLP.

The length of the C-terminal fragment of the HPV L1 protein derived from the second type is determined in the following manner: The natural sequence of the L1 protein is truncated within its α5 region and nearby regions thereof, then the sequence from the newly generated N-terminus within its α5 region to the C-terminus is retained. Such a truncated sequence does not have the major neutralizing antigenic epitope so that does not interfere with the immunogenicity of the resulting chimeric protein.

The C-terminal fragment of the HPV L1 protein derived from the second type can be further mutated, deleted and/or added, preferably retaining at least one of its nuclear localization sequences. Yang et al. predicted the nuclear localization sequences of 107 HPV subtypes (Yang et al. Predicting the nuclear localization signals of 107 types of HPV L1 proteins by bioinformatic analysis. Geno. Prot. Bioinfo. Vol. 4 No. 1 2006, incorporated herein by reference in its entirety). The nuclear localization sequences of each type of HPV L1 protein can be conveniently determined by sequence analysis software commonly used in the field.

The above-described connection of the N-terminal fragment to the C-terminal fragment occurs at the newly generated C-terminus of the former and at the newly generated N-terminus of the latter. This can be a direct connection or a connection via a linker. The site where the connection occurs is defined as the origin coordinate, the N-terminal side of the origin is regarded as minus while the C-terminal side as plus.

The following shows the sequence of amino acids 453-469 of the HPV6 L1 protein and the corresponding sequences of L1 proteins of other HPV types. These sequence overlap with their α5 region respectively. It can be seen these sequences are highly similar. The numbers in brackets indicate the positions of the last amino acid residue of the listed sequences, where for HPV Type 45, an additional 26 amino acids are present at the N-terminus of the L1 protein of some HPV Type 45 strains, while at the N-terminus of the L1 protein of other HPV Type 45 strains, the said additional 26 amino acids are not present, therefore the number is indicated as (478)+26.

```
HPV6
                              (SEQ ID NO: 184)
ELDQYPLGRKFLLQSGY(469)

HPV11
                              (SEQ ID NO: 185)
ELDQFPLGRKFLLQSGY(470)

HPV16
                              (SEQ ID NO: 186)
DLDQFPLGRKFLLQAGL(474)

HPV18
                              (SEQ ID NO: 187)
DLDQYPLGRKFLVQAGL(475)

HPV31
                              (SEQ ID NO: 188)
DLDQFPLGRKFLLQAGY(475)

HPV35
                              (SEQ ID NO: 189)
DLDQFPLGRKFLLQAGL(472)

HPV39
                              (SEQ ID NO: 190)
ELDQFPLGRKFLLQARV(474)

HPV45
                              (SEQ ID NO: 191)
DLDQYPLGRKFLVQAGL(478) + 26
```

-continued

```
HPV51
                              (SEQ ID NO: 192)
DLDQFALGRKFLLQVGV(474)

HPV52
                              (SEQ ID NO: 193)
DLDQFPLGRKFLLQAGL(478)

HPV56
                              (SEQ ID NO: 194)
DLDQFPLGRKFLMQLGTRS(474)

HPV58
                              (SEQ ID NO: 195)
DLDQFPLGRKFLLQSGL(473)

HPV33
                              (SEQ ID NO: 197)
DLDQFPLGRKFLLQAGL(473)

KAKPKLKRAAPTSTRTSSAKRKKVKK
``` wherein KR at positions 480-481 and KRKK (SEQ ID NO: 197) at positions 493-496 are nuclear localization sequences.

```
HPV59
                              (SEQ ID NO: 198)
DLDQFPPLGRKFLLQLGA(475)

RPKPTIGPRKRAAPAPTSTPSPKRVKRRKSSRK
``` wherein RKR at positions 484-486 and KRVKRRK (SEQ ID NO: 199) at positions 498-504 are nuclear localization sequences.

In one embodiment of the present invention, the inventors have completed C-terminus substitutions of L1 proteins between different HPV types by taking advantage of sequence similarity of the α5 region and nearby regions between the HPV types.

In the most preferred embodiment of the present invention, the inventors have noted that L1 protein of each HPV type has a tetrapeptide RKFL (SEQ ID NO: 157) or, more advantageously, a hexapeptide LGRKFL (SEQ ID NO: 158), at a similar position. The inventors have skillfully exploited this highly conserved sequence to locate the chimeric protein connection point at any amino acid position within this oligopeptide. On one hand, the sequence starting from the N-terminus of the chimeric protein to RKFL (SEQ ID NO: 157) or LGRKFL (SEQ ID NO: 158) is identical to the sequence of the N-terminal fragment derived from L1 protein of the first HPV type, while on the other hand, the sequence starting from RKFL (SEQ ID NO: 157) or LGRKFL (SEQ ID NO: 158) to the C-terminus of the chimeric protein is identical to the sequence of the C-terminal fragment derived from L1 protein of the second type.

The chimeric protein thus produced maintains a high degree of similarity to the natural HPV L1 protein, and it can be expected to perform well in production and even in medical or prophylactic procedures thereafter.

It will be understandable for those skilled in the art that there are different strains with different natural sequences of a given HPV type, chimeric proteins constructed using different strains also fall within the scope of the present invention.

It will be understandable for those skilled in the art that because of the high degree of similarity between L1 protein of different HPV types, if, during the construction of the chimeric proteins, the N-terminal fragment derived from L1 protein of the first HPV type is extended by more amino acid residues towards the C-terminus, or the C-terminal fragment derived from L1 protein of the second HPV type is extended by more amino acid residues towards the N-terminus, it is also possible to form chimeric proteins that are structurally identical to the present invention due to identical or similar amino acids at the corresponding sites. The chimeric proteins thus formed also fall within the scope of the present invention.

It will be understandable for those skilled in the art that on the basis of the chimeric proteins of the above described embodiments, variants of the chimeric proteins may be formed by mutations, deletions and/or additions of amino acid residues. These variants are likely to have the immunogenicity of L1 protein of the first HPV type, can form VLP, and have a good yield and solubility. The chimeric proteins such formed also fall within the scope of the present invention.

The Beneficial Effects of the Invention

The expression systems commonly used for producing virus-like particles are classified into eukaryotic expression systems and prokaryotic expression systems. The papilloma virus L proteins expressed by the eukaryotic expression systems can spontaneously assemble into viral-like particles, but have the disadvantage of low expression level thus are not suitable for mass production. The papilloma virus L protein expressed by the prokaryotic expression system requires in vitro processing to obtain virus-like particles because of often destroyed natural conformation, and has low yield, being difficult to be used in industrialization.

The present invention modifies the C-terminus of the L protein of the papilloma virus (e.g. human papilloma virus), for example by replacing it with the C-terminal fragment of HPV Type 16 L1 protein, HPV Type 28 L1 protein, HPV Type 33 L1 protein, HPV Type 59 L1 protein or HPV Type 68 L1 protein, thus can be used in expression systems (e.g. host cells, e.g. insect cells) to improve the expression level and the solubility of the papilloma virus L protein in expression systems (for example, host cells, e.g. insect cells). This can be used for the mass production of vaccines such as HPV vaccines.

The inventors found that the HPV Type 16 L1 protein, the HPV Type 28 L1 protein, the HPV Type 33 L1 protein, the HPV Type 59 L1 protein and the HPV Type 68 L1 protein have increased expression level and increased solubility compared to L1 proteins of other HPV types, and that said increased protein expression level and increased solubility was found to be depend on the C-terminal sequence of said HPV L1 protein. Among 107 HPV Type L1 proteins, most of them have nuclear localization sequences at the C-termini, and the C-terminal sequences have some similarities.

For papilloma virus L proteins that are currently inexpressible, very low in expression level or insoluble after expression, replacement of their C-terminal fragments with C-terminal fragments of the HPV Type 16 L1 protein, HPV Type 28 L1 protein, HPV Type 33 L1 protein, HPV Type 59 L1 protein or HPV Type 68 L1 protein makes it possible for soluble expression and subsequent purification. This strategy can be used for the mass production of polyvalent vaccines (e.g. HPV vaccines), making it possible to provide more comprehensive protection against a wide range of papilloma virus infections, especially HPV.

There needs to increase the expression level and the solubility of the HPV L1 protein in insect cells for mass production purpose. In addition, the virus-like particles assembled by the HPV L protein lack good conformation in yeast cells due to failure to form correct disulphide bonds.

For the HPV L1 proteins that are poorly expressed and insoluble in insect cells, a significant increase in expression level and solubility can be resulted after the modification of its C-terminal fragment into the C-terminal fragment of the HPV Type 33 or 59 L1 protein, thus they could be used for mass production of HPV vaccines.

For HPV L1 proteins that are better expressed and better soluble in insect cells compared to L1 proteins of other HPV types, such as HPV Type 16 protein, HPV Type 28 L1 protein, HPV Type 68 L1 protein, etc., there are needs to further improve the expression level and the solubility in order to achieve mass production of vaccines. In the present invention, for example, after modifying the C-terminal fragment of the HPV Type 16 L1 protein to the C-terminal fragment of the HPV Type 33 L1 protein, the expression level and the solubility of the modified chimeric HPV Type 16 protein are improved, which is conducive to the mass production of HPV vaccines.

To sum up, the chimeric HPV L1 proteins showed much higher expression level and solubility in insect cells compared to the unmodified HPV L1 protein. It can be used for the mass production of HPV vaccines. In addition, the chimeric HPV L1 proteins can correctly form disulfide bonds thus be assembled into HPV virus-like particles with good conformations in insect cells. This can improve the immunogenicity of HPV virus-like particles and trigger better immune responses.

Definition

Unless otherwise stated, all technical and scientific terms used herein have the meanings normally understood by a person of ordinary skill in the art to which the invention belongs. For the convenience of understanding the present invention, the following terms are cited below for their ordinary meaning.

When used herein and in the attached claims, the singular forms "a/an", "another" and "said/the" include the plural designations of the objects unless the context clearly indicates otherwise. Unless otherwise expressly stated, the terms "include/comprise/have", "for example", etc. are intended to convey inclusion rather than limitation.

The term "immunogenicity" refers to the ability of a substance, for example a protein or a peptide, to trigger an immune response, i.e. the ability to trigger the production of antibodies, in particular the ability to trigger humoral- or cell-mediated response.

The term "antibody" refers to an immunoglobulin molecule that binds an antigen. Antibodies may be polyclonal mixtures or monoclonal. Antibodies may be intact immunoglobulins of natural origin or of recombinant origin or may be immunoreactive portions of intact immunoglobulins. Antibodies may be present in a variety of forms including, for example, Fv, Fab', F(ab')2 and as single chains.

The term "antigenicity" refers to the ability of a substance, for example a protein or a peptide, to trigger the production of antibodies that bind specifically to it.

The term "epitope" includes any protein determinant cluster that specifically binds to an antibody or T-cell receptor. Epitope determinants typically consist of chemically active surface groups (e.g. amino acids or sugar side chains, or combinations thereof) of the molecule and typically have specific three-dimensional structural characteristics as well as specific charge characteristics.

The terms "subtype" or "type" are used interchangeably herein to refer to genetic variant of virus that allows it can be recognized by the immune system as distinct antigen from type to type. For example, HPV 16 is immunologically distinguishable from HPV 33.

The term "HPV L1 protein", as used herein, the term "HPV" and "human papilloma virus" refer to envelope-free double-stranded DNA viruses of the Papillomavirus family. Their genomes are circular and approximately 8 kilobase pairs in size. Most HPVs encode eight major proteins, six in the "early" region (E1-E2) and two in the "late" region (L1 (major capsid protein) and L2 (minor capsid protein)). Over 120 HPV types have been identified and they are labelled by numbers (e.g. HPV-16, HPV-18, etc.).

The term "HPV" or "HPV virus" refers to papilloma viruses of the Papillomaviridae Family, which are envelope-free DNA viruses with a double-stranded closed circular DNA genome of approximately 8 kb in size that is usually classified into three regions: (i) the early region (E), which contains six open reading frames E1, E2, E4-E7, encoding non-structural proteins related to viral replication, transcription and transformation, as well as open reading frames E3 and E8; (ii) the late region (L), which contains reading frames encoding the major capsid protein L1 and the minor capsid protein L2; and (iii) the long regulatory region (LCR), which does not encode any proteins but has the origin of replication and multiple transcription factor binding sites.

The terms "HPV L1 protein" and "HPV L2 protein" refer to proteins encoded by the late region (L) of the HPV gene and synthesized late in the HPV infection cycle. The L2 protein is the minor capsid protein. 72 L1 pentamers form the outer shell of the icosahedral HPV particles, which encloses the closed circular double-stranded DNA micro-chromosome.

The term "virus-like particle" refers to a hollow particle-containing one or plurality of structural proteins of a virus, without viral nucleic acids.

"HPV pseudovirus" is an ideal model for in vitro neutralization of HPV, by taking advantages of the non-specific nucleic acid encapsulation property of HPV VLP, HPV pseudovirus is formed by wrapping free DNA or introducing an exogenous plasmid into a VLP composed of intracellularly-expressed HPV L1 and L2.

The "pseudovirus neutralization assay" is a method for evaluating the neutralizing activity of antibodies. After incubation of immunized animal serum with a certain amount of pseudovirus and then infection of the cells, the amount of the cells decreases when serum neutralizing antibodies increases, showing a linear negative correlation in a certain range. The neutralizing activity of antibodies in serum can therefore be assessed by measuring changes in the amounts of cells.

The term "fragment thereof" or "variant thereof" refers to a deletion, insertion and/or substitution of nucleotides or amino acids sequence of the present invention. Preferably, the fragment or variant of the polypeptide provided by the present invention is capable of triggering the humoral- and/or the cellular-immune response in animals or humans.

The term "chimeric" means that sequences of polypeptides or nucleotides derived from different parental molecules are connected together by —CO—NH— or 3',5'-phosphodiester bonds, respectively. Preferably, they are not spaced by additional linker sequences, but are directly adjacent to each other.

The term "truncation" refers to the removal of one or plurality of amino acids from the N- and/or C-terminus of a polypeptide or the deletion of one or plurality of amino acids from the interior of a polypeptide.

The term "nuclear localization sequence" refers to an amino acid sequence that directs the protein into the nucleus. In some HPV L1 proteins, two tight clusters of basic residues (i.e. nuclear localization sequences) (e.g. one is KRKR (SEQ ID NO: 200), KRKK (SEQ ID NO: 197), KRKRK (SEQ ID NO: 201), KRKKRK (SEQ ID NO: 202), KRVKRRK (SEQ ID NO: 199), etc. and the other is KR, RKR, KRK, etc.) have a spacer region of 10-14 amino acids between them. The above clusters of basic residues belong to nuclear localization sequences. In some other HPV L1 proteins, the nuclear localization sequence is a tight cluster of basic residues formed by arginines and/or lysines. Nuclear localization sequences include, but are not limited to, examples of clusters of basic residues as described above. See Jun Yang et al, Predicting the Nuclear Localization Signals of 107 Types of HPV L1 Proteins by Bioinformatic Analysis, Genomics, Proteomics & Bioinformatics Volume 4, Issue 1, 2006, Pages 34-41, the entire contents of which are incorporated herein by reference.

The term "functional variant" refers to a version of a polypeptide or a protein that retains the desired activities or characteristics after truncation, mutation, deletion and/or addition.

"Sequence identity" between two sequences of polypeptides or nucleic acids indicates the number of identical residues between said sequences as a percentage of the total number of residues, and is calculated based on the size of the smaller one of the compared molecules. When calculating the percentage identity, the sequences being compared are matched in such a way as to produce the maximum match between the sequences, with the vacant positions (if present) in the match being resolved by a specific algorithm. Preferred computer program methods for determining identity between two sequences include, but are not limited to, GCG program packages including GAP, BLASTP, BLASTN and FASTA (Altschul et al., 1990, J. Mol. Biol. 215: 403-410). The above programs are publicly available from the National Center of Biotechnology Information (NCBI) and other sources. The well-known Smith Waterman Algorithm can also be used to determine the identity.

Non-critical amino acids can be conservatively substituted without affecting the normal function of the protein. Conservative substitution means replacing amino acids with chemically or functionally similar amino acids. Tables for conservative substitutions that provide similar amino acids are well known in the art. By way of example, in some embodiments, the groups of amino acids provided in Tables 1-3 are considered to be conservative substitutions for each other.

TABLE 1

In some embodiments, the selected groups of amino acids that are considered to be conservative substitutions for each other

| | |
|---|---|
| Acid residues | D and E |
| Basic residues | K, R and H |
| Hydrophilic uncharged residues | S, T, N and Q |
| Aliphatic uncharged residues | G, A, V, L and I |
| Non-polar uncharged residues | C, M and P |
| Aromatic residues | F, Y and W |

TABLE 2

In some embodiments, other selected groups of amino acids considered to be conservative substitutions for each other

| | |
|---|---|
| Group 1 | A, S and T |
| Group 2 | D and E |
| Group 3 | N and Q |
| Group 4 | R and K |
| Group 5 | I, L and M |
| Group 6 | F, Y and W |

TABLE 3

In some embodiments, other selected groups of amino acids considered to be conservative substitutions for each other

| | |
|---|---|
| Group A | A and G |
| Group B | D and E |
| Group C | N and Q |
| Group D | R, K and H |
| Group E | I, L, M and V |
| Group F | F, Y and W |
| Group G | S and T |
| Group H | C and M |

The term "amino acids" refers to the twenty common naturally occurring amino acids. Naturally occurring amino acids include alanine (Ala; A), arginine (Arg; R), asparagine (Asn; N), aspartic acid (Asp; D), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y) and valine (Val; V).

The term "adjuvant" refers to a compound or mixture that enhances immune responses. In particular, a vaccine may comprise an adjuvant. Adjuvants for use in the present invention may include, but are not limited to, one or plurality of the following: mineral-containing adjuvant compositions, oil-emulsion adjuvants, saponin adjuvant formulations, derivatives of bacteria or microbes.

The term "vector" refers to a nucleic acid molecule capable of proliferating another nucleic acid connected to it. The term includes vectors as self-replicating nucleic acid structures and as vectors integrated into the genome of host cells into which the vector has been introduced. Certain vectors are capable of directing the expression of nucleic acids to which such vectors are operatively connected.

The term "host cell" refers to a cell into which an exogenous nucleic acid has been introduced, as well as to the progeny of such a cell. Host cells include "transformants" (or "transformed cells"), "transfectants" (or "transfected cells") or "infectants" (or "infected cells"), each of which includes primary transformed, transfected or infected cells and the progeny derived from them. Such progeny may not be identical to the parental cells in terms of nucleic acid content and may contain mutations.

The administration amount is preferably a "prophylactically effective amount" (herein the prophylaxis may be considered as treatment and the two may be used interchangeably), which is sufficient to show benefit to the individual.

EXAMPLES

Example 1 Construction of Chimeric Genes

Example 1.1: Construction of a Chimeric Gene with the C-Terminus of HPV6 L1 Substituted with the C-Terminus of HPV33 L1

1.1.1 Construction of pFB-HPV6 L1 as the Template

The HPV6 L1 gene with the KpnI and XbaI cleavage sites at both ends of the synthesized sequences was synthesized by Thermo Fisher [formerly Invitrogen (Shanghai) Trading Co.], its sequence is shown in SEQ ID NO: 5. The plasmid pcDNA3-HPV6-L1 comprising the nucleotide sequence encoding amino acid 1-500 of HPV6 L1 was obtained by ligating the synthesized gene fragment with pcDNA3 vector (distributor: Thermo Fisher) at KpnI and XbaI cleavage sites.

The obtained pcDNA3-HPV6-L1 plasmid was subjected to double enzyme digestion with KpnI and XbaI to obtain a gene fragment of HPV6 L1 (1-500). The fragment was then ligated with the KpnI/XbaI double digested pFastBac™ 1 vector (distributor: Thermo Fisher) to obtain a rod vector containing the HPV6 L1 (1-500) gene fragment, named as pFB-HPV6 L1.

1.1.2 Construction of pFB-HPV33 L1 as the Template

The HPV33 L1 gene with the Kpn I and XbaI cleavage sites at both ends of the synthesized sequences was synthesized by Thermo Fisher [formerly Invitrogen (Shanghai) Trading Co.), its sequence is shown as SEQ ID NO: 6. The plasmid pcDNA3-HPV33-L1 comprising the nucleotide sequence encoding amino acids 1-499 of HPV33 L1 was obtained by ligating the synthesized gene fragment with pcDNA3 vector (distributor: Thermo Fisher) at Kpn I and XbaI cleavage sites.

The pcDNA3-HPV33-L1 plasmid was subjected to double enzyme digestion with KpnI and XbaI to obtain a fragment of the HPV33 L1 (1-499) gene. The fragment was then ligated to the KpnI and XbaI double digested pFastBac™ 1 vector (distributor: Thermo Fisher) to obtain a rod vector containing the HPV33 L1 (1-499) gene fragment, named as pFB-HPV33 L1.

1.1.3 Construction of pFB-HPV6 L1: 33C

Chimeric gene with HPV6 L1 C-terminus substituted with HPV33 L1 C-terminus: the constructed recombinant plasmid pFB-HPV6 L1 was used as the gene template to amplify a 1426 bp gene fragment using primers F1 and R1, the primer sequence F1 is shown in SEQ ID No: 7 and R1 is shown in SEQ ID No: 8.

This gene fragment contains a fragment encoding amino acids 1-469 of HPV6 L1, 10 bases overlapping with the gene fragment encoding amino acids 474-499 of HPV33 L1, and a fragment of the KpnI digest site (GGTACAC), the amplified sequence is shown in SEQ ID No: 9.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

The recombinant plasmid pFB-HPV33 L1 was used as the gene template to amplify a gene fragment of 101 bp in length using primers F2 and R2, the primer sequence of F2 is shown in SEQ ID No: 10 and the primer sequence of R2 is shown in SEQ ID No: 11.

This gene fragment contains a gene fragment encoding 26 C-terminal amino acids (474-499) of HPV33 L1, a 10 bp base overlapping with the gene fragment encoding the C-terminus of amino acids 1-469 of HPV6 L1 and the XbaI (TACTAGA) digest site, the amplified sequence is shown in SEQ ID No: 12.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

PCR Ligating Sequences:

The ligating primers were F1 and R2, and the fragments amplified using the above primers (amplified fragments of F1 and R1, amplified fragments of F2 and R2) were used as templates.

PCR ligating parameters: pre-denaturation at 94° C. for 5 min; denaturation at 98° C. for 10 s, annealing at 52° C. for 15 s, 72° C. for 1 kb/1 min, for 5 cycles; denaturation at 98° C. for 10 s, annealing at 68° C. for 15 s, 72° C. for 1 kb/1 min, for 25 cycles; extension at 72° C. for 5 min; end at 16° C.

The final result was SEQ ID NO: 4, a nucleotide sequence encoding amino acids 1-469 of HPV6 L1 and 26 C-terminal amino acids of HPV33 L1(aa 474-499), with KpnI and XbaI cleavage sites at both ends (hereafter referred to as the ligating sequence).

The recombinant plasmid pFB-HPV6 L1: 33C was obtained by double digesting the pFastBac™ 1 vector and the ligating sequence fragment with KpnI+XbaI enzymes and cloning the ligating sequence into the pFastBac™ 1 vector to obtain pFB-HPV6 L1: 33C, which is a chimeric gene with the C-terminus of HPV6 L1 substituted by the C-terminus of HPV33 L1.

Example 1.2: Construction of Chimeric Gene with the C-Terminus of HPV11 L1 Substituted by the C-Terminus of HPV33 L1

The experimental methods and procedures were the same as in Example 1.1, see Appendix 2 for relevant sequences.

Example 1.3: Construction of a Chimeric Gene with the C-Terminus of HPV16 L1 Substituted by the C-Terminus of HPV33 L1

The experimental method and procedure were the same as in Example 1.1, see Appendix 3 for relevant sequences.

Example 1.4: Construction of a Chimeric Gene with the C-Terminus of HPV18 L1 Substituted by the C-Terminus of HPV33 L1

The experimental method and procedure were the same as in Example 1.1, see Appendix 4 for relevant sequences.

Example 1.5: Construction of a Chimeric Gene with the C-Terminus of HPV31 L1 Substituted by the C-Terminus of HPV33 L1

The experimental method and procedure were the same as in Example 1.1, see Appendix 5 for relevant sequences.

Example 1.6: Construction of a Chimeric Gene with the C-Terminus of HPV35 L1 Substituted by the C-Terminus of HPV33 L1

The experimental methods and procedures were the same as in Example 1.1, see Appendix 6 for relevant sequences.

Example 1.7: Construction of Chimeric Gene with the C-Terminus of HPV39 L1 Substituted by the C-Terminus of HPV59L1

1.7.1 Construction of pFB-HPV39 L1 Used as the Template

The HPV39 L1 gene with the KpnI and XbaI cleavage sites at both ends of the synthesized sequences was synthesized by Thermo Fisher [formerly Invitrogen (Shanghai) Trading Co.), its sequence is shown as SEQ ID NO: 83. The plasmid pcDNA3-HPV39-L1 containing a nucleotide sequence encoding amino acids 1-505 of HPV39 L1 was obtained by ligating the synthesized gene fragment with pcDNA3 vector (distributor: Thermo Fisher) at Kpn I and XbaI cleavage sites.

The pcDNA3-HPV39-L1 plasmid was subjected to double digestion with KpnI and XbaI to obtain a fragment of the HPV39 L1 (1-505) gene. The fragment was then ligated to the KpnI and XbaI double digested pFastBac™ 1 vector (distributor: Thermo Fisher) to obtain a rod vector containing the HPV39 L1 (1-505) gene fragment, named as pFB-HPV39 L1.

1.7.2 Construction of pFB-HPV59L1 as the Template

The HPV59L1 gene was synthesized by Thermo Fisher [formerly Invitrogen (Shanghai) Trading Co.) to obtain plasmid pcDNA3-HPV59-L1 containing the nucleotide sequence encoding amino acids 1-508 of HPV59L1.

The pcDNA3-HPV59-L1 plasmid was double digested with KpnI and XbaI to obtain a fragment of the HPV59L1 (1-508) gene. The fragment was then ligated to the KpnI/XbaI double digested pFastBac™ 1 vector (distributor: Thermo Fisher) to obtain a rod vector containing the HPV59L1 (1-508) gene fragment, named as pFB-HPV59L1.

1.7.3 Construction of pFB-HPV39 L1: 59C

Chimeric gene with HPV39 L1 C-terminus substituted with HPV59L1 C-terminus: The constructed recombinant plasmid pFB-HPV39 L1 was used as the gene template to amplify a 1428 bp gene fragment using primers F1 and R1, the primer sequence F1 is shown in SEQ ID No: 85 and the primer sequence R1 is shown in SEQ ID No: 86.

This fragment contains a fragment encoding amino acids 1-469 of HPV39 L1, a 12-base overlapping with a fragment encoding amino acids 471-508 of HPV59L1 and a segment of the KpnI digest site (GGTACAC), the amplified sequence is shown in SEQ ID No: 87.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

The recombinant plasmid pFB-HPV59L1 was used as the gene template to amplify a gene fragment of 139 bp in length using primers F2 and R2. The primer sequence F2 is shown in SEQ ID No: 88 and R2 is shown in SEQ ID No: 89.

This gene fragment contains a gene fragment encoding 38 C-terminal amino acids (471-508) of the HPV59L1, a 12 bp base overlapping with the gene fragment encoding amino acids 1-469 of HPV39 L1 and the XbaI (TACTAGA) digest site, and the amplified sequence is shown in SEQ ID No: 90.

PCR amplification parameters: pre-denaturation at 94° C. for 5 min; denaturation at 98° C. for 10 s, annealing at 69° C. for 15 s, 1 kb/1 min at 72° C. for 30 cycles; extension at 72° C. for 5 min; end at 16° C.

PCR Ligating Sequence

The ligating primers were F1 and R2, and the fragments amplified by using the above primers (F1 and R1 amplified fragments, F2 and R2 amplified fragments) were used as templates.

PCR ligating parameters: pre-denaturation at 94° C. for 5 min; denaturation at 98° C. for 10 s, annealing at 52° C. for 15 s, 72° C. for 1 kb/1 min, for 5 cycles; denaturation at 98° C. for 10 s, annealing at 68° C. for 15 s, 72° C. for 1 kb/1 min, for 25 cycles; extension at 72° C. for 5 min; end at 16° C.

The final result was SEQ ID NO: 82, a nucleotide sequence encoding amino acids 1-469 of HPV39 L1 and 38 C-terminal amino acids of HPV59L1(471-508) with KpnI and XbaI enzyme cleavage sites at both ends (hereafter referred to as the ligating sequence).

The recombinant plasmid pFB-HPV39 L1: 59C was obtained by double digesting the pFastBac™ 1 vector and the ligating sequence fragment with KpnI+XbaI enzymes and the ligating sequence was cloned into the pFastBac™ 1 vector o obtain pFB-HPV39 L1: 59C, which is a chimeric gene with the C-terminus of HPV39 L1 substituted by the C-terminus of HPV59L1.

Example 1.8: Construction of Chimeric Gene with the C-Terminus of HPV45L1 Substituted by the C-Terminus of HPV33 L1

The experimental methods and procedures were the same as in Example 1.1, see Appendix 8 for relevant sequences.

Example 1.9: Construction of a Chimeric Gene with the C-Terminus of HPV51L1 Substituted by the C-Terminus of HPV33 L1

The experimental methods and procedures were the same as in Example 1.1, see Appendix 9 for relevant sequences.

Example 1.10: Construction of a Chimeric Gene with the C-Terminus of HPV52L1 Substituted by the C-Terminus of HPV33 L1

The experimental methods and procedures were the same as in Example 1.1, see Appendix 10 for relevant sequences.

Example 1.11: Construction of a Chimeric Gene with the C-Terminus of HPV56L1 Substituted by the C-Terminus of HPV33 L1

The experimental methods and procedures were the same as in Example 1.1, see Appendix 11 for relevant sequences.

Example 1.12: Construction of a Chimeric Gene with the C-Terminus of HPV58L1 Substituted by the C-Terminus of HPV33 L1

The experimental methods and procedures were the same as in Example 1.1, see Appendix 12 for relevant sequences.

Example 2 Recombinant Baculovirus Packaging

Example 2.1: HPV6 L1: 33C Recombinant Baculovirus Packaging of

The recombinant plasmid of pFB-HPV6 L1: 33C constructed in Example 1 was identified and sequenced to be correct, and was transformed into DH10Bac bacteria competent cells (Bac-to-Bac® kit, purchased from Thermo Fisher), incubated at 37° C. for proliferation, and incubated in a flat dish for streak culture. White colonies was selected, incubated overnight. The bacterial culture was collected and the recombinant baculovirus DNA was extracted using alkaline lysis method.

The recombinant baculovirus DNA was transfected into insect cells SF9 using a cationic transfection reagent (purchased from Sino Biological) to package the recombinant baculovirus virulent strains. The procedure was as follows:

a. SF9 cells at log phase were inoculated in dishes at a density of $0.6 \times 10^6$ cell/dish. The dish inoculated with SF9 cells were left at room temperature for 2 hrs. for the cell's adhering to the dish wall.

b. 20 µL of extracted plasmid Bacmid DNA was added to 200 µL Grace's Medium (no serum, no additives, purchased from Gibico) and mixed and inverted 5 times.

c. 25 µL of 0.2× TF1 (transfection reagent, purchased from Sino Biological) was added dropwise to 200 µL of Grace's Medium and mixed gently.

d. Mixed b and c. Incubated at room temperature for 15-45 min.

e. During the incubation of DNA with cellfectin (purchased from Sino Biological), the cell supernatant was discarded and 0.8 mL of Grace Medium (serum additive free) was added into the dish.

f. The incubated mixture of DNA and transfection reagent of d was added to the dish dropwise.

g. Incubated at 27° C. for 2 hr.

h. Cell culture medium was discarded and 2.5 mL complete growth media/dish (SCD6 SF+10% FBS) (SCD6 SF was purchased from Sino Biological, FBS was purchased from Gibico) a was added.

i. Culture was performed at 27° C. for 7 days and whether the viral infection occurred was observed.

Virus supernatant was collected after visible lesions were observed in the transfected cells, typically after 7-11 days of culturing. The viral supernatant, i.e., the P1 generation virus strain of HPV6 L1: 33C is collected aseptically with a pipette. SF9 cells, at a density of $2 \times 10^6$ cells/mL, were infected using P1 generation virus strain of HPV6 L1: 33C at a ratio of 1:50 (V/V), cultured at 27° C. for 3 days, and centrifuged at 1000 g±200 g for 10 min at room temperature. The collected virus supernatant was the P2 generation virus and could be used for infecting the host cells and production.

Example 2.2: Packaging of HPV11 L1: 33C Recombinant Baculovirus

The experimental methods and procedures were the same as in Example 2.1.

Example 2.3: Packaging of HPV 16L1: 33C Recombinant Baculovirus

The experimental methods and procedures were the same as those of Example 2.1.

Example 2.4: Packaging of HPV18 L1: 33C Recombinant Baculovirus

The experimental methods and procedures were the same as those of Example 2.1.

Example 2.5: Packaging of HPV31 L1: 33C Recombinant Baculovirus

The experimental methods and procedures were the same as those of Example 2.1.

Example 2.6: Packaging of HPV35 L1: 33C Recombinant Baculovirus

The experimental methods and procedures were the same as those of Example 2.1.

Example 2.7: Packaging of HPV39 L1: 59C Recombinant Baculovirus

The experimental methods and procedures were the same as those of Example 2.1.

Example 2.8: Packaging of HPV45 L1: 33C Recombinant Baculovirus

The experimental methods and procedures were the same as those of Example 2.1.

Example 2.9: Packaging of HPV51 L1: 33C Recombinant Baculovirus

The experimental methods and procedures were the same as those of Example 2.1.

Example 2.10: Packaging of HPV52 L1: 33C Recombinant Baculovirus

The experimental methods and procedures were the same as those of Example 2.1.

Example 2.11: Packaging of HPV56 L1: 33C Recombinant Baculovirus

The experimental methods and procedures were the same as those of Example 2.1.

Example 2.12: Packaging of HPV58 L1: 33C Recombinant Baculovirus

The experimental methods and procedures were the same as those of Example 2.1.

Example 3 Expression of Chimeric Proteins

Example 3.1: Expression of HPV6 L1: 33C

High Five cells were infected with baculovirus containing the HPV6 L1: 33C recombinant gene obtained in Example 2 at a ratio of 1:200 (V/V), and the cell precipitate was collected by centrifugation at 1000 g±100 g at room temperature. The cells were broken up by sonication at low temperature for 3 min, centrifuged at >10,000 g for 10 min and the supernatant was collected for SDS-PAGE. Lane 1: Marker (The marker is a mixture of 7 purified proteins with molecular weights ranging from 14.4 kDa to 116 kDa, produced by Thermo Scientific); Lane 2: cell lysate; Lane 3: supernatant of the lysate collected by centrifugation.

The result is shown in FIG. 1A. The HPV6 L1: 33C L1 protein prepared by this method has a yield of >100 mg/L and a protein size of approximate 56 KD, which can be used for mass production.

Example 3.2: Expression and Production of HPV11 L1: 33C

The experimental methods and procedures were the same as in Example 3.1.

Figure 1B:
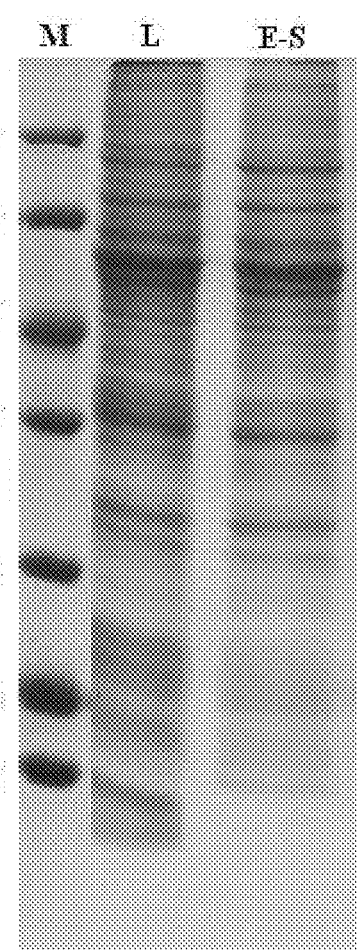
FIG. 1B: Expression of L1 protein of HPV 11 L1: 33C. M: Marker; L: cell lysate; E-S: supernatant collected after centrifugation of the lysate.

The result is shown in FIG. 1B. The HPV11 L1: 33C L1 protein prepared by this method has a yield of >100 mg/L and a protein size of approximate 56 KD, which can be used for mass production.

Example 3.3: Expression and Production of HPV 16L1: 33C

The experimental methods and procedures were the same as in Example 3.1.

Figure 1C:
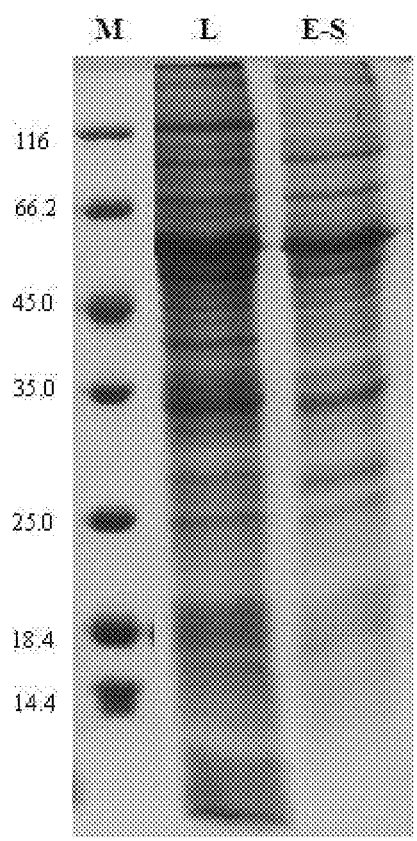
FIG. 1C: Expression of L1 protein of HPV 16 L1: 33C. M: Marker; L: cell lysate; E-S: supernatant collected after centrifugation of the lysate.

The result is shown in FIG. 1C. The HPV 16L1: 33C L1 protein prepared by this method has a yield of >100 mg/L and a protein size of approximate 56 KD, which can be used for mass production.

Example 3.4: Expression and Production of HPV18 L1: 33C

The experimental methods and procedures were the same as in Example 3.1.

Figure 1D:
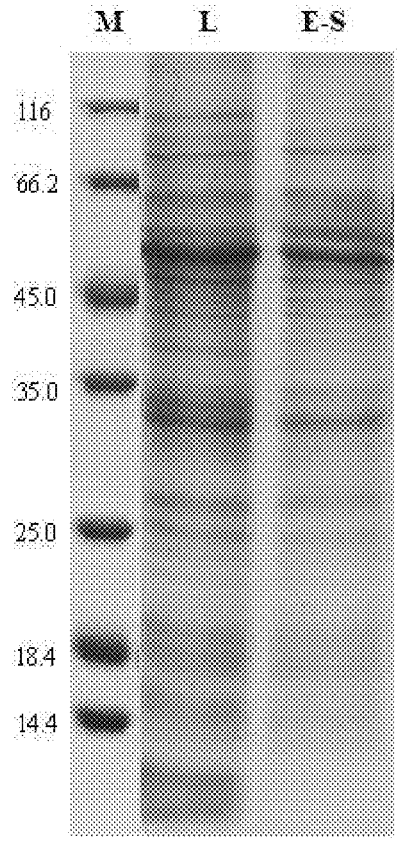
FIG. 1D: Expression of L1 protein of HPV 18 L1: 33C. M: Marker; L: cell lysate; E-S: supernatant collected after centrifugation of the lysate.

The result is shown in FIG. 1D. The HPV18 L1: 33C L1 protein prepared method has a yield of >100 mg/L and a protein size of approximate 56 KD, which can be used for mass production.

Example 3.5: Expression and Production of HPV31 L1: 33C

The experimental methods and procedures were the same as in Example 3.1.

Figure 1E:
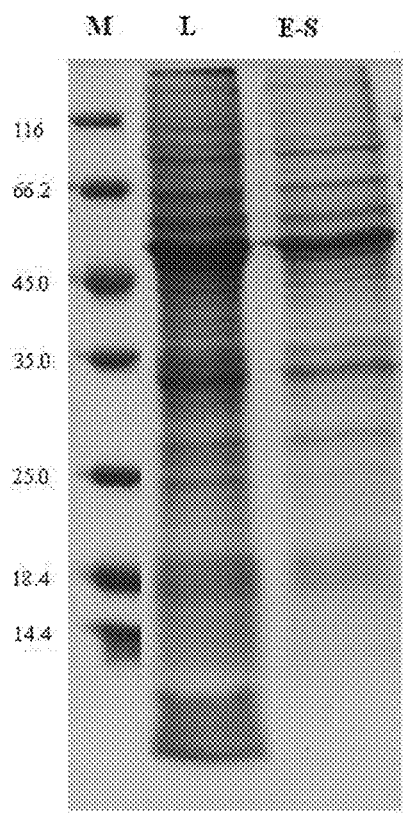
FIG. 1E: Expression of L1 protein of HPV 31 L1: 33C. M: Marker; L: cell lysate; E-S: supernatant collected after centrifugation of the lysate.

The result is shown in FIG. 1E. The HPV31 L1: 33C L1 protein prepared by this method has a yield of >100 mg/L and a protein size of approximate 56 KD, which can be used for mass production.

Example 3.6: Expression and Production of HPV35 L1: 33C

The experimental methods and procedures were the same as in Example 3.1.

Figure 1F:
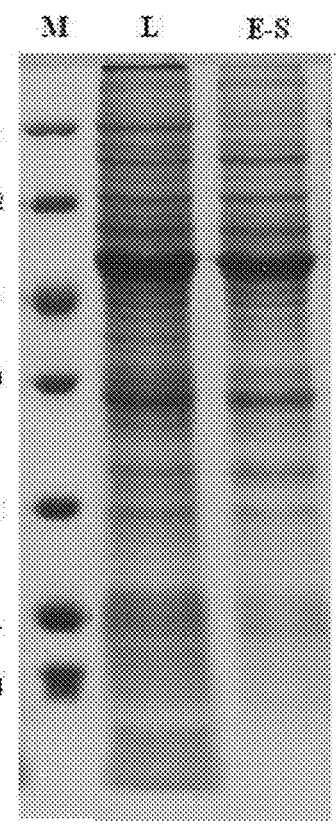
FIG. 1F: Expression of L1 protein of HPV 35 L1: 33C. M: Marker; L: cell lysate; E-S: supernatant collected after centrifugation of the lysate.

The result is shown in FIG. 1F. The HPV35 L1: 33C L1 protein prepared by this method has a yield of >100 mg/L and a protein size of approximate 56 KD, which can be used for mass production.

Example 3.7: Expression and Production of HPV39 L1: 59C

The experimental methods and procedures were the same as in Example 3.1.

Figure 1G:
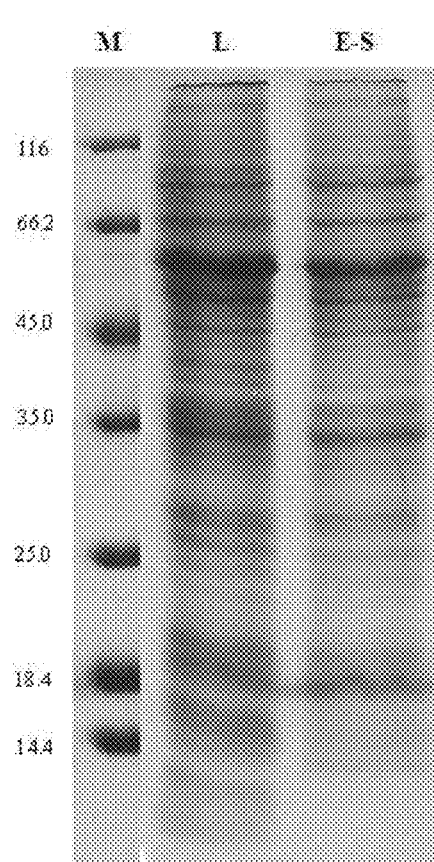
FIG. 1G: Expression of L1 protein of HPV 39 L1: 59C. M: Marker; L: cell lysate; E-S: supernatant collected after centrifugation of the lysate.

The result is shown in FIG. 1G. The HPV39 L1: 59C L1 protein prepared by this method has a yield of >100 mg/L and a protein size of approximate 56 KD, which can be used for mass production.

Example 3.8: Expression and Production of HPV45 L1: 33C

The experimental methods and procedures were the same as in Example 3.1.

Figure 1H:
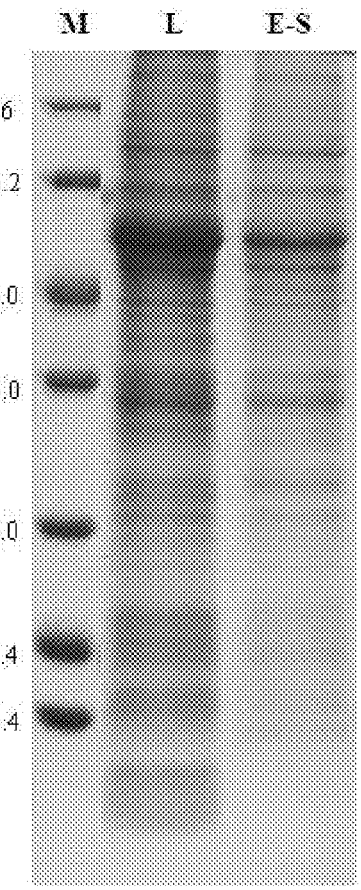
FIG. 1H: Expression of L1 protein of HPV 45 L1: 33C. M: Marker; L: cell lysate; E-S: supernatant collected after centrifugation of the lysate.

The result is shown in FIG. 1H. The HPV45 L1: 33C L1 protein prepared by this method has a yield of >100 mg/L and a protein size of approximate 56 KD, which can be used for mass production.

Example 3.9: Expression and Production of HPV51 L1: 33C

The experimental methods and procedures were the same as in Example 3.1.

Figure 1I:
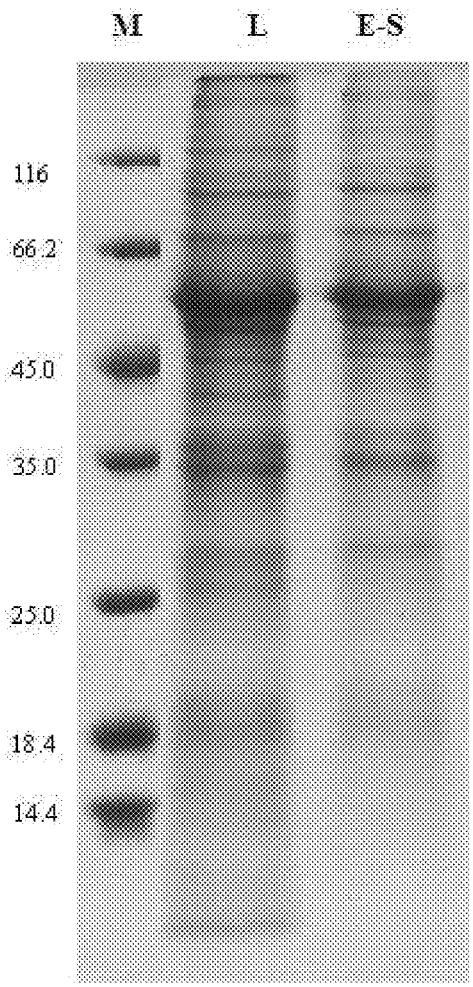
FIG. 1I: Expression of L1 protein of HPV 51 L1: 33C. M: Marker; L: cell lysate; E-S: supernatant collected after centrifugation of the lysate.

The result is shown in FIG. 1I. The HPV51 L1: 33C L1 protein prepared by this method has a yield of >100 mg/L and a protein size of approximate 56 KD, which can be used for mass production.

Example 3.10: Expression and Production of HPV52 L1: 33C

The experimental methods and procedures were the same as in Example 3.1.

Figure 1J:
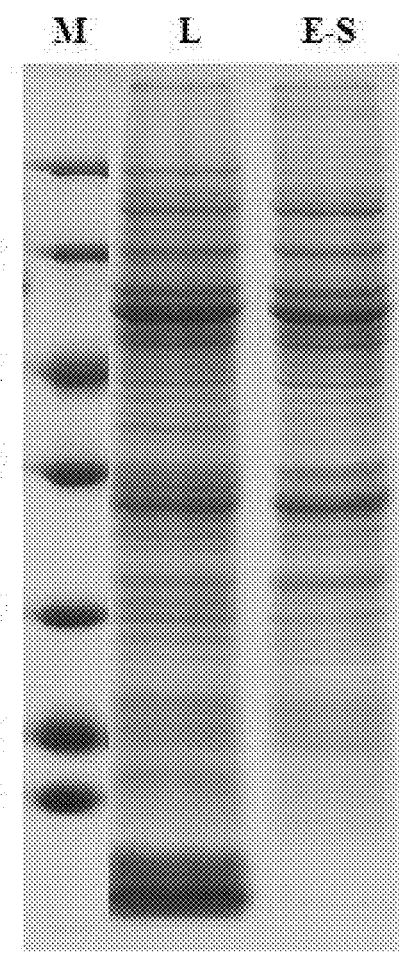
FIG. 1J: Expression of L1 protein of HPV 52 L1: 33C. M: Marker; L: cell lysate; E-S: supernatant collected after centrifugation of the lysate.

The result is shown in FIG. 1J. The HPV52 L1: 33C L1 protein prepared by this method has a yield of >100 mg/L and a protein size of approximate 56 KD, which can be used for mass production.

Example 3.11: Expression and Production of HPV56 L1: 33C

The experimental methods and procedures were the same as in Example 3.1.

Figures 1K, 1L:
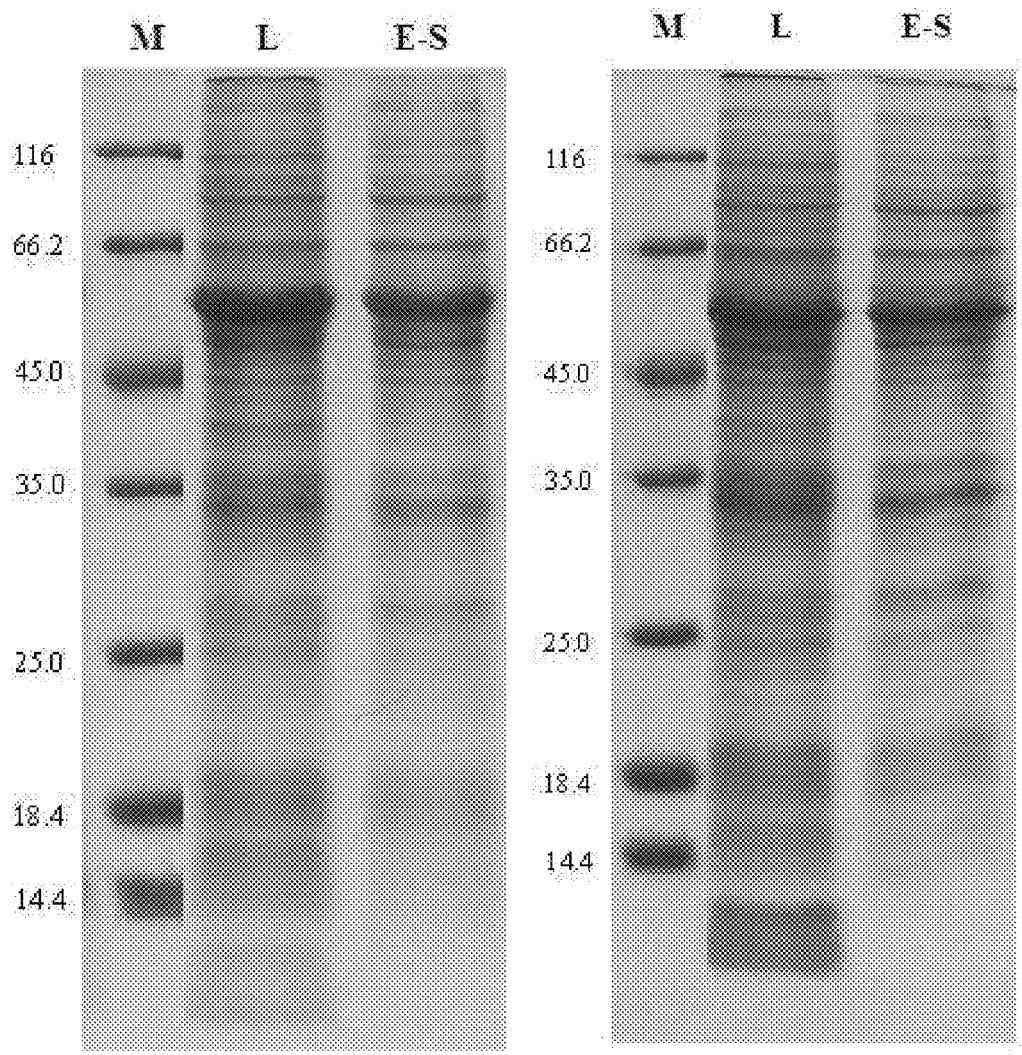
FIG. 1K: Expression of L1 protein of HPV 56 L1: 33C. M: Marker; L: cell lysate; E-S: supernatant collected after centrifugation of the lysate.
FIG. 1L: Expression of L1 protein of HPV 58 L1: 33C. M: Marker; L: cell lysate; E-S: supernatant collected after centrifugation of the lysate.

The result is shown in FIG. 1K. The HPV56 L1: 33C L1 protein prepared by this method has a yield of >100 mg/L and a protein size of approximate 56 KD, which can be used for mass production.

Example 3.12: Expression and Production of HPV58 L1: 33C

The experimental methods and procedures were the same as in Example 3.1.

The result is shown in FIG. 1L. The HPV58 L1: 33C L1 protein prepared by this method has a yield of >100 mg/L and a protein size of approximate 56 KD, which can be used for mass production.

Example 4 Preparation of Purified Virus-Like Particles

Example 4.1: Preparation of Purified HPV6 L1: 33C Virus-Like Particles

The HPV6 L1: 33C virus-like particles were purified by a two-step chromatography method, i.e. HS-MMA method, the supernatant collected in Example 3 was purified, and finally, high purity virus-like particles were obtained.
First Step Chromatography:
  Medium: POROS® 50 HS strong cation exchange media produced by Thermo Fisher was used.
  Medium volume: 150 mL of media volume, 30 mL/min of linear flow rate.
  Chromatography conditions: equilibration buffer (pH 6.2, the salt concentration is 50 mM phosphate, 0.5 M NaCl); wash buffer (the salt concentration is 50 mM phosphate, 0.75 M NaCl, pH 6.2).
  The chromatography column was first equilibrated with 5 CV of equilibration buffer and then the sample was loaded. After loading, the column was then eluted with 5 CV of equilibration buffer and wash buffer, respectively, to remove the protein impurities.
  Elution conditions: a 50 mM phosphate buffer containing 50 mM arginine hydrochloride, pH 6.2, with an elution salt concentration being of 1.25 M NaCl, was used.
Second Step Chromatography.
  Medium: MMA ion exchange media produced by Bestchrom (Shanghai) Biosciences Co., Ltd was used.
  Medium volume: media volume is 150 mL, while linear flow rate is 30 mL/min.
  Chromatography conditions: equilibration buffer: 50 mM PB, 1.25 M NaCl, pH 6.2. The chromatography column was first equilibrated with 4 CV equilibration buffer and then the sample was loaded. After loading, protein impurities were rinsed off with 5 CV equilibration buffer and then the target protein was eluted with elution buffer and collected.
  Elution conditions: 100 mM NaAC, 150 mM NaCl, 0.01% Tween 80, pH 4.5.

Example 4.2: Preparation of Purified HPV11 L1: 33C Virus-Like Particles

The experimental methods and procedures were the same as in Example 4.1.

Example 4.3: Purification and Preparation of HPV 16L1: 33C Virus-Like Particles

The experimental methods and procedures were the same as in Example 4.1.

Example 4.4: Purification and Preparation of HPV18 L1: 33C Virus-Like Particles

The experimental methods and procedures were the same as in Example 4.1.

Example 4.5: Purification and Preparation of HPV31 L1: 33C Virus-Like Particles

The experimental methods and procedures were the same as in Example 4.1.

Example 4.6: Preparation of Purified HPV35 L1: 33C Virus-Like Particles

The experimental methods and procedures were the same as in Example 4.1.

Example 4.7: Preparation of Purified HPV39 L1: 59C Virus-Like Particles

The experimental methods and procedures were the same as in Example 4.1.

Example 4.8: Preparation of Purified HPV45 L1: 33C Virus-Like Particles

The experimental methods and procedures were the same as in Example 4.1.

Example 4.9: Preparation of Purified HPV51 L1: 33C Virus-Like Particles

The experimental methods and procedures were the same as in Example 4.1.

Example 4.10: Preparation of Purified HPV52 L1: 33C Virus-Like Particles

The experimental methods and procedures were the same as in Example 4.1.

Example 4.11: Preparation of Purified HPV56 L1: 33C Virus-Like Particles

The experimental methods and procedures were the same as in Example 4.1.

Example 4.12: Preparation of Purified HPV58 L1: 33C Virus-Like Particles

The experimental methods and procedures were the same as in Example 4.1.

Example 5 Morphological Observation of Virus-Like Particles

Example 5.1: Morphological Observation of HPV6 L1: 33C Virus-Like Particles

10 μL sample was taken for transmission electron microscopy. The sample was fixed onto a carbon coated copper grid for 2 min, the rest liquid was absorbed off with filter paper, and then stained twice with phosphotungstic acid (Beijing Electron Microscopy China Technology Co., Ltd., concentration 2%, pH 6.5) for 30 seconds each time, the rest staining solution was absorbed off with filter paper, left the sample for drying, then performed transmission electron microscopy observation. The transmission electron microscope (Brand: Hitachi, Model No.: H-7650) was 80 KV with a magnification of 80,000×.

Figure 2A:
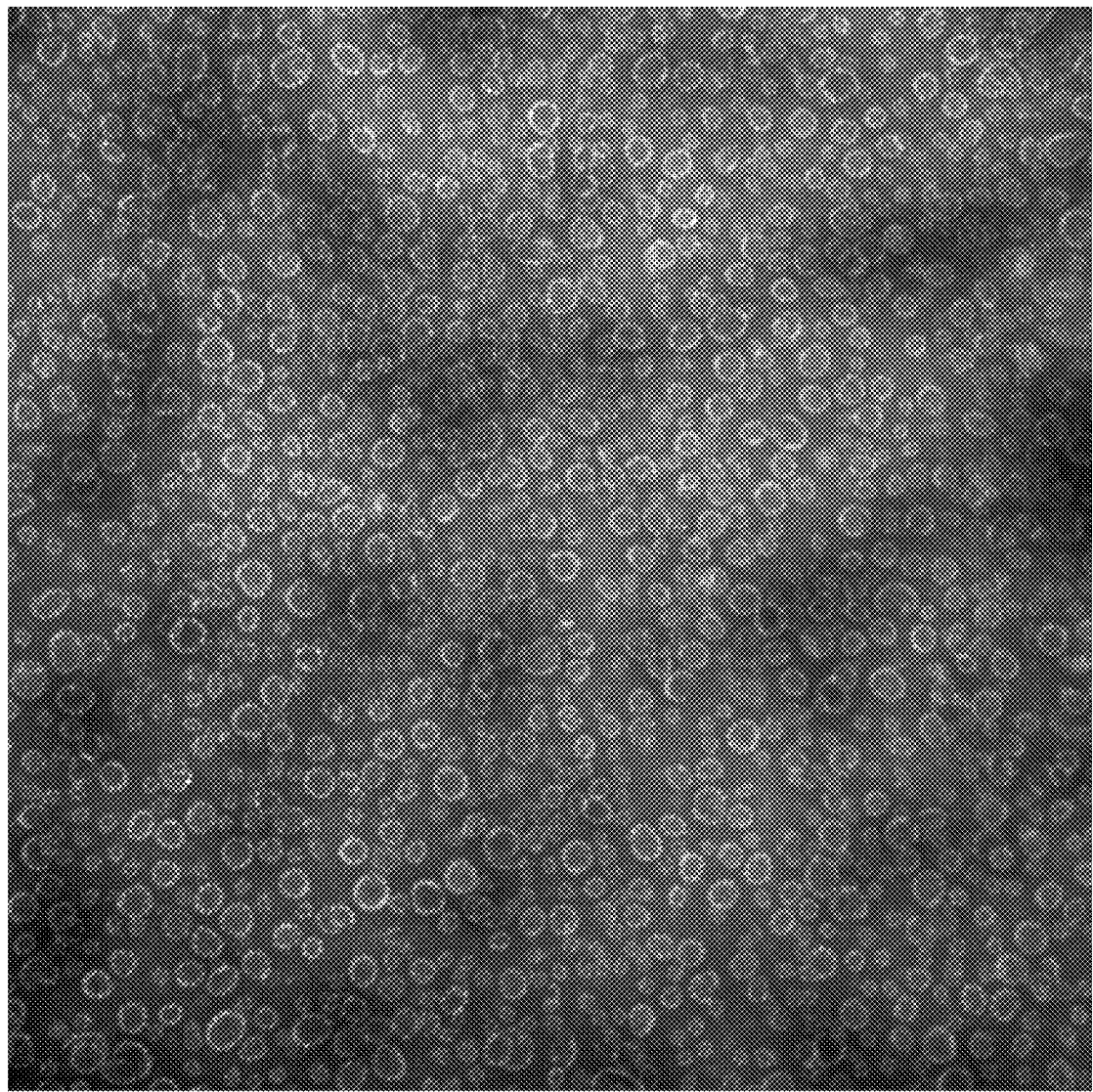
FIG. 2A: Transmission electron microscopy of HPV 6 L1: 33C virus-like particles.

The electron microscopy observation is shown in FIG. 2A. As can be seen in FIG. 2A, the C-terminal-modified HPV6 L1: 33C can form uniform-sized virus-like particles with an average diameter of approximate 60 nm.

Example 5.2: Morphological Observation of HPV11 L1: 33C Virus-Like Particles The experimental methods and procedures were the same as in Example 5.1.

Figure 2B:
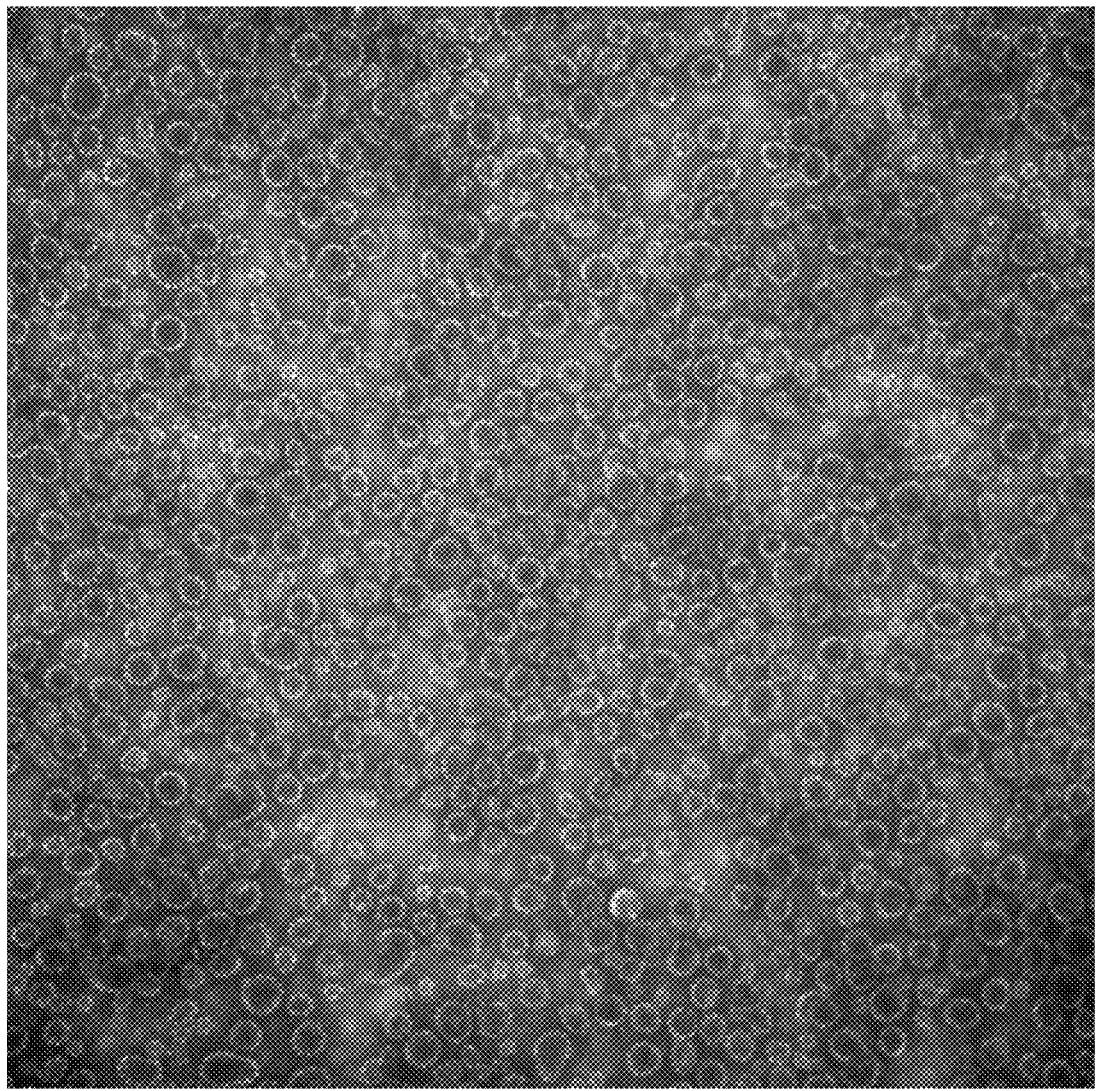
FIG. 2B: Transmission electron microscopy of HPV 11 L1: 33C virus-like particles.

The electron microscopy observation is shown in FIG. 2B. As can be seen in FIG. 2B, the C-terminal-modified HPV11 L1: 33C can form uniform-sized virus-like particles, with an average diameter of approximate 60 nm.

Example 5.3: Morphological Observation of HPV 16L1: 33C Virus-Like Particles The experimental methods and procedures were the same as in Example 5.1.

Figure 2C:
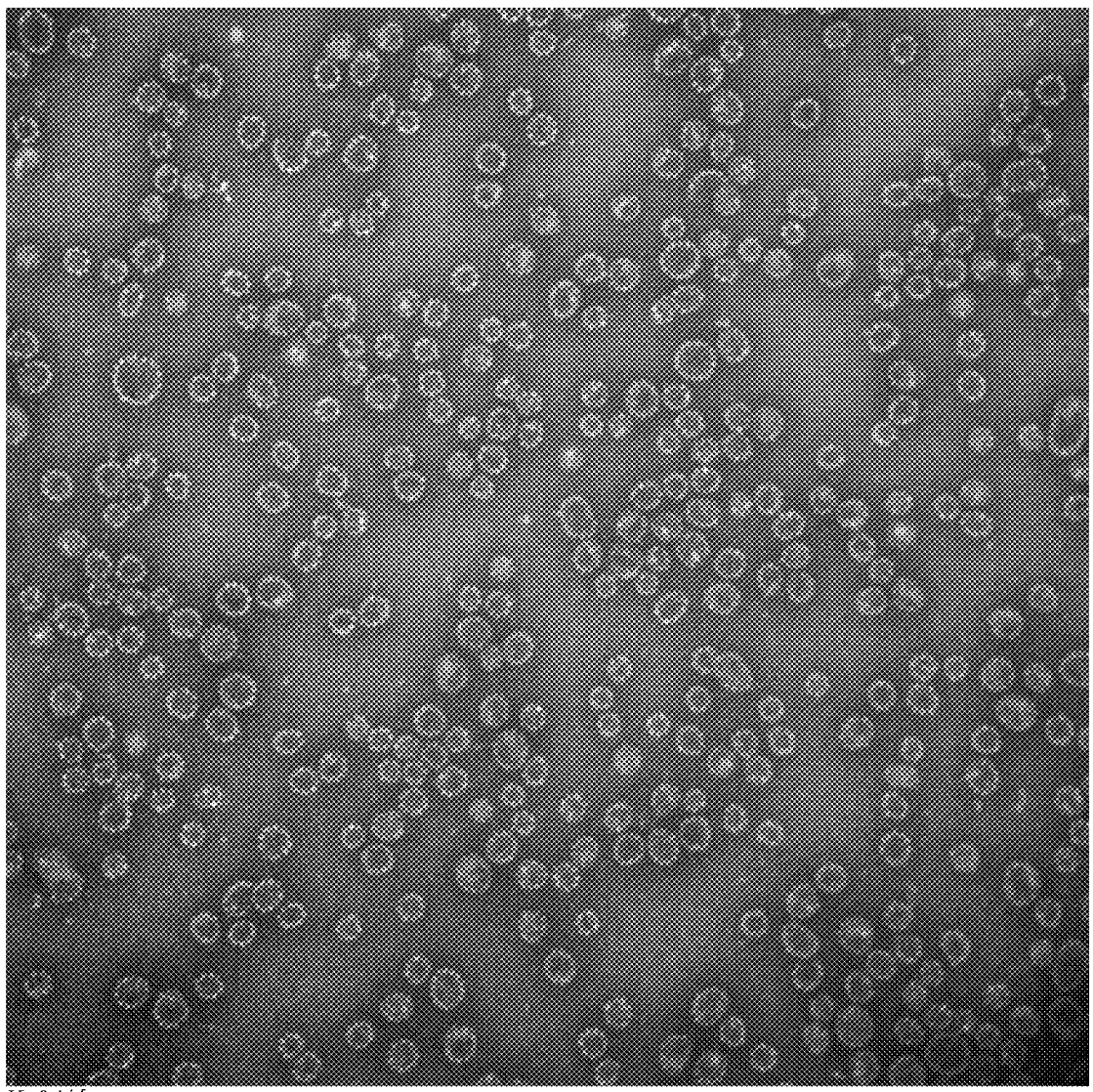
FIG. 2C: Transmission electron microscopy of HPV 16 L1: 33C virus-like particles.

The electron microscopy observation is shown in FIG. 2C. As can be seen in FIG. 2C, the C-terminal-modified HPV 16L1: 33C can form uniform-sized virus-like particles with an average diameter of approximate 60 nm.

Example 5.4: Morphological Observation of HPV18 L1: 33C Virus-Like Particles The experimental methods and procedures were the same as in Example 5.1.

Figure 2D:
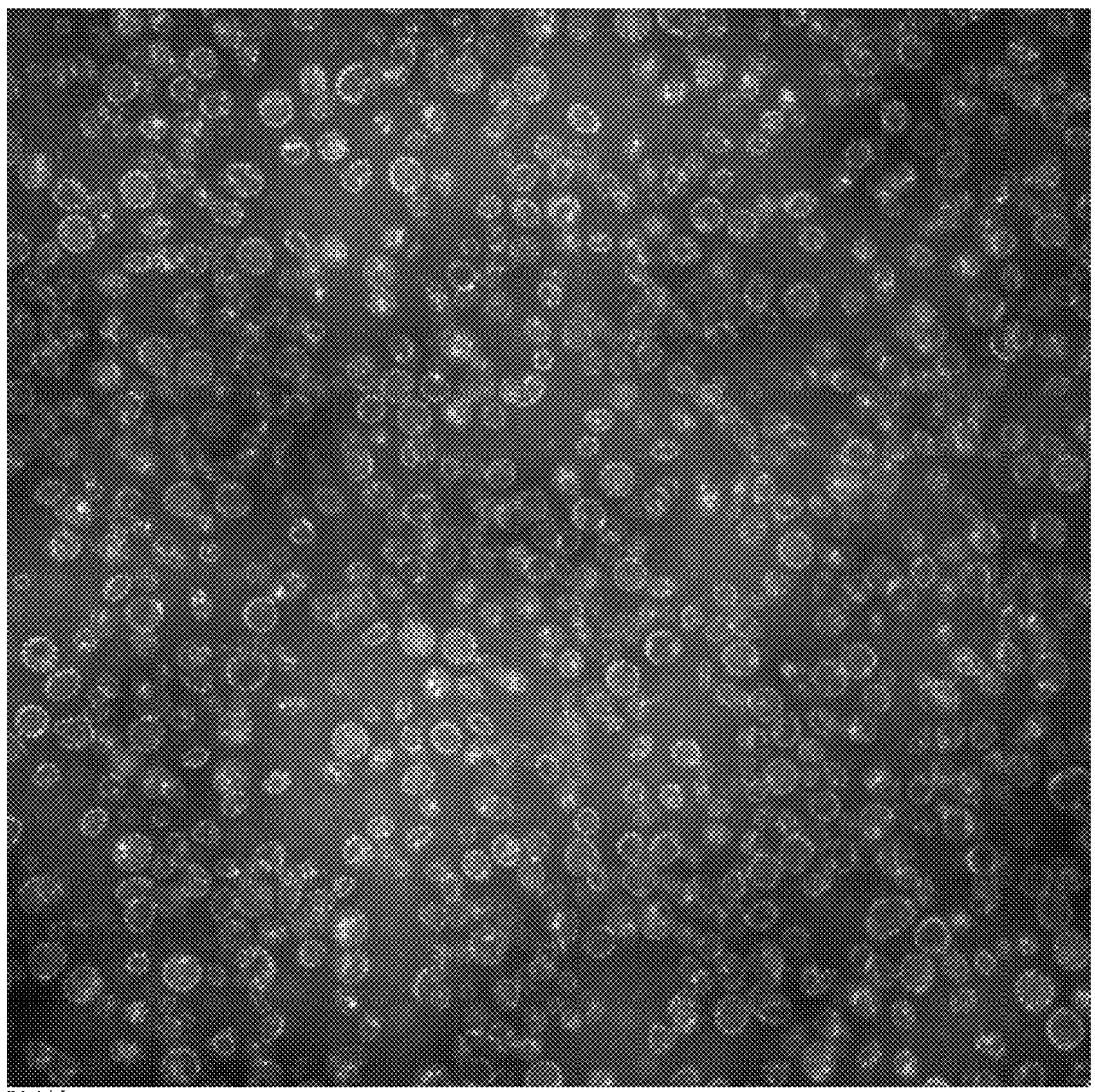
FIG. 2D: Transmission electron microscopy of HPV 18 L1: 33C virus-like particles.

The electron microscopy observation is shown in FIG. 2D. As can be seen in FIG. 2D, the C-terminal-modified HPV18 L1: 33C can form uniform-sized virus-like particles with an average diameter of approximate 60 nm.

Example 5.5: Morphological Observation of HPV31 L1: 33C Virus-Like Particles The experimental methods and procedures were the same as in Example 5.1.

Figure 2E:
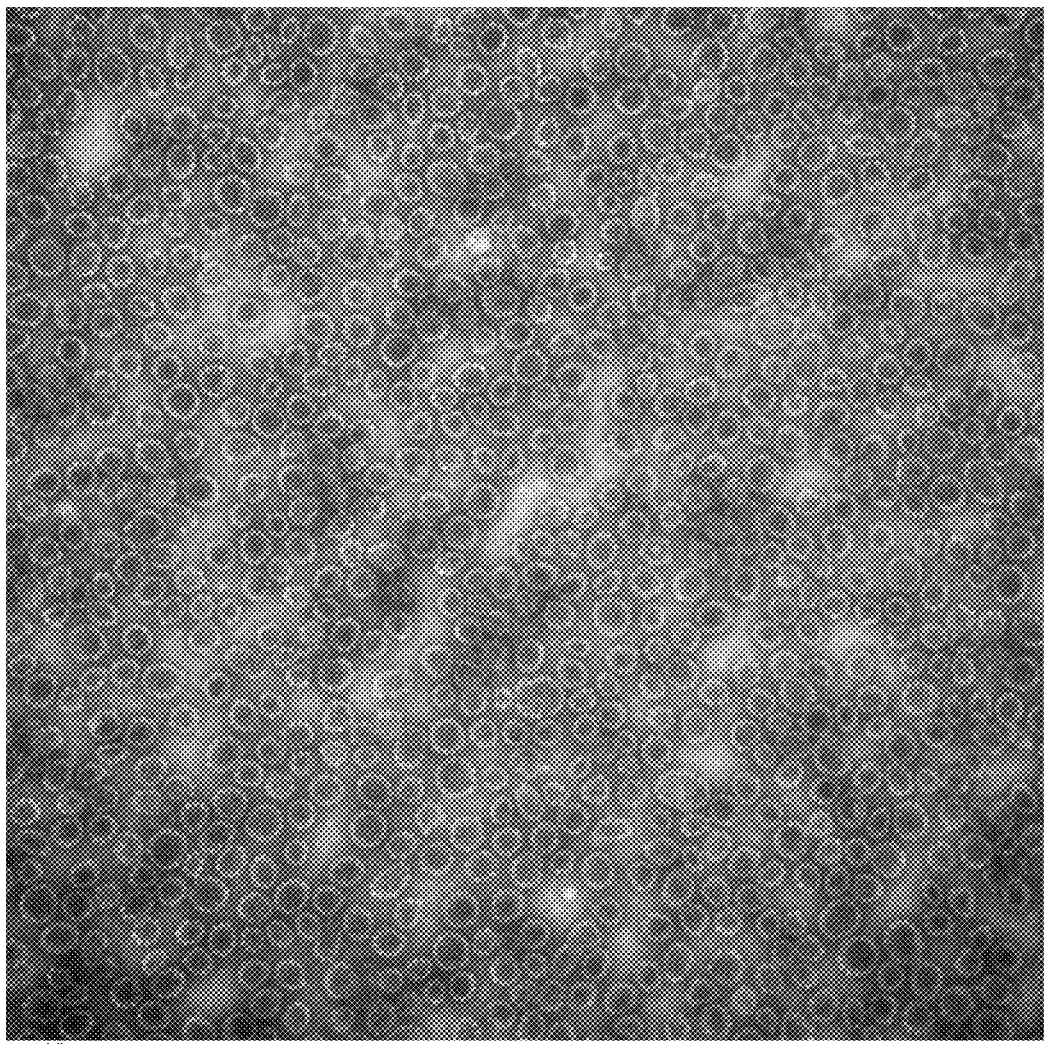
FIG. 2E: Transmission electron microscopy of HPV 31 L1: 33C virus-like particles.

The electron microscopy observation is shown in FIG. 2E. As can be seen in FIG. 2E, the C-terminal-modified HPV31 L1: 33C can form uniform-sized virus-like particles with an average diameter of approximate 60 nm.

Example 5.6: Morphological Observation of HPV35 L1: 33C Virus-Like Particles The experimental methods and procedures were the same as in Example 5.1.

Figure 2F:
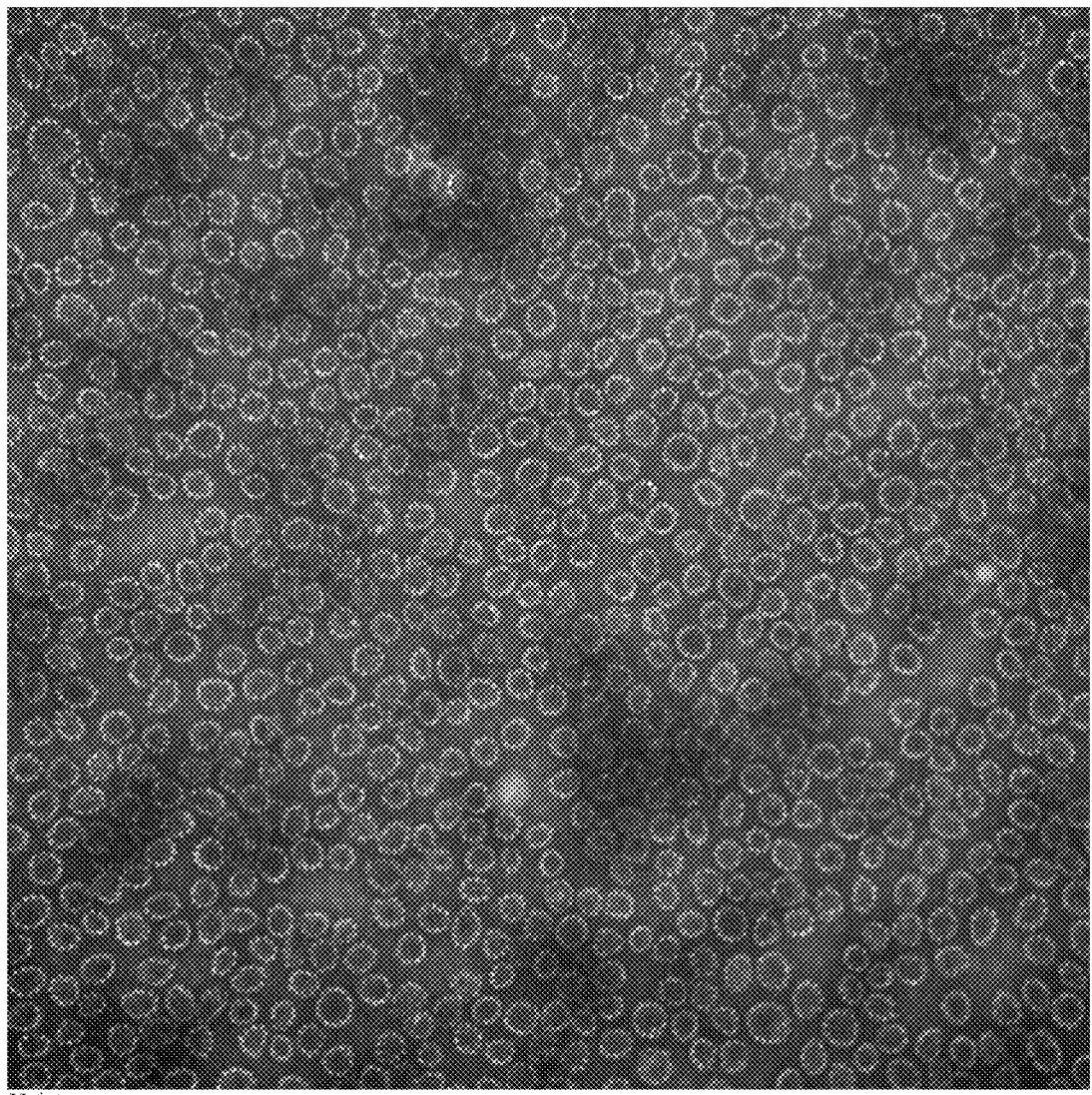
FIG. 2F: Transmission electron microscopy of HPV 35 L1: 33C virus-like particles.

The electron microscopy observation is shown in FIG. 2F. As can be seen in FIG. 2F, the C-terminally modified HPV35 L1: 33C can form uniform-sized virus-like particles with an average diameter of approximate 60 nm.

Example 5.7: Morphological Observation of HPV39 L1: 59C Virus-Like Particles The experimental methods and procedures were the same as in Example 5.1.

Figure 2G:
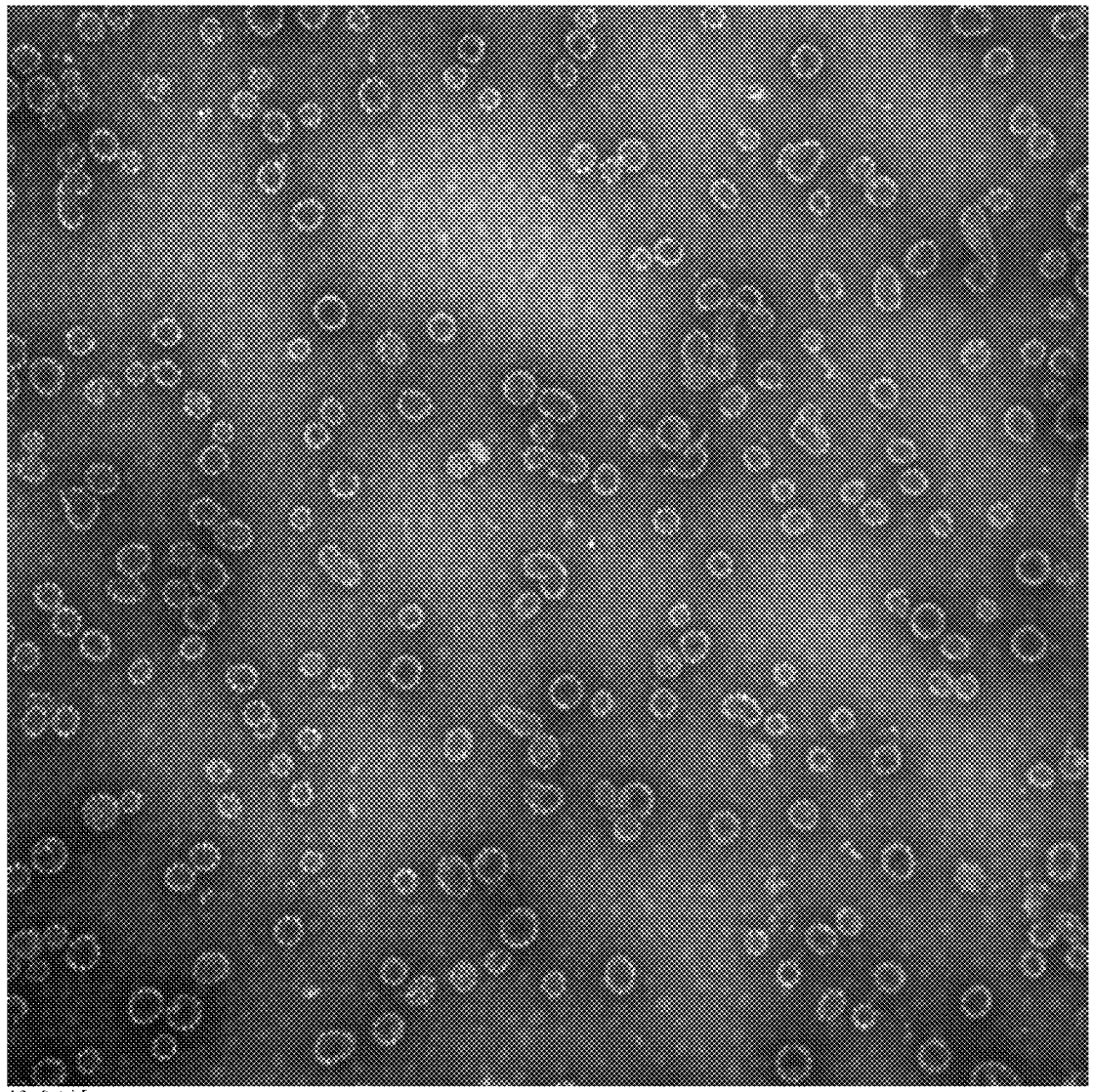
FIG. 2G: Transmission electron microscopy of HPV 39 L1: 59C virus-like particles.

The electron microscopy observation is shown in FIG. 2G. As can be seen in FIG. 2G, the C-terminal-modified HPV39 L1: 59C can form uniform-sized virus-like particles with an average diameter of approximate 60 nm.

Example 5.8: Morphological Observation of HPV45 L1: 33C Virus-Like Particles The experimental methods and procedures were the same as in Example 5.1.

Figure 2H:
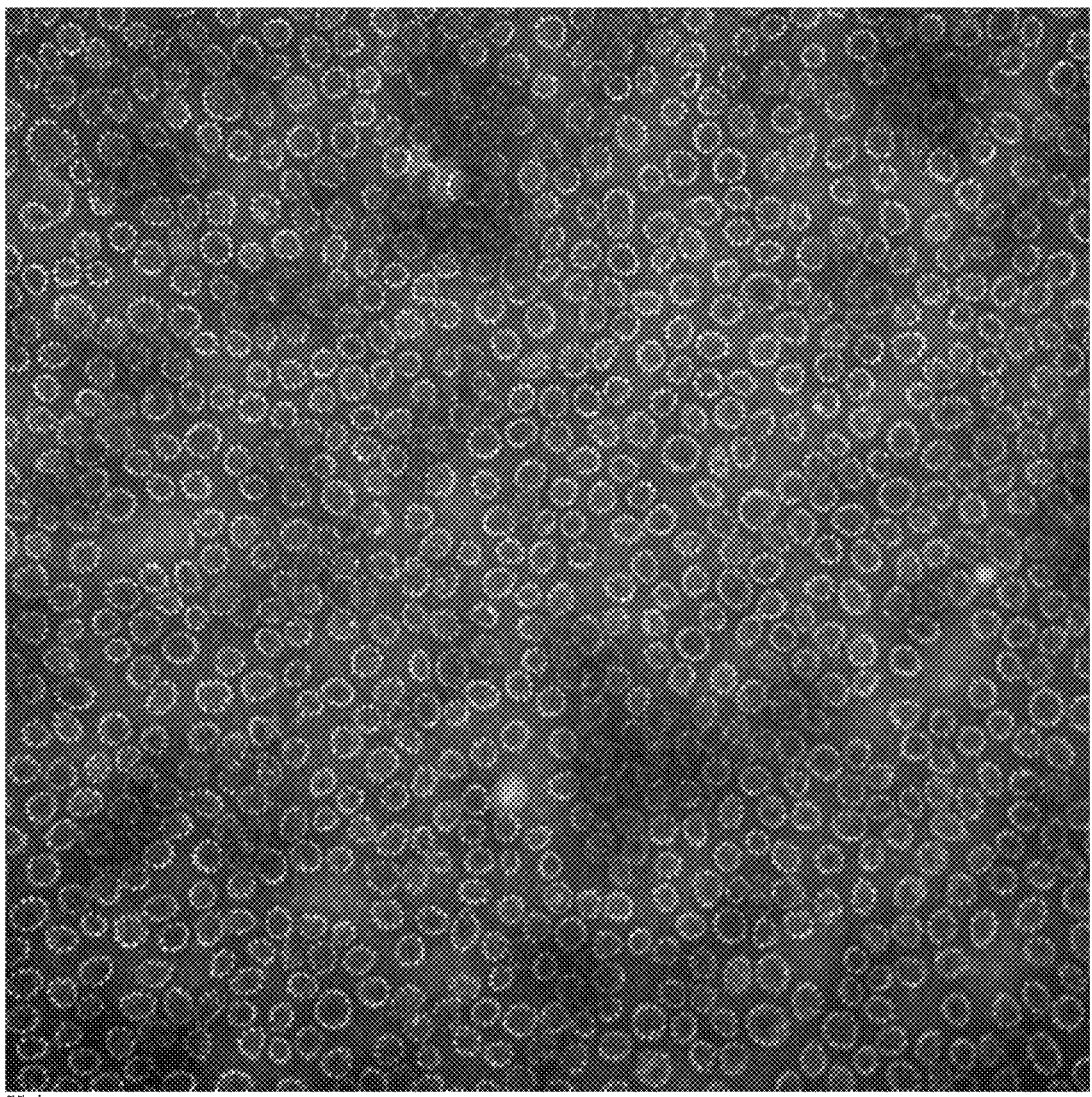
FIG. 2H: Transmission electron microscopy of HPV 45 L1: 33C virus-like particles.

The electron microscopy observation is shown in FIG. 2H. As can be seen in FIG. 2H, the C-terminal-modified HPV45 L1: 33C can form uniform-sized virus-like particles with an average diameter of approximate 60 nm.

Example 5.9: Morphological Observation of HPV51 L1: 33C Virus-Like Particles The experimental methods and procedures were the same as in Example 5.1.

Figure 2I:
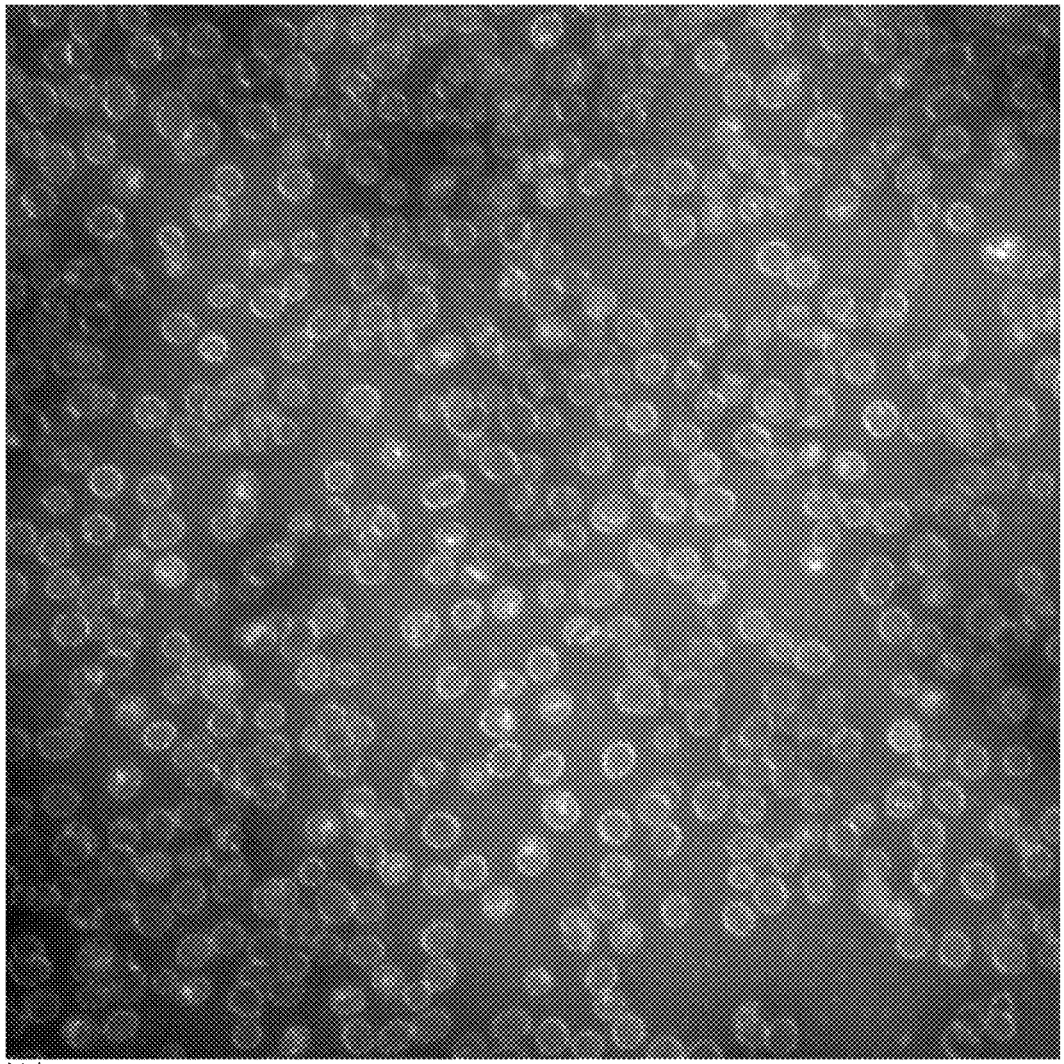
FIG. 2I: Transmission electron microscopy of HPV 51 L1: 33C virus-like particles.

The electron microscopy observation is shown in FIG. 2I. As can be seen in FIG. 2I, the C-terminal-modified HPV51 L1: 33C can form uniform-sized virus-like particles with an average diameter of approximate 60 nm.

Example 5.10: Morphological Observation of HPV52 L1: 33C Virus-Like Particles The experimental methods and procedures were the same as in Example 5.1.

Figure 2J:
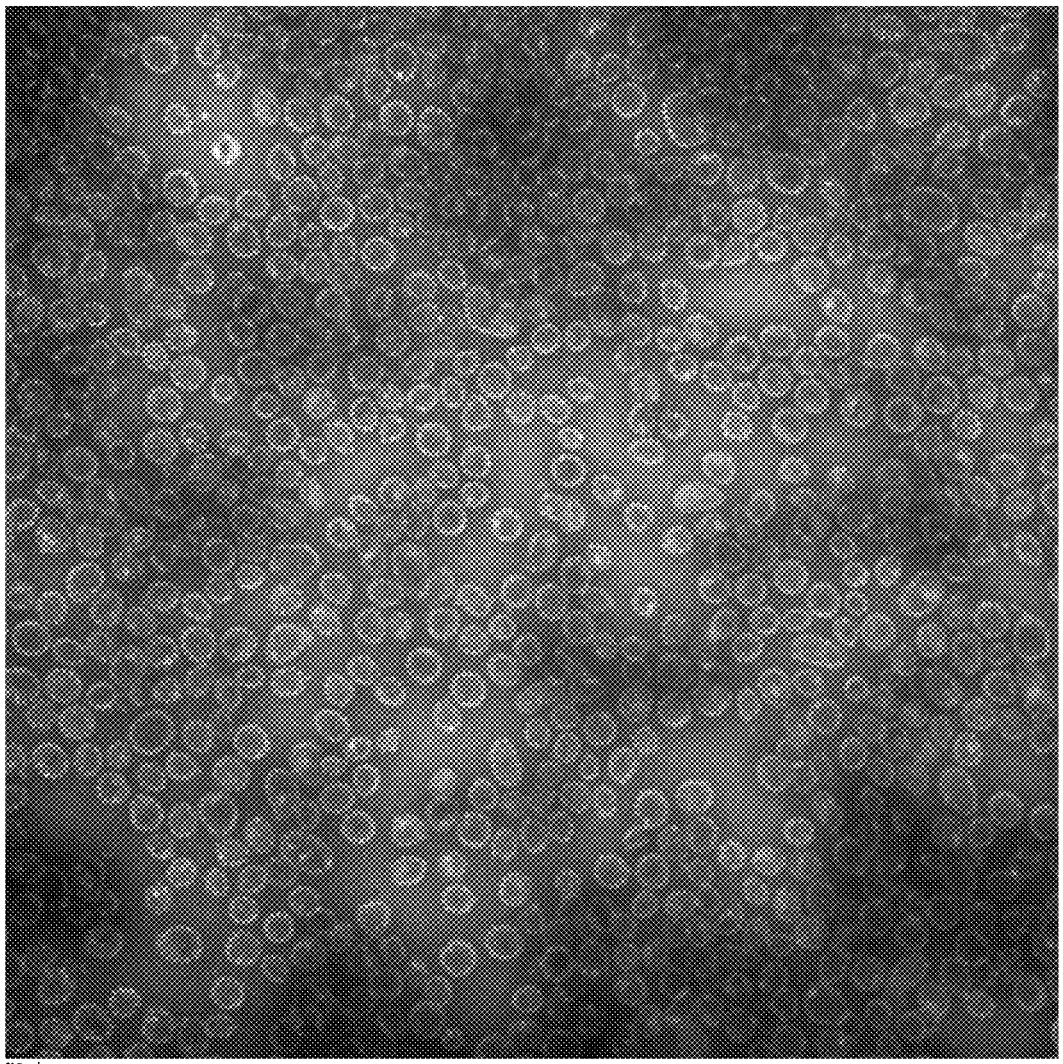
FIG. 2J: Transmission electron microscopy of HPV 52 L1: 33C virus-like particles.

The electron microscopy observation is shown in FIG. 2J. As can be seen in FIG. 2J, the C-terminal-modified HPV52 L1: 33C can form uniform-sized virus-like particles with an average diameter of approximate 60 nm.

Example 5.11: Morphological Observation of HPV56 L1: 33C Virus-Like Particles The experimental methods and procedures were the same as in Example 5.1.

Figure 2K:
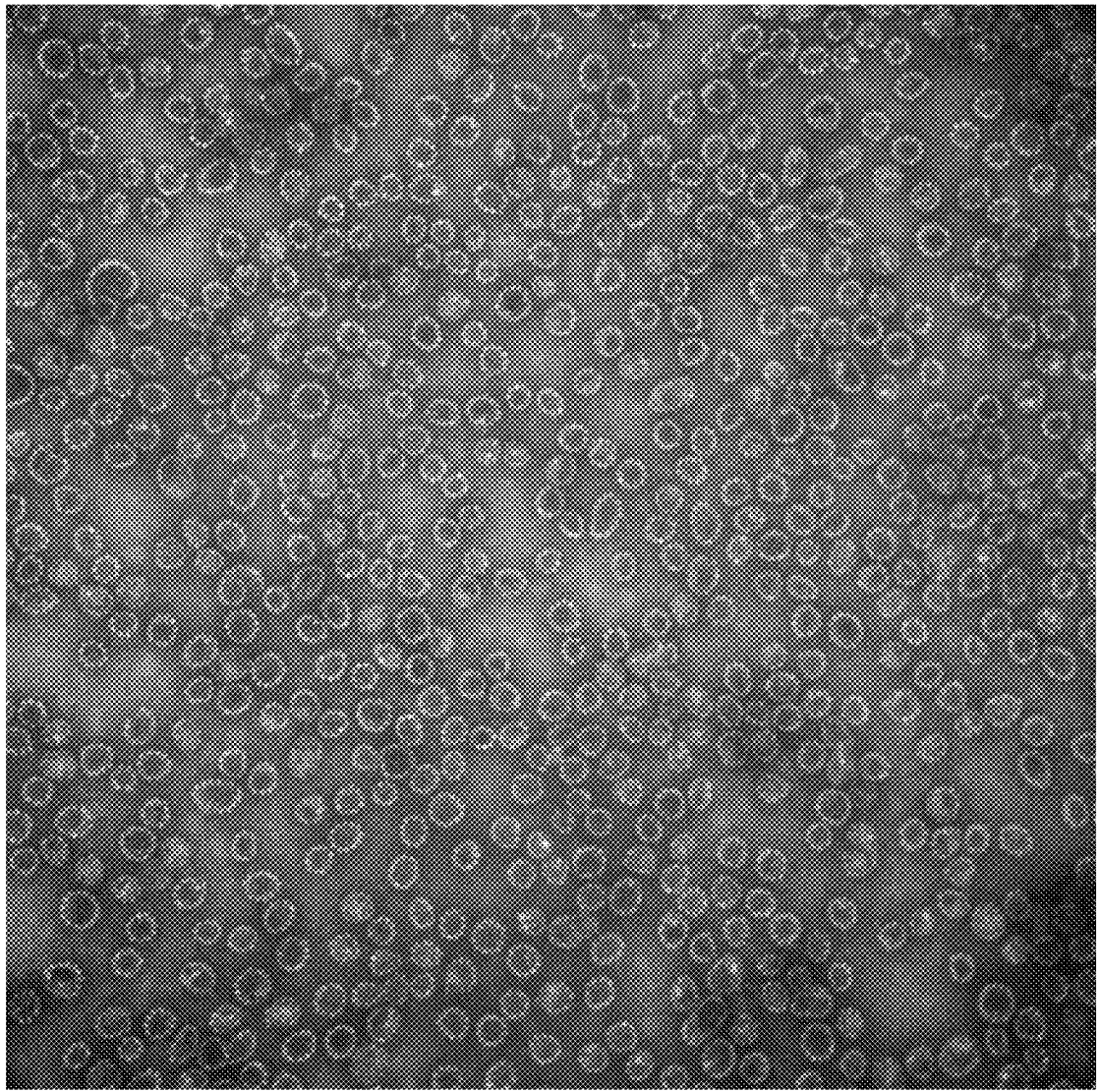
FIG. 2K: Transmission electron microscopy of HPV 56 L1: 33C virus-like particles.

The electron microscopy observation is shown in FIG. 2K. As can be seen in FIG. 2K, the C-terminal-modified HPV56 L1: 33C can form uniform-sized virus-like particles with an average diameter of approximate 60 nm.

Example 5.12: Morphological Observation of HPV58 L1: 33C Virus-Like Particles The experimental methods and procedures were the same as in Example 5.1.

Figure 2L:
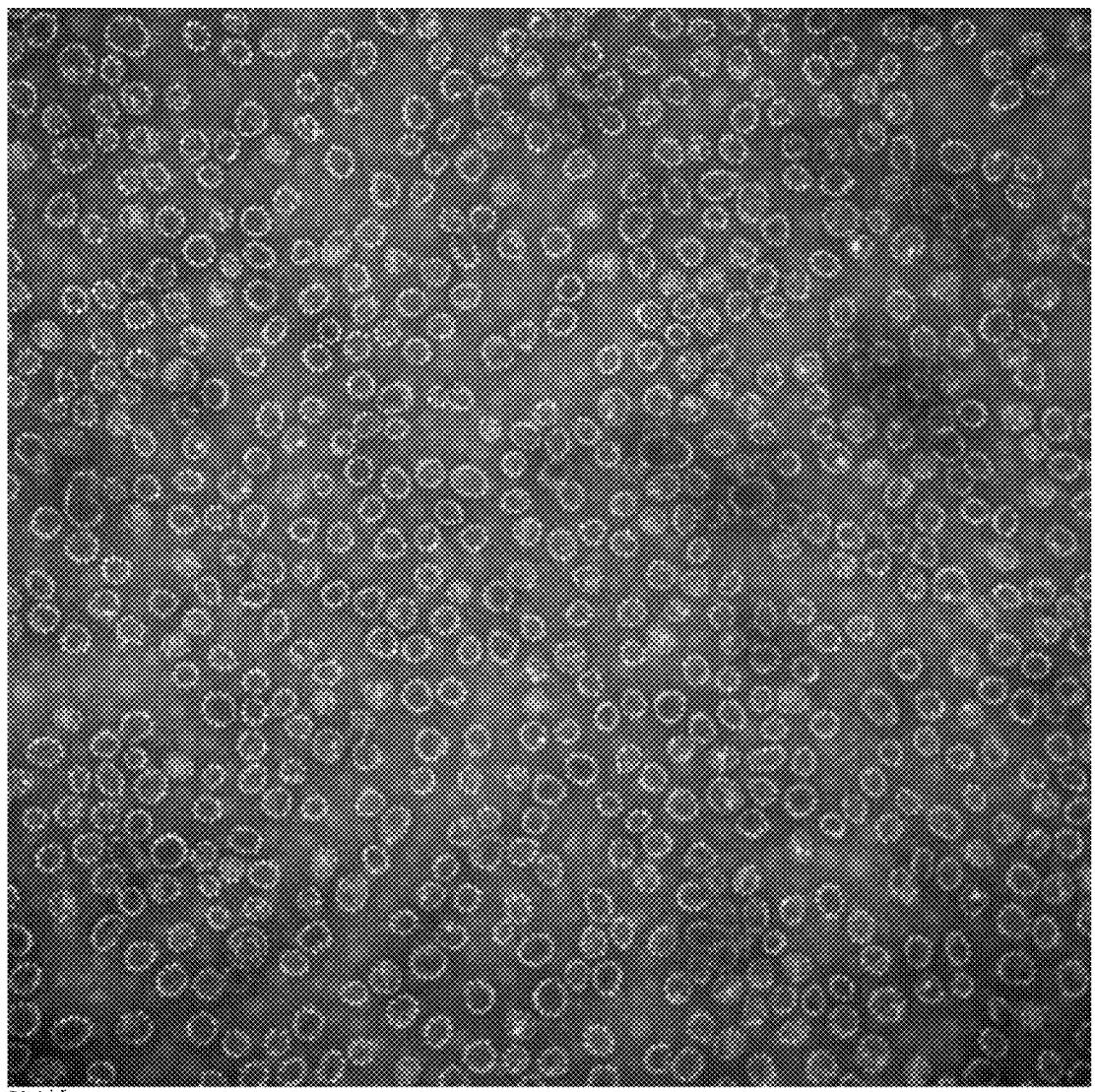
FIG. 2L: Transmission electron microscopy of HPV 58 L1: 33C virus-like particles.

The electron microscopy observation is shown in FIG. 2L. As can be seen in FIG. 2L, the C-terminal-modified HPV58 L1: 33C can form uniform-sized virus-like particles with an average diameter of approximate 60 nm.

Example 6 Immunogenicity Evaluation of Virus-Like Particles in Animals

Example 6.1: Immunogenicity Evaluation of HPV6 L1: 33C Virus-Like Particles in Animals 6.1.1 Modeling of Pseudovirus-Neutralizing Cells As HPV is difficult to be cultured in vitro and has a strong host specificity, it is difficult to be reproduced in organisms other than humans, thus there is a lack of suitable animal models. Therefore, there is a need to establish suitable and effective in vitro neutralization experimental models for the evaluation of vaccine immunoprotectivity.

HPV pseudovirus is an ideal model for HPV in vitro neutralization: Thanks to the HPV VLP's characteristic of non-specifically encapsulating nucleic acids, HPV pseudovirus can be formed from the VLPs, composed of HPV L1 and L2 expressed in cells, by encapsulating free DNA or introducing exogenous plasmid.

The immunogenicity of immunized animal serum samples was analyzed by pseudovirus neutralization assay. The animal immunized with HPV6 virus-like particles can produce neutralizing antibodies against HPV6 which can neutralize HPV6 pseudovirus. When the immunized animal serum is incubated with a certain amount of pseudovirus and then infects cells, the number of cells capable of expressing GFP fluorescence decreases when neutralization antibodies in the serum increases, showing a linear negative correlation in a certain range, so the neutralizing activity of antibodies in the serum can be evaluated by detecting the change in the number of cells expressing GFP.

Construction method of pseudovirus: The HPV6 pCMV3-3-HPV6 L1+L2 (L1 sequence was from Uniprot P69898, L2 sequence was from Uniprot Q84297) plasmid (purchased from Sino Biological) and the fluorescent plasmid (PSEU-GFP Spark, purchased from Sino Biological) were co-transfected into 293FT adherent cells (purchased from Thermo Fisher). The specific methods refer to the published literature (Pastrana D V, Buck C B, Pang Y S, Thompson C D, Castle P E, FitzGerald P C, Kjaer S K, Lowy D R, Schiller J T. Reactivity of human sera in a sensitive, high-throughput pseudovirus-based papilloma virus neutralization assay for HPV16 and HPV18. [J] Virology 2004, 321:205-216.). The pseudovirus supernatant was collected and aliquoted, and stored in a −80° C. refrigerator for stock.

6.1.2 Immunoprotective Evaluation of HPV6 L1: 33C Virus-Like Particles in Animals Immunization Procedures in Mice:

HPV6 L1: 33C virus-like particles were adsorpted onto aluminium phosphate adjuvant, mixed, and used to immunize mice at a dose of 0.15 μg/200 μL per mouse, 10 mice in total. The mice were immunized with the diluted samples on Days 0, 7 and 21, with control mice immunized with blank serum. Blood was collected from the eyes of the mice on Day 28 and the sera were isolated for pseudovirus neutralization titers assay.

EC50 Assay of Mice:

The murine serum was inactivated at 56° C. for 30 minutes, centrifuged at 6000 g, 5 mins, and the supernatant was collected for assaying. 4-8 hours prior to the assay, 293FT cells were inoculated at a density of 15,000 cells/well into 96-well plates and incubated at 37° C. in a $CO_2$ incubator with 5% $CO_2$. The post-immune murine serum and blank control serum were serial diluted with neutralizing media respectively, then mixed with the HPV6 pseudovirus prepared in 6.1 at a volume ratio of 1:1, incubated at 2-8° C. for 1 hrs., then 100 μL/well of the mixture were added to 293FT cells, which had been inoculated for 4-8 hrs in advance. Each sample was in replicate, and blank serum control group, pseudovirus positive control group and pseudovirus negative control group were used. The cells infected by pseudovirus were incubated at 37° C. in a $CO_2$ incubator with 5% $CO_2$ for 62-96 hrs, fluorescence scanning photographed and counted in an ELISPOT analyzer (Model No.: S6 Universal-V Analyzer, Manufacturer: CTL). On the basis of the neutralization inhibition of each murine serum sample, the maximum dilution of the serum at 50% neutralization inhibition was calculated for each murine serum sample according to the Reed-Muench method, i.e. the half efficacy dilution EC50.

The results of the HPV6 serum pseudovirus neutralization titer assay are detailed in Table 4.

TABLE 4

EC50 of Serum Neutralization Titer Assay in Mice (GMT ± SEM)

| HPV Type | $EC_{50}$ Value |
| --- | --- |
| Type 6 | 4948 ± 1831 |

Notes:
1. number of animals, N = 10.
2. GMT (Geometric Mean Titer): geometric mean titer.
3. SEM (Standard Error of Mean): standard error.

The above evaluation results show that the HPV6 L1: 33C virus-like particles prepared by the present invention have good immunogenicity and can produce neutralizing antibodies with high titers in animals, which can be used to prepare into a vaccine for preventing HPV infections.

Example 6.2: Evaluation of Immunogenicity of HPV11 L1: 33C Virus-Like Particles in Animals The experimental methods and procedures were the same as in Example 6.1. The L1 sequence was from Uniprot P04012 and the L2 sequence was from Uniprot P04013.

The results of HPV11 serum pseudovirus neutralization titer assay are detailed in Table 5.

TABLE 5

EC50 of Serum Neutralization Titer Assay in Mice (GMT ± SEM)

| HPV Type | $EC_{50}$ Value |
| --- | --- |
| Type 11 | 15024 ± 8400 |

The above evaluation results show that the HPV11 L1: 33C virus-like particles prepared by the present invention have good immunogenicity, can produce high titers of neutralizing antibodies in animals, and can be used to prepare into a vaccine for the prevention of HPV infection.

Example 6.3: Evaluation of Immunogenicity of HPV 16L1: 33C Virus-Like Particles in Animals The experimental methods and procedures were the same as in Example 6.1. The L1 sequence was from Uniprot P03101 and the L2 sequence was from Uniprot P03107.

The results of HPV16 serum pseudovirus neutralization titer assay are detailed in Table 6.

TABLE 6

EC50 of Serum Neutralization Titer Assay in Mice (GMT ± SEM)

| HPV Type | $EC_{50}$ Value |
|---|---|
| Type 16 | 32449 ± 7224 |

The above evaluation results show that the HPV 16L1: 33C virus-like particles prepared by the present invention have good immunogenicity and can produce high titers of neutralizing antibodies in animals, which can be used to prepare into a vaccine for the prevention of HPV infection.

Example 6.4: Evaluation of Immunogenicity of HPV18 L1: 33C Virus-Like Particles in Animals The experimental methods and procedures were the same as in Example 6.1. The L1 sequence was from Uniprot Q80B70 and the L2 sequence was from Uniprot P06793.

The results of HPV18 serum pseudovirus neutralization titer assay are detailed in Table 7.

TABLE 7

EC50 of Serum Neutralization Titer Assay in Mice (GMT ± SEM)

| HPV Type | $EC_{50}$ Value |
|---|---|
| Type 18 | 18480 ± 4051 |

The above evaluation results show that the HPV18 L1: 33C virus-like particles prepared by the present invention have good immunogenicity, can produce high titers of neutralizing antibodies in animals, and can be used to prepare into a vaccine for preventing HPV infection.

Example 6.5: Evaluation of Immunogenicity of HPV31 L1: 33C Virus-Like Particles in Animals The experimental methods and procedures were the same as in Example 6.1. The L1 sequence was from Uniprot P17388 and the L2 sequence was from Uniprot P17389.

The results of HPV31 serum pseudovirus neutralization titer assay are detailed in Table 8.

TABLE 8

EC50 of Serum Neutralization Titer Assay in Mice (GMT ± SEM)

| HPV Type | $EC_{50}$ Value |
|---|---|
| Type 31 | 5210 ± 1147 |

The above evaluation results show that the HPV31 L1: 33C virus-like particles prepared by the present invention have good immunogenicity, can produce high titers of neutralizing antibodies in animals, and can be used to prepare into a vaccine for preventing HPV infection.

Example 6.6: Evaluation of Immunogenicity of HPV35 L1: 33C Virus-Like Particles in Animals The experimental methods and procedures were the same as in Example 6.1. The L1 sequence was from Uniprot P27232 and the L2 sequence was from Uniprot P27234.

The results of HPV35 serum pseudovirus neutralization titer assay are detailed in Table 9.

TABLE 9

EC50 of Serum Neutralization Titer Assay in Mice (GMT ± SEM)

| HPV Type | $EC_{50}$ Value |
|---|---|
| Type 35 | 2293 ± 1448 |

The above evaluation results show that the HPV35 L1: 33C virus-like particles prepared by the present invention have good immunogenicity, can produce high titers of neutralizing antibodies in animals, and can be used to prepare into a vaccine for preventing HPV infection.

Example 6.7: Immunogenicity Evaluation of HPV39 L1: 59C Virus-Like Particles in Animals The experimental methods and procedures were the same as in Example 6.1. The L1 sequence was from Uniprot P24838 and the L2 sequence was from Uniprot P24839.

The results of HPV39 serum pseudovirus neutralization titer assay are detailed in Table 10.

TABLE 10

EC50 of Serum Neutralization Titer Assay in Mice (GMT ± SEM)

| HPV Type | $EC_{50}$ Value |
|---|---|
| Type 39 | 25526 ± 5857 |

The above evaluation results show that the HPV39 L1: 59C virus-like particles prepared by the present invention have good immunogenicity, can produce high titers of neutralizing antibodies in animals, and can be used to prepare into a vaccine for preventing HPV infection.

Example 6.8: Immunogenicity Evaluation of HPV45 L1: 33C Virus-Like Particles in Animals The experimental methods and procedures were the same as in Example 6.1. The L1 sequence was from Uniprot P36741 and the L2 sequence was from Uniprot P36761.

The results of HPV45 serum pseudovirus neutralization titer assay are detailed in Table 11.

TABLE 11

EC50 of Serum Neutralization Titer Assay in Mice (GMT ± SEM)

| HPV Type | $EC_{50}$ Value |
|---|---|
| Type 45 | 755 ± 935 |

The above evaluation results show that the HPV45 L1: 33C virus-like particles prepared by the present invention have good immunogenicity, can produce high titers of neutralizing antibodies in animals, and can be used to prepare into a vaccine for preventing HPV infection.

Example 6.9: Evaluation of Immunogenicity of HPV51 L1: 33C Virus-Like Particles in Animals The experimental methods and procedures were the same as in Example 6.1. The L1 sequence was from Uniprot P26536 and the L2 sequence was from Uniprot P26539.

The results of HPV51 serum pseudovirus neutralization titer assay are detailed in Table 12.

TABLE 12

EC50 of Serum Neutralization Titer Assay in Mice (GMT ± SEM)

| HPV Type | $EC_{50}$ Value |
|---|---|
| Type 51 | 5528 ± 1572 |

The above evaluation results show that the HPV51 L1: 33C virus-like particles prepared by the present invention have good immunogenicity, can produce high titers of neutralizing antibodies in animals, and can be used to prepare into a vaccine for preventing HPV infection.

Example 6.10: Evaluation of Immunogenicity of HPV52 L1: 33C Virus-Like Particles in Animals The experimental methods and procedures were the same as in Example 6.1. The L1 sequence was from Uniprot Q05138 and the L2 sequence was from Uniprot F8S4U2.

The results of HPV52 serum pseudovirus neutralization titer assay are detailed in Table 13.

TABLE 13

EC50 of Serum Neutralization Titer Assay in Mice (GMT ± SEM)

| HPV Type | $EC_{50}$ Value |
|---|---|
| Type 52 | 19019 ± 8604 |

The above evaluation results show that the HPV52 L1: 33C virus-like particles prepared by the present invention have good immunogenicity, can produce high titers of neutralizing antibodies in animals, and can be used to prepare into a vaccine for preventing HPV infection.

Example 6.11: Evaluation of Immunogenicity of HPV56 L1: 33C Virus-Like Particles in Animals The experimental methods and procedures were the same as in Example 6.1. The L1 sequence was from Uniprot P36743 and the L2 sequence was from Uniprot P36765.

The results of HPV56 serum pseudovirus neutralization titer assay are detailed in Table 14.

TABLE 14

EC50 of Serum Neutralization Titer Assay in Mice (GMT ± SEM)

| HPV Type | $EC_{50}$ Value |
|---|---|
| Type 56 | 2497 ± 612 |

The above evaluation results show that the HPV56 L1: 33C virus-like particles prepared by the present invention have good immunogenicity, can produce high titers of neutralizing antibodies in animals, and can be used to prepare into a vaccine for preventing HPV infection.

Example 6.12: Evaluation of Immunogenicity of HPV58 L1: 33C Virus-Like Particles in Animals The experimental methods and procedures were the same as in Example 6.1. The L1 sequence was from Uniprot P26535 and the L2 sequence was from Uniprot B6ZB12.

The results of HPV58 serum pseudovirus neutralization titer assay are detailed in Table 15.

TABLE 15

EC50 of Serum Neutralization Titer Assay in Mice (GMT ± SEM)

| HPV Type | $EC_{50}$ Value |
|---|---|
| Type 58 | 19939 ± 8459 |

The above evaluation results show that the HPV58 L1: 33C virus-like particles prepared by the present invention have good immunogenicity, can produce high titers of neutralizing antibodies in animals, and can be used to prepare into a vaccine for the prevention of HPV infection.

Comparative Example 1: Expression of C-Terminal Truncated HPV16L1 (aa 1-474)

Figure 3:
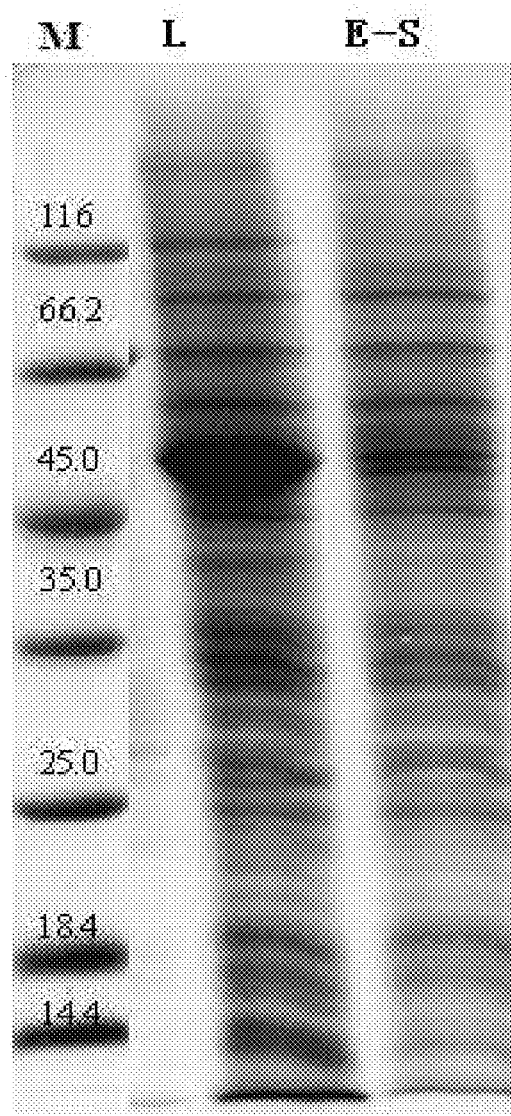
FIG. 3: Expression of C-terminal truncated HPV 16L1 (1-474). M: Marker; L: cell lysates; E-S: supernatant collected after centrifugation of the lysates.

The inventors attempted to truncate the C-terminus of HPV16L1 by 31 amino acids and named it HPV16L1 (1-474) (SEQ ID NO: 27). However, it was found in the study that the truncated HPV16L1 (1-474) protein was highly expressed but has very poor solubility, and is difficult to extract and purify, the detailed results of expression and extraction are shown in FIG. 3.

Although the present invention has been described in detail by way of illustration and embodiments in the foregoing, it is intended to facilitate understanding. It is obvious to those skilled in the art that various modifications and improvements can be made to the technical solutions of the present invention are apparently possible for those of ordinary skill in the art without deviating from the spirit or scope of the attached claims.

What is claimed is:

1. A chimeric human papillomavirus L1 protein comprising, from its N-terminus to C-terminus orientation, (a) an N-terminal fragment derived from an L1 protein of HPV Type 6, wherein said fragment is encoded by the gene in SEQ ID No:5; and (b) a C-terminal fragment, which is selected from the sequences shown in SEQ ID No: 2 or SEQ ID No: 132, wherein said chimeric human papillomavirus L1 protein has the immunogenicity of the L1 protein of HPV Type 6.

2. The chimeric human papillomavirus L1 protein according to claim 1, wherein the sequence of the N-terminal fragment derived from HPV type 6 L1 protein is shown in SEQ ID No: 1.

3. The chimeric human papillomavirus L1 protein according to claim 1, wherein said C-terminus of said N-terminal fragment is connected to the N-terminus of said C-terminal fragment directly or via a linker.

4. The chimeric human papillomavirus L1 protein according to claim 1, wherein the sequence of the chimeric HPV L1.

5. An immunogenic composition for the prevention of papillomavirus-associated diseases, comprising:

(a) an adjuvant; and (b) the chimeric human papillomavirus L1 protein according to claim 1.

6. An immunogenic composition for the prevention of papillomavirus-associated diseases, comprising;

(a) an adjuvant; and (b) the chimeric human papillomavirus L1 protein according to claim 2.

7. An immunogenic composition for the prevention of papillomavirus-associated diseases, comprising:

(a) an adjuvant; and (b) the chimeric human papillomavirus L1 protein according to claim 3.

8. An immunogenic composition for the prevention of papillomavirus-associated diseases, comprising:

(a) an adjuvant; and (b) the chimeric human papillomavirus L1 protein according to claim 4.

* * * * *

SEQUENCE LISTING

```
<160> NUMBER OF SEQ ID NOS: 202

<210> SEQ ID NO 1
<211> LENGTH: 469
<212> TYPE: PRT
<213> ORGANISM: Homo sapiens
<220> FEATURE:
<221> NAME/KEY: misc_feature
```

<223> OTHER INFORMATION: 0601 Amino acid sequence of HPV type 6 L1 protein aa 1-469

<400> SEQUENCE: 1

```
Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
            35                  40                  45

Phe Ser Ile Lys Arg Ala Asn Lys Thr Val Val Pro Lys Val Ser Gly
        50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
                100                 105                 110

Gly Val Ser Gly His Pro Phe Leu Asn Lys Tyr Asp Asp Val Glu Asn
            115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400
```

```
Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr
465

<210> SEQ ID NO 2
<211> LENGTH: 26
<212> TYPE: PRT
<213> ORGANISM: Homo sapiens
<220> FEATURE:
<221> NAME/KEY: misc_feature
<223> OTHER INFORMATION: 0602 Amino acid sequence of HPV type 33 L1
      protein aa 474-499

<400> SEQUENCE: 2

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 3
<211> LENGTH: 495
<212> TYPE: PRT
<213> ORGANISM: Artificial sequence
<220> FEATURE:
<223> OTHER INFORMATION: 0603 Amino acid sequence of chimeric HPV type 6
      L1 protein

<400> SEQUENCE: 3

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
```

```
                    180                 185                 190
Asp Gly Asp Met Val Asp Thr Gly Phe Gly Ala Met Asn Phe Ala Asp
                195                 200                 205
Leu Gln Thr Asn Lys Ser Asp Val Pro Ile Asp Ile Cys Gly Thr Thr
            210                 215                 220
Cys Lys Tyr Pro Asp Tyr Leu Gln Met Ala Ala Asp Pro Tyr Gly Asp
225                 230                 235                 240
Arg Leu Phe Phe Phe Leu Arg Lys Glu Gln Met Phe Ala Arg His Phe
                245                 250                 255
Phe Asn Arg Ala Gly Glu Val Gly Glu Pro Val Pro Asp Thr Leu Ile
            260                 265                 270
Ile Lys Gly Ser Gly Asn Arg Thr Ser Val Gly Ser Ser Ile Tyr Val
        275                 280                 285
Asn Thr Pro Ser Gly Ser Leu Val Ser Ser Glu Ala Gln Leu Phe Asn
        290                 295                 300
Lys Pro Tyr Trp Leu Gln Lys Ala Gln Gly His Asn Asn Gly Ile Cys
305                 310                 315                 320
Trp Gly Asn Gln Leu Phe Val Thr Val Val Asp Thr Thr Arg Ser Thr
                325                 330                 335
Asn Met Thr Leu Cys Ala Ser Val Thr Thr Ser Ser Thr Tyr Thr Asn
            340                 345                 350
Ser Asp Tyr Lys Glu Tyr Met Arg His Val Glu Glu Tyr Asp Leu Gln
        355                 360                 365
Phe Ile Phe Gln Leu Cys Ser Ile Thr Leu Ser Ala Glu Val Met Ala
        370                 375                 380
Tyr Ile His Thr Met Asn Pro Ser Val Leu Glu Asp Trp Asn Phe Gly
385                 390                 395                 400
Leu Ser Pro Pro Pro Asn Gly Thr Leu Glu Asp Thr Tyr Arg Tyr Val
                405                 410                 415
Gln Ser Gln Ala Ile Thr Cys Gln Lys Pro Thr Pro Glu Lys Glu Lys
            420                 425                 430
Pro Asp Pro Tyr Lys Asn Leu Ser Phe Trp Glu Val Asn Leu Lys Glu
        435                 440                 445
Lys Phe Ser Ser Glu Leu Asp Gln Tyr Pro Leu Gly Arg Lys Phe Leu
    450                 455                 460
Leu Gln Ser Gly Tyr Lys Ala Lys Pro Lys Leu Lys Arg Ala Ala Pro
465                 470                 475                 480
Thr Ser Thr Arg Thr Ser Ser Ala Lys Arg Lys Lys Val Lys Lys
                485                 490                 495

<210> SEQ ID NO 4
<211> LENGTH: 1488
<212> TYPE: DNA
<213> ORGANISM: Artificial sequence
<220> FEATURE:
<223> OTHER INFORMATION: 0604 Nucleotide sequence of chimeric HPV type 6
      L1 protein

<400> SEQUENCE: 4
atgtggagac catctgacag cacagtctat gtgcctcctc caaaccctgt gagcaaggtg      60
gtggctacag atgcctatgt gaccaggacc aacatcttct accatgcctc ctccagcaga    120
ctgctggctg tgggacaccc atacttcagc atcaagaggg ctaacaagac agtggtgcca    180
aaggtgtctg ctaccaata cagggtgttc aaggtggtgc tgcctgaccc aaacaagttt    240
gccctgcctg actcctccct gtttgaccca accacccaga gactggtgtg ggcttgtact    300
```

```
ggattggagg tgggcagggg acaaccactg ggagtgggag tgtctggaca cccattcctg      360
aacaaatatg atgatgtgga gaactctggc tctggaggca ccctggaca agacaacagg       420 gtgaatgtgg ggatggacta caagcagacc caactttgta tggtgggctg tgcccctcca     480 ctggggagaac actggggcaa gggcaagcag tgtaccaaca cacctgtcca ggctggagac    540
tgtcctccat tggaactgat tacctctgtg attcaggatg agatatggt ggacacaggc      600 tttggagcta tgaactttgc tgacctccaa accaacaagt ctgatgtgcc aattgacatc     660
tgtggcacca cttgtaaata ccctgactac ctccaaatgg ctgctgaccc atatggagac    720
agactgttct tcttcctgag gaaggaacag atgtttgcca gacacttctt caacagggct    780
ggagaggtgg gagaacctgt gcctgacacc ctgattatca agggctctgg caacaggacc    840
tctgtgggct ccagcatcta tgtgaacaca ccatctggct ccctggtgtc ctctgaggct    900
caacttttca caagccata ctggctccaa aaggctcaag acacaacaa tggcatctgt     960 tggggcaacc aactttttgt gacagtggtg gacaccacca ggagcaccaa tatgacctg   1020 tgtgcctctg tgaccacctc cagcacctac accaactctg actacaagga atatatgagg   1080
catgtggagg aatatgacct ccaattcatc ttccaacttt gtagcatcac cctgtctgct   1140
gaggtgatgg cttacatcca cacaatgaac ccatctgtgt tggaggactg gaactttgga  1200
ctgagccctc ctccaaatgg caccttggag gacacctaca gatatgtcca gagccaggct  1260
atcacttgtc agaagccaac acctgagaag gagaagcctg acccatacaa gaacctgtcc  1320
ttctgggagg tgaacctgaa agagaagttc tcctctgaac tggaccaata ccccactgggc 1380 aggaagttcc tgctccaatc tggctacaaa gccaagccaa aactgaaaag ggctgcccca  1440
accagcacca ggacctcctc tgccaagagg aagaaggtga agaagtaa               1488
```

<210> SEQ ID NO 5
<211> LENGTH: 1522
<212> TYPE: DNA
<213> ORGANISM: Artificial sequence
<220> FEATURE:
<223> OTHER INFORMATION: 0605 Synthetic HPV6 L1 gene

<400> SEQUENCE: 5

```
ctgggtacca tgtggagacc atctgacagc acagtctatg tgcctcctcc aaaccctgtg    60
agcaaggtgg tggctacaga tgcctatgtg accaggacca acatcttcta ccatgcctcc   120
tccagcagac tgctggctgt gggacaccca tacttcagca tcaagagggc taacaagaca   180
gtggtgccaa aggtgtctgg ctaccaatac agggtgttca aggtggtgct gcctgaccca   240
aacaagtttg ccctgcctga ctcctccctg tttgacccaa ccacccagag actggtgtgg   300
gcttgtactg gattggaggt gggcagggga caaccactgg gagtgggagt gtctggacac   360
ccattcctga caaatatga tgatgtggag aactctggct ctggaggcaa ccctggacaa    420
gacaacaggg tgaatgtggg gatggactac aagcagaccc aactttgtat ggtgggctgt   480
gcccctccac tggggagaaca ctggggcaag ggcaagcagt gtaccaacac acctgtccag  540
gctggagact gtcctccatt ggaactgatt acctctgtga ttcaggatgg agatatggtg   600
gacacaggct ttggagctat gaactttgct gacctccaaa ccaacaagtc tgatgtgcca   660
attgacatct gtggcaccac ttgtaaatac cctgactacc tccaaatggc tgctgaccca   720
tatggagaca gactgttctt cttcctgagg aaggaacaga tgtttgccag acacttcttc   780
aacagggctg gagaggtggg agaacctgtg cctgacaccc tgattatcaa gggctctggc   840
```

```
aacaggacct ctgtgggctc cagcatctat gtgaacacac catctggctc cctggtgtcc    900
tctgaggctc aacttttcaa caagccatac tggctccaaa aggctcaagg acacaacaat    960
ggcatctgtt ggggcaacca acttttttgtg acagtggtgg acaccaccag gagcaccaat   1020
atgaccctgt gtgcctctgt gaccaccctcc agcacctaca ccaactctga ctacaaggaa   1080
tatatgaggc atgtggagga atatgacctc caattcatct ccaactttg tagcatcacc     1140 ctgtctgctg aggtgatggc ttacatccac acaatgaacc catctgtgtt ggaggactgg    1200
aactttggac tgagccctcc tccaaatggc accttggagg acacctacag atatgtccag    1260
agccaggcta tcacttgtca gaagccaaca cctgagaagg agaagcctga cccatacaag    1320
aacctgtcct tctgggaggt gaacctgaaa gagaagttct cctctgaact ggaccaatac    1380
ccactgggca ggaagttcct gctccaatct ggctacaggg caggtccag catcaggaca     1440 ggagtgaaga gacctgctgt gagcaaggca tctgctgccc caaagaggaa gagggctaag    1500
accaagaggt aaactcgagc tc                                             1522
```

```
<210> SEQ ID NO 6
<211> LENGTH: 1519
<212> TYPE: DNA
<213> ORGANISM: Artificial sequence
<220> FEATURE:
<223> OTHER INFORMATION: 0606 Synthetic HPV33 L1 gene

<400> SEQUENCE: 6
ctgggtacca tgagtgtgtg gagaccatct gaggctacag tctacctgcc tcctgtgcct    60
gtgagcaagg tggtgagcac agatgaatat gtgagcagga ccagcatcta ctactatgct   120
ggctccagca gactgctggc tgtgggacac ccatacttca gcatcaagaa cccaaccaat   180
gccaagaaac tgctggtgcc aaaggtgtct ggactccaat acagggtgtt cagggtgaga   240
ctgcctgacc caaacaagtt tggctttcct gacacctcct tctacaaccc tgacacccag   300
agactggtgt gggcttgtgt gggattggag attggcaggg acaaccact gggagtgggc    360 atctctggac acccactgct gaacaagttt gatgacacag agacaggcaa caaatacccct  420 ggacaacctg agcagacaa cagggagtgt ctgagtatgg actacaagca gacccaactt    480
tgtctgctgg gctgtaagcc tccaacagga gaacactggg gcaagggagt ggcttgtacc   540
aatgctgccc ctgccaatga ctgtcctcca ttggaactga taaacaccat cattgaggat   600
ggagatatgg tggacacagg cttgggctgt atggacttca gaccctcca gccaacaag    660 tctgatgtgc caattgacat ctgtggcagc acttgtaaat accctgacta cctgaaaatg   720
acctctgaac catatggaga ctccctgttc ttcttcctga ggagggaaca gatgtttgtg   780
agacacttct tcaacagggc tggcaccctg ggagaggctg tgcctgatga cctctacatc   840
aagggctctg gcaccacagc cagcatccag tcctctgcct tctttccaac cacatctggc   900
agtatggtga cctctgagag ccaactttttc aacaagccat actggctcca aagggctcaa   960
ggacacaaca atggcatctg ttggggcaac caggtgtttg tgacagtggt ggacaccacc   1020
aggagcacca atatgaccct gtgtacccag gtgacctctg acagcaccta caagaatgag   1080
aacttcaagg aatacatcag gcatgtggag gaatatgacc tccaatttgt gttccaactt   1140
tgtaaggtga ccctgacagc agaggtgatg acctacatcc atgctatgaa ccctgacatc   1200
ttggaggact ggcagtttgg actgacacct cctccatctg cctccctcca agacacctac   1260
aggtttgtga ccagccaggc tatcacttgt cagaagacag tgcctccaaa ggagaaggag   1320
gacccactgg gcaaatacac cttctgggag gtggacctga agagaagtt ctctgctgac   1380
```

```
ctggaccagt tccactggg caggaagttc ctgctccaag caggactgaa agccaagcca    1440
aaactgaaaa gggctgcccc aaccagcacc aggacctcct ctgccaagag gaagaaggtg    1500
aagaagtaaa ctcgagctc                                                 1519
```

<210> SEQ ID NO 7
<211> LENGTH: 35
<212> TYPE: DNA
<213> ORGANISM: Artificial sequence
<220> FEATURE:
<223> OTHER INFORMATION: 0607 HPV6L1 F1

<400> SEQUENCE: 7

```
cttggtacca tgtggagacc atctgacagc acagt                                35
```

<210> SEQ ID NO 8
<211> LENGTH: 36
<212> TYPE: DNA
<213> ORGANISM: Artificial sequence
<220> FEATURE:
<223> OTHER INFORMATION: 0608 HPV6L1 R1

<400> SEQUENCE: 8

```
gcttggcttt gtagccagat tggagcagga acttcc                               36
```

<210> SEQ ID NO 9
<211> LENGTH: 1426
<212> TYPE: DNA
<213> ORGANISM: Artificial sequence
<220> FEATURE:
<223> OTHER INFORMATION: 0609 HPV6L1 amplified sequence 1

<400> SEQUENCE: 9

```
cttggtacca tgtggagacc atctgacagc acagtctatg tgcctcctcc aaaccctgtg      60
agcaaggtgg tggctacaga tgcctatgtg accaggacca acatcttcta ccatgcctcc     120
tccagcagac tgctggctgt gggacaccca tacttcagca tcaagagggc taacaagaca     180
gtggtgccaa aggtgtctgg ctaccaatac agggtgttca aggtggtgct gcctgaccca     240
aacaagtttg ccctgcctga ctcctccctg tttgacccaa ccaccagag actggtgtgg     300 gcttgtactg gattggaggt gggcaggga caaccactgg gagtgggagt gtctggacac     360
ccattcctga caaatatga tgatgtggag aactctggct ctggaggcaa ccctggacaa     420
gacaacaggg tgaatgtggg gatggactac aagcagaccc aactttgtat ggtgggctgt     480
gcccctccac tggagaaca ctggggcaag ggcaagcagt gtaccaacac acctgtccag     540
gctggagact gtcctccatt ggaactgatt acctctgtga ttcaggatgg agatatggtg     600
gacacaggct tggagctat gaactttgct gacctccaaa ccaacaagtc tgatgtgcca     660
attgacatct gtggcaccac ttgtaaatac cctgactacc tccaaatggc tgctgaccca     720 tatgagaca gactgttctt cttcctgagg aaggaacaga tgtttgccag acacttcttc     780
aacagggctg gagaggtggg agaacctgtg cctgacaccc tgattatcaa gggctctggc     840
aacaggacct ctgtgggctc cagcatctat gtgaacacac catctggctc cctggtgtcc     900
tctgaggctc aactttttcaa caagccatac tggctccaaa aggctcaagg acacaacaat     960
ggcatctgtt gggcaaccaa cttttttgtg acagtggtgg acaccaccag gagcaccaat    1020
atgaccctgt gtgcctctgt gaccacctcc agcacctaca ccaactctga ctacaaggaa    1080
tatatgaggc atgtggagga atatgacctc caattcatct tccaactttg tagcatcacc    1140
```

```
ctgtctgctg aggtgatggc ttacatccac acaatgaacc catctgtgtt ggaggactgg      1200
aactttggac tgagccctcc tccaaatggc accttggagg acacctacag atatgtccag      1260
agccaggcta tcacttgtca gaagccaaca cctgagaagg agaagcctga cccatacaag      1320
aacctgtcct tctgggaggt gaacctgaaa gagaagttct cctctgaact ggaccaatac      1380
ccactgggca ggaagttcct gctccaatct ggctacaaag ccaagc                     1426
```

<210> SEQ ID NO 10
<211> LENGTH: 35
<212> TYPE: DNA
<213> ORGANISM: Artificial sequence
<220> FEATURE:
<223> OTHER INFORMATION: 0610 HPV6L1 F2

<400> SEQUENCE: 10

```
atctggctac aaagccaagc caaaactgaa aaggg                                 35
```

<210> SEQ ID NO 11
<211> LENGTH: 37
<212> TYPE: DNA
<213> ORGANISM: Artificial sequence
<220> FEATURE:
<223> OTHER INFORMATION: 0611 HPV6L1 R2

<400> SEQUENCE: 11

```
ctgtctagat ttacttcttc accttcttcc tcttggc                               37
```

<210> SEQ ID NO 12
<211> LENGTH: 101
<212> TYPE: DNA
<213> ORGANISM: Artificial sequence
<220> FEATURE:
<223> OTHER INFORMATION: 0612 HPV6L1 amplified sequence 2

<400> SEQUENCE: 12

```
atctggctac aaagccaagc caaaactgaa aagggctgcc ccaaccagca ccaggacctc      60
ctctgccaag aggaagaagg tgaagaagta aatctagaca g                          101
```

<210> SEQ ID NO 13
<211> LENGTH: 38
<212> TYPE: PRT
<213> ORGANISM: Homo sapiens
<220> FEATURE:
<221> NAME/KEY: misc_feature
<223> OTHER INFORMATION: 0613 Amino acid sequence of HPV type 59 L1
      protein aa 471-508

<400> SEQUENCE: 13

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 14
<211> LENGTH: 470
<212> TYPE: PRT
<213> ORGANISM: Homo sapiens
<220> FEATURE:
<221> NAME/KEY: misc_feature
<223> OTHER INFORMATION: 1101 Amino acid sequence of HPV type 11 L1
      protein aa 1-470

<400> SEQUENCE: 14

```
Met Trp Arg Pro Ser Asp Ser Thr Val Tyr Val Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
                100                 105                 110

Gly Val Ser Gly His Pro Leu Leu Asn Lys Tyr Asp Asp Val Glu Asn
            115                 120                 125

Ser Gly Gly Tyr Gly Gly Asn Pro Gly Gln Asp Asn Arg Val Asn Val
130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
    195                 200                 205

Asp Leu Gln Thr Asn Lys Ser Asp Val Pro Leu Asp Ile Cys Gly Thr
210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
    275                 280                 285

Val His Thr Pro Ser Gly Ser Leu Val Ser Ser Glu Ala Gln Leu Phe
290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
    355                 360                 365

Gln Phe Ile Phe Gln Leu Cys Ser Ile Thr Leu Ser Ala Glu Val Met
370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415
```

```
Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
            435                 440                 445

Glu Lys Phe Ser Ser Glu Leu Asp Gln Phe Pro Leu Gly Arg Lys Phe
450                 455                 460

Leu Leu Gln Ser Gly Tyr
465                 470

<210> SEQ ID NO 15
<211> LENGTH: 26
<212> TYPE: PRT
<213> ORGANISM: Homo sapiens
<220> FEATURE:
<221> NAME/KEY: misc_feature
<223> OTHER INFORMATION: 1102 Amino acid sequence of HPV type 33 L1
      protein aa 474-499

<400> SEQUENCE: 15

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 16
<211> LENGTH: 496
<212> TYPE: PRT
<213> ORGANISM: Artificial sequence
<220> FEATURE:
<223> OTHER INFORMATION: 1103 Amino acid sequence of chimeric HPV type
      11 L1 protein

<400> SEQUENCE: 16

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
```

```
        195                 200                 205
Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Lys Ala Lys Pro Lys Leu Lys Arg Ala Ala
465                 470                 475                 480

Pro Thr Ser Thr Arg Thr Ser Ser Ala Lys Arg Lys Lys Val Lys Lys
                485                 490                 495
```

<210> SEQ ID NO 17
<211> LENGTH: 1492
<212> TYPE: DNA
<213> ORGANISM: Artificial sequence
<220> FEATURE:
<223> OTHER INFORMATION: 1104 Nucleotide sequence of chimeric HPV type 11 L1 protein

<400> SEQUENCE: 17

```
atgtggagac catctgacag cacagtctat gtgcctcctc aaaccctgt gagcaaggtg    60 gtggctacag atgcctatgt gaagaggacc aacatcttct accatgcctc ctccagcaga   120
ctgctggctg tgggacaccc atactacagc atcaagaagg tgaacaagac agtggtgcca   180
aaggtgtctg gctaccaata cagggtgttc aaggtggtgc tgcctgaccc aaacaagttt   240
gccctgcctg actcctccct gtttgaccca accaccaga gactggtgtg gcttgtact    300 ggattggagg tgggcagggg acaaccactg ggagtgggag tgtctggaca cccactgctg   360
```

```
aacaaatatg atgatgtgga gaactctgga ggctatggag gcaaccctgg acaagacaac      420
agggtgaatg tggggatgga ctacaagcag acccaacttt gtatggtggg ctgtgcccct      480
ccactgggag aacactgggg caagggcacc cagtgtagca cacctctgt ccagaatgga       540 gactgtcctc cattggaact gattacctct gtgattcagg atggagatat ggtggacaca     600
ggctttggag ctatgaactt tgctgacctc caaaccaaca agtctgatgt gccactggac     660
atctgtggca cagtgtgtaa atacctgac tacctccaaa tggctgctga cccatatgga      720
gacagactgt tcttctacct gaggaaggaa cagatgtttg ccagacactt cttcaacagg     780
gctggcacag tgggagaacc tgtgcctgat gacctgctgg tgaagggagg caacaacagg     840
tcctctgtgg catccagcat ctatgtgcat acaccatctg gctccctggt gtcctctgag     900
gctcaacttt tcaacaagcc atactggctc aaaaggctc aaggacacaa caatggcatc      960
tgttggggca ccacctgtt tgtgacagtg gtggacacca ccaggagcac caatatgacc     1020
ctgtgtgcct ctgtgagcaa gtctgccacc tacaccaact tgactacaa ggaatatatg      1080 aggcatgtgg aggagtttga cctccaattc atcttccaac tttgtagcat caccctgtct    1140
gctgaggtga tggcttacat ccacacaatg aacccatctg tgttggagga ctggaacttt    1200
ggactgagcc ctcctccaaa tggcacctt gaggacacct acagatatgt ccagagccag     1260
gctatcactt gtcagaagcc aacacctgag aaggagaagc aggacccata caaggatatg    1320
agtttctggg aggtgaacct gaaagagaag ttctcctctg aactggacca gtttccactg    1380
ggcaggaagt tcctgctcca atctggctac aaagccaagc caaaactgaa agggctgcc     1440 ccaaccagca ccaggacctc ctctgccaag aggaagaagg tgaagaagta aa             1492

<210> SEQ ID NO 18
<211> LENGTH: 1525
<212> TYPE: DNA
<213> ORGANISM: Artificial sequence
<220> FEATURE:
<223> OTHER INFORMATION: 1105 Synthetic HPV11 L1 gene

<400> SEQUENCE: 18
ctgggtacca tgtggagacc atctgacagc acagtctatg tgcctcctcc aaaccctgtg      60
agcaaggtgg tggctacaga tgcctatgtg aagaggacca acatcttcta ccatgcctcc     120
tccagcagac tgctggctgt gggacaccca tactacagca tcaagaaggt gaacaagaca    180
gtggtgccaa aggtgtctgg ctaccaatac agggtgttca aggtggtgct gcctgaccca    240
aacaagtttg ccctgcctga ctcctccctg tttgacccaa ccaccagag actggtgtgg     300 gcttgtactg gattggaggt gggcagggga caaccactgg gagtgggagt gtctggacac    360
ccactgctga acaaatatga tgatgtggag aactctggag ctatggagg caaccctgga     420 caagacaaca gggtgaatgt ggggatggac tacaagcaga cccaactttg tatggtgggc    480
tgtgcccctc cactgggaga acactggggc aagggcaccc agtgtagcaa cacctctgtc    540
cagaatggag actgtcctcc attggaactg attacctctg tgattcagga tggagatatg    600
gtggacacag gctttggagc tatgaacttt gctgacctcc aaaccaacaa gtctgatgtg    660
ccactggaca tctgtggcac agtgtgtaaa taccctgact acctccaaat ggctgctgac   720
ccatatggag acagactgtt cttctacctg aggaaggaac agatgtttgc cagacacttc    780
ttcaacaggg ctggcacagt gggagaacct gtgcctgatg acctgctggt gaagggaggc    840
aacaacaggt cctctgtggc atccagcatc tatgtgcata caccatctgg ctccctggtg    900
tcctctgagg ctcaactttt caacaagcca tactggctcc aaaaggctca aggacacaac    960
```

```
aatggcatct gttggggcaa ccacctgttt gtgacagtgg tggacaccac caggagcacc    1020
aatatgaccc tgtgtgcctc tgtgagcaag tctgccacct acaccaactc tgactacaag    1080
gaatatatga ggcatgtgga ggagtttgac ctccaattca tcttccaact ttgtagcatc    1140
accctgtctg ctgaggtgat ggcttacatc cacacaatga acccatctgt gttggaggac    1200
tggaactttg gactgagccc tcctccaaat ggcaccttgg aggacaccta cagatatgtc    1260
cagagccagg ctatcacttg tcagaagcca acacctgaga aggagaagca ggacccatac    1320
aaggatatga gtttctggga ggtgaacctg aaagagaagt tctcctctga actggaccag    1380
tttccactgg gcaggaagtt cctgctccaa tctggctaca ggggcaggac ctctgccagg    1440
acaggcatca agagacctgc tgtgagcaag ccaagcacag ccccaaagag aagaggacc     1500 aagaccaaga agtaaactcg agctc                                          1525
```

<210> SEQ ID NO 19
<211> LENGTH: 1519
<212> TYPE: DNA
<213> ORGANISM: Artificial sequence
<220> FEATURE:
<223> OTHER INFORMATION: 1106 Synthetic HPV33 L1 gene

<400> SEQUENCE: 19

```
ctgggtacca tgagtgtgtg gagaccatct gaggctacag tctacctgcc tcctgtgcct     60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360 atctctggac acccactgct gaacaagttt gatgacacag agacaggcaa caaataccct    420
ggacaacctg gagcagacaa cagggagtgt ctgagtatgg actacaagca gacccaactt    480
tgtctgctgg gctgtaagcc tccaacagga gaacactggg gcaagggagt ggcttgtacc    540
aatgctgccc ctgccaatga ctgtcctcca ttggaactga taaacaccat cattgaggat    600
ggagatatgg tggacacagg ctttggctgt atggacttca gaccctccaa gccaacaag     660 tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcaccctg ggagaggctg tgcctgatga cctctacatc    840
aagggctctg gcaccacagc cagcatccag tcctctgcct tctttccaac accatctggc    900
agtatggtga cctctgagag ccaacttttc aacaagccat actggctcca aagggctcaa    960
ggacacaaca atggcatctg ttggggcaac caggtgtttg tgacagtggt ggacaccacc    1020
aggagcacca atatgaccct gtgtacccag gtgacctctg cagcacccta caagaatgag    1080
aacttcaagg aatacatcag gcatgtggag gaatatgacc tccaatttgt gttccaactt    1140
tgtaaggtga ccctgacagc agaggtgatg acctacatcc atgctatgaa ccctgacatc    1200
ttggaggact ggcagtttgg actgacacct cctccatctg cctccctcca agacacctac    1260
aggtttgtga ccagccaggc tatcacttgt cagaagacag tgcctccaaa ggagaaggag    1320
gacccactgg gcaaatacac cttctgggag gtggacctga agagaagtt ctctgctgac    1380 ctggaccagt ttccactggg caggaagttc ctgctccaag caggactgaa agccaagcca    1440
```
aaactgaaaa gggctgcccc aaccagcacc aggacctcct ctgccaagag gaagaaggtg    1500
aagaagtaaa ctcgagctc    1519

<210> SEQ ID NO 20
<211> LENGTH: 35
<212> TYPE: DNA
<213> ORGANISM: Artificial sequence
<220> FEATURE:
<223> OTHER INFORMATION: 1107 HPV11L1 F1

<400> SEQUENCE: 20
cttggtacca tgtggagacc atctgacagc acagt    35

<210> SEQ ID NO 21
<211> LENGTH: 36
<212> TYPE: DNA
<213> ORGANISM: Artificial sequence
<220> FEATURE:
<223> OTHER INFORMATION: 1108 HPV11L1 R1

<400> SEQUENCE: 21
gcttggcttt gtagccagat tggagcagga acttcc    36

<210> SEQ ID NO 22
<211> LENGTH: 1429
<212> TYPE: DNA
<213> ORGANISM: Artificial sequence
<220> FEATURE:
<223> OTHER INFORMATION: 1109 HPV11L1 amplified sequence 1

<400> SEQUENCE: 22
cttggtacca tgtggagacc atctgacagc acagtctatg tgcctcctcc aaaccctgtg    60
agcaaggtgg tggctacaga tgcctatgtg aagaggacca acatcttcta ccatgcctcc    120
tccagcagac tgctggctgt gggacaccca tactacagca tcaagaaggt gaacaagaca    180
gtggtgccaa aggtgtctgg ctaccaatac agggtgttca aggtggtgct gcctgaccca    240
aacaagtttg ccctgcctga ctcctccctg tttgacccaa ccacccagag actggtgtgg    300
gcttgtactg gattggaggt gggcagggga caaccactgg gagtgggagt gtctggacac    360
ccactgctga caaaatatga tgatgtggag aactctggag gctatggagg caaccctgga    420
caagacaaca gggtgaatgt ggggatggac tacaagcaga cccaactttg tatggtgggc    480
tgtgcccctc cactgggaga acactggggc aagggcaccc agtgtagcaa cacctctgtc    540
cagaatggag actgtcctcc attggaactg attacctctg tgattcagga tggagatatg    600
gtggacacag gctttggagc tatgaacttt gctgacctcc aaaccaacaa gtctgatgtg    660
ccactggaca tctgtggcac agtgtgtaaa tacccctgact acctccaaat ggctgctgac    720
ccatatggag acagactgtt cttctacctg aggaaggaac agatgtttgc cagacacttc    780
ttcaacaggg ctggcacagt gggagaacct gtgcctgatg acctgctggt gaagggaggc    840
aacaacaggt cctctgtggc atccagcatc tatgtgcata ccatctggg ctccctggtg    900 tcctctgagg ctcaactttt caacaagcca tactggctcc aaaaggctca aggacacaac    960
aatggcatct gttgggggcaa ccacctgttt gtgacagtgg tggacaccac caggagcacc    1020
aatatgaccc tgtgtgcctc tgtgagcaag tctgccacct acaccaactc tgactacaag    1080
gaatatatga ggcatgtgga ggagtttgac ctccaattca tcttccaact tgtagcatc    1140 accctgtctg ctgaggtgat ggcttacatc cacacaatga acccatctgt gttgaggac    1200 tggaactttg gactgagccc tcctccaaat ggcaccttgg aggacaccta cagatatgtc    1260

```
cagagccagg ctatcacttg tcagaagcca acacctgaga aggagaagca ggacccatac    1320
aaggatatga gtttctggga ggtgaacctg aaagagaagt tctcctctga actggaccag    1380
tttccactgg gcaggaagtt cctgctccaa tctggctaca aagccaagc                1429

<210> SEQ ID NO 23
<211> LENGTH: 35
<212> TYPE: DNA
<213> ORGANISM: Artificial sequence
<220> FEATURE:
<223> OTHER INFORMATION: 1110 HPV11L1 F2

<400> SEQUENCE: 23
atctggctac aaagccaagc caaaactgaa aaggg                               35

<210> SEQ ID NO 24
<211> LENGTH: 37
<212> TYPE: DNA
<213> ORGANISM: Artificial sequence
<220> FEATURE:
<223> OTHER INFORMATION: 1111 HPV11L1 R2

<400> SEQUENCE: 24
ctgtctagat ttacttcttc accttcttcc tcttggc                             37

<210> SEQ ID NO 25
<211> LENGTH: 101
<212> TYPE: DNA
<213> ORGANISM: Artificial sequence
<220> FEATURE:
<223> OTHER INFORMATION: 1112 HPV11L1 amplified sequence 2

<400> SEQUENCE: 25
atctggctac aaagccaagc caaaactgaa aagggctgcc ccaaccagca ccaggacctc    60
ctctgccaag aggaagaagg tgaagaagta aatctagaca g                        101

<210> SEQ ID NO 26
<211> LENGTH: 38
<212> TYPE: PRT
<213> ORGANISM: Homo sapiens
<220> FEATURE:
<221> NAME/KEY: misc_feature
<223> OTHER INFORMATION: 1113 Amino acid sequence of HPV type 59 L1
      protein aa 471-508

<400> SEQUENCE: 26

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 27
<211> LENGTH: 474
<212> TYPE: PRT
<213> ORGANISM: Homo sapiens
<220> FEATURE:
<221> NAME/KEY: misc_feature
<223> OTHER INFORMATION: 1601 Amino acid sequence of HPV type 16 L1
      protein aa 1-474

<400> SEQUENCE: 27

Met Ser Leu Trp Leu Pro Ser Glu Ala Thr Val Tyr Leu Pro Pro Val
```

-continued

```
1               5                   10                  15
    Pro Val Ser Lys Val Ser Thr Asp Glu Tyr Val Ala Arg Thr Asn
                    20                  25                  30
    Ile Tyr Tyr His Ala Gly Thr Ser Arg Leu Leu Ala Val Gly His Pro
                    35                  40                  45
    Tyr Phe Pro Ile Lys Lys Pro Asn Asn Asn Lys Ile Leu Val Pro Lys
                50                  55                  60
    Val Ser Gly Leu Gln Tyr Arg Val Phe Arg Ile His Leu Pro Asp Pro
    65                  70                  75                  80
    Asn Lys Phe Gly Phe Pro Asp Thr Ser Phe Tyr Asn Pro Asp Thr Gln
                        85                  90                  95
    Arg Leu Val Trp Ala Cys Val Gly Val Glu Val Gly Arg Gly Gln Pro
                    100                 105                 110
    Leu Gly Val Gly Ile Ser Gly His Pro Leu Leu Asn Lys Leu Asp Asp
                    115                 120                 125
    Thr Glu Asn Ala Ser Ala Tyr Ala Ala Asn Ala Gly Val Asp Asn Arg
                130                 135                 140
    Glu Cys Ile Ser Met Asp Tyr Lys Gln Thr Gln Leu Cys Leu Ile Gly
    145                 150                 155                 160
    Cys Lys Pro Pro Ile Gly Glu His Trp Gly Lys Gly Ser Pro Cys Thr
                        165                 170                 175
    Asn Val Ala Val Asn Pro Gly Asp Cys Pro Pro Leu Glu Leu Ile Asn
                    180                 185                 190
    Thr Val Ile Gln Asp Gly Asp Met Val Asp Thr Gly Phe Gly Ala Met
                    195                 200                 205
    Asp Phe Thr Thr Leu Gln Ala Asn Lys Ser Glu Val Pro Leu Asp Ile
                210                 215                 220
    Cys Thr Ser Ile Cys Lys Tyr Pro Asp Tyr Ile Lys Met Val Ser Glu
    225                 230                 235                 240
    Pro Tyr Gly Asp Ser Leu Phe Phe Tyr Leu Arg Arg Glu Gln Met Phe
                        245                 250                 255
    Val Arg His Leu Phe Asn Arg Ala Gly Ala Val Gly Glu Asn Val Pro
                    260                 265                 270
    Asp Asp Leu Tyr Ile Lys Gly Ser Gly Ser Thr Ala Asn Leu Ala Ser
                275                 280                 285
    Ser Asn Tyr Phe Pro Thr Pro Ser Gly Ser Met Val Thr Ser Asp Ala
    290                 295                 300
    Gln Ile Phe Asn Lys Pro Tyr Trp Leu Gln Arg Ala Gln Gly His Asn
    305                 310                 315                 320
    Asn Gly Ile Cys Trp Gly Asn Gln Leu Phe Val Thr Val Val Asp Thr
                        325                 330                 335
    Thr Arg Ser Thr Asn Met Ser Leu Cys Ala Ala Ile Ser Thr Ser Glu
                    340                 345                 350
    Thr Thr Tyr Lys Asn Thr Asn Phe Lys Glu Tyr Leu Arg His Gly Glu
                    355                 360                 365
    Glu Tyr Asp Leu Gln Phe Ile Phe Gln Leu Cys Lys Ile Thr Leu Thr
                370                 375                 380
    Ala Asp Val Met Thr Tyr Ile His Ser Met Asn Ser Thr Ile Leu Glu
    385                 390                 395                 400
    Asp Trp Asn Phe Gly Leu Gln Pro Pro Gly Gly Thr Leu Glu Asp
                        405                 410                 415
    Thr Tyr Arg Phe Val Thr Ser Gln Ala Ile Ala Cys Gln Lys His Thr
                    420                 425                 430
```

-continued

```
Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu
465                 470

<210> SEQ ID NO 28
<211> LENGTH: 26
<212> TYPE: PRT
<213> ORGANISM: Homo sapiens
<220> FEATURE:
<221> NAME/KEY: misc_feature
<223> OTHER INFORMATION: 1602 Amino acid sequence of HPV type 33 L1
      protein aa 474-499

<400> SEQUENCE: 28

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 29
<211> LENGTH: 500
<212> TYPE: PRT
<213> ORGANISM: Artificial sequence
<220> FEATURE:
<223> OTHER INFORMATION: 1603 Amino acid sequence of chimeric HPV type
      16 L1 protein

<400> SEQUENCE: 29

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
```

```
        210                 215                 220
Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
                340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
        450                 455                 460

Gly Arg Lys Phe Leu Leu Gln Ala Gly Leu Lys Ala Lys Pro Lys Leu
465                 470                 475                 480

Lys Arg Ala Ala Pro Thr Ser Thr Arg Thr Ser Ser Ala Lys Arg Lys
                485                 490                 495

Lys Val Lys Lys
            500

<210> SEQ ID NO 30
<211> LENGTH: 1504
<212> TYPE: DNA
<213> ORGANISM: Artificial sequence
<220> FEATURE:
<223> OTHER INFORMATION: 1604 Nucleotide sequence of chimeric HPV type
      16 L1 protein

<400> SEQUENCE: 30
atgagtctgt ggctgccatc tgaggctaca gtctacctgc ctcctgtgcc tgtgagcaag      60
gtggtgagca cagatgaata tgtggcaagg accaacatct actaccatgc tggcaccagc     120
agactgctgg ctgtgggaca cccatacttt ccaatcaaga agccaaacaa caacaagatt     180
ctggtgccaa aggtgtctgg actccaatac agggtgttca ggattcacct gcctgaccca     240
aacaagtttg gctttcctga cacctccttc tacaaccctg acaccagag actggtgtgg     300 gcttgtgtgg gagtggaggt gggcaggga caaccactgg gagtgggcat ctctggacac     360
```

```
ccactgctga caaaactgga tgacacagag aatgcctctg cctatgctgc caatgctgga    420
gtggacaaca gggagtgtat cagtatggac tacaagcaga cccaactttg tctgattggc    480
tgtaagcctc caattggaga acactggggc aagggcagcc catgtaccaa tgtggctgtg    540
aaccctggag actgtcctcc attggaactg ataaacacag tgattcagga tggagatatg    600
gtggacacag gctttggagc tatggacttc accaccctcc aagccaacaa gtctgaggtg    660
ccactggaca tctgtaccag catctgtaaa taccctgact acatcaagat ggtgtctgaa    720
ccatatggag actccctgtt cttctacctg aggagggaac agatgtttgt gagacacctg    780
ttcaacaggg ctggagcagt gggagagaat gtgcctgatg acctctacat caagggctct    840
ggcagcacag ccaacctggc atccagcaac tactttccaa caccatctgg cagtatggtg    900
acctctgatg cccagatttt caacaagcca tactggctcc aaagggctca aggacacaac    960
aatggcatct gttggggcaa ccaactttt gtgacagtgg tggacaccac caggagcacc   1020
aatatgagtc tgtgtgctgc catcagcacc tctgagacca cctacaagaa caccaacttc   1080
aaggaatacc tgagacatgg agaggaatat gacctccaat tcatcttcca actttgtaag   1140
attaccctga cagcagatgt gatgacctac atccacagta tgaacagcac catcttggag   1200
gactggaact ttggactcca acctcctcct ggaggcacct tggaggacac ctacaggttt   1260
gtgaccagcc aggctattgc ctgtcagaaa cacacacctc ctgccccaaa ggaggaccca   1320
ctgaaaaaat acaccttctg ggaggtgaac ctgaaagaga gttctctgc tgacctggac   1380 cagtttccac tgggcaggaa gttcctgctc aagcaggac tgaaagccaa gccaaaactg   1440
aaaagggctg ccccaaccag caccaggacc tcctctgcca agaggaagaa ggtgaagaag   1500
taaa                                                                1504

<210> SEQ ID NO 31
<211> LENGTH: 1537
<212> TYPE: DNA
<213> ORGANISM: Artificial sequence
<220> FEATURE:
<223> OTHER INFORMATION: 1605 Synthetic HPV16 L1 gene

<400> SEQUENCE: 31
ctgggtacca tgagtctgtg gctgccatct gaggctacag tctacctgcc tcctgtgcct     60
gtgagcaagg tggtgagcac agatgaatat gtggcaagga ccaacatcta ctaccatgct    120
ggcaccagca gactgctggc tgtgggacac ccatactttc aatcaagaa gccaaacaac    180 aacaagattc tggtgccaaa ggtgtctgga ctccaataca gggtgttcag gattcacctg    240
cctgacccaa acaagtttgg ctttcctgac acctccttct acaaccctga cacccagaga    300
ctggtgtggg cttgtgtggg agtggaggtg ggcagggac aaccactggg agtgggcatc    360
tctggacacc cactgctgaa caaactggat gacacagaga atgcctctgc ctatgctgcc    420
aatgctggag tggacaacag ggagtgtatc agtatggact acaagcagac ccaactttgt    480
ctgattggct gtaagcctcc aattggagaa cactggggca agggcagccc atgtaccaat    540
gtggctgtga accctggaga ctgtcctcca ttggaactga taaacacagt gattcaggat    600
ggagatatgg tggacacagg ctttggagct atggacttca ccaccctcca agccaacaag    660
tctgaggtgc cactggacat ctgtaccagc atctgtaaat accctgacta catcaagatg    720
gtgtctgaac catatggaga ctccctgttc ttctacctga ggagggaaca gatgtttgtg    780
agacacctgt tcaacagggc tggagcagtg ggagagaatg tgcctgatga cctctacatc    840
aagggctctg gcagcacagc caacctggca tccagcaact actttccaac accatctggc    900
```

```
agtatggtga cctctgatgc ccagattttc aacaagccat actggctcca aagggctcaa    960
ggacacaaca atggcatctg ttggggcaac caacttttg tgacagtggt ggacaccacc    1020
aggagcacca atatgagtct gtgtgctgcc atcagcacct ctgagaccac ctacaagaac    1080
accaacttca aggaatacct gagacatgga gaggaatatg acctccaatt catcttccaa    1140
ctttgtaaga ttaccctgac agcagatgtg atgacctaca tccacagtat gaacagcacc    1200
atcttggagg actggaactt tggactccaa cctcctcctg gaggcacctt ggaggacacc    1260
tacaggtttg tgaccagcca ggctattgcc tgtcagaaac acacacctcc tgccccaaag    1320
gaggacccac tgaaaaaata caccttctgg gaggtgaacc tgaaagagaa gttctctgct    1380
gacctggacc agtttccact gggcaggaag ttcctgctcc aagcaggact gaaagccaag    1440
ccaaagttca ccctgggcaa gaggaaggct acaccaacca cctccagcac cagcaccaca    1500
gccaagagga agaagaggaa actgtaaact cgagctc                             1537
```

<210> SEQ ID NO 32
<211> LENGTH: 1519
<212> TYPE: DNA
<213> ORGANISM: Artificial sequence
<220> FEATURE:
<223> OTHER INFORMATION: 1606 Synthetic HPV33 L1 gene

<400> SEQUENCE: 32

```
ctgggtacca tgagtgtgtg gaggccatct gaggctacag tctacctgcc tcctgtgcct    60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360
atctctggac acccactgct gaacaagttt gatgacacag agacaggcaa caaatacct    420
ggacaacctg gagcagacaa cagggagtgt ctgagtatgg actacaagca gacccaactt    480
tgtctgctgg gctgtaagcc tccaacagga gaacactggg gcaagggagt ggcttgtacc    540
aatgctgccc ctgccaatga ctgtcctcca ttggaactga taaacaccat cattgaggat    600
ggagatatgt ggacacaggg ctttggctgt atggacttca gaccctcca gccaacaag    660
tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcacccctg ggagaggctg tgcctgatga cctctacatc    840
aagggctctg gcaccacagc cagcatccag tcctctgcct ctttccaac accatctggc    900
agtatggtga cctctgagag ccaacttttc aacaagccat actggctcca aagggctcaa    960
ggacacaaca atggcatctg ttggggcaac caggtgtttg tgacagtggt ggacaccacc    1020
aggagcacca atatgaccct gtgtacccag gtgacctctg acagcaccta caagaatgag    1080
aacttcaagg aatacatcag gcatgtggag gaatatgacc tccaatttgt gttccaactt    1140
tgtaaggtga ccctgacagc agaggtgatg acctacatcc atgctatgaa ccctgacatc    1200
ttggaggact ggcagtttgg actgacacct cctccatctg cctccctcca agacacctac    1260
aggtttgtga ccagccaggc tatcacttgt cagaagacag tgcctccaaa ggagaaggag    1320
gacccactgg gcaaatacac cttctgggag gtggacctga agagaagtt ctctgctgac    1380
```

| | |
|---|---|
| ctggaccagt tccactggg caggaagttc ctgctccaag caggactgaa agccaagcca | 1440 |
| aaactgaaaa gggctgcccc aaccagcacc aggacctcct ctgccaagag gaagaaggtg | 1500 |
| aagaagtaaa ctcgagctc | 1519 |

<210> SEQ ID NO 33
<211> LENGTH: 34
<212> TYPE: DNA
<213> ORGANISM: Artificial sequence
<220> FEATURE:
<223> OTHER INFORMATION: 1607 HPV16L1 F1

<400> SEQUENCE: 33

| | |
|---|---|
| cttggtacca tgagtctgtg gctgccatct gagg | 34 |

<210> SEQ ID NO 34
<211> LENGTH: 36
<212> TYPE: DNA
<213> ORGANISM: Artificial sequence
<220> FEATURE:
<223> OTHER INFORMATION: 1608 HPV16L1 R1

<400> SEQUENCE: 34

| | |
|---|---|
| gcttggcttt cagtcctgct tggagcagga acttcc | 36 |

<210> SEQ ID NO 35
<211> LENGTH: 1441
<212> TYPE: DNA
<213> ORGANISM: Artificial sequence
<220> FEATURE:
<223> OTHER INFORMATION: 1609 HPV16L1 amplified sequence 1

<400> SEQUENCE: 35

| | |
|---|---|
| cttggtacca tgagtctgtg gctgccatct gaggctacag tctacctgcc tcctgtgcct | 60 |
| gtgagcaagg tggtgagcac agatgaatat gtggcaagga ccaacatcta ctaccatgct | 120 |
| ggcaccagca gactgctggc tgtgggacac ccatactttc aatcaagaa gccaaacaac | 180 |
| aacaagattc tggtgccaaa ggtgtctgga ctccaataca gggtgttcag gattcacctg | 240 |
| cctgacccaa acaagtttgg ctttcctgac acctccttct acaaccctga cacccagaga | 300 |
| ctggtgtggg cttgtgtggg agtggaggtg ggcagggac aaccactggg agtgggcatc | 360 |
| tctggacacc cactgctgaa caaactggat gacacagaga atgcctctgc ctatgctgcc | 420 |
| aatgctggag tggacaacag ggagtgtatc agtatggact acaagcagac ccaactttgt | 480 |
| ctgattggct gtaagcctcc aattggagaa cactggggca agggcagccc atgtaccaat | 540 |
| gtggctgtga accctggaga ctgtcctcca ttggaactga taaacacagt gattcaggat | 600 |
| ggagatatgg tggacacagg cttttggagct atggacttca ccaccctcca agccaacaag | 660 |
| tctgaggtgc cactggacat ctgtaccagc atctgtaaat accctgacta catcaagatg | 720 |
| gtgtctgaac catatggaga ctccctgttc ttctacctga ggagggaaca gatgtttgtg | 780 |
| agacacctgt tcaacagggc tggagcagtg ggagagaatg tgcctgatga cctctacatc | 840 |
| aagggctctg gcagcacagc caacctggca tccagcaact actttccaac accatctggc | 900 |
| agtatggtga cctctgatgc ccagattttc aacaagccat actggctcca aagggctcaa | 960 |
| ggacacaaca tggcatctg ttggggcaac caacttttt tgacagtggt ggacaccacc | 1020 |
| aggagcacca atatgagtct gtgtgctgcc atcagcacct ctgagaccac ctacaagaac | 1080 |
| accaacttca ggaataccct gagacatgga gaggaatatg acctccaatt catcttccaa | 1140 |
| cttttgtaaga ttaccctgac agcagatgtg atgacctaca tccacagtat gaacagcacc | 1200 |

```
atcttggagg actggaactt tggactccaa cctcctcctg gaggcaccft ggaggacacc    1260 tacaggtttg tgaccagcca ggctattgcc tgtcagaaac acacacctcc tgccccaaag    1320
gaggacccac tgaaaaaata caccttctgg gaggtgaacc tgaaagagaa gttctctgct    1380
gacctggacc agtttccact gggcaggaag ttcctgctcc aagcaggact gaaagccaag    1440
c                                                                    1441
```

<210> SEQ ID NO 36
<211> LENGTH: 35
<212> TYPE: DNA
<213> ORGANISM: Artificial sequence
<220> FEATURE:
<223> OTHER INFORMATION: 1610 HPV16L1 F2

<400> SEQUENCE: 36

```
agcaggactg aaagccaagc caaaactgaa aaggg                               35
```

<210> SEQ ID NO 37
<211> LENGTH: 36
<212> TYPE: DNA
<213> ORGANISM: Artificial sequence
<220> FEATURE:
<223> OTHER INFORMATION: 1611 HPV16L1 R2

<400> SEQUENCE: 37

```
ctgtctagat ttacttcttc accttcttcc tcttgg                              36
```

<210> SEQ ID NO 38
<211> LENGTH: 101
<212> TYPE: DNA
<213> ORGANISM: Artificial sequence
<220> FEATURE:
<223> OTHER INFORMATION: 1612 HPV16L1 amplified sequence 2

<400> SEQUENCE: 38

```
agcaggactg aaagccaagc caaaactgaa aagggctgcc ccaaccagca ccaggacctc    60
ctctgccaag aggaagaagg tgaagaagta aatctagaca g                        101
```

<210> SEQ ID NO 39
<211> LENGTH: 38
<212> TYPE: PRT
<213> ORGANISM: Homo sapiens
<220> FEATURE:
<221> NAME/KEY: misc_feature
<223> OTHER INFORMATION: 1613 Amino acid sequence of HPV type 59 L1
      protein aa 471-508

<400> SEQUENCE: 39

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 40
<211> LENGTH: 470
<212> TYPE: PRT
<213> ORGANISM: Homo sapiens
<220> FEATURE:
<221> NAME/KEY: misc_feature
<223> OTHER INFORMATION: 1801 Amino acid sequence of HPV type 18 L1
      protein aa 1-470

```
<400> SEQUENCE: 40

Met Ala Leu Trp Arg Pro Ser Asp Asn Thr Val Tyr Leu Pro Pro
1               5                   10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
                35                  40                  45

Tyr Phe Arg Val Pro Ala Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
                100                 105                 110

Leu Gly Val Gly Leu Ser Gly His Pro Phe Tyr Asn Lys Leu Asp Asp
                115                 120                 125

Thr Glu Ser Ser His Ala Ala Thr Ser Asn Val Ser Glu Asp Val Arg
130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
                180                 185                 190

Thr Val Leu Glu Asp Gly Asp Met Val Asp Thr Gly Tyr Gly Ala Met
                195                 200                 205

Asp Phe Ser Thr Leu Gln Asp Thr Lys Cys Glu Val Pro Leu Asp Ile
210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
                260                 265                 270

Gln Ser Leu Tyr Ile Lys Gly Thr Gly Met Arg Ala Ser Pro Gly Ser
                275                 280                 285

Cys Val Tyr Ser Pro Ser Pro Ser Gly Ser Ile Val Thr Ser Asp Ser
                290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Asp Thr
                325                 330                 335

Thr Arg Ser Thr Asn Leu Thr Ile Cys Ala Ser Thr Gln Ser Pro Val
                340                 345                 350

Pro Gly Gln Tyr Asp Ala Thr Lys Phe Lys Gln Tyr Ser Arg His Val
                355                 360                 365

Glu Glu Tyr Asp Leu Gln Phe Ile Phe Gln Leu Cys Thr Ile Thr Leu
                370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
```

```
                    405                 410                 415
Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
            435                 440                 445

Asn Val Asp Leu Lys Glu Lys Phe Ser Leu Asp Leu Asp Gln Tyr Pro
        450                 455                 460

Leu Gly Arg Lys Phe Leu
465             470

<210> SEQ ID NO 41
<211> LENGTH: 26
<212> TYPE: PRT
<213> ORGANISM: Homo sapiens
<220> FEATURE:
<221> NAME/KEY: misc_feature
<223> OTHER INFORMATION: 1802 Amino acid sequence of HPV type 33 L1
      protein aa 474-499

<400> SEQUENCE: 41

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 42
<211> LENGTH: 496
<212> TYPE: PRT
<213> ORGANISM: Artificial sequence
<220> FEATURE:
<223> OTHER INFORMATION: 1803 Amino acid sequence of chimeric HPV type
      18 L1 protein

<400> SEQUENCE: 42

Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
        35                  40                  45

Tyr Phe Arg Val Pro Ala Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125

Thr Glu Ser Ser His Ala Ala Thr Ser Asn Val Ser Glu Asp Val Arg
    130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190
```

```
Thr Val Leu Glu Asp Gly Asp Met Val Asp Thr Gly Tyr Gly Ala Met
            195                 200                 205

Asp Phe Ser Thr Leu Gln Asp Thr Lys Cys Glu Val Pro Leu Asp Ile
210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
            245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
            275                 280                 285

Cys Val Tyr Ser Pro Ser Pro Ser Gly Ser Ile Val Thr Ser Asp Ser
290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
            325                 330                 335

Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
            355                 360                 365

Glu Glu Tyr Asp Leu Gln Phe Ile Phe Gln Leu Cys Thr Ile Thr Leu
            370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
            405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
            435                 440                 445

Asn Val Asp Leu Lys Glu Lys Phe Ser Leu Asp Leu Asp Gln Tyr Pro
450                 455                 460

Leu Gly Arg Lys Phe Leu Lys Ala Lys Pro Lys Leu Lys Arg Ala Ala
465                 470                 475                 480

Pro Thr Ser Thr Arg Thr Ser Ser Ala Lys Arg Lys Lys Val Lys Lys
            485                 490                 495
```

<210> SEQ ID NO 43
<211> LENGTH: 1492
<212> TYPE: DNA
<213> ORGANISM: Artificial sequence
<220> FEATURE:
<223> OTHER INFORMATION: 1804 Nucleotide sequence of chimeric HPV type
   18 L1 protein

<400> SEQUENCE: 43

```
atggccctct ggagaccatc cgataacaca gtgtacttgc ccccacccag cgtcgcccgg      60
gtggtgaaca cagacgacta cgtcaccaga acctcaatct ctaccaccgc cgggtccagc     120
cggctgctga ccgtgggcaa ccctacttc cgcgtgcccg ccggcggcgg aaacaaacaa     180
gacatcccca agtcagcgc ctatcagtac cgggtgttcc gcgtccaact gcccgatccc     240
aacaagttcg gcctgcccga cacctccatc tacaaccccg agaccagag ctggtctgg     300 gcttgcgccg cgtcgagat cgggagggc caacccctgg gcgtggggtt gtccggccac     360
```

```
cccttctaca acaagctgga cgataccgag tccagccacg cagcaaccag caacgtctcc    420
gaagatgtgc gcgataacgt cagcgtggac tacaaacaaa cccaactgtg catcctggga    480
tgcgcacccg ccatcggcga gcattgggcc aaggggaccg cctgcaagag caggcccctg    540
agccaagggg actgtccacc cctggagttg aagaataccg tgctcgagga cggcgacatg    600
gtggacaccg gctacggcgc tatggatttc tccaccctcc aggacaccaa gtgcgaagtg    660
cccctcgaca tctgccaaag catctgcaag taccccgact acctccagat gagcgccgac    720
ccctacggcg acagcatgtt cttctgtctc agaagggaac aattgttcgc ccgccacttc    780
tggaaccggg ccggcacaat gggagataca gtccccagag cctgtacat caaggggacc    840 ggaatgaggg ccagcccggg tcctgcgtc tacagcccaa gccctccgg gagcatcgtc    900 acaagcgata gccaactctt caacaagccc tactggctcc acaaagccca aggccacaat    960
aacggggtgt gttggcacaa ccagctgttc gtgaccgtcg tggacacaac caggtccaca   1020
aacctgacca tctgcgccag cacccaaagc cccgtgcccg ccagtacga cgccacaaag   1080 ttcaaacaat actctcggca cgtggaagag tacgacctcc aattcatctt ccaactctgc   1140
accatcaccc tcaccgccga cgtgatgagc tacatccact ccatgaactc ctccatcctg   1200
gaagactgga atttcggcgt gccaccaccc cctaccacct ccctcgtcga cacctacaga   1260
ttcgtgcaga gcgtggccat cacatgccag aaagacgccg ccccgccga gaacaaagac   1320 ccatacgaca aactgaaatt ctggaacgtc gacctgaaag agaaattcag cctggatctg   1380
gaccagtacc cattgggcag gaagttcctc aaagccaagc caaaactgaa aagggctgcc   1440
ccaaccagca ccaggacctc ctctgccaag aggaagaagg tgaagaagta aa            1492

<210> SEQ ID NO 44
<211> LENGTH: 1543
<212> TYPE: DNA
<213> ORGANISM: Artificial sequence
<220> FEATURE:
<223> OTHER INFORMATION: 1805 Synthetic HPV18 L1 gene

<400> SEQUENCE: 44
ctgggtacca tggccctctg gagaccatcc gataacacag tgtacttgcc cccacccagc     60
gtcgcccggg tggtgaacac agacgactac gtcaccagaa cctcaatctt ctaccacgcc    120
gggtccagcc ggctgctgac cgtgggcaac ccctacttcc gcgtgcccgc cggcggcgga    180
aacaaacaag acatccccaa agtcagcgcc tatcagtacc gggtgttccg cgtccaactg    240
cccgatccca caagttcgg cctgcccgac acctccatct acaacccga cccagagg       300 ctggtctggg cttgcgccgg cgtcgagatc ggggaggggcc aaccctggg cgtggggttg    360 tccggccacc ccttctacaa caagctggac gataccgagt ccagccacgc agcaaccagc    420
aacgtctccg aagatgtgcg cgataacgtc agcgtggact acaaacaaac ccaactgtgc    480
atcctgggat gcgcacccgc catcggcgag cattgggcca aggggaccgc ctgcaagagc    540
aggcccctga gccaagggga ctgtccaccc ctggagttga agaataccgt gctcgaggac    600
ggcgacatgg tggacaccgg ctacggcgct atggatttct ccaccctcca ggacaccaag    660
tgcgaagtgc ccctcgacat ctgccaaagc atctgcaagt accccgacta cctccagatg    720
agcgccgacc cctacggcga cagcatgttc ttctgtctca gaagggaaca attgttcgcc    780
cgccacttct ggaaccgggc cggcacaatg ggagatacag tccccagagc ctgtacatc    840 aaggggaccg gaatgagggc cagcccgggt cctgcgtct acagcccaag ccctccggg    900
```

```
agcatcgtca caagcgatag ccaactcttc aacaagccct actggctcca caaagcccaa    960
ggccacaata acgggtgtg ttggcacaac cagctgttcg tgaccgtcgt ggacacaacc   1020
aggtccacaa acctgaccat ctgcgccagc acccaaagcc ccgtgcccgg ccagtacgac   1080
gccacaaagt tcaaacaata ctctcggcac gtggaagagt acgacctcca attcatcttc   1140
caactctgca ccatcaccct caccgccgac gtgatgagct acatccactc catgaactcc   1200
tccatcctgg aagactggaa tttcggcgtg ccaccacccc ctaccacctc cctcgtcgac   1260
acctacagat tcgtgcagag cgtggccatc acatgccaga agacgccgc cccgccgag   1320 aacaaagacc catacgacaa actgaaattc tggaacgtcg acctgaaaga gaaattcagc   1380
ctggatctgg accagtaccc attgggcagg aagttcctcg tgcaagccgg cctcaggaga   1440
aaaccaacaa tcgggcccag gaagaggagc gcccccagcg caaccaccag cagcaagccc   1500
gcaaaaaggg tcagagtgag ggcacgcaaa taaactcgag ctc                     1543
```

<210> SEQ ID NO 45
<211> LENGTH: 1519
<212> TYPE: DNA
<213> ORGANISM: Artificial sequence
<220> FEATURE:
<223> OTHER INFORMATION: 1806 Synthetic HPV33 L1 gene

<400> SEQUENCE: 45

```
ctgggtacca tgagtgtgtg gagaccatct gaggctacag tctacctgcc tcctgtgcct     60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360 atctctggac acccactgct gaacaagttt gatgacacag agacaggcaa caatacccct    420
ggacaacctg agcagacaa cagggagtgt ctgagtatgg actacaagca gacccaactt    480
tgtctgctgg gctgtaagcc tccaacagga gaacactggg caagggagt ggcttgtacc    540 aatgctgccc ctgccaatga ctgtcctcca ttggaactga taaacaccat cattgaggat    600
ggagatatgg tggacacagg cttttggctgt atggacttca agaccctcca agccaacaag    660
tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcacctg ggagaggctg tgcctgatga cctctacatc    840
aagggctctg gcaccacagc cagcatccag tcctctgcct ctttccaac accatctggc    900 agtatggtga cctctgagag ccaacttttc aacaagccat actggctcca aagggctcaa    960
ggacacaaca atggcatctg ttggggcaac caggtgtttg tgacagtggt ggacaccacc   1020
aggagcacca atatgaccct gtgtacccag gtgacctctg acagcaccta caagaatgag   1080
aacttcaagg aatacatcag gcatgtggag gaatatgacc tccaatttgt gttccaactt   1140
tgtaaggtga ccctgacagc agaggtgatg acctacatcc atgctatgaa ccctgacatc   1200
ttggaggact ggcagtttgg actgacacct cctccatctg cctccctcca agacacctac   1260
aggtttgtga ccagccaggc tatcacttgt cagaagacag tgcctccaaa ggagaaggag   1320
gacccactgg gcaaatacac cttctgggag gtggacctga agagaagtt ctctgctgac   1380 ctggaccagt ttccactggg caggaagttc ctgctccaag caggactgaa agccaagcca   1440
```

```
aaactgaaaa gggctgcccc aaccagcacc aggacctcct ctgccaagag gaagaaggtg    1500
aagaagtaaa ctcgagctc                                                 1519

<210> SEQ ID NO 46
<211> LENGTH: 34
<212> TYPE: DNA
<213> ORGANISM: Artificial sequence
<220> FEATURE:
<223> OTHER INFORMATION: 1807 HPV18L1 F1

<400> SEQUENCE: 46
cttggtacca tggccctctg gagaccatcc gata                                34

<210> SEQ ID NO 47
<211> LENGTH: 35
<212> TYPE: DNA
<213> ORGANISM: Artificial sequence
<220> FEATURE:
<223> OTHER INFORMATION: 1808 HPV18L1 R1

<400> SEQUENCE: 47
gcttggcttt gaggaacttc ctgcccaatg ggtac                               35

<210> SEQ ID NO 48
<211> LENGTH: 1429
<212> TYPE: DNA
<213> ORGANISM: Artificial sequence
<220> FEATURE:
<223> OTHER INFORMATION: 1809 HPV18L1 amplified sequence 1

<400> SEQUENCE: 48
cttggtacca tggccctctg gagaccatcc gataacacag tgtacttgcc cccacccagc    60
gtcgcccggg tggtgaacac agacgactac gtcaccagaa cctcaatctt ctaccacgcc    120
gggtccagcc ggctgctgac cgtgggcaac ccctacttcc gcgtgcccgc cggcggcgga    180
aacaaacaag acatccccaa agtcagcgcc tatcagtacc gggtgttccg cgtccaactg    240
cccgatccca caagttcgg cctgcccgac acctccatct acaaccccga gacccagagg    300
ctggtctggg cttgcgccgg cgtcgagatc ggggggggcc aacccctggg cgtggggttg    360
tccggccacc ccttctacaa caagctggac gataccgagt ccagccacgc agcaaccagc    420
aacgtctccg aagatgtgcg cgataacgtc agcgtggact acaaacaaac ccaactgtgc    480
atcctgggat gcgcacccgc catcggcgag cattgggcca aggggaccgc ctgcaagagc    540
aggcccctga ccaagggga ctgtccaccc ctggagttga agaataccgt gctcgaggac    600
ggcgacatgg tggacaccgg ctacggcgct atggatttct ccaccctcca ggacaccaag    660
tgcgaagtgc ccctcgacat ctgccaaagc atctgcaagt ccccgactac ctccagatg    720 agcgccgacc cctacggcga cagcatgttc ttctgtctca agggaaca attgttcgcc    780 cgccacttct ggaaccgggc cggcacaatg ggagatacag tccccagag cctgtacatc    840 aaggggaccg gaatgagggc cagccccggg tcctgcgtct acagcccaag cccctccggg    900
agcatcgtca aagcgatag ccaactcttc aacaagccct actggctcca caaagcccaa    960
ggccacaata cggggtgtg ttggcacaac cagctgttcg tgaccgtcgt ggacacaacc    1020
aggtccacaa acctgaccat ctgcgccagc acccaaagcc ccgtgcccgg ccagtacgac    1080
gccacaaagt tcaaacaata ctctcggcac gtggaagagt acgacctcca attcatcttc    1140
caactctgca ccatcaccct caccgccgac gtgatgagct acatccactc catgaactcc    1200
```

```
tccatcctgg aagactggaa tttcggcgtg ccaccacccc ctaccacctc cctcgtcgac    1260
acctacagat tcgtgcagag cgtggccatc acatgccaga aagacgccgc ccccgccgag    1320
aacaaagacc catacgacaa actgaaattc tggaacgtcg acctgaaaga gaaattcagc    1380
ctggatctgg accagtaccc attgggcagg aagttcctca agccaagc                1429
```

```
<210> SEQ ID NO 49
<211> LENGTH: 35
<212> TYPE: DNA
<213> ORGANISM: Artificial sequence
<220> FEATURE:
<223> OTHER INFORMATION: 1810 HPV18L1 F2

<400> SEQUENCE: 49
gaagttcctc aaagccaagc caaaactgaa aaggg                              35
```

```
<210> SEQ ID NO 50
<211> LENGTH: 36
<212> TYPE: DNA
<213> ORGANISM: Artificial sequence
<220> FEATURE:
<223> OTHER INFORMATION: 1811 HPV18L1 R2

<400> SEQUENCE: 50
ctgtctagat ttacttcttc accttcttcc tcttgg                             36
```

```
<210> SEQ ID NO 51
<211> LENGTH: 101
<212> TYPE: DNA
<213> ORGANISM: Artificial sequence
<220> FEATURE:
<223> OTHER INFORMATION: 1812 HPV18L1 amplified sequence 2

<400> SEQUENCE: 51
gaagttcctc aaagccaagc caaaactgaa aagggctgcc ccaaccagca ccaggacctc    60
ctctgccaag aggaagaagg tgaagaagta aatctagaca g                       101
```

```
<210> SEQ ID NO 52
<211> LENGTH: 38
<212> TYPE: PRT
<213> ORGANISM: Homo sapiens
<220> FEATURE:
<221> NAME/KEY: misc_feature
<223> OTHER INFORMATION: 1813 Amino acid sequence of HPV type 59 L1
      protein aa 471-508

<400> SEQUENCE: 52

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35
```

```
<210> SEQ ID NO 53
<211> LENGTH: 475
<212> TYPE: PRT
<213> ORGANISM: Homo sapiens
<220> FEATURE:
<221> NAME/KEY: misc_feature
<223> OTHER INFORMATION: 3101 Amino acid sequence of HPV type 31 L1
      protein aa 1-475

<400> SEQUENCE: 53
```

```
Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
            35                  40                  45

Tyr Tyr Ser Ile Pro Lys Ser Asp Asn Pro Lys Lys Ile Val Val Pro
        50                  55                  60

Lys Val Ser Gly Leu Gln Tyr Arg Val Phe Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
                100                 105                 110

Pro Leu Gly Val Gly Ile Ser Gly His Pro Leu Leu Asn Lys Phe Asp
            115                 120                 125

Asp Thr Glu Asn Ser Asn Arg Tyr Ala Gly Gly Pro Gly Thr Asp Asn
            130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
            195                 200                 205

Met Asp Phe Thr Ala Leu Gln Asp Thr Lys Ser Asn Val Pro Leu Asp
210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
                260                 265                 270

Pro Thr Asp Leu Tyr Ile Lys Gly Ser Gly Ser Thr Ala Thr Leu Ala
            275                 280                 285

Asn Ser Thr Tyr Phe Pro Thr Pro Ser Gly Ser Met Val Thr Ser Asp
            290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
            355                 360                 365

Glu Glu Phe Asp Leu Gln Phe Ile Phe Gln Leu Cys Lys Ile Thr Leu
370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Ser
```

```
            420               425               430
Ala Pro Gln Lys Pro Lys Glu Asp Pro Phe Lys Asp Tyr Val Phe Trp
            435               440               445

Glu Val Asn Leu Lys Glu Lys Phe Ser Ala Asp Leu Asp Gln Phe Pro
        450               455               460

Leu Gly Arg Lys Phe Leu Leu Gln Ala Gly Tyr
465             470             475

<210> SEQ ID NO 54
<211> LENGTH: 26
<212> TYPE: PRT
<213> ORGANISM: Homo sapiens
<220> FEATURE:
<221> NAME/KEY: misc_feature
<223> OTHER INFORMATION: 3102 Amino acid sequence of HPV type 33 L1
      protein aa 474-499

<400> SEQUENCE: 54

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 55
<211> LENGTH: 501
<212> TYPE: PRT
<213> ORGANISM: Artificial sequence
<220> FEATURE:
<223> OTHER INFORMATION: 3103 Amino acid sequence of chimeric HPV type
      31 L1 protein

<400> SEQUENCE: 55

Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45

Tyr Tyr Ser Ile Pro Lys Ser Asp Asn Pro Lys Lys Ile Val Val Pro
50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205
```

```
Met Asp Phe Thr Ala Leu Gln Asp Thr Lys Ser Asn Val Pro Leu Asp
    210                 215                 220
Ile Cys Asn Ser Ile Cys Lys Tyr Pro Asp Tyr Leu Lys Met Val Ala
225                 230                 235                 240
Glu Pro Tyr Gly Asp Thr Leu Phe Phe Tyr Leu Arg Arg Glu Gln Met
                245                 250                 255
Phe Val Arg His Phe Asn Arg Ser Gly Thr Val Gly Glu Ser Val
            260                 265                 270
Pro Thr Asp Leu Tyr Ile Lys Gly Ser Gly Ser Thr Ala Thr Leu Ala
                275                 280                 285
Asn Ser Thr Tyr Phe Pro Thr Pro Ser Gly Ser Met Val Thr Ser Asp
290                 295                 300
Ala Gln Ile Phe Asn Lys Pro Tyr Trp Met Gln Arg Ala Gln Gly His
305                 310                 315                 320
Asn Asn Gly Ile Cys Trp Gly Asn Gln Leu Phe Val Thr Val Val Asp
                325                 330                 335
Thr Thr Arg Ser Thr Asn Met Ser Val Cys Ala Ala Ile Ala Asn Ser
            340                 345                 350
Asp Thr Thr Phe Lys Ser Ser Asn Phe Lys Glu Tyr Leu Arg His Gly
            355                 360                 365
Glu Glu Phe Asp Leu Gln Phe Ile Phe Gln Leu Cys Lys Ile Thr Leu
    370                 375                 380
Ser Ala Asp Ile Met Thr Tyr Ile His Ser Met Asn Pro Ala Ile Leu
385                 390                 395                 400
Glu Asp Trp Asn Phe Gly Leu Thr Thr Pro Pro Ser Gly Ser Leu Glu
                405                 410                 415
Asp Thr Tyr Arg Phe Val Thr Ser Gln Ala Ile Thr Cys Gln Lys Ser
            420                 425                 430
Ala Pro Gln Lys Pro Lys Glu Asp Pro Phe Lys Asp Tyr Val Phe Trp
            435                 440                 445
Glu Val Asn Leu Lys Glu Lys Phe Ser Ala Asp Leu Asp Gln Phe Pro
    450                 455                 460
Leu Gly Arg Lys Phe Leu Leu Gln Ala Gly Tyr Lys Ala Lys Pro Lys
465                 470                 475                 480
Leu Lys Arg Ala Ala Pro Thr Ser Thr Arg Thr Ser Ser Ala Lys Arg
                485                 490                 495
Lys Lys Val Lys Lys
            500

<210> SEQ ID NO 56
<211> LENGTH: 1507
<212> TYPE: DNA
<213> ORGANISM: Artificial sequence
<220> FEATURE:
<223> OTHER INFORMATION: 3104 Nucleotide sequence of chimeric HPV type
      31 L1 protein

<400> SEQUENCE: 56
atgagcctgt ggaggcccag cgaggccacc gtgtacctgc ccccgtgcc cgtgagcaag      60 gtggtgagca ccgacgagta cgtgaccagg accaacatct actaccacgc cggcagcgcc     120
aggctgctga ccgtgggcca ccctactac agcatcccca agagcgacaa ccccaagaag     180
atcgtggtgc ccaaggtgag cggcctgcag tacagggtgt tcagggtgag gctgcccgac     240
cccaacaagt tcggcttccc cgacaccagc ttctacaacc ccgagaccca gaggctggtg     300
tgggcctgcg tgggcctgga ggtgggcagg ggccagcccc tgggcgtggg catcagcggc     360
```

```
caccccctgc tgaacaagtt cgacgacacc gagaacagca acaggtacgc cggcggcccc        420
ggcaccgaca caggagtg catcagcatg gactacaagc agacccagct gtgcctgctg         480
ggctgcaagc ccccatcgg cgagcactgg gcaagggca gccctgcag caacaacgcc          540 atcacccccg cgactgccc ccccctggag ctgaagaaca cgtgatcca ggacggcgac         600 atggtggaca ccggcttcgg cgccatggac ttcaccgccc tgcaggacac caagagcaac       660
gtgcccctgg acatctgcaa cagcatctgc aagtaccccg actacctgaa gatggtggcc      720
gagccctacg gcgacaccct gttcttctac ctgaggaggg agcagatgtt cgtgaggcac      780
ttcttcaaca ggagcggcac cgtgggcgag agcgtgccca ccgacctgta catcaagggc      840
agcggcagca ccgccaccct ggccaacagc acctacttcc ccaccccag cggcagcatg       900 gtgaccagcg acgccagat cttcaacaag ccctactgga tgcagagggc ccagggccac      960
aacaacggca tctgctgggg caaccagctg ttcgtgaccg tggtggacac caccaggagc     1020
accaacatga gcgtgtgcgc cgccatcgcc aacagcgaca ccaccttcaa gagcagcaac      1080
ttcaaggagt acctgaggca cggcgaggag ttcgacctgc agttcatctt ccagctgtgc      1140
aagatcaccc tgagcgccga catcatgacc tacatccaca gcatgaaccc cgccatcctg     1200
gaggactgga acttcggcct gaccaccccc ccagcggca gcctggagga cacctacagg      1260
ttcgtgacca gccaggccat cacctgccag aagtccgccc ccagaagcc caaggaggac      1320 cccttcaagg actacgtgtt ctgggaggtg aacctgaagg agaagttcag cgccgacctg     1380
gaccagttcc ccctgggcag gaagttcctg ctgcaggccg gctacaaagc caagccaaaa    1440
ctgaaaaggg ctgccccaac cagcaccagg acctcctctg ccaagaggaa gaaggtgaag    1500
aagtaaa                                                                   1507
```

<210> SEQ ID NO 57
<211> LENGTH: 1534
<212> TYPE: DNA
<213> ORGANISM: Artificial sequence
<220> FEATURE:
<223> OTHER INFORMATION: 3105 Synthetic HPV31 L1 gene

<400> SEQUENCE: 57

```
ctgggtacca tgagcctgtg gaggcccagc gaggccaccg tgtacctgcc ccccgtgccc         60
gtgagcaagg tggtgagcac cgacgagtac gtgaccagga ccaacatcta ctaccacgcc       120
ggcagcgcca ggctgctgac cgtgggccac ccctactaca gcatccccaa gagcgacaac       180
cccaagaaga tcgtggtgcc caaggtgagc ggcctgcagt acagggtgtt cagggtgagg       240
ctgcccgacc ccaacaagtt cggcttcccc gacaccagct tctacaaccc cgagacccag       300
aggctggtgt gggcctgcgt gggcctggag gtgggcaggg ccagcccct gggcgtgggc        360 atcagcggcc accccctgct gaacaagttc gacgacaccg agaacagcaa caggtacgcc      420
ggcggccccg gcaccgacaa cagggagtgc atcagcatgg actacaagca gacccagctg      480
tgcctgctgg gctgcaagcc ccccatcggc gagcactggg gcaagggcag ccctgcagc        540 aacaacgcca tcaccccgg cgactgcccc cccctggagc tgaagaacag cgtgatccag       600
gacggcgaca tggtggacac cggcttcggc gccatggact tcaccgccct gcaggacacc     660
aagagcaacg tgcccctgga catctgcaac agcatctgca agtaccccga ctacctgaag     720
atggtggccg agccctacgg cgacaccctg ttcttctacc tgaggaggga gcagatgttc     780
gtgaggcact tcttcaacag gagcggcacc gtgggcgaga gcgtgcccac cgacctgtac    840
```

| atcaagggca gcggcagcac cgccaccctg gccaacagca cctacttccc cacccccagc | 900 |
| ggcagcatgg tgaccagcga cgcccagatc ttcaacaagc cctactggat gcagagggcc | 960 |
| cagggccaca acaacggcat ctgctgggc aaccagctgt tcgtgaccgt ggtggacacc | 1020 |
| accaggagca ccaacatgag cgtgtgcgcc gccatcgcca acagcgacac caccttcaag | 1080 |
| agcagcaact tcaaggagta cctgaggcac ggcgaggagt tcgacctgca gttcatcttc | 1140 |
| cagctgtgca agatcaccct gagcgccgac atcatgacct acatccacag catgaacccc | 1200 |
| gccatcctgg aggactggaa cttcggcctg accacccccc cagcggcag cctggaggac | 1260 |
| acctacaggt tcgtgaccag ccaggccatc acctgccaga gtccgcccc ccagaagccc | 1320 |
| aaggaggacc ccttcaagga ctacgtgttc tgggaggtga acctgaagga aagttcagc | 1380 |
| gccgacctgg accagttccc cctgggcagg aagttcctgc tgcaggccgg ctacagggcc | 1440 |
| aggcccaagt tcaaggccgg caagaggagc gcccccagcg ccagcaccac cacccccgcc | 1500 |
| aagaggaaga agaccaagaa gtaaactcga gctc | 1534 |

<210> SEQ ID NO 58
<211> LENGTH: 1519
<212> TYPE: DNA
<213> ORGANISM: Artificial sequence
<220> FEATURE:
<223> OTHER INFORMATION: 3106 Synthetic HPV33 L1 gene

<400> SEQUENCE: 58

| ctgggtacca tgagtgtgtg gagaccatct gaggctacag tctacctgcc tcctgtgcct | 60 |
| gtgagcaagg tggtgagcac agatgaatat gtgagcagga ccagcatcta ctactatgct | 120 |
| ggctccagca gactgctggc tgtgggacac ccatacttca gcatcaagaa cccaaccaat | 180 |
| gccaagaaac tgctggtgcc aaaggtgtct ggactccaat acagggtgtt cagggtgaga | 240 |
| ctgcctgacc caaacaagtt tggctttcct gacacctcct tctacaaccc tgacacccag | 300 |
| agactggtgt gggcttgtgt gggattggag attggcaggg acaaccact gggagtgggc | 360 |
| atctctggac acccactgct gaacaagttt gatgacacag agacaggcaa caaataccct | 420 |
| ggacaacctg gagcagacaa cagggagtgt ctgagtatgg actacaagca gacccaactt | 480 |
| tgtctgctgg gctgtaagcc tccaacagga gaacactggg caagggagt ggcttgtacc | 540 |
| aatgctgccc ctgccaatga ctgtcctcca ttggaactga taaacaccat cattgaggat | 600 |
| ggagatatgg tggacacagg cttggctgt atggacttca gaccctcca agccaacaag | 660 |
| tctgatgtgc caattgacat ctgtggcagc acttgtaaat accctgacta cctgaaaatg | 720 |
| acctctgaac catatggaga ctccctgttc ttcttcctga ggagggaaca gatgtttgtg | 780 |
| agacacttct tcaacagggc tggcaccctg ggagaggctg tgcctgatga cctctacatc | 840 |
| aagggctctg gcaccacagc cagcatccag tcctctgcct tcttccaac accatctggc | 900 |
| agtatggtga cctctgagag ccaacttttc aacaagccat actggctcca aagggctcaa | 960 |
| ggacacaaca atggcatctg ttggggcaac caggtgtttg tgacagtggt ggacaccacc | 1020 |
| aggagcacca atatgaccct gtgtacccag gtgacctctg acagcaccta caagaatgag | 1080 |
| aacttcaagg aatacatcag gcatgtggag gaatatgacc tccaatttgt gttccaactt | 1140 |
| tgtaaggtga ccctgacagc agaggtgatg acctacatcc atgctatgaa ccctgacatc | 1200 |
| ttggaggact ggcagtttgg actgacacct cctccatctg cctccctcca agacacctac | 1260 |
| aggtttgtga ccagccaggc tatcacttgt cagaagacag tgcctccaaa ggagaaggag | 1320 |
| gacccactgg gcaaatacac cttctgggag gtggacctga agagaagtt ctctgctgac | 1380 |

```
ctggaccagt tccactggg caggaagttc ctgctccaag caggactgaa agccaagcca    1440
aaactgaaaa gggctgcccc aaccagcacc aggacctcct ctgccaagag gaagaaggtg    1500
aagaagtaaa ctcgagctc                                                  1519
```

<210> SEQ ID NO 59
<211> LENGTH: 33
<212> TYPE: DNA
<213> ORGANISM: Artificial sequence
<220> FEATURE:
<223> OTHER INFORMATION: 3107 HPV31L1 F1

<400> SEQUENCE: 59

```
cttggtacca tgagcctgtg gaggcccagc gag                                  33
```

<210> SEQ ID NO 60
<211> LENGTH: 38
<212> TYPE: DNA
<213> ORGANISM: Artificial sequence
<220> FEATURE:
<223> OTHER INFORMATION: 3108 HPV31L1 R1

<400> SEQUENCE: 60

```
gcttggcttt gtagccggcc tgcagcagga acttcctg                             38
```

<210> SEQ ID NO 61
<211> LENGTH: 1444
<212> TYPE: DNA
<213> ORGANISM: Artificial sequence
<220> FEATURE:
<223> OTHER INFORMATION: 3109 HPV31L1 amplified sequence 1

<400> SEQUENCE: 61

```
cttggtacca tgagcctgtg gaggcccagc gaggccaccg tgtacctgcc ccccgtgccc     60
gtgagcaagg tggtgagcac cgacgagtac gtgaccagga ccaacatcta ctaccacgcc    120
ggcagcgcca ggctgctgac cgtgggccac ccctactaca gcatccccaa gagcgacaac    180
cccaagaaga tcgtggtgcc caaggtgagc ggcctgcagt acagggtgtt cagggtgagg    240
ctgcccgacc ccaacaagtt cggcttcccc gacaccagct tctacaaccc cgagacccag    300
aggctggtgt gggcctgcgt gggcctggag gtgggcaggg ccagcccct gggcgtgggc    360 atcagcggcc accccctgct gaacaagttc gacgacaccg agaacagcaa caggtacgcc    420
ggcggccccg gcaccgacaa cagggagtgc atcagcatgg actacaagca gacccagctg    480
tgcctgctgg gctgcaagcc ccccatcggc gagcactggg gcaagggcag ccctgcagc    540 aacaacgcca tcacccccgg cgactgcccc cccctggagc tgaagaacag cgtgatccag    600
gacggcgaca tggtggacac cggcttcggc gccatggact tcaccgccct gcaggacacc    660
aagagcaacg tgcccctgga catctgcaac agcatctgca gtaccccga ctacctgaag    720 atggtggccg agccctacgg cgacacactg ttcttctacc tgaggaggga gcagatgttc    780
gtgaggcact tcttcaacag gagcggcacc gtgggcgaga gcgtgcccac cgacctgtac    840
atcaagggca gcggcagcac cgccaccctg gccaacagca cctacttccc caccccagc    900 ggcagcatgg tgaccagcga cgcccagatc ttcaacaagc cctactggat gcagagggcc    960
cagggccaca caacggcat ctgctgggc aaccagctgt tcgtgaccgt ggtggacacc    1020
accaggagca ccaacatgag cgtgtgcgcc gccatcgcca acagcgacac caccttcaag    1080
agcagcaact tcaaggagta cctgaggcac ggcgaggagt tcgacctgca gttcatcttc    1140
```

```
cagctgtgca agatcaccct gagcgccgac atcatgacct acatccacag catgaacccc    1200
gccatcctgg aggactggaa cttcggcctg accacccccc ccagcggcag cctggaggac    1260
acctacaggt tcgtgaccag ccaggccatc acctgccaga agtccgcccc ccagaagccc    1320
aaggaggacc ccttcaagga ctacgtgttc tgggaggtga acctgaagga gaagttcagc    1380
gccgacctgg accagttccc cctgggcagg aagttcctgc tgcaggccgg ctacaaagcc    1440
aagc                                                                 1444
```

<210> SEQ ID NO 62
<211> LENGTH: 35
<212> TYPE: DNA
<213> ORGANISM: Artificial sequence
<220> FEATURE:
<223> OTHER INFORMATION: 3110 HPV31L1 F2

<400> SEQUENCE: 62

```
ggccggctac aaagccaagc caaaactgaa aaggg                                 35
```

<210> SEQ ID NO 63
<211> LENGTH: 41
<212> TYPE: DNA
<213> ORGANISM: Artificial sequence
<220> FEATURE:
<223> OTHER INFORMATION: 3111 HPV31L1 R2

<400> SEQUENCE: 63

```
ctgtctagat ttacttcttc accttcttcc tcttggcaga g                          41
```

<210> SEQ ID NO 64
<211> LENGTH: 101
<212> TYPE: DNA
<213> ORGANISM: Artificial sequence
<220> FEATURE:
<223> OTHER INFORMATION: 3112 HPV31L1 amplified sequence 2

<400> SEQUENCE: 64

```
ggccggctac aaagccaagc caaaactgaa aagggctgcc ccaaccagca ccaggacctc      60
ctctgccaag aggaagaagg tgaagaagta aatctagaca g                         101
```

<210> SEQ ID NO 65
<211> LENGTH: 38
<212> TYPE: PRT
<213> ORGANISM: Homo sapiens
<220> FEATURE:
<221> NAME/KEY: misc_feature
<223> OTHER INFORMATION: 3113 Amino acid sequence of HPV type 59 L1
      protein aa 471-508

<400> SEQUENCE: 65

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 66
<211> LENGTH: 472
<212> TYPE: PRT
<213> ORGANISM: Homo sapiens
<220> FEATURE:
<221> NAME/KEY: misc_feature
<223> OTHER INFORMATION: 3501 Amino acid sequence of HPV type 35 L1 protein aa 1-472

<400> SEQUENCE: 66

```
Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
            35                  40                  45

Tyr Tyr Ala Ile Lys Lys Gln Asp Ser Asn Lys Ile Ala Val Pro Lys
        50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
            115                 120                 125

Thr Glu Asn Ser Asn Lys Tyr Val Gly Asn Ser Gly Thr Asp Asn Arg
        130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
        210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Gly Thr Leu Pro Ser Thr Ser
        275                 280                 285

Tyr Phe Pro Thr Pro Ser Gly Ser Met Val Thr Ser Asp Ala Gln Ile
        290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
        370                 375                 380

Val Met Thr Tyr Ile His Ser Met Asn Pro Ser Ile Leu Glu Asp Trp
385                 390                 395                 400
```

```
Asn Phe Gly Leu Thr Pro Pro Ser Gly Thr Leu Glu Asp Thr Tyr
            405                 410                 415

Arg Tyr Val Thr Ser Gln Ala Val Thr Cys Gln Lys Pro Ser Ala Pro
        420                 425                 430

Lys Pro Lys Asp Asp Pro Leu Lys Asn Tyr Thr Phe Trp Glu Val Asp
            435                 440                 445

Leu Lys Glu Lys Phe Ser Ala Asp Leu Asp Gln Phe Pro Leu Gly Arg
        450                 455                 460

Lys Phe Leu Leu Gln Ala Gly Leu
465             470

<210> SEQ ID NO 67
<211> LENGTH: 26
<212> TYPE: PRT
<213> ORGANISM: Homo sapiens
<220> FEATURE:
<221> NAME/KEY: misc_feature
<223> OTHER INFORMATION: 3502 Amino acid sequence of HPV type 33 L1
      protein aa 474-499

<400> SEQUENCE: 67

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 68
<211> LENGTH: 498
<212> TYPE: PRT
<213> ORGANISM: Artificial sequence
<220> FEATURE:
<223> OTHER INFORMATION: 3503 Amino acid sequence of chimeric HPV type
      35 L1 protein

<400> SEQUENCE: 68

Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
        35                  40                  45

Tyr Tyr Ala Ile Lys Lys Gln Asp Ser Asn Lys Ile Ala Val Pro Lys
    50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ser Asn Lys Tyr Val Gly Asn Ser Gly Thr Asp Asn Arg
    130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190
```

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
    210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
    370                 375                 380

Val Met Thr Tyr Ile His Ser Met Asn Pro Ser Ile Leu Glu Asp Trp
385                 390                 395                 400

Asn Phe Gly Leu Thr Pro Pro Pro Ser Gly Thr Leu Glu Asp Thr Tyr
                405                 410                 415

Arg Tyr Val Thr Ser Gln Ala Val Thr Cys Gln Lys Pro Ser Ala Pro
            420                 425                 430

Lys Pro Lys Asp Asp Pro Leu Lys Asn Tyr Thr Phe Trp Glu Val Asp
        435                 440                 445

Leu Lys Glu Lys Phe Ser Ala Asp Leu Asp Gln Phe Pro Leu Gly Arg
    450                 455                 460

Lys Phe Leu Leu Gln Ala Gly Leu Lys Ala Lys Pro Lys Leu Lys Arg
465                 470                 475                 480

Ala Ala Pro Thr Ser Thr Arg Thr Ser Ser Ala Lys Arg Lys Lys Val
                485                 490                 495

Lys Lys

<210> SEQ ID NO 69
<211> LENGTH: 1498
<212> TYPE: DNA
<213> ORGANISM: Artificial sequence
<220> FEATURE:
<223> OTHER INFORMATION: 3504 Nucleotide sequence of chimeric HPV type
      35 L1 protein

<400> SEQUENCE: 69
atgagtctgt ggaggagcaa tgaggctaca gtctacctgc ctcctgtgtc tgtgagcaag      60
gtggtgagca cagatgaata tgtgaccagg accaacatct actaccatgc tggctccagc     120
agactgctgg ctgtgggaca cccatactat gccatcaaga agcaggacag caacaagatt     180
gctgtgccaa aggtgtctgg actccaaata agggtgttca gggtgaaact gcctgaccca     240

-continued

```
aacaagtttg ctttcctga cacctccttc tatgaccctg ccagccagag actggtgtgg      300
gcttgtactg gagtggaggt gggcagggga caaccactgg gagtgggcat ctctggacac      360
ccactgctga acaaactgga tgacacagag aacagcaaca aatatgtggg caactctggc      420
acagacaaca gggagtgtat cagtatggac tacaagcaga cccaactttg tctgattggc      480
tgtagacctc caattggaga cactggggc aagggcacac catgtaatgc caaccaggtg      540
aaggctggag agtgtcctcc attggaactg ctgaacacag tgctccaaga tggagatatg      600
gtggacacag gctttggagc tatggacttc accaccctcc aagccaacaa gtctgatgtg      660
ccactggaca tctgttccag catctgtaaa taccctgact acctgaaaat ggtgtctgaa      720
ccatatggag atatgctgtt cttctacctg aggagggaac agatgtttgt gagacacctg      780
ttcaacaggg ctggcacagt gggagagaca gtgcctgctg acctctacat caagggcacc      840
acaggcaccc tgccaagcac ctcctacttt ccaacaccat ctggcagtat ggtgacctct      900
gatgcccaga ttttcaacaa gccatactgg ctccaaaggg ctcaaggaca caacaatggc      960
atctgttgga gcaaccaact ttttgtgaca gtggtggaca ccaccaggag caccaatatg      1020
agtgtgtgtt ctgctgtgtc ctcctctgac agcacctaca agaatgacaa cttcaaggaa      1080
tacctgagac atggagagga atatgacctc caattcatct ccaactttg taagattacc      1140 ctgacagcag atgtgatgac ctacatccac agtatgaacc caagcatctt ggaggactgg      1200
aactttggac tgacacctcc tccatctggc accttgaggg acacctacag atatgtgacc      1260
agccaggctg tgacttgtca gaagccatct gccccaaagc caaggatga cccactgaaa      1320 aactacaccct tctgggaggt ggacctgaaa gagaagttct ctgctgacct ggaccagttt      1380
ccactgggca ggaagttcct gctccaagca ggactgaaag ccaagccaaa actgaaaagg      1440
gctgccccaa ccagcaccag gacctcctct gccaagagga agaaggtgaa gaagtaaa      1498
```

<210> SEQ ID NO 70
<211> LENGTH: 1528
<212> TYPE: DNA
<213> ORGANISM: Artificial sequence
<220> FEATURE:
<223> OTHER INFORMATION: 3505 Synthetic HPV35 L1 gene

<400> SEQUENCE: 70

```
ctgggtacca tgagtctgtg gaggagcaat gaggctacag tctacctgcc tcctgtgtct       60
gtgagcaagg tggtgagcac agatgaatat gtgaccagga ccaacatcta ctaccatgct      120
ggctccagca gactgctggc tgtgggacac ccatactatg ccatcaagaa gcaggacagc      180
aacaagattg ctgtgccaaa ggtgtctgga ctccaataca gggtgttcag ggtgaaactg      240
cctgacccaa acaagtttgg ctttcctgac acctccttct atgaccctgc agccagaga      300 ctggtgtggg cttgtactgg agtggaggtg ggcagggac aaccactggg agtgggcatc      360
tctggacacc cactgctgaa caaactggat gacacagaga acagcaacaa atatgtgggc      420
aactctggca cagacaacag ggagtgtatc agtatggact acaagcagac ccaactttgt      480
ctgattggct gtagacctcc aattggagaa cactggggca gggcacacc atgtaatgcc      540 aaccaggtga aggctggaga gtgtcctcca ttggaactgc tgaacacagt gctccaagat      600
ggagatatgg tggacacagg ctttggagct atggacttca ccaccctcca agccaacaag      660
tctgatgtgc cactggacat ctgttccagc atctgtaaat accctgacta cctgaaaatg      720
gtgtctgaac catatggaga tatgctgttc ttctacctga ggagggaaca gatgtttgtg      780
agacacctgt tcaacagggc tggcacagtg ggagagacag tgcctgctga cctctacatc      840
```

| aagggcacca caggcaccct gccaagcacc tcctactttc aacaccatc tggcagtatg | 900 |
| gtgacctctg atgcccagat tttcaacaag ccatactggc tccaaagggc tcaaggacac | 960 |
| aacaatggca tctgttggag caaccaactt tttgtgacag tggtggacac caccaggagc | 1020 |
| accaatatga gtgtgtgttc tgctgtgtcc tcctctgaca gcacctacaa gaatgacaac | 1080 |
| ttcaaggaat acctgagaca tggagaggaa tatgacctcc aattcatctt ccaactttgt | 1140 |
| aagattaccc tgacagcaga tgtgatgacc tacatccaca gtatgaaccc aagcatcttg | 1200 |
| gaggactgga actttggact gacacctcct ccatctggca ccttggagga cacctacaga | 1260 |
| tatgtgacca gccaggctgt gacttgtcag aagccatctg ccccaaagcc aaaggatgac | 1320 |
| ccactgaaaa actacacctt ctgggaggtg gacctgaaag agaagttctc tgctgacctg | 1380 |
| gaccagtttc cactgggcag gaagttcctg ctccaagcag gactgaaagc cagaccaaac | 1440 |
| ttcagactgg gcaagagggc tgcccctgcc agcaccagca agaagtccag caccaagagg | 1500 |
| aggaaggtga agagctaaac tcgagctc | 1528 |

<210> SEQ ID NO 71
<211> LENGTH: 1519
<212> TYPE: DNA
<213> ORGANISM: Artificial sequence
<220> FEATURE:
<223> OTHER INFORMATION: 3506 Synthetic HPV33 L1 gene

<400> SEQUENCE: 71

| ctgggtacca tgagtgtgtg gagaccatct gaggctacag tctacctgcc tcctgtgcct | 60 |
| gtgagcaagg tggtgagcac agatgaatat gtgagcagga ccagcatcta ctactatgct | 120 |
| ggctccagca gactgctggc tgtgggacac ccatacttca gcatcaagaa cccaaccaat | 180 |
| gccaagaaac tgctggtgcc aaaggtgtct ggactccaat acagggtgtt cagggtgaga | 240 |
| ctgcctgacc caaacaagtt tggctttcct gacacctcct tctacaaccc tgacacccag | 300 |
| agactggtgt gggcttgtgt gggattggag attggcaggg acaaccact gggagtgggc | 360 |
| atctctggac acccactgct gaacaagttt gatgacacag agacaggcaa caaatacccct | 420 |
| ggacaacctg agcagacaa cagggagtgt ctgagtatgg actacaagca gacccaactt | 480 |
| tgtctgctgg gctgtaagcc tccaacagga gaacactggg gcaagggagt ggcttgtacc | 540 |
| aatgctgccc tgccaatga ctgtcctcca ttggaactga taaacaccat cattgaggat | 600 |
| ggagatatgg tggacacagg ctttggctgt atggacttca gaccctcca gccaacaag | 660 |
| tctgatgtgc caattgacat ctgtggcagc acttgtaaat accctgacta cctgaaaatg | 720 |
| acctctgaac catatggaga ctccctgttc ttcttcctga ggagggaaca gatgtttgtg | 780 |
| agacacttct tcaacagggc tggcacccctg ggagaggctg tgcctgatga cctctacatc | 840 |
| aagggctctg gcaccacagc cagcatccag tcctctgcct tctttccaac accatctggc | 900 |
| agtatggtga cctctgagag ccaacttttc aacaagccat actggctcca aagggctcaa | 960 |
| ggacacaaca atggcatctg ttggggcaac caggtgtttg tgacagtggt ggacaccacc | 1020 |
| aggagccacca atatgaccct gtgtaccag gtgacctctg acagcaccta caagaatgag | 1080 |
| aacttcaagg aatacatcag gcatgtggag gaatatgacc tccaatttgt gttccaactt | 1140 |
| tgtaaggtga ccctgacagc agaggtgatg acctacatcc atgctatgaa ccctgacatc | 1200 |
| ttggaggact ggcagtttgg actgacacct cctccatctg cctccctcca agacacctac | 1260 |
| aggtttgtga ccagccaggc tatcacttgt cagaagacag tgcctccaaa ggagaaggag | 1320 |

```
gacccactgg gcaaatacac cttctgggag gtggacctga agagaagtt ctctgctgac    1380 ctggaccagt ttccactggg caggaagttc ctgctccaag caggactgaa agccaagcca    1440
aaactgaaaa gggctgcccc aaccagcacc aggacctcct ctgccaagag gaagaaggtg    1500
aagaagtaaa ctcgagctc                                                 1519

<210> SEQ ID NO 72
<211> LENGTH: 34
<212> TYPE: DNA
<213> ORGANISM: Artificial sequence
<220> FEATURE:
<223> OTHER INFORMATION: 3507 HPV35L1 F1

<400> SEQUENCE: 72
cttggtacca tgagtctgtg gaggagcaat gagg                                34

<210> SEQ ID NO 73
<211> LENGTH: 36
<212> TYPE: DNA
<213> ORGANISM: Artificial sequence
<220> FEATURE:
<223> OTHER INFORMATION: 3508 HPV35L1 R1

<400> SEQUENCE: 73
gcttggcttt cagtcctgct tggagcagga acttcc                              36

<210> SEQ ID NO 74
<211> LENGTH: 1435
<212> TYPE: DNA
<213> ORGANISM: Artificial sequence
<220> FEATURE:
<223> OTHER INFORMATION: 3509 HPV35L1 amplified sequence 1

<400> SEQUENCE: 74
cttggtacca tgagtctgtg gaggagcaat gaggctacag tctacctgcc tcctgtgtct    60
gtgagcaagg tggtgagcac agatgaatat gtgaccagga ccaacatcta ctaccatgct    120
ggctccagca gactgctggc tgtgggacac ccatactatg ccatcaagaa gcaggacagc    180
aacaagattg ctgtgccaaa ggtgtctgga ctccaataca gggtgttcag ggtgaaactg    240
cctgacccaa acaagtttgg cttttcctga cctccttct atgaccctgc cagccagaga    300
ctggtgtggg cttgtactgg agtggaggtg ggcaggggac aaccactggg agtgggcatc    360
tctggacacc cactgctgaa caaactggat gacacagaga acagcaacaa atatgtgggc    420
aactctggca gacaacag ggagtgtatc agtatggact acaagcagac ccaactttgt    480
ctgattggct gtagacctcc aattggagaa cactggggca agggcacacc atgtaatgcc    540
aaccaggtga aggctggaga gtgtcctcca ttgaactgc tgaacacagt gctccaagat    600
ggagatatgg tggacacagg cttggagct atggacttca ccaccctcca agccaacaag    660
tctgatgtgc cactggacat ctgttccagc atctgtaaat accctgacta cctgaaaatg    720
gtgtctgaac catatggaga tatgctgttc ttctacctga ggagggaaca gatgtttgtg    780
agacacctgt tcaacagggc tggcacagtg ggagagacag tgcctgctga cctctacatc    840
aagggcacca caggcaccct gccaagcacc tcctactttc caacaccatc tggcagtatg    900
gtgacctctg atgcccagat tttcaacaag ccatactggc tccaagggc tcaaggacac    960 aacaatggca tctgttggag caaccaactt tttgtgacag tggtggacac caccaggagc    1020
accaatatga gtgtgtgttc tgctgtgtcc cctctgaca gcacctacaa gaatgacaac    1080
ttcaaggaat acctgagaca tggagaggaa tatgacctcc aattcatctt ccaactttgt    1140
```

-continued

```
aagattaccc tgacagcaga tgtgatgacc tacatccaca gtatgaaccc aagcatcttg    1200
gaggactgga actttggact gacacctcct ccatctggca ccttggagga cacctacaga    1260
tatgtgacca gccaggctgt gacttgtcag aagccatctg ccccaaagcc aaggatgac     1320 ccactgaaaa actacacctt ctgggaggtg gacctgaaag agaagttctc tgctgacctg    1380
gaccagtttc cactgggcag gaagttcctg ctccaagcag gactgaaagc caagc         1435
```

```
<210> SEQ ID NO 75
<211> LENGTH: 35
<212> TYPE: DNA
<213> ORGANISM: Artificial sequence
<220> FEATURE:
<223> OTHER INFORMATION: 3510 HPV35L1 F2

<400> SEQUENCE: 75
agcaggactg aaagccaagc caaaactgaa aaggg                               35
```

```
<210> SEQ ID NO 76
<211> LENGTH: 36
<212> TYPE: DNA
<213> ORGANISM: Artificial sequence
<220> FEATURE:
<223> OTHER INFORMATION: 3511 HPV35L1 R2

<400> SEQUENCE: 76
ctgtctagat ttacttcttc accttcttcc tcttgg                              36
```

```
<210> SEQ ID NO 77
<211> LENGTH: 101
<212> TYPE: DNA
<213> ORGANISM: Artificial sequence
<220> FEATURE:
<223> OTHER INFORMATION: 3512 HPV35L1 amplified sequence 2

<400> SEQUENCE: 77
agcaggactg aaagccaagc caaaactgaa aagggctgcc ccaaccagca ccaggacctc    60
ctctgccaag aggaagaagg tgaagaagta aatctagaca g                        101
```

```
<210> SEQ ID NO 78
<211> LENGTH: 38
<212> TYPE: PRT
<213> ORGANISM: Homo sapiens
<220> FEATURE:
<221> NAME/KEY: misc_feature
<223> OTHER INFORMATION: 3513 Amino acid sequence of HPV type 59 L1
      protein aa 471-508

<400> SEQUENCE: 78

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35
```

```
<210> SEQ ID NO 79
<211> LENGTH: 469
<212> TYPE: PRT
<213> ORGANISM: Homo sapiens
<220> FEATURE:
<221> NAME/KEY: misc_feature
<223> OTHER INFORMATION: 3901 Amino acid sequence of HPV type 39 L1
      protein aa 1-469
```

<400> SEQUENCE: 79

```
Met Ala Met Trp Arg Ser Ser Asp Ser Met Val Tyr Leu Pro Pro
1               5                   10                  15

Ser Val Ala Lys Val Val Asn Thr Asp Asp Tyr Val Thr Arg Thr Gly
            20                  25                  30

Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Gly Met Val Gly Asp Ala Ile Pro Ala
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Asp Thr Thr
                325                 330                 335

Arg Ser Thr Asn Phe Thr Leu Ser Thr Ile Glu Ser Ile Pro
            340                 345                 350

Ser Thr Tyr Asp Pro Ser Lys Phe Lys Glu Tyr Thr Arg His Val Glu
        355                 360                 365

Glu Tyr Asp Leu Gln Phe Ile Phe Gln Leu Cys Thr Val Thr Leu Thr
370                 375                 380

Thr Asp Val Met Ser Tyr Ile His Thr Met Asn Ser Ser Ile Leu Asp
385                 390                 395                 400

Asn Trp Asn Phe Ala Val Ala Pro Pro Pro Ser Ala Ser Leu Val Asp
```

```
                            405                 410                 415

Thr Tyr Arg Tyr Leu Gln Ser Ala Ala Ile Thr Cys Gln Lys Asp Ala
            420                 425                 430

Pro Ala Pro Glu Lys Lys Asp Pro Tyr Asp Gly Leu Lys Phe Trp Asn
        435                 440                 445

Val Asp Leu Arg Glu Lys Phe Ser Leu Glu Leu Asp Gln Phe Pro Leu
    450                 455                 460

Gly Arg Lys Phe Leu
465

<210> SEQ ID NO 80
<211> LENGTH: 38
<212> TYPE: PRT
<213> ORGANISM: Homo sapiens
<220> FEATURE:
<221> NAME/KEY: misc_feature
<223> OTHER INFORMATION: 3902 Amino acid sequence of HPV type 59 L1
      protein aa 471-508

<400> SEQUENCE: 80

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 81
<211> LENGTH: 507
<212> TYPE: PRT
<213> ORGANISM: Artificial sequence
<220> FEATURE:
<223> OTHER INFORMATION: 3903 Amino acid sequence of chimeric HPV type
      39 L1 protein

<400> SEQUENCE: 81

Met Ala Met Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
            20                  25                  30

Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175
```

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
    210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Met Val Gly Asp Ala Ile Pro Ala
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
    290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
                325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
        355                 360                 365

Glu Tyr Asp Leu Gln Phe Ile Phe Gln Leu Cys Thr Val Thr Leu Thr
    370                 375                 380

Thr Asp Val Met Ser Tyr Ile His Thr Met Asn Ser Ser Ile Leu Asp
385                 390                 395                 400

Asn Trp Asn Phe Ala Val Ala Pro Pro Ser Ala Ser Leu Val Asp
                405                 410                 415

Thr Tyr Arg Tyr Leu Gln Ser Ala Ala Ile Thr Cys Gln Lys Asp Ala
            420                 425                 430

Pro Ala Pro Glu Lys Lys Asp Pro Tyr Asp Gly Leu Lys Phe Trp Asn
        435                 440                 445

Val Asp Leu Arg Glu Lys Phe Ser Leu Glu Leu Asp Gln Phe Pro Leu
    450                 455                 460

Gly Arg Lys Phe Leu Leu Gln Leu Gly Ala Arg Pro Lys Pro Thr Ile
465                 470                 475                 480

Gly Pro Arg Lys Arg Ala Ala Pro Ala Pro Thr Ser Thr Pro Ser Pro
                485                 490                 495

Lys Arg Val Lys Arg Arg Lys Ser Ser Arg Lys
            500                 505

<210> SEQ ID NO 82
<211> LENGTH: 1525
<212> TYPE: DNA
<213> ORGANISM: Artificial sequence
<220> FEATURE:
<223> OTHER INFORMATION: 3904 Nucleotide sequence of chimeric HPV type
      39 L1 protein

<400> SEQUENCE: 82
atggctatgt ggaggtcctc tgacagtatg gtctacctgc ctcctccatc tgtggctaag    60
gtggtgaaca cagatgacta tgtgaccagg acaggcatct actactatgc tggctccagc   120
agactgctga cagtgggaca cccatacttc aaggtgggga tgaatggagg caggaagcag   180

```
gacatcccaa aggtgtctgc ctaccaatac agggtgttca gggtgaccct gcctgaccca      240
aacaagttca gcatccctga tgcctccctc tacaaccctg agacccagag actggtgtgg      300
gcttgtgtgg gagtggaggt gggcagggga caaccactgg gagtgggcat ctctggacac      360
ccactctaca acagacagga tgacacagag aacagcccat tctccagcac caccaacaag      420
gacagcaggg acaatgtgtc tgtggactac aagcagaccc aactttgtat cattggctgt      480
gtgcctgcca ttggagaaca ctggggcaag gcaaggcttg taagccaaac aatgtgagc       540 acaggagact gtcctccatt ggaactggtg aacacaccaa ttgaggatgg agatatgatt      600
gacacaggct atggagctat ggactttgga gccctccaag agaccaagtc tgaggtgcca      660
ctggacatct gtcagagcat ctgtaaatac cctgactacc tccaaatgag tgctgatgtc      720
tatgagacag tatgttcttc tgtctgagg agggaacaac ttttgccag acacttctgg       780 aacaggggag ggatggtggg agatgccatc cctgcccaac tctacatcaa gggcacagac      840
atcagggcta accctggctc ctctgtctac tgtccaagcc catctggcag tatggtgacc      900
tctgacagcc aacttttcaa caagccatac tggctgcaca aggctcaagg acacaacaat      960
ggcatctgtt ggcacaacca acttttcctg acagtggtgg acaccaccag gagcaccaac     1020
ttcaccctga gcaccagcat tgagtccagc atcccaagca cctatgaccc aagcaagttc     1080
aaggaataca ccaggcatgt ggaggaatat gacctccaat tcatcttcca actttgtact     1140
gtgaccctga ccacagatgt gatgagttac atccacacaa tgaactccag catcctggac     1200
aactggaact tgctgtggc tcctcctcca tctgcctccc tggtgacac ctacagatac       1260 ctccaatctg ctgccatcac ttgtcagaag gatgcccctg ccctgagaa aaggaccca       1320 tatgatggac tgaagttctg gaatgtggac ctgagggaga gttctcctt ggaactggac      1380 cagtttccac tgggcaggaa gttcctgctc caacttggag ccagaccaaa gccaaccatt     1440
ggaccaagga gagggctgc ccctgcccca accagcacac caagcccaaa gagggtgaag      1500
aggaggaagt ccagcaggaa gtaaa                                          1525
```

<210> SEQ ID NO 83
<211> LENGTH: 1537
<212> TYPE: DNA
<213> ORGANISM: Artificial sequence
<220> FEATURE:
<223> OTHER INFORMATION: 3905 Synthetic HPV39 L1 gene

<400> SEQUENCE: 83

```
ctgggtacca tggctatgtg gaggtcctct gacagtatgg tctacctgcc tcctccatct       60
gtggctaagg tggtgaacac agatgactat gtgaccagga caggcatcta ctactatgct      120
ggctccagca gactgctgac agtgggacac ccatacttca aggtggggat gaatggaggc      180
aggaagcagg acatcccaaa ggtgtctgcc taccaataca gggtgttcag ggtgaccctg      240
cctgacccaa caagttcag catccctgat gcctccctct acaaccctga gacccagaga       300
ctggtgtggg cttgtgtggg agtggaggtg ggcagggac aaccactggg agtgggcatc       360
tctggacacc cactctacaa cagacaggat gacacagaga acagcccatt ctccagcacc      420
accaacaagg acagcaggga caatgtgtct gtggactaca agcagaccca actttgtatc      480
attggctgtg tgcctgccat tggagaacac tggggcaagg caaggcttg taagccaaac       540 aatgtgagca caggagactg tcctccattg gaactggtga acacaccaat tgaggatgga      600
gatatgattg acacaggcta tggagctatg gactttggag ccctccaaga gaccaagtct     660
```

```
gaggtgccac tggacatctg tcagagcatc tgtaaatacc ctgactacct ccaaatgagt    720
gctgatgtct atggagacag tatgttcttc tgtctgagga gggaacaact ttttgccaga    780
cacttctgga cagggaggg atggtggga gatgccatcc ctgcccaact ctacatcaag      840
ggcacagaca tcagggctaa ccctggctcc tctgtctact gtccaagccc atctggcagt    900
atggtgacct ctgacagcca acttttcaac aagccatact ggctgcacaa ggctcaagga    960
cacaacaatg gcatctgttg gcacaaccaa cttttcctga cagtggtgga caccaccagg   1020
agcaccaact tcaccctgag caccagcatt gagtccagca tcccaagcac ctatgaccca   1080
agcaagttca aggaatacac caggcatgtg gaggaatatg acctccaatt catcttccaa   1140
ctttgtactg tgaccctgac cacagatgtg atgagttaca tccacacaat gaactccagc   1200
atcctggaca actggaactt tgctgtggct cctcctccat ctgcctccct ggtggacacc   1260
tacagatacc tccaatctgc tgccatcact tgtcagaagg atgcccctgc ccctgagaag   1320
aaggacccat atgatggact gaagttctgg aatgtggacc tgagggagaa gttctccttg   1380
gaactggacc agtttccact gggcaggaag ttcctgctcc aagccagggt gaggaggaga   1440
ccaaccattg gaccaaggaa gagacctgct gccagcacct cctcctcctc tgccaccaaa   1500
cacaagagga gagggtgag caagtaaact cgagctc                             1537
```

<210> SEQ ID NO 84
<211> LENGTH: 1546
<212> TYPE: DNA
<213> ORGANISM: Artificial sequence
<220> FEATURE:
<223> OTHER INFORMATION: 3906 Synthetic HPV59 L1 gene

<400> SEQUENCE: 84

```
ctgggtacca tggctctgtg gaggtcctct gacaacaagg tctacctgcc tcctccatct     60
gtggctaagg tggtgagcac agatgaatat gtgaccagga ccagcatctt ctaccatgct   120
ggctccagca gactgctgac agtgggacac ccatacttca aggtgccaaa gggaggcaat   180
ggcagacagg atgtgccaaa ggtgtctgcc taccaataca gggtgttcag ggtgaaactg   240
cctgacccaa acaagtttgg actgcctgac aacacagtct atgacccaaa cagccagaga   300
ctggtgtggg cttgtgtggg agtggagatt ggcaggggac aaccactggg agtgggactg   360
tctggacacc cactctacaa caaactggat gacacagaga ctctcatgt ggcatctgct   420 gtggacacca aggacaccag ggacaatgtg tctgtggact acaagcagac ccaactttgt   480
atcattggct gtgtgcctgc cattggagaa cactggacca agggcacagc ctgtaagcca   540
accacagtgg tccagggaga ctgtcctcca ttggaactga taaacacacc aattgaggat   600
ggagatatgg tggacacagg ctatggagct atggacttca aactgctcca agacaacaag   660
tctgaggtgc cactggacat ctgtcagagc atctgtaaat accctgacta cctccaaatg   720
agtgctgatg cctatggaga cagtatgttc ttctgtctga ggagggaaca ggtgttttgcc   780 agacacttct ggaacaggtc tggcacaatg ggagaccaac ttcctgagtc cctctacatc   840
aagggcacag acatcagggc taaccctggc tcctacctct cagcccaag cccatctggc    900 tctgtggtga cctctgacag ccaacttttc aacaagccat actggctgca caaggctcaa    960
ggactgaaca atggcatctg ttggcacaac caacttttcc tgacagtggt ggacaccacc   1020
aggagcacca acctgtctgt gtgtgccagc accacctcca gcatcccaaa tgtctacaca   1080
ccaacctcct tcaaggaata tgccaggcat gtggaggagt tgacctcca attcatcttc   1140 caactttgta agattaccct gaccacagag gtgatgagtt acatccacaa tatgaacacc   1200
```

```
accatcttgg aggactggaa ctttggagtg acacctcctc caacagcctc cctggtggac    1260
acctacaggt ttgtccagtc tgctgctgtg acttgtcaga aggacacagc ccctcctgtg    1320
aagcaggacc catatgacaa actgaagttc tggcctgtgg acctgaaaga gaggttctct    1380
gctgacctgg accagtttcc actgggcagg aagttcctgc tccaacttgg agccagacca    1440
aagccaacca ttggaccaag gaagagggct gcccctgccc caaccagcac accaagccca    1500
aagagggtga agaggaggaa gtccagcagg aagtaaactc gagctc                   1546

<210> SEQ ID NO 85
<211> LENGTH: 38
<212> TYPE: DNA
<213> ORGANISM: Artificial sequence
<220> FEATURE:
<223> OTHER INFORMATION: 3907 HPV39L1 F1

<400> SEQUENCE: 85
cttggtacca tggctatgtg gaggtcctct gacagtat                              38

<210> SEQ ID NO 86
<211> LENGTH: 38
<212> TYPE: DNA
<213> ORGANISM: Artificial sequence
<220> FEATURE:
<223> OTHER INFORMATION: 3908 HPV39L1 R1

<400> SEQUENCE: 86
tccaagttgg agcaggaact tcctgcccag tggaaact                              38

<210> SEQ ID NO 87
<211> LENGTH: 1428
<212> TYPE: DNA
<213> ORGANISM: Artificial sequence
<220> FEATURE:
<223> OTHER INFORMATION: 3909 HPV39L1 amplified sequence 1

<400> SEQUENCE: 87
cttggtacca tggctatgtg gaggtcctct gacagtatgg tctacctgcc tcctccatct      60
gtggctaagg tggtgaacac agatgactat gtgaccagga caggcatcta ctactatgct     120
ggctccagca gactgctgac agtgggacac ccatacttca aggtggggat gaatggaggc     180
aggaagcagg acatcccaaa ggtgtctgcc taccaataca gggtgttcag ggtgaccctg     240
cctgacccaa acaagttcag catccctgat gcctccctct acaaccctga gacccagaga     300
ctggtgtggg cttgtgtggg agtggaggtg gcaggggac aaccactggg agtgggcatc      360
tctggacacc cactctacaa cagacaggat gacacagaga cagcccatt ctccagcacc      420 accaacaagg acagcaggga caatgtgtct gtggactaca gcagaccca actttgtatc      480 attggctgtg tgcctgccat tggagaacac tggggcaagg gcaaggcttg taagccaaac    540
aatgtgagca caggagactg tcctccattg gaactggtga acacaccaat tgaggatgga    600
gatatgattg acacaggcta tggagctatg gactttggag ccctccaaga gaccaagtct    660
gaggtgccac tggacatctg tcagagcatc tgtaaatacc ctgactacct ccaaatgagt    720
gctgatgtct atgagacag tatgttcttc tgtctgagga gggaacaact tttttgccaga    780 cacttctgga acaggggagg gatggtggga gatgccatcc ctgcccaact ctacatcaag    840
ggcacagaca tcagggctaa ccctggctcc tctgtctact gtccaagccc atctggcagt    900
atggtgacct ctgacagcca acttttcaac aagccatact ggctgcacaa ggctcaagga    960
```

```
cacaacaatg gcatctgttg gcacaaccaa cttttcctga cagtggtgga caccaccagg    1020
agcaccaact tcaccctgag caccagcatt gagtccagca tcccaagcac ctatgaccca    1080
agcaagttca aggaatacac caggcatgtg gaggaatatg acctccaatt catcttccaa    1140
ctttgtactg tgaccctgac cacagatgtg atgagttaca tccacacaat gaactccagc    1200
atcctggaca actggaactt tgctgtggct cctcctccat ctgcctccct ggtggacacc    1260
tacagatacc tccaatctgc tgccatcact tgtcagaagg atgcccctgc ccctgagaag    1320
aaggacccat atgatggact gaagttctgg aatgtggacc tgagggagaa gttctccttg    1380
gaactggacc agtttccact gggcaggaag ttcctgctcc aacttgga                1428

<210> SEQ ID NO 88
<211> LENGTH: 37
<212> TYPE: DNA
<213> ORGANISM: Artificial sequence
<220> FEATURE:
<223> OTHER INFORMATION: 3910 HPV39L1 F2

<400> SEQUENCE: 88
aggaagttcc tgctccaact tggagccaga ccaaagc                              37

<210> SEQ ID NO 89
<211> LENGTH: 40
<212> TYPE: DNA
<213> ORGANISM: Artificial sequence
<220> FEATURE:
<223> OTHER INFORMATION: 3911 HPV39L1 R2

<400> SEQUENCE: 89
ctgtctagat ttacttcctg ctggacttcc tcctcttcac                           40

<210> SEQ ID NO 90
<211> LENGTH: 139
<212> TYPE: DNA
<213> ORGANISM: Artificial sequence
<220> FEATURE:
<223> OTHER INFORMATION: 3912 HPV39L1 amplified sequence 2

<400> SEQUENCE: 90
aggaagttcc tgctccaact tggagccaga ccaaagccaa ccattggacc aaggaagagg     60 gctgccctg ccccaaccag cacaccaagc ccaaagaggg tgaagaggag gaagtccagc    120
aggaagtaaa tctagacag                                                 139

<210> SEQ ID NO 91
<211> LENGTH: 26
<212> TYPE: PRT
<213> ORGANISM: Homo sapiens
<220> FEATURE:
<221> NAME/KEY: misc_feature
<223> OTHER INFORMATION: 3913 Amino acid sequence of HPV type 33 L1
      protein aa 474-499

<400> SEQUENCE: 91

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 92
<211> LENGTH: 478
<212> TYPE: PRT
<213> ORGANISM: Homo sapiens
```

```
<220> FEATURE:
<221> NAME/KEY: misc_feature
<223> OTHER INFORMATION: 4501 Amino acid sequence of HPV type 45 L1
      protein aa 1-478

<400> SEQUENCE: 92
```

| | | | | | | | | | | | | | | |
|---|---|---|---|---|---|---|---|---|---|---|---|---|---|---|
| Met | Ala | Leu | Trp | Arg | Pro | Ser | Asp | Ser | Thr | Val | Tyr | Leu | Pro | Pro |
| 1 | | | | 5 | | | | | 10 | | | | | 15 |
| Ser | Val | Ala | Arg | Val | Val | Asn | Thr | Asp | Asp | Tyr | Val | Ser | Arg | Thr | Ser |
| | | | 20 | | | | | 25 | | | | | 30 | | |
| Ile | Phe | Tyr | His | Ala | Gly | Ser | Ser | Arg | Leu | Leu | Thr | Val | Gly | Asn | Pro |
| | | | 35 | | | | 40 | | | | | 45 | | | |
| Tyr | Phe | Arg | Val | Val | Pro | Ser | Gly | Ala | Gly | Asn | Lys | Gln | Ala | Val | Pro |
| | 50 | | | | | 55 | | | | | 60 | | | | |
| Lys | Val | Ser | Ala | Tyr | Gln | Tyr | Arg | Val | Phe | Arg | Val | Ala | Leu | Pro | Asp |
| 65 | | | | | 70 | | | | | 75 | | | | | 80 |
| Pro | Asn | Lys | Phe | Gly | Leu | Pro | Asp | Ser | Thr | Ile | Tyr | Asn | Pro | Glu | Thr |
| | | | | 85 | | | | | 90 | | | | | 95 | |
| Gln | Arg | Leu | Val | Trp | Ala | Cys | Val | Gly | Met | Glu | Ile | Gly | Arg | Gly | Gln |
| | | | 100 | | | | | 105 | | | | | 110 | | |
| Pro | Leu | Gly | Ile | Gly | Leu | Ser | Gly | His | Pro | Phe | Tyr | Asn | Lys | Leu | Asp |
| | | | 115 | | | | | 120 | | | | | 125 | | |
| Asp | Thr | Glu | Ser | Ala | His | Ala | Ala | Thr | Ala | Val | Ile | Thr | Gln | Asp | Val |
| | 130 | | | | | 135 | | | | | 140 | | | | |
| Arg | Asp | Asn | Val | Ser | Val | Asp | Tyr | Lys | Gln | Thr | Gln | Leu | Cys | Ile | Leu |
| 145 | | | | | 150 | | | | | 155 | | | | | 160 |
| Gly | Cys | Val | Pro | Ala | Ile | Gly | Glu | His | Trp | Ala | Lys | Gly | Thr | Leu | Cys |
| | | | | 165 | | | | | 170 | | | | | 175 | |
| Lys | Pro | Ala | Gln | Leu | Gln | Pro | Gly | Asp | Cys | Pro | Pro | Leu | Glu | Leu | Lys |
| | | | 180 | | | | | 185 | | | | | 190 | | |
| Asn | Thr | Ile | Ile | Glu | Asp | Gly | Asp | Met | Val | Asp | Thr | Gly | Tyr | Gly | Ala |
| | | | 195 | | | | | 200 | | | | | 205 | | |
| Met | Asp | Phe | Ser | Thr | Leu | Gln | Asp | Thr | Lys | Cys | Glu | Val | Pro | Leu | Asp |
| | 210 | | | | | 215 | | | | | 220 | | | | |
| Ile | Cys | Gln | Ser | Ile | Cys | Lys | Tyr | Pro | Asp | Tyr | Leu | Gln | Met | Ser | Ala |
| 225 | | | | | 230 | | | | | 235 | | | | | 240 |
| Asp | Pro | Tyr | Gly | Asp | Ser | Met | Phe | Phe | Cys | Leu | Arg | Arg | Glu | Gln | Leu |
| | | | | 245 | | | | | 250 | | | | | 255 | |
| Phe | Ala | Arg | His | Phe | Trp | Asn | Arg | Ala | Gly | Val | Met | Gly | Asp | Thr | Val |
| | | | 260 | | | | | 265 | | | | | 270 | | |
| Pro | Thr | Asp | Leu | Tyr | Ile | Lys | Gly | Thr | Ser | Ala | Asn | Met | Arg | Glu | Thr |
| | | | | 275 | | | | | 280 | | | | | 285 | |
| Pro | Gly | Ser | Cys | Val | Tyr | Ser | Pro | Ser | Pro | Ser | Gly | Ser | Ile | Thr | Thr |
| | 290 | | | | | 295 | | | | | 300 | | | | |
| Ser | Asp | Ser | Gln | Leu | Phe | Asn | Lys | Pro | Tyr | Trp | Leu | His | Lys | Ala | Gln |
| 305 | | | | | 310 | | | | | 315 | | | | | 320 |
| Gly | His | Asn | Asn | Gly | Ile | Cys | Trp | His | Asn | Gln | Leu | Phe | Val | Thr | Val |
| | | | | 325 | | | | | 330 | | | | | 335 | |
| Val | Asp | Thr | Thr | Arg | Ser | Thr | Asn | Leu | Thr | Leu | Cys | Ala | Ser | Thr | Gln |
| | | | 340 | | | | | 345 | | | | | 350 | | |
| Asn | Pro | Val | Pro | Asn | Thr | Tyr | Asp | Pro | Thr | Lys | Phe | Lys | His | Tyr | Ser |
| | | | | 355 | | | | | 360 | | | | | 365 | |
| Arg | His | Val | Glu | Glu | Tyr | Asp | Leu | Gln | Phe | Ile | Phe | Gln | Leu | Cys | Thr |
| | 370 | | | | | 375 | | | | | 380 | | | | |

```
Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Thr Thr
            405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
            435                 440                 445

Lys Phe Trp Thr Val Asp Leu Lys Glu Lys Phe Ser Ser Asp Leu Asp
            450                 455                 460

Gln Tyr Pro Leu Gly Arg Lys Phe Leu Val Gln Ala Gly Leu
465                 470                 475

<210> SEQ ID NO 93
<211> LENGTH: 26
<212> TYPE: PRT
<213> ORGANISM: Homo sapiens
<220> FEATURE:
<221> NAME/KEY: misc_feature
<223> OTHER INFORMATION: 4502 Amino acid sequence of HPV type 33 L1
      protein aa 474-499

<400> SEQUENCE: 93

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 94
<211> LENGTH: 504
<212> TYPE: PRT
<213> ORGANISM: Artificial sequence
<220> FEATURE:
<223> OTHER INFORMATION: 4503 Amino acid sequence of chimeric HPV type
      45 L1 protein

<400> SEQUENCE: 94

Met Ala Leu Trp Arg Pro Ser Asp Ser Thr Val Tyr Leu Pro Pro Pro
1               5                   10                  15

Ser Val Ala Arg Val Val Asn Thr Asp Asp Tyr Val Ser Arg Thr Ser
            20                  25                  30

Ile Phe Tyr His Ala Gly Ser Ser Arg Leu Leu Thr Val Gly Asn Pro
            35                  40                  45

Tyr Phe Arg Val Val Pro Ser Gly Ala Gly Asn Lys Gln Ala Val Pro
50                  55                  60

Lys Val Ser Ala Tyr Gln Tyr Arg Val Phe Arg Val Ala Leu Pro Asp
65                  70                  75                  80

Pro Asn Lys Phe Gly Leu Pro Asp Ser Thr Ile Tyr Asn Pro Glu Thr
            85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
            115                 120                 125

Asp Thr Glu Ser Ala His Ala Ala Thr Ala Val Ile Thr Gln Asp Val
            130                 135                 140

Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
            165                 170                 175
```

Lys Pro Ala Gln Leu Gln Pro Gly Asp Cys Pro Leu Glu Leu Lys
            180                 185                 190

Asn Thr Ile Ile Glu Asp Gly Asp Met Val Asp Thr Gly Tyr Gly Ala
            195                 200                 205

Met Asp Phe Ser Thr Leu Gln Asp Thr Lys Cys Glu Val Pro Leu Asp
210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
            245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
            275                 280                 285

Pro Gly Ser Cys Val Tyr Ser Pro Ser Pro Ser Gly Ser Ile Thr Thr
            290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
            325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
            355                 360                 365

Arg His Val Glu Glu Tyr Asp Leu Gln Phe Ile Phe Gln Leu Cys Thr
            370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Thr Thr
            405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
            435                 440                 445

Lys Phe Trp Thr Val Asp Leu Lys Glu Lys Phe Ser Ser Asp Leu Asp
450                 455                 460

Gln Tyr Pro Leu Gly Arg Lys Phe Leu Val Gln Ala Gly Leu Lys Ala
465                 470                 475                 480

Lys Pro Lys Leu Lys Arg Ala Ala Pro Thr Ser Thr Arg Thr Ser Ser
            485                 490                 495

Ala Lys Arg Lys Lys Val Lys Lys
            500

<210> SEQ ID NO 95
<211> LENGTH: 1516
<212> TYPE: DNA
<213> ORGANISM: Artificial sequence
<220> FEATURE:
<223> OTHER INFORMATION: 4504 Nucleotide sequence of chimeric HPV type
      45 L1 protein

<400> SEQUENCE: 95
atggctctgt ggagaccatc tgacagcaca gtctacctgc ctcctccatc tgtggcaagg        60
gtggtgaaca cagatgacta tgtgagcagg accagcatct tctaccatgc tggctccagc      120

| | |
|---|---|
| agactgctga cagtgggcaa cccatacttc agggtggtgc caagtggagc aggcaacaag | 180 |
| caggctgtgc caaaggtgtc tgcctaccaa tacagggtgt tcagggtggc tctgcctgac | 240 |
| ccaaacaagt ttggactgcc tgacagcacc atctacaacc ctgagaccca gagactggtg | 300 |
| tgggcttgtg tggggatgga gattggcagg ggacaaccac tgggcattgg actgtctgga | 360 |
| cacccattct acaacaaact ggatgacaca gagtctgccc atgctgccac agcagtgatt | 420 |
| acccaggatg tgagggacaa tgtgtctgtg gactacaagc agacccaact ttgtatcctg | 480 |
| ggctgtgtgc ctgccattgg agaacactgg gctaagggca cctgtgtaa gcctgcccaa | 540 |
| ctccaacctg gagactgtcc tccattggaa ctgaaaaaca ccatcattga ggatggagat | 600 |
| atggtggaca caggctatgg agctatggac ttcagcaccc tccaagacac caagtgtgag | 660 |
| gtgccactgg acatctgtca gagcatctgt aaatacctg actacctcca aatgagtgct | 720 |
| gacccatatg agacagtat gttcttctgt ctgaggaggg aacaactttt tgccagacac | 780 |
| ttctggaaca gggctggagt gatgggagac acagtgccaa cagacctcta catcaagggc | 840 |
| acctctgcca atatgaggga cacctggc tcctgtgtct acagcccaag cccatctggc | 900 |
| agcatcacca cctctgacag ccaacttttc aacaagccat actggctgca caaggctcaa | 960 |
| ggacacaaca atggcatctg ttggcacaac caacttttg tgacagtggt ggacaccacc | 1020 |
| aggagcacca acctgaccct gtgtgccagc acccagaacc ctgtgccaaa cacctatgac | 1080 |
| ccaaccaagt tcaagcacta cagcaggcat gtggaggaat atgacctcca attcatcttc | 1140 |
| caactttgta ccatcaccct gacagcagag gtgatgagtt acatccacag tatgaactcc | 1200 |
| agcatcttgg agaactggaa ctttggagtg cctcctcctc caaccacctc cctggtggac | 1260 |
| acctacaggt tgtccagtc tgtggctgtg acttgtcaga aggacaccac acctcctgag | 1320 |
| aagcaggacc catatgacaa actgaagttc tggacagtgg acctgaaaga gaagttctcc | 1380 |
| tctgacctgg accaatacccc actgggcagg aagttcctgg tccaggctgg actgaaagcc | 1440 |
| aagccaaaac tgaaagggc tgccccaacc agcaccagga cctcctctgc caagaggaag | 1500 |
| aaggtgaaga agtaaa | 1516 |

<210> SEQ ID NO 96
<211> LENGTH: 1552
<212> TYPE: DNA
<213> ORGANISM: Artificial sequence
<220> FEATURE:
<223> OTHER INFORMATION: 4505 Synthetic HPV45 L1 gene

<400> SEQUENCE: 96

| | |
|---|---|
| ctgggtacca tggctctgtg gagaccatct gacagcacag tctacctgcc tcctccatct | 60 |
| gtggcaaggg tggtgaacac agatgactat gtgagcagga ccagcatctt ctaccatgct | 120 |
| ggctccagca gactgctgac agtgggcaac ccatacttca gggtggtgcc aagtggagca | 180 |
| ggcaacaagc aggctgtgcc aaaggtgtct gcctaccaat acagggtgtt cagggtggct | 240 |
| ctgcctgacc caaacaagtt tggactgcct gacagcacca tctacaaccc tgagacccag | 300 |
| agactggtgt gggcttgtgt ggggatggag attggcaggg gacaaccact gggcattgga | 360 |
| ctgtctggac acccattcta caacaaactg gatgacacag agtctgccca tgctgccaca | 420 |
| gcagtgatta cccaggatgt gagggacaat gtgtctgtgg actacaagca gacccaactt | 480 |
| tgtatcctgg gctgtgtgcc tgccattgga gaacactggg ctaagggcac ctgtgtaag | 540 |
| cctgcccaac tccaacctgg agactgtcct ccattggaac tgaaaaacac catcattgag | 600 |
| gatggagata tggtggacac aggctatgga gctatggact tcagcaccct ccaagacacc | 660 |

```
aagtgtgagg tgccactgga catctgtcag agcatctgta aatacccctga ctacctccaa    720 atgagtgctg acccatatgg agacagtatg ttcttctgtc tgaggaggga caacttttt     780 gccagacact tctggaacag ggctggagtg atgggagaca cagtgccaac agacctctac    840
atcaagggca cctctgccaa tatgaggag acacctggct cctgtgtcta cagcccaagc     900
ccatctggca gcatcaccac ctctgacagc caacttttca acaagccata ctggctgcac    960
aaggctcaag acacaacaa tggcatctgt tggcacaacc aacttttgt gacagtggtg      1020 gacaccacca ggagcaccaa cctgaccctg tgtgccagca cccagaaccc tgtgccaaac    1080
acctatgacc caaccaagtt caagcactac agcaggcatg tggaggaata tgacctccaa    1140
ttcatcttcc aactttgtac catcaccctg acagcagagg tgatgagtta catccacagt    1200
atgaactcca gcatcttgga gaactggaac tttggagtgc ctcctcctcc aaccacctcc    1260
ctggtggaca cctacaggtt tgtccagtct gtggctgtga cttgtcagaa ggacaccaca    1320
cctcctgaga agcaggaccc atatgacaaa ctgaagttct ggacagtgga cctgaaagag    1380
aagttctcct ctgacctgga ccaatacca ctgggcagga agttcctggt ccaggctgga    1440
ctgaggagga gaccaaccat tggaccaagg aagagacctg ctgccagcac cagcacagcc    1500
agcagacctg ccaagagggt gaggattagg agcaagaagt aaaactcgagc tc          1552

<210> SEQ ID NO 97
<211> LENGTH: 1519
<212> TYPE: DNA
<213> ORGANISM: Artificial sequence
<220> FEATURE:
<223> OTHER INFORMATION: 4506 Synthetic HPV33 L1 gene

<400> SEQUENCE: 97
ctgggtacca tgagtgtgtg gagaccatct gaggctacag tctacctgcc tcctgtgcct    60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360 atctctggac acccactgct gaacaagttt gatgacacag acaggcaa caaataccct    420 ggacaacctg agcagacaa cagggagtgt ctgagtatgg actacaagca gacccaactt    480
tgtctgctgg gctgtaagcc tccaacagga gaacactggg gcaagggagt ggcttgtacc    540
aatgctgccc ctgccaatga ctgtcctcca ttggaactga taaacaccat cattgaggat    600
ggagatatgt ggacacagg ctttggctgt atggacttca gaccctcca gccaacaag     660 tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcacctg ggagaggctg tgcctgatga cctctacatc     840
aagggctctg gcaccacagc cagcatccag tcctctgcct tctttccaac accatctggc    900
agtatggtga cctctgagag ccaacttttc aacaagccat actggctcca aagggctcaa    960
ggacacaaca atggcatctg ttggggcaac caggtgtttg tgacagtggt ggacaccacc    1020
aggagcacca atatgaccct gtgtacccag gtgacctctg acagcaccta caagaatgag    1080
aacttcaagg aatacatcag gcatgtggag gaatatgacc tccaatttgt gttccaactt    1140
```

```
tgtaaggtga ccctgacagc agaggtgatg acctacatcc atgctatgaa ccctgacatc    1200
ttggaggact ggcagtttgg actgacacct cctccatctg cctccctcca agacacctac    1260
aggtttgtga ccagccaggc tatcacttgt cagaagacag tgcctccaaa ggagaaggag    1320
gacccactgg gcaaatacac cttctgggag gtggacctga agagaagtt ctctgctgac     1380 ctggaccagt ttccactggg caggaagttc ctgctccaag caggactgaa agccaagcca    1440
aaactgaaaa gggctgcccc aaccagcacc aggacctcct ctgccaagag gaagaaggtg    1500
aagaagtaaa ctcgagctc                                                 1519
```

<210> SEQ ID NO 98
<211> LENGTH: 33
<212> TYPE: DNA
<213> ORGANISM: Artificial sequence
<220> FEATURE:
<223> OTHER INFORMATION: 4507 HPV45L1 F1

<400> SEQUENCE: 98

```
cttggtacca tggctctgtg gagaccatct gac                                 33
```

<210> SEQ ID NO 99
<211> LENGTH: 32
<212> TYPE: DNA
<213> ORGANISM: Artificial sequence
<220> FEATURE:
<223> OTHER INFORMATION: 4508 HPV45L1 R1

<400> SEQUENCE: 99

```
gcttggcttt cagtccagcc tggaccagga ac                                  32
```

<210> SEQ ID NO 100
<211> LENGTH: 1453
<212> TYPE: DNA
<213> ORGANISM: Artificial sequence
<220> FEATURE:
<223> OTHER INFORMATION: 4509 HPV45L1 amplified sequence 1

<400> SEQUENCE: 100

```
cttggtacca tggctctgtg gagaccatct gacagcacag tctacctgcc tcctccatct    60
gtggcaaggg tggtgaacac agatgactat gtgagcagga ccagcatctt ctaccatgct    120
ggctccagca gactgctgac agtgggcaac ccatacttca ggtggtgcc aagtggagca     180 ggcaacaagc aggctgtgcc aaaggtgtct gcctaccaat acagggtgtt cagggtggct    240
ctgcctgacc caaacaagtt tggactgcct gacagcacca tctacaaccc tgagacccag    300
agactggtgt gggcttgtgt ggggatggag attggcaggg acaaccact gggcattgga     360 ctgtctggac acccattcta caacaaactg gatgacacag agtctgccca tgctgccaca    420
gcagtgatta cccaggatgt gagggacaat gtgtctgtgg actacaagca gacccaactt    480
tgtatcctgg gctgtgtgcc tgccattgga gaacactggg ctaagggcac cctgtgtaag    540
cctgcccaac tccaacctgg agactgtcct ccattggaac tgaaaacac catcattgag      600 gatggagata tggtggacac aggctatgga gctatggact tcagcaccct ccaagacacc    660
aagtgtgagg tgccactgga catctgtcag agcatctgta ataccctga ctacctccaa     720 atgagtgctg acccatatgg agacagtatg ttcttctgtc tgaggaggga caacttttt    780 gccagacact tctggaacag ggctggagtg atgggagaca cagtgccaac agacctctac    840
atcaagggca cctctgccaa tatgagggag acacctggct cctgtgtcta cagcccaagc    900
ccatctggca gcatcaccac ctctgacagc caacttttca caagccata ctggctgcac    960
```

```
aaggctcaag gacacaacaa tggcatctgt tggcacaacc aacttttgt gacagtggtg    1020 gacaccacca ggagcaccaa cctgaccctg tgtgccagca cccagaaccc tgtgccaaac    1080
acctatgacc caaccaagtt caagcactac agcaggcatg tggaggaata tgacctccaa    1140
ttcatcttcc aactttgtac catcaccctg acagcagagg tgatgagtta catccacagt    1200
atgaactcca gcatcttgga gaactggaac tttggagtgc tcctcctcc aaccacctcc    1260 ctggtggaca cctacaggtt tgtccagtct gtggctgtga cttgtcagaa ggacaccaca    1320
cctcctgaga agcaggaccc atatgacaaa ctgaagttct ggacagtgga cctgaaagag    1380
aagttctcct ctgacctgga ccaataccca ctgggcagga gttcctggt ccaggctgga    1440 ctgaaagcca agc                                                       1453
```

<210> SEQ ID NO 101
<211> LENGTH: 35
<212> TYPE: DNA
<213> ORGANISM: Artificial sequence
<220> FEATURE:
<223> OTHER INFORMATION: 4510 HPV45L1 F2

<400> SEQUENCE: 101

```
ggctggactg aaagccaagc caaaactgaa aaggg                                35
```

<210> SEQ ID NO 102
<211> LENGTH: 37
<212> TYPE: DNA
<213> ORGANISM: Artificial sequence
<220> FEATURE:
<223> OTHER INFORMATION: 4511 HPV45L1 R2

<400> SEQUENCE: 102

```
ctgtctagat ttacttcttc accttcttcc tcttggc                              37
```

<210> SEQ ID NO 103
<211> LENGTH: 101
<212> TYPE: DNA
<213> ORGANISM: Artificial sequence
<220> FEATURE:
<223> OTHER INFORMATION: 4512 HPV45L1 amplified sequence 2

<400> SEQUENCE: 103

```
ggctggactg aaagccaagc caaaactgaa aagggctgcc ccaaccagca ccaggacctc    60
ctctgccaag aggaagaagg tgaagaagta aatctagaca g                        101
```

<210> SEQ ID NO 104
<211> LENGTH: 38
<212> TYPE: PRT
<213> ORGANISM: Homo sapiens
<220> FEATURE:
<221> NAME/KEY: misc_feature
<223> OTHER INFORMATION: 4513 Amino acid sequence of HPV type 59 L1
      protein aa 471-508

<400> SEQUENCE: 104

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 105
<211> LENGTH: 474
<212> TYPE: PRT
<213> ORGANISM: Homo sapiens
<220> FEATURE:
<221> NAME/KEY: misc_feature
<223> OTHER INFORMATION: 5101 Amino acid sequence of HPV type 51 L1 protein aa 1-474

<400> SEQUENCE: 105

| | | | | | | | | | | | | | | |
|---|---|---|---|---|---|---|---|---|---|---|---|---|---|---|
| Met | Ala | Leu | Trp | Arg | Thr | Asn | Asp | Ser | Lys | Val | Tyr | Leu | Pro | Pro | Ala |
| 1 | | | | 5 | | | | | 10 | | | | | 15 | |
| Pro | Val | Ser | Arg | Ile | Val | Asn | Thr | Glu | Glu | Tyr | Ile | Thr | Arg | Thr | Gly |
| | | | 20 | | | | | 25 | | | | | 30 | | |
| Ile | Tyr | Tyr | Tyr | Ala | Gly | Ser | Ser | Arg | Leu | Ile | Thr | Leu | Gly | His | Pro |
| | | 35 | | | | | 40 | | | | | 45 | | | |
| Tyr | Phe | Pro | Ile | Pro | Lys | Thr | Ser | Thr | Arg | Ala | Ala | Ile | Pro | Lys | Val |
| 50 | | | | | 55 | | | | | 60 | | | | | |
| Ser | Ala | Phe | Gln | Tyr | Arg | Val | Phe | Arg | Val | Gln | Leu | Pro | Asp | Pro | Asn |
| 65 | | | | | 70 | | | | | 75 | | | | | 80 |
| Lys | Phe | Gly | Leu | Pro | Asp | Pro | Asn | Leu | Tyr | Asn | Pro | Asp | Thr | Asp | Arg |
| | | | | 85 | | | | | 90 | | | | | 95 | |
| Leu | Val | Trp | Gly | Cys | Val | Gly | Val | Glu | Val | Gly | Arg | Gly | Gln | Pro | Leu |
| | | | 100 | | | | | 105 | | | | | 110 | | |
| Gly | Val | Gly | Leu | Ser | Gly | His | Pro | Leu | Phe | Asn | Lys | Tyr | Asp | Asp | Thr |
| | | | 115 | | | | | 120 | | | | | 125 | | |
| Glu | Asn | Ser | Arg | Ile | Ala | Asn | Gly | Asn | Ala | Gln | Gln | Asp | Val | Arg | Asp |
| | 130 | | | | | 135 | | | | | 140 | | | | |
| Asn | Thr | Ser | Val | Asp | Asn | Lys | Gln | Thr | Gln | Leu | Cys | Ile | Ile | Gly | Cys |
| 145 | | | | | 150 | | | | | 155 | | | | | 160 |
| Ala | Pro | Pro | Ile | Gly | Glu | His | Trp | Gly | Ile | Gly | Thr | Thr | Cys | Lys | Asn |
| | | | | 165 | | | | | 170 | | | | | 175 | |
| Thr | Pro | Val | Pro | Pro | Gly | Asp | Cys | Pro | Pro | Leu | Glu | Leu | Val | Ser | Ser |
| | | | 180 | | | | | 185 | | | | | 190 | | |
| Val | Ile | Gln | Asp | Gly | Asp | Met | Ile | Asp | Thr | Gly | Phe | Gly | Ala | Met | Asp |
| | | 195 | | | | | 200 | | | | | 205 | | | |
| Phe | Ala | Ala | Leu | Gln | Ala | Thr | Lys | Ser | Asp | Val | Pro | Leu | Asp | Ile | Ser |
| | 210 | | | | | 215 | | | | | 220 | | | | |
| Gln | Ser | Val | Cys | Lys | Tyr | Pro | Asp | Tyr | Leu | Lys | Met | Ser | Ala | Asp | Thr |
| 225 | | | | | 230 | | | | | 235 | | | | | 240 |
| Tyr | Gly | Asn | Ser | Met | Phe | Phe | His | Leu | Arg | Arg | Glu | Gln | Ile | Phe | Ala |
| | | | | 245 | | | | | 250 | | | | | 255 | |
| Arg | His | Tyr | Tyr | Asn | Lys | Leu | Val | Gly | Val | Gly | Glu | Asp | Ile | Pro | Asn |
| | | | 260 | | | | | 265 | | | | | 270 | | |
| Asp | Tyr | Tyr | Ile | Lys | Gly | Ser | Gly | Asn | Gly | Arg | Asp | Pro | Ile | Glu | Ser |
| | | 275 | | | | | 280 | | | | | 285 | | | |
| Tyr | Ile | Tyr | Ser | Ala | Thr | Pro | Ser | Gly | Ser | Met | Ile | Thr | Ser | Asp | Ser |
| | 290 | | | | | 295 | | | | | 300 | | | | |
| Gln | Ile | Phe | Asn | Lys | Pro | Tyr | Trp | Leu | His | Arg | Ala | Gln | Gly | His | Asn |
| 305 | | | | | 310 | | | | | 315 | | | | | 320 |
| Asn | Gly | Ile | Cys | Trp | Asn | Asn | Gln | Leu | Phe | Ile | Thr | Cys | Val | Asp | Thr |
| | | | | 325 | | | | | 330 | | | | | 335 | |
| Thr | Arg | Ser | Thr | Asn | Leu | Thr | Ile | Ser | Thr | Ala | Thr | Ala | Ala | Val | Ser |
| | | | 340 | | | | | 345 | | | | | 350 | | |
| Pro | Thr | Phe | Thr | Pro | Ser | Asn | Phe | Lys | Gln | Tyr | Ile | Arg | His | Gly | Glu |
| | | | 355 | | | | | 360 | | | | | 365 | | |

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
            420                 425                 430

Pro Pro Gln Ala Lys Pro Asp Pro Leu Ala Lys Tyr Lys Phe Trp Asp
        435                 440                 445

Val Asp Leu Lys Glu Arg Phe Ser Leu Asp Leu Asp Gln Phe Ala Leu
    450                 455                 460

Gly Arg Lys Phe Leu Leu Gln Val Gly Val
465                 470

<210> SEQ ID NO 106
<211> LENGTH: 26
<212> TYPE: PRT
<213> ORGANISM: Homo sapiens
<220> FEATURE:
<221> NAME/KEY: misc_feature
<223> OTHER INFORMATION: 5102 Amino acid sequence of HPV type 33 L1
      protein aa 474-499

<400> SEQUENCE: 106

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 107
<211> LENGTH: 500
<212> TYPE: PRT
<213> ORGANISM: Artificial sequence
<220> FEATURE:
<223> OTHER INFORMATION: 5103 Amino acid sequence of chimeric HPV type
      51 L1 protein

<400> SEQUENCE: 107

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65              70                  75                  80

Lys Phe Gly Leu Pro Asp Pro Asn Leu Tyr Asn Pro Asp Thr Asp Arg
            85                  90                  95

Leu Val Trp Gly Cys Val Gly Val Glu Val Gly Arg Gly Gln Pro Leu
        100                 105                 110

Gly Val Gly Leu Ser Gly His Pro Leu Phe Asn Lys Tyr Asp Asp Thr
    115                 120                 125

Glu Asn Ser Arg Ile Ala Asn Gly Asn Ala Gln Gln Asp Val Arg Asp
130                 135                 140

Asn Thr Ser Val Asp Asn Lys Gln Thr Gln Leu Cys Ile Ile Gly Cys

```
            145                 150                 155                 160
        Ala Pro Pro Ile Gly Glu His Trp Gly Ile Gly Thr Thr Cys Lys Asn
                        165                 170                 175

Thr Pro Val Pro Pro Gly Asp Cys Pro Pro Leu Glu Leu Val Ser Ser
                        180                 185                 190

Val Ile Gln Asp Gly Asp Met Ile Asp Thr Gly Phe Gly Ala Met Asp
                        195                 200                 205

Phe Ala Ala Leu Gln Ala Thr Lys Ser Asp Val Pro Leu Asp Ile Ser
                210                 215                 220

Gln Ser Val Cys Lys Tyr Pro Asp Tyr Leu Lys Met Ser Ala Asp Thr
        225                 230                 235                 240

Tyr Gly Asn Ser Met Phe Phe His Leu Arg Arg Glu Gln Ile Phe Ala
                        245                 250                 255

Arg His Tyr Tyr Asn Lys Leu Val Gly Val Gly Glu Asp Ile Pro Asn
                        260                 265                 270

Asp Tyr Tyr Ile Lys Gly Ser Gly Asn Gly Arg Asp Pro Ile Glu Ser
                        275                 280                 285

Tyr Ile Tyr Ser Ala Thr Pro Ser Gly Ser Met Ile Thr Ser Asp Ser
                290                 295                 300

Gln Ile Phe Asn Lys Pro Tyr Trp Leu His Arg Ala Gln Gly His Asn
        305                 310                 315                 320

Asn Gly Ile Cys Trp Asn Asn Gln Leu Phe Ile Thr Cys Val Asp Thr
                        325                 330                 335

Thr Arg Ser Thr Asn Leu Thr Ile Ser Thr Ala Thr Ala Ala Val Ser
                        340                 345                 350

Pro Thr Phe Thr Pro Ser Asn Phe Lys Gln Tyr Ile Arg His Gly Glu
                        355                 360                 365

Glu Tyr Glu Leu Gln Phe Ile Phe Gln Leu Cys Lys Ile Thr Leu Thr
                        370                 375                 380

Thr Glu Val Met Ala Tyr Leu His Thr Met Asp Pro Thr Ile Leu Glu
        385                 390                 395                 400

Gln Trp Asn Phe Gly Leu Thr Leu Pro Pro Ser Ala Ser Leu Glu Asp
                        405                 410                 415

Ala Tyr Arg Phe Val Arg Asn Ala Ala Thr Ser Cys Gln Lys Asp Thr
                        420                 425                 430

Pro Pro Gln Ala Lys Pro Asp Pro Leu Ala Lys Tyr Lys Phe Trp Asp
                        435                 440                 445

Val Asp Leu Lys Glu Arg Phe Ser Leu Asp Leu Asp Gln Phe Ala Leu
        450                 455                 460

Gly Arg Lys Phe Leu Leu Gln Val Gly Val Lys Ala Lys Pro Lys Leu
        465                 470                 475                 480

Lys Arg Ala Ala Pro Thr Ser Thr Arg Thr Ser Ser Ala Lys Arg Lys
                        485                 490                 495

Lys Val Lys Lys
                        500

<210> SEQ ID NO 108
<211> LENGTH: 1504
<212> TYPE: DNA
<213> ORGANISM: Artificial sequence
<220> FEATURE:
<223> OTHER INFORMATION: 5104 Nucleotide sequence of chimeric HPV type
      51 L1 protein

<400> SEQUENCE: 108
```

```
atggctctgt ggaggaccaa tgacagcaag gtctacctgc ctcctgcccc tgtgagcagg      60
attgtgaaca cagaggaata catcaccagg acaggcatct actactatgc tggctccagc     120
agactgatta ccctgggaca cccatacttt ccaatcccaa agaccagcac cagggctgcc     180
atcccaaagg tgtctgcctt ccaatacagg gtgttcaggg tccaacttcc tgacccaaac     240
aagtttggac tgcctgaccc aaacctctac aaccctgaca cagacagact ggtgtggggc     300
tgtgtgggag tggaggtggg caggggacaa ccactgggag tgggactgtc tggacaccca     360
ctgttcaaca aatatgatga cacagagaac agcaggattg ccaatggcaa tgcccaacag     420
gatgtgaggg acaacacctc tgtggacaac aagcagaccc aactttgtat cattggctgt     480
gcccctccaa ttggagaaca ctggggcatt ggcaccactt gtaagaacac acctgtgcct     540
cctggagact gtcctccatt ggaactggtg tcctctgtga ttcaggatgg agatatgatt     600
gacacaggct ttggagctat ggactttgct gccctccaag ccaccaagtc tgatgtgcca     660
ctggacatca gccagtctgt gtgtaaatac cctgactacc tgaaaatgag tgctgacacc     720
tatggcaaca gtatgttctt ccacctgagg agggaacaga ttttttgccag acactactac     780 aacaaactgg tgggagtggg agaggacatc ccaaatgact actacatcaa gggctctggc     840
aatggcaggg acccaattga gtcctacatc tactctgcca ccatctggg cagtatgatt     900 acctctgaca gccagatttt caacaagcca tactggctgc agggctca aggacacaac     960 aatggcatct gttggaacaa ccaactttc atcacttgtg tggacaccac caggagcacc    1020
aacctgacca tcagcacagc cacagcagca gtgagcccaa ccttcacacc aagcaacttc    1080
aagcaataca tcagacatgg agaggaatat gaactccaat tcatcttcca actttgtaag    1140
attaccctga ccacagaggt gatggcttac ctgcacacaa tggacccaac catcttggaa    1200
cagtggaact ttggactgac cctgcctcca tctgcctcct tggaggatgc ctacaggttt    1260
gtgaggaatg ctgccacctc ctgtcagaag acacacctc acaggctaa gcctgaccca    1320 ctggctaaat acaagttctg ggatgtggac ctgaaagaga ggttctccct ggacctggac    1380
cagtttgccc tgggcaggaa gttcctgctc caagtgggag tcaaagccaa gccaaaactg    1440
aaaagggctg ccccaaccag caccaggacc tcctctgcca agaggaagaa ggtgaagaag    1500
taaa                                                                 1504
```

<210> SEQ ID NO 109
<211> LENGTH: 1534
<212> TYPE: DNA
<213> ORGANISM: Artificial sequence
<220> FEATURE:
<223> OTHER INFORMATION: 5105 Synthetic HPV51 L1 gene

<400> SEQUENCE: 109

```
ctgggtacca tggctctgtg gaggaccaat gacagcaagg tctacctgcc tcctgcccct      60
gtgagcagga ttgtgaacac agaggaatac atcaccagga caggcatcta ctactatgct     120
ggctccagca gactgattac cctgggacac ccatactttc caatcccaaa gaccagcacc     180
agggctgcca tcccaaaggt gtctgccttc aatacaggg tgttcagggt ccaacttcct     240
gacccaaaca gtttggact gcctgaccca aacctctaca accctgacac agacagactg     300
gtgtggggct gtgtgggagt ggaggtgggc aggggacaac cactgggagt gggactgtct     360
ggacacccac tgttcaacaa atatgatgac acagagaaca gcaggattgc caatggcaat     420
gcccaacagg atgtgaggga caacacctct gtggacaaca agcagaccca actttgtatc     480
attggctgtg cccctccaat tggagaacac tggggcattg gcaccacttg taagaacaca     540
```

```
cctgtgcctc ctggagactg tcctccattg gaactggtgt cctctgtgat tcaggatgga      600
gatatgattg acacaggctt tggagctatg gactttgctg ccctccaagc caccaagtct      660
gatgtgccac tggacatcag ccagtctgtg tgtaaatacc ctgactacct gaaaatgagt      720
gctgacacct atggcaacag tatgttcttc cacctgagga gggaacagat ttttgccaga      780
cactactaca acaaactggt gggagtggga gaggacatcc caaatgacta ctacatcaag      840
ggctctggca atggcaggga cccaattgag tcctacatct actctgccac accatctggc      900
agtatgatta cctctgacag ccagattttc aacaagccat actggctgca gggctcaa       960 ggacacaaca atggcatctg ttggaacaac caacttttca tcacttgtgt ggacaccacc     1020
aggagcacca acctgaccat cagcacagcc acagcagcag tgagcccaac cttcacacca     1080
agcaacttca gcaatacat cagacatgga gaggaatatg aactccaatt catcttccaa      1140
ctttgtaaga ttaccctgac cacagaggtg atggcttacc tgcacacaat ggacccaacc     1200
atcttggaac agtggaactt tggactgacc ctgcctccat ctgcctcctt ggaggatgcc     1260
tacaggtttg tgaggaatgc tgccacctcc tgtcagaagg acacacctcc acaggctaag     1320
cctgacccac tggctaaata caagttctgg gatgtggacc tgaaagagag gttctccctg     1380
gacctggacc agtttgccct gggcaggaag ttcctgctcc aagtgggagt ccagaggaag     1440
ccaagacctg gactgaaaag acctgcctcc tctgcctcct cctcctcctc ctcctctgcc     1500
aagaggaaga gggtgaagaa gtaaactcga gctc                                 1534

<210> SEQ ID NO 110
<211> LENGTH: 1519
<212> TYPE: DNA
<213> ORGANISM: Artificial sequence
<220> FEATURE:
<223> OTHER INFORMATION: 5106 Synthetic HPV33 L1 gene

<400> SEQUENCE: 110
ctgggtacca tgagtgtgtg gagaccatct gaggctacag tctacctgcc tcctgtgcct       60
gtgagcaagg tggtgagcac agatgaatat gtgagcagga ccagcatcta ctactatgct      120
ggctccagca gactgctggc tgtgggacac ccatacttca gcatcaagaa cccaaccaat      180
gccaagaaac tgctggtgcc aaaggtgtct ggactccaat acagggtgtt cagggtgaga      240
ctgcctgacc caaacaagtt tggctttcct gacacctcct tctacaaccc tgacacccag      300
agactggtgt gggcttgtgt gggattggag attggcaggg acaaccact gggagtgggc      360 atctctggac acccactgct gaacaagttt gatgacacag agacaggcaa caatacccct     420
ggacaacctg agcagacaa cagggagtgt ctgagtatgg actacaagca gacccaactt      480
tgtctgctgg gctgtaagcc tccaacagga gaacactggg gcaagggagt ggcttgtacc     540
aatgctgccc ctgccaatga ctgtcctcca ttggaactga taaacaccat cattgaggat     600
ggagatatgg tggacacagg ctttggctgt atggacttca gaccctcca agccaacaag     660 tctgatgtgc caattgacat ctgtggcagc acttgtaaat accctgacta cctgaaaatg     720
acctctgaac catatggaga ctccctgttc ttcttcctga ggagggaaca gatgtttgtg     780
agacacttct tcaacagggc tggcacccct ggagaggctg ccctgatga cctctacatc     840 aagggctctg gcaccacagc cagcatccag tcctctgcct tctttccaac accatctggc     900
agtatggtga cctctgagag ccaacttttc aacaagccat actggctcca aagggctcaa     960
ggacacaaca atggcatctg ttgggcaac caggtgtttg tgacagtggt ggacaccacc     1020
```

-continued

| | |
|---|---|
| aggagcacca atatgaccct gtgtacccag gtgacctctg acagcaccta caagaatgag | 1080 |
| aacttcaagg aatacatcag gcatgtggag gaatatgacc tccaatttgt gttccaactt | 1140 |
| tgtaaggtga ccctgacagc agaggtgatg acctacatcc atgctatgaa ccctgacatc | 1200 |
| ttggaggact ggcagtttgg actgacacct cctccatctg cctccctcca agacacctac | 1260 |
| aggtttgtga ccagccaggc tatcacttgt cagaagacag tgcctccaaa ggagaaggag | 1320 |
| gacccactgg gcaaatacac cttctgggag gtggacctga agagaagtt ctctgctgac | 1380 |
| ctggaccagt ttccactggg caggaagttc ctgctccaag caggactgaa agccaagcca | 1440 |
| aaactgaaaa gggctgcccc aaccagcacc aggacctcct ctgccaagag gaagaaggtg | 1500 |
| aagaagtaaa ctcgagctc | 1519 |

<210> SEQ ID NO 111
<211> LENGTH: 34
<212> TYPE: DNA
<213> ORGANISM: Artificial sequence
<220> FEATURE:
<223> OTHER INFORMATION: 5107 HPV51L1 F1

<400> SEQUENCE: 111

| | |
|---|---|
| cttggtacca tggctctgtg gaggaccaat gaca | 34 |

<210> SEQ ID NO 112
<211> LENGTH: 32
<212> TYPE: DNA
<213> ORGANISM: Artificial sequence
<220> FEATURE:
<223> OTHER INFORMATION: 5108 HPV51L1 R1

<400> SEQUENCE: 112

| | |
|---|---|
| gcttggcttt gactcccact tggagcagga ac | 32 |

<210> SEQ ID NO 113
<211> LENGTH: 1441
<212> TYPE: DNA
<213> ORGANISM: Artificial sequence
<220> FEATURE:
<223> OTHER INFORMATION: 5109 HPV51L1 amplified sequence 1

<400> SEQUENCE: 113

| | |
|---|---|
| cttggtacca tggctctgtg gaggaccaat gacagcaagg tctacctgcc tcctgcccct | 60 |
| gtgagcagga ttgtgaacac agaggaatac atcaccagga caggcatcta ctactatgct | 120 |
| ggctccagca gactgattac cctgggacac ccatactttc caatcccaaa gaccagcacc | 180 |
| agggctgcca tcccaaaggt gtctgccttc aatacaggg tgttcagggt ccaacttcct | 240 |
| gacccaaaca gtttggact gcctgaccca aacctctaca ccctgacac agacagactg | 300 |
| gtgtggggct gtgtgggagt ggaggtgggc aggggacaac cactgggagt gggactgtct | 360 |
| ggacacccac tgttcaacaa atatgatgac acagagaaca gcaggattgc caatggcaat | 420 |
| gcccaacagg atgtgaggga caacacctct gtggacaaca agcagaccca actttgtatc | 480 |
| attggctgtg cccctccaat tggagaacac tggggcattg gcaccacttg taagaacaca | 540 |
| cctgtgcctc ctggagactg tcctccattg gaactggtgt cctctgtgat tcaggatgga | 600 |
| gatatgattg acacaggctt tggagctatg gactttgctg ccctccaagc caccaagtct | 660 |
| gatgtgccac tggacatcag ccagtctgtg tgtaaatacc ctgactacct gaaaatgagt | 720 |
| gctgacacct atggcaacag tatgttcttc ccacctgagga gggaacagat ttttgccaga | 780 |
| cactactaca acaaactggt gggagtggga gaggacatcc caaatgacta ctacatcaag | 840 |

-continued

```
ggctctggca atggcaggga cccaattgag tcctacatct actctgccac accatctggc    900
agtatgatta cctctgacag ccagattttc aacaagccat actggctgca cagggctcaa    960
ggacacaaca atggcatctg ttggaacaac caacttttca tcacttgtgt ggacaccacc   1020
aggagcacca acctgaccat cagcacagcc acagcagcag tgagcccaac cttcacacca   1080
agcaacttca gcaatacat cagacatgga gaggaatatg aactccaatt catcttccaa    1140
ctttgtaaga ttaccctgac cacagaggtg atggcttacc tgcacacaat ggacccaacc   1200
atcttggaac agtggaactt tggactgacc ctgcctccat ctgcctcctt ggaggatgcc   1260
tacaggtttg tgaggaatgc tgccacctcc tgtcagaagg acacacctcc acaggctaag   1320
cctgacccac tggctaaata caagttctgg gatgtggacc tgaaagagag gttctccctg   1380
gacctggacc agtttgccct gggcaggaag ttcctgctcc aagtgggagt caaagccaag   1440
c                                                                   1441
```

<210> SEQ ID NO 114
<211> LENGTH: 35
<212> TYPE: DNA
<213> ORGANISM: Artificial sequence
<220> FEATURE:
<223> OTHER INFORMATION: 5110 HPV51L1 F2

<400> SEQUENCE: 114

```
agtgggagtc aaagccaagc caaaactgaa aaggg                               35
```

<210> SEQ ID NO 115
<211> LENGTH: 36
<212> TYPE: DNA
<213> ORGANISM: Artificial sequence
<220> FEATURE:
<223> OTHER INFORMATION: 5111 HPV51L1 R2

<400> SEQUENCE: 115

```
ctgtctagat ttacttcttc accttcttcc tcttgg                              36
```

<210> SEQ ID NO 116
<211> LENGTH: 101
<212> TYPE: DNA
<213> ORGANISM: Artificial sequence
<220> FEATURE:
<223> OTHER INFORMATION: 5112 HPV51L1 amplified sequence 2

<400> SEQUENCE: 116

```
agtgggagtc aaagccaagc caaaactgaa aagggctgcc ccaaccagca ccaggacctc    60
ctctgccaag aggaagaagg tgaagaagta aatctagaca g                       101
```

<210> SEQ ID NO 117
<211> LENGTH: 38
<212> TYPE: PRT
<213> ORGANISM: Homo sapiens
<220> FEATURE:
<221> NAME/KEY: misc_feature
<223> OTHER INFORMATION: 5113 Amino acid sequence of HPV type 59 L1
     protein aa 471-508

<400> SEQUENCE: 117

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
            35

<210> SEQ ID NO 118
<211> LENGTH: 478
<212> TYPE: PRT
<213> ORGANISM: Homo sapiens
<220> FEATURE:
<221> NAME/KEY: misc_feature
<223> OTHER INFORMATION: 5201 Amino acid sequence of HPV type 52 L1
      protein aa 1-478

<400> SEQUENCE: 118

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Thr Val Gly His Pro
        35                  40                  45

Tyr Phe Ser Ile Lys Asn Thr Ser Gly Asn Gly Lys Lys Val Leu
    50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95

Glu Thr Gln Arg Leu Val Trp Ala Cys Thr Gly Leu Glu Ile Gly Arg
            100                 105                 110

Gly Gln Pro Leu Gly Val Gly Ile Ser Gly His Pro Leu Leu Asn Lys
        115                 120                 125

Phe Asp Asp Thr Glu Thr Ser Asn Lys Tyr Ala Gly Lys Pro Gly Ile
    130                 135                 140

Asp Asn Arg Glu Cys Leu Ser Met Asp Tyr Lys Gln Thr Gln Leu Cys
145                 150                 155                 160

Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
            180                 185                 190

Leu Ile Asn Ser Val Ile Gln Asp Gly Asp Met Val Asp Thr Gly Phe
        195                 200                 205

Gly Cys Met Asp Phe Asn Thr Leu Gln Ala Ser Lys Ser Asp Val Pro
    210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
        275                 280                 285

Ala Thr Val Gln Ser Ser Ala Phe Phe Pro Thr Pro Ser Gly Ser Met
    290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu

```
                    340             345             350
Val Lys Lys Glu Ser Thr Tyr Lys Asn Glu Asn Phe Lys Glu Tyr Leu
                355             360             365

Arg His Gly Glu Glu Phe Asp Leu Gln Phe Ile Phe Gln Leu Cys Lys
        370             375             380

Ile Thr Leu Thr Ala Asp Val Met Thr Tyr Ile His Lys Met Asp Ala
385             390             395             400

Thr Ile Leu Glu Asp Trp Gln Phe Gly Leu Thr Pro Pro Pro Ser Ala
            405             410             415

Ser Leu Glu Asp Thr Tyr Arg Phe Val Thr Ser Thr Ala Ile Thr Cys
        420             425             430

Gln Lys Asn Thr Pro Pro Lys Gly Lys Glu Asp Pro Leu Lys Asp Tyr
    435             440             445

Met Phe Trp Glu Val Asp Leu Lys Glu Lys Phe Ser Ala Asp Leu Asp
    450             455             460

Gln Phe Pro Leu Gly Arg Lys Phe Leu Leu Gln Ala Gly Leu
465             470             475

<210> SEQ ID NO 119
<211> LENGTH: 26
<212> TYPE: PRT
<213> ORGANISM: Homo sapiens
<220> FEATURE:
<221> NAME/KEY: misc_feature
<223> OTHER INFORMATION: 5202 Amino acid sequence of HPV type 33 L1
      protein aa 474-499

<400> SEQUENCE: 119

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 120
<211> LENGTH: 504
<212> TYPE: PRT
<213> ORGANISM: Artificial sequence
<220> FEATURE:
<223> OTHER INFORMATION: 5203 Amino acid sequence of chimeric HPV type
      52 L1 protein

<400> SEQUENCE: 120

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Thr Val Gly His Pro
        35                  40                  45

Tyr Phe Ser Ile Lys Asn Thr Ser Ser Gly Asn Gly Lys Lys Val Leu
    50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95

Glu Thr Gln Arg Leu Val Trp Ala Cys Thr Gly Leu Glu Ile Gly Arg
            100                 105                 110

Gly Gln Pro Leu Gly Val Gly Ile Ser Gly His Pro Leu Leu Asn Lys
        115                 120                 125
```

Phe Asp Asp Thr Glu Thr Ser Asn Lys Tyr Ala Gly Lys Pro Gly Ile
130                 135                 140

Asp Asn Arg Glu Cys Leu Ser Met Asp Tyr Lys Gln Thr Gln Leu Cys
145                 150                 155                 160

Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
            180                 185                 190

Leu Ile Asn Ser Val Ile Gln Asp Gly Asp Met Val Asp Thr Gly Phe
        195                 200                 205

Gly Cys Met Asp Phe Asn Thr Leu Gln Ala Ser Lys Ser Asp Val Pro
210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Leu Arg Arg Glu
                245                 250                 255

Gln Met Phe Val Arg His Phe Asn Arg Ala Gly Thr Leu Gly Asp
        260                 265                 270

Pro Val Pro Gly Asp Leu Tyr Ile Gln Gly Ser Asn Ser Gly Asn Thr
            275                 280                 285

Ala Thr Val Gln Ser Ser Ala Phe Phe Pro Thr Pro Ser Gly Ser Met
290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350

Val Lys Lys Glu Ser Thr Tyr Lys Asn Glu Asn Phe Lys Glu Tyr Leu
        355                 360                 365

Arg His Gly Glu Glu Phe Asp Leu Gln Phe Ile Phe Gln Leu Cys Lys
370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445

Met Phe Trp Glu Val Asp Leu Lys Glu Lys Phe Ser Ala Asp Leu Asp
450                 455                 460

Gln Phe Pro Leu Gly Arg Lys Phe Leu Leu Gln Ala Gly Leu Lys Ala
465                 470                 475                 480

Lys Pro Lys Leu Lys Arg Ala Ala Pro Thr Ser Thr Arg Thr Ser Ser
                485                 490                 495

Ala Lys Arg Lys Lys Val Lys Lys
            500

<210> SEQ ID NO 121
<211> LENGTH: 1516
<212> TYPE: DNA
<213> ORGANISM: Artificial sequence
<220> FEATURE:
<223> OTHER INFORMATION: 5204 Nucleotide sequence of chimeric HPV type 52 L1 protein

<400> SEQUENCE: 121

| | | | | | |
|---|---|---|---|---|---|
| atgagcgtgt | ggaggcccag | cgaggccacc | gtgtacctgc | ccccgtgcc | cgtgagcaag | 60 |
| gtggtgagca | ccgacgagta | cgtgagcagg | accagcatct | actactacgc | cggcagcagc | 120 |
| aggctgctga | ccgtgggcca | ccctacttc | agcatcaaga | acaccagcag | cggcaacggc | 180 |
| aagaaggtgc | tggtgcccaa | ggtgagcggc | tgcagtaca | gggtgttcag | gatcaagctg | 240 |
| cccgacccca | acaagttcgg | cttccccgac | accagcttct | acaaccccga | cccagagg | 300 |
| ctggtgtggg | cctgcaccgg | cctggagatc | ggcaggggcc | agcccctggg | cgtgggcatc | 360 |
| agcggccacc | ccctgctgaa | caagttcgac | gacaccgaga | ccagcaacaa | gtacgccggc | 420 |
| aagcccggca | tcgacaacag | ggagtgcctg | agcatggact | acaagcagac | ccagctgtgc | 480 |
| atcctgggct | gcaagccccc | catcggcgag | cactggggca | agggcacccc | ctgcaacaac | 540 |
| aacagcggca | ccccggcga | ctgccccccc | ctgcagctga | tcaacagcgt | gatccaggac | 600 |
| ggcgacatgg | tggacaccgg | cttcggctgc | atggacttca | cacccctgca | ggccagcaag | 660 |
| agcgacgtgc | ccatcgacat | ctgcagcagc | gtgtgcaagt | accccgacta | cctgcagatg | 720 |
| gccagcgagc | cctacggcga | cagcctgttc | ttcttcctga | ggaggagca | gatgttcgtg | 780 |
| aggcacttct | tcaacagggc | cggcaccctg | ggcgaccccg | tgcccggcga | cctgtacatc | 840 |
| cagggcagca | cagcggcaa | caccgccacc | gtgcagagca | gcgccttctt | ccccacccc | 900 |
| agcggcagca | tggtgaccag | cgagagccag | ctgttcaaca | gccctactg | gctgcagagg | 960 |
| gcccagggcc | acaacaacgg | catctgctgg | ggcaaccagc | tgttcgtgac | cgtggtggac | 1020 |
| accaccagga | gcaccaacat | gaccctgtgc | gccgaggtga | agaaggagag | cacctacaag | 1080 |
| aacgagaact | tcaaggagta | cctgaggcac | ggcgaggagt | tcgacctgca | gttcatcttc | 1140 |
| cagctgtgca | agatcaccct | gaccgccgac | gtgatgacct | acatccacaa | gatggacgcc | 1200 |
| accatcctgg | aggactggca | gttcggcctg | accccccc | ccagcgccag | cctggaggac | 1260 |
| acctacaggt | tcgtgaccag | caccgccatc | acctgccaga | gaacacccc | cccaagggc | 1320 |
| aaggaggacc | ccctgaagga | ctacatgttc | tgggaggtgg | acctgaagga | gaagttcagc | 1380 |
| gccgacctgg | accagttccc | cctgggcagg | aagttcctgc | tgcaggccgg | cctgaaagcc | 1440 |
| aagccaaaac | tgaaaagggc | tgccccaacc | agcaccagga | cctcctctgc | caagaggaag | 1500 |
| aaggtgaaga | agtaaa | | | | | 1516 |

<210> SEQ ID NO 122
<211> LENGTH: 1531
<212> TYPE: DNA
<213> ORGANISM: Artificial sequence
<220> FEATURE:
<223> OTHER INFORMATION: 5205 Synthetic HPV52 L1 gene

<400> SEQUENCE: 122

| | | | | | |
|---|---|---|---|---|---|
| ctgggtacca | tgagcgtgtg | gaggcccagc | gaggccaccg | tgtacctgcc | ccccgtgccc | 60 |
| gtgagcaagg | tggtgagcac | cgacgagtac | gtgagcagga | ccagcatcta | ctactacgcc | 120 |
| ggcagcagca | ggctgctgac | cgtgggccac | ccctacttca | gcatcaagaa | caccagcagc | 180 |
| ggcaacggca | agaaggtgct | ggtgcccaag | gtgagcggc | tgcagtacag | ggtgttcagg | 240 |
| atcaagctgc | ccgaccccaa | caagttcggc | ttccccgaca | ccagcttcta | caaccccgag | 300 |
| acccagaggc | tggtgtgggc | ctgcaccggc | ctggagatcg | gcaggggcca | gcccctgggc | 360 |
| gtgggcatca | gcggccaccc | cctgctgaac | aagttcgacg | acaccgagac | cagcaacaag | 420 |

```
tacgccggca agcccggcat cgacaacagg gagtgcctga gcatggacta caagcagacc    480
cagctgtgca tcctgggctg caagcccccc atcggcgagc actggggcaa ggcaccccc     540 tgcaacaaca acagcggcaa ccccggcgac tgccccccccc tgcagctgat aacagcgtg    600 atccaggacg gcgacatggt ggacaccggc ttcggctgca tggacttcaa caccctgcag    660
gccagcaaga gcgacgtgcc catcgacatc tgcagcagcg tgtgcaagta ccccgactac    720
ctgcagatgg ccagcgagcc ctacggcgac agcctgttct tcttcctgag gagggagcag    780
atgttcgtga ggcacttctt caacagggcc ggcacccctgg gcgaccccgt gcccggcgac    840
ctgtacatcc agggcagcaa cagcggcaac accgccaccg tgcagagcag cgccttcttc    900 cccacccccca gcggcagcat ggtgaccagc gagagccagc tgttcaacaa gccctactgg    960
ctgcagaggg cccagggcca caacaacggc atctgctggg gcaaccagct gttcgtgacc   1020
gtggtggaca ccaccaggag caccaacatg accctgtgcg ccgaggtgaa gaaggagagc   1080
acctacaaga cgagaacttt caaggagtac ctgaggcacg gcgaggagtt cgacctgcag   1140
ttcatcttcc agctgtgcaa gatcaccctg accgccgacg tgatgaccta catccacaag   1200
atggacgcca ccatcctgga ggactggcag ttcggcctga cccccccccc cagcgccagc   1260
ctggaggaca cctacaggtt cgtgaccagc accgccatca cctgccagaa gaacaccccc   1320
cccaagggca aggaggaccc cctgaaggac tacatgttct gggaggtgga cctgaaggag   1380
aagttcagcg ccgacctgga ccagttcccc ctgggcagga agttcctgct gcaggccggc   1440
ctgcaggcca ggcccaagct gaagaggccc gccagcagcg ccccccaggac cagcaccaag   1500 aagaagaagg tgaagaggta aactcgagct c                                  1531
```

<210> SEQ ID NO 123
<211> LENGTH: 1519
<212> TYPE: DNA
<213> ORGANISM: Artificial sequence
<220> FEATURE:
<223> OTHER INFORMATION: 5206 Synthetic HPV33 L1 gene

<400> SEQUENCE: 123

```
ctgggtacca tgagtgtgtg gagaccatct gaggctacag tctacctgcc tcctgtgcct     60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360 atctctggac acccactgct gaacaagttt gatgacacag agacaggcaa caatacccct    420
ggacaacctg gagcagacaa cagggagtgt ctgagtatgg actacaagca gacccaactt    480
tgtctgctgg gctgtaagcc tccaacagga gaacactggg gcaagggagt ggcttgtacc    540
aatgctgccc ctgccaatga ctgtcctcca ttggaactga taaacaccat cattgaggat    600
ggagatatgg tggacacagg ctttggctgt atggacttca gaccctcca agccaacaag    660 tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcacccctg ggagaggctg tgcctgatga cctctacatc    840
aagggctctg gcaccacagc cagcatccag tcctctgcct tctttccaac accatctggc    900
```

| | |
|---|---|
| agtatggtga cctctgagag ccaacttttc aacaagccat actggctcca aagggctcaa | 960 |
| ggacacaaca atggcatctg ttggggcaac caggtgtttg tgacagtggt ggacaccacc | 1020 |
| aggagcacca atatgaccct gtgtacccag gtgacctctg acagcaccta caagaatgag | 1080 |
| aacttcaagg aatacatcag gcatgtggag gaatatgacc tccaatttgt gttccaactt | 1140 |
| tgtaaggtga ccctgacagc agaggtgatg acctacatcc atgctatgaa ccctgacatc | 1200 |
| ttggaggact ggcagtttgg actgacacct cctccatctg cctccctcca agacacctac | 1260 |
| aggtttgtga ccagccaggc tatcacttgt cagaagacag tgcctccaaa ggagaaggag | 1320 |
| gaccccactgg gcaaatacac cttctgggag gtggacctga agagaagtt ctctgctgac | 1380 |
| ctggaccagt ttccactggg caggaagttc ctgctccaag caggactgaa agccaagcca | 1440 |
| aaactgaaaa gggctgcccc aaccagcacc aggacctcct ctgccaagag gaagaaggtg | 1500 |
| aagaagtaaa ctcgagctc | 1519 |

<210> SEQ ID NO 124
<211> LENGTH: 34
<212> TYPE: DNA
<213> ORGANISM: Artificial sequence
<220> FEATURE:
<223> OTHER INFORMATION: 5207 HPV52L1 F1

<400> SEQUENCE: 124

| | |
|---|---|
| cttggtacca tgagcgtgtg gaggcccagc gagg | 34 |

<210> SEQ ID NO 125
<211> LENGTH: 35
<212> TYPE: DNA
<213> ORGANISM: Artificial sequence
<220> FEATURE:
<223> OTHER INFORMATION: 5208 HPV52L1 R1

<400> SEQUENCE: 125

| | |
|---|---|
| gcttggcttt caggccggcc tgcagcagga acttc | 35 |

<210> SEQ ID NO 126
<211> LENGTH: 1453
<212> TYPE: DNA
<213> ORGANISM: Artificial sequence
<220> FEATURE:
<223> OTHER INFORMATION: 5209 HPV52L1 amplified sequence 1

<400> SEQUENCE: 126

| | |
|---|---|
| cttggtacca tgagcgtgtg gaggcccagc gaggccaccg tgtacctgcc ccccgtgccc | 60 |
| gtgagcaagg tggtgagcac cgacgagtac gtgagcagga ccagcatcta ctactacgcc | 120 |
| ggcagcagca ggctgctgac cgtgggccac ccctacttca gcatcaagaa caccagcagc | 180 |
| ggcaacggca agaaggtgct ggtgcccaag gtgagcggcc tgcagtacag ggtgttcagg | 240 |
| atcaagctgc ccgaccccaa caagttcggc ttccccgaca ccagcttcta caaccccgag | 300 |
| acccagaggc tggtgtgggc ctgcaccggc ctggagatcg gcaggggcca gcccctgggc | 360 |
| gtgggcatca gcggccaccc cctgctgaac aagttcgacg acaccgagac cagcaacaag | 420 |
| tacgccggca gcccggcat cgacaacagg gagtgcctga gcatggacta caagcagacc | 480 |
| cagctgtgca tcctgggctg caagcccccc atcggcgagc actggggcaa gggcacccc | 540 |
| tgcaacaaca acagcggcaa ccccggcgac tgcccccccc tgcagctgat caacagcgtg | 600 |
| atccaggacg gcgacatggt ggacaccggc ttcggctgca tggacttcaa caccctgcag | 660 |
| gccagcaaga gcgacgtgcc catcgacatc tgcagcagcg tgtgcaagta ccccgactac | 720 |

```
ctgcagatgg ccagcgagcc ctacggcgac agcctgttct tcttcctgag gagggagcag    780
atgttcgtga ggcacttctt caacagggcc ggcaccctgg cgacccccgt gcccggcgac    840
ctgtacatcc agggcagcaa cagcggcaac accgccaccg tgcagagcag cgccttcttc    900
cccaccccca gcggcagcat ggtgaccagc gagagccagc tgttcaacaa gccctactgg    960
ctgcagaggg cccagggcca acaacggca tctgctgggg caaccagct gttcgtgacc    1020 gtggtggaca ccaccaggag caccaacatg accctgtgcg ccgaggtgaa gaaggagagc   1080
acctacaaga cgagaactt caaggagtac ctgaggcacg gcgaggagtt cgacctgcag   1140
ttcatcttcc agctgtgcaa gatcaccctg accgccgacg tgatgaccta catccacaag   1200
atggacgcca ccatcctgga ggactggcag ttcggcctga ccccccccc cagcgccagc   1260 ctggaggaca cctacaggtt cgtgaccagc accgccatca cctgccagaa gaacaccccc   1320
cccaagggca aggaggaccc cctgaaggac tacatgttct gggaggtgga cctgaaggag   1380
aagttcagcg ccgacctgga ccagttcccc ctgggcagga agttcctgct gcaggccggc   1440
ctgaaagcca agc                                                     1453

<210> SEQ ID NO 127
<211> LENGTH: 35
<212> TYPE: DNA
<213> ORGANISM: Artificial sequence
<220> FEATURE:
<223> OTHER INFORMATION: 5210 HPV52L1 F2

<400> SEQUENCE: 127
ggccggcctg aaagccaagc caaaactgaa aaggg                               35

<210> SEQ ID NO 128
<211> LENGTH: 36
<212> TYPE: DNA
<213> ORGANISM: Artificial sequence
<220> FEATURE:
<223> OTHER INFORMATION: 5211 HPV52L1 R2

<400> SEQUENCE: 128
ctgtctagat ttacttcttc accttcttcc tcttgg                              36

<210> SEQ ID NO 129
<211> LENGTH: 101
<212> TYPE: DNA
<213> ORGANISM: Artificial sequence
<220> FEATURE:
<223> OTHER INFORMATION: 5212 HPV52L1 amplified sequence 2

<400> SEQUENCE: 129
ggccggcctg aaagccaagc caaaactgaa aagggctgcc ccaaccagca ccaggacctc    60
ctctgccaag aggaagaagg tgaagaagta aatctagaca g                       101

<210> SEQ ID NO 130
<211> LENGTH: 38
<212> TYPE: PRT
<213> ORGANISM: Homo sapiens
<220> FEATURE:
<221> NAME/KEY: misc_feature
<223> OTHER INFORMATION: 5213 Amino acid sequence of HPV type 59 L1
      protein aa 471-508

<400> SEQUENCE: 130

Leu Gln Leu Gly Ala Arg Pro Lys Pro Thr Ile Gly Pro Arg Lys Arg
1               5                   10                  15
```

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 131
<211> LENGTH: 467
<212> TYPE: PRT
<213> ORGANISM: Homo sapiens
<220> FEATURE:
<221> NAME/KEY: misc_feature
<223> OTHER INFORMATION: 5601 Amino acid sequence of HPV type 56 L1
      protein aa 1-467

<400> SEQUENCE: 131

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
            20                  25                  30

Ile Phe Tyr His Ala Gly Ser Ser Arg Leu Leu Ala Val Gly His Pro
        35                  40                  45

Tyr Tyr Ser Val Thr Lys Asp Asn Thr Lys Thr Asn Ile Pro Lys Val
    50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
                85                  90                  95

Leu Val Trp Ala Cys Val Gly Leu Glu Val Gly Arg Gly Gln Pro Leu
            100                 105                 110

Gly Ala Gly Leu Ser Gly His Pro Leu Phe Asn Arg Leu Asp Asp Thr
        115                 120                 125

Glu Ser Ser Asn Leu Ala Asn Asn Asn Val Ile Glu Asp Ser Arg Asp
    130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Pro Leu Ala Leu Ile Asn Thr
            180                 185                 190

Pro Ile Glu Asp Gly Asp Met Ile Asp Thr Gly Phe Gly Ala Met Asp
        195                 200                 205

Phe Lys Val Leu Gln Glu Ser Lys Ala Glu Val Pro Leu Asp Ile Val
    210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
            260                 265                 270

Glu Leu Tyr Leu Lys Gly Ser Asn Gly Arg Glu Pro Pro Pro Ser Ser
        275                 280                 285

Val Tyr Val Ala Thr Pro Ser Gly Ser Met Ile Thr Ser Glu Ala Gln
    290                 295                 300

Leu Phe Asn Lys Pro Tyr Trp Leu Gln Arg Ala Gln Gly His Asn Asn
305                 310                 315                 320

```
Gly Ile Cys Trp Gly Asn Gln Leu Phe Val Thr Val Asp Thr Thr
            325                 330                 335

Arg Ser Thr Asn Met Thr Ile Ser Thr Ala Thr Glu Gln Leu Ser Lys
        340                 345                 350

Tyr Asp Ala Arg Lys Ile Asn Gln Tyr Leu Arg His Val Glu Glu Tyr
            355                 360                 365

Glu Leu Gln Phe Val Phe Gln Leu Cys Lys Ile Thr Leu Ser Ala Glu
        370                 375                 380

Val Met Ala Tyr Leu His Asn Met Asn Ala Asn Leu Leu Glu Asp Trp
385                 390                 395                 400

Asn Ile Gly Leu Ser Pro Val Ala Thr Ser Leu Glu Asp Lys Tyr
            405                 410                 415

Arg Tyr Val Arg Ser Thr Ala Ile Thr Cys Gln Arg Glu Gln Pro Pro
        420                 425                 430

Thr Glu Lys Gln Asp Pro Leu Ala Lys Tyr Lys Phe Trp Asp Val Asn
            435                 440                 445

Leu Gln Asp Ser Phe Ser Thr Asp Leu Asp Gln Phe Pro Leu Gly Arg
        450                 455                 460

Lys Phe Leu
465

<210> SEQ ID NO 132
<211> LENGTH: 31
<212> TYPE: PRT
<213> ORGANISM: Homo sapiens
<220> FEATURE:
<221> NAME/KEY: misc_feature
<223> OTHER INFORMATION: 5602 Amino acid sequence of HPV type 33 L1
      protein aa 469-499

<400> SEQUENCE: 132

Leu Gln Ala Gly Leu Lys Ala Lys Pro Lys Leu Lys Arg Ala Ala Pro
1               5                   10                  15

Thr Ser Thr Arg Thr Ser Ser Ala Lys Arg Lys Lys Val Lys Lys
            20                  25                  30

<210> SEQ ID NO 133
<211> LENGTH: 498
<212> TYPE: PRT
<213> ORGANISM: Artificial sequence
<220> FEATURE:
<223> OTHER INFORMATION: 5603 Amino acid sequence of chimeric HPV type
      56 L1 protein

<400> SEQUENCE: 133

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
            20                  25                  30

Ile Phe Tyr His Ala Gly Ser Ser Arg Leu Leu Ala Val Gly His Pro
        35                  40                  45

Tyr Tyr Ser Val Thr Lys Asp Asn Thr Lys Thr Asn Ile Pro Lys Val
    50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
            85                  90                  95

Leu Val Trp Ala Cys Val Gly Leu Glu Val Gly Arg Gly Gln Pro Leu
        100                 105                 110
```

Gly Ala Gly Leu Ser Gly His Pro Leu Phe Asn Arg Leu Asp Asp Thr
            115                 120                 125

Glu Ser Ser Asn Leu Ala Asn Asn Val Ile Glu Asp Ser Arg Asp
        130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Leu Ala Leu Ile Asn Thr
            180                 185                 190

Pro Ile Glu Asp Gly Asp Met Ile Asp Thr Gly Phe Gly Ala Met Asp
            195                 200                 205

Phe Lys Val Leu Gln Glu Ser Lys Ala Glu Val Pro Leu Asp Ile Val
            210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
                260                 265                 270

Glu Leu Tyr Leu Lys Gly Ser Asn Gly Arg Glu Pro Pro Pro Ser Ser
            275                 280                 285

Val Tyr Val Ala Thr Pro Ser Gly Ser Met Ile Thr Ser Glu Ala Gln
            290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Ile Ser Thr Ala Thr Glu Gln Leu Ser Lys
            340                 345                 350

Tyr Asp Ala Arg Lys Ile Asn Gln Tyr Leu Arg His Val Glu Glu Tyr
            355                 360                 365

Glu Leu Gln Phe Val Phe Gln Leu Cys Lys Ile Thr Leu Ser Ala Glu
            370                 375                 380

Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
            420                 425                 430

Thr Glu Lys Gln Asp Pro Leu Ala Lys Tyr Lys Phe Trp Asp Val Asn
            435                 440                 445

Leu Gln Asp Ser Phe Ser Thr Asp Leu Asp Gln Phe Pro Leu Gly Arg
450                 455                 460

Lys Phe Leu Leu Gln Ala Gly Leu Lys Ala Lys Pro Lys Leu Lys Arg
465                 470                 475                 480

Ala Ala Pro Thr Ser Thr Arg Thr Ser Ser Ala Lys Arg Lys Lys Val
                485                 490                 495

Lys Lys

<210> SEQ ID NO 134
<211> LENGTH: 1498
<212> TYPE: DNA

<213> ORGANISM: Artificial sequence
<220> FEATURE:
<223> OTHER INFORMATION: 5604 Nucleotide sequence of chimeric HPV type 56 L1 protein

<400> SEQUENCE: 134

```
atggctacct ggagaccatc tgagaacaag gtctacctgc ctccaacacc tgtgagcaag      60
gtggtggcta cagactccta tgtgaagagg accagcatct tctaccatgc tggctccagc     120
agactgctgg ctgtgggaca cccatactac tctgtgacca aggacaacac caagaccaac     180
atcccaaagg tgtctgccta ccaatacagg gtgttcaggg tgagactgcc tgacccaaac     240
aagtttggac tgcctgacac caacatctac aaccctgacc aggagagact ggtgtgggct     300
tgtgtgggat tggaggtggg caggggacaa ccactgggag caggactgtc tggacaccca     360
ctgttcaaca gactggatga cacagagtcc agcaacctgg ctaacaacaa tgtgattgag     420
gacagcaggg acaacatctc tgtggatggc aagcagaccc aactttgtat tgtgggctgt     480
actcctgcta tgggagaaca ctggaccaag ggagcagtgt gtaagagcac ccaggtgacc     540
acaggagact gtcctccact ggctctgata aacacaccaa ttgaggatgg agatatgatt     600
gacacaggct ttggagctat ggacttcaag gtgctccaag agcaaggc tgaggtgcca      660
ctggacattg tccagagcac ttgtaaatac cctgactacc tgaaaatgag tgctgatgcc     720
tatgtagaca gtatgtggtt ctacctgagg agggaacaac tttttgccag acactacttc     780
aacagggctg gcaaggtggg agagaccatc cctgctgaac tctacctgaa aggcagcaat     840
ggcagggaac ctcctccatc ctctgtctat gtggctacac catctggcag tatgattacc     900
tctgaggctc aacttttcaa caagccatac tggctccaaa gggctcaagg acacaacaat     960
ggcatctgtt ggggcaacca acttttgtg acagtggtgg acaccaccag agcaccaat     1020
atgaccatca gcacagccac agaacaactt agcaaatatg atgccaggaa gataaaccaa    1080
tacctgaggc atgtgagga atatgaactc caatttgtgt ccaactttg taagattacc    1140
ctgtctgctg aggtgatggc ttacctgcac aatatgaatg ccaacctgtt ggaggactgg    1200
aacattggac tgagccctcc tgtggctacc tccttggagg acaaatacag atatgtgagg    1260
agcacagcca tcacttgtca gagggaacaa cctccaacag agaagcagga cccactggct    1320
aaatacaagt tctgggatgt gaacctccaa gactccttca gcacagacct ggaccagttt    1380
ccactgggca ggaagttcct gctccaagca ggactgaaaa ccaagccaaa actgaaaagg    1440
gctgccccaa ccagcaccag gacctcctct gccaagagga gaaggtgaa gaagtaaa    1498
```

<210> SEQ ID NO 135
<211> LENGTH: 1519
<212> TYPE: DNA
<213> ORGANISM: Artificial sequence
<220> FEATURE:
<223> OTHER INFORMATION: 5605 Synthetic HPV56 L1 gene

<400> SEQUENCE: 135

```
ctgggtacca tggctacctg agaccatct gagaacaagg tctacctgcc tccaacacct      60
gtgagcaagg tggtggctac agactccat gtgaagagga ccagcatctt ctaccatgct    120
ggctccagca gactgctggc tgtgggacac ccatactact ctgtgaccaa ggacaacacc    180
aagaccaaca tcccaaaggt gtctgcctac caatacaggg tgttcagggt gagactgcct    240
gacccaaaca gtttggact gcctgacacc aacatctaca accctgacca ggagagactg    300
gtgtgggctt gtgtgggatt ggaggtgggc aggggacaac cactgggagc aggactgtct    360
```

```
ggacacccac tgttcaacag actggatgac acagagtcca gcaacctggc taacaacaat    420
gtgattgagg acagcaggga caacatctct gtggatggca agcagaccca actttgtatt    480
gtgggctgta ctcctgctat gggagaacac tggaccaagg gagcagtgtg taagagcacc    540
caggtgacca caggagactg tcctccactg gctctgataa acacaccaat tgaggatgga    600
gatatgattg acacaggctt tggagctatg gacttcaagg tgctccaaga gagcaaggct    660
gaggtgccac tggacattgt ccagagcact tgtaaatacc ctgactacct gaaaatgagt    720
gctgatgcct atggagacag tatgtggttc tacctgaggg gggaacaact ttttgccaga    780
cactacttca cagggctgg caaggtggga gagaccatcc tgctgaact ctacctgaaa    840
ggcagcaatg cagggaacc tcctccatcc tctgtctatg tggctacacc atctggcagt    900
atgattacct ctgaggctca acttttcaac aagccatact ggctccaaag ggctcaagga    960
cacaacaatg gcatctgttg gggcaaccaa cttttttgtga cagtggtgga caccaccagg   1020
agcaccaata tgaccatcag cacagccaca gaacaactta gcaaatatga tgccaggaag   1080
ataaaccaat acctgaggca tgtggaggaa atgaactcc aatttgtgtt ccaactttgt    1140
aagattaccc tgtctgctga ggtgatggct tacctgcaca atatgaatgc caacctgttg   1200
gaggactgga acattggact gagccctcct gtggctacct ccttggagga caaatacaga   1260
tatgtgagga gcacagccat cacttgtcag agggaacaac ctccaacaga gaagcaggac   1320
ccactggcta atacaagtt ctgggatgtg aacctccaag actccttcag cacagacctg   1380
gaccagttc cactgggcag gaagttcctg atgcaacttg gcaccaggag caagcctgct   1440
gtggctacca gcaagaagag gtctgcccca accagcacca gcacacctgc caagaggaag   1500
aggaggtaaa ctcgagctc                                                1519
```

<210> SEQ ID NO 136
<211> LENGTH: 1519
<212> TYPE: DNA
<213> ORGANISM: Artificial sequence
<220> FEATURE:
<223> OTHER INFORMATION: 5606 Synthetic HPV33 L1 gene

<400> SEQUENCE: 136

```
ctgggtacca tgagtgtgtg agaccatct gaggctacag tctacctgcc tcctgtgcct     60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg acaaccact gggagtgggc    360
atctctggac acccactgct gaacaagttt gatgacacag agacaggcaa caatacccct    420
ggacaacctg agcagacaa cagggagtgt ctgagtatgg actacaagca gacccaactt    480
tgtctgctgg gctgtaagcc tccaacagga gaacactggg gcagggagt ggcttgtacc    540
aatgctgccc ctgccaatga ctgtcctcca ttggaactga taaacaccat cattgaggat    600
ggagatatgg tggacacagg ctttggctgt atggacttca gaccctcca gccaacaag    660
tctgatgtgc caattgacat ctgtggcagc acttgtaaat accctgacta cctgaaaatg    720
acctctgaac catatggaga ctcccctgttc ttcttcctga ggagggaaca gatgtttgtg    780
agacacttct tcaacagggc tggcaccctg ggagaggctg tgcctgatga cctctacatc    840
aagggctctg gcaccacagc cagcatccag tcctctgcct tctttccaac accatctggc    900
```

-continued

```
agtatggtga cctctgagag ccaacttttc aacaagccat actggctcca aagggctcaa    960
ggacacaaca atggcatctg ttggggcaac caggtgtttg tgacagtggt ggacaccacc   1020
aggagcacca atatgaccct gtgtacccag gtgacctctg acagcaccta caagaatgag   1080
aacttcaagg aatacatcag gcatgtggag gaatatgacc tccaatttgt gttccaactt   1140
tgtaaggtga ccctgacagc agaggtgatg acctacatcc atgctatgaa ccctgacatc   1200
ttggaggact ggcagtttgg actgacacct cctccatctg cctccctcca agacacctac   1260
aggtttgtga ccagccaggc tatcacttgt cagaagacag tgcctccaaa ggagaaggag   1320
gacccactgg gcaaatacac cttctgggag gtggacctga agagaagtt ctctgctgac   1380
ctggaccagt ttccactggg caggaagttc ctgctccaag caggactgaa agccaagcca   1440
aaactgaaaa gggctgcccc aaccagcacc aggacctcct ctgccaagag gaagaaggtg   1500
aagaagtaaa ctcgagctc                                               1519
```

<210> SEQ ID NO 137
<211> LENGTH: 33
<212> TYPE: DNA
<213> ORGANISM: Artificial sequence
<220> FEATURE:
<223> OTHER INFORMATION: 5607 HPV56L1 F1

<400> SEQUENCE: 137

```
cttggtacca tggctacctg gagaccatct gag                                 33
```

<210> SEQ ID NO 138
<211> LENGTH: 31
<212> TYPE: DNA
<213> ORGANISM: Artificial sequence
<220> FEATURE:
<223> OTHER INFORMATION: 5608 HPV56L1 R1

<400> SEQUENCE: 138

```
ctgcttggag caggaacttc ctgcccagtg g                                   31
```

<210> SEQ ID NO 139
<211> LENGTH: 1420
<212> TYPE: DNA
<213> ORGANISM: Artificial sequence
<220> FEATURE:
<223> OTHER INFORMATION: 5609 HPV56L1 amplified sequence 1

<400> SEQUENCE: 139

```
cttggtacca tggctacctg gagaccatct gagaacaagg tctacctgcc tccaacacct     60
gtgagcaagg tggtggctac agactcctat gtgaaggga ccagcatctt ctaccatgct    120
ggctccagca gactgctggc tgtgggacac ccatactact ctgtgaccaa ggacaacacc    180
aagaccaaca tcccaaaggt gtctgcctac caatacaggg tgttcagggt gagactgcct    240
gacccaaaca gtttggact gcctgacacc aacatctaca ccctgacca ggagagactg    300
gtgtgggctt gtgtgggatt ggaggtgggc aggggacaac cactgggagc aggactgtct    360
ggacacccac tgttcaacag actggatgac acagagtcca gcaacctggc taacaacaat    420
gtgattgagg acagcaggga caacatctct gtggatggca agcagaccca actttgtatt    480
gtgggctgta ctcctgctat gggagaacac tggaccaagg agcagtgtg taagagcacc    540
caggtgacca caggagactg tcctccactg gctctgataa acaccaat tgaggatgga    600
gatatgattg acacaggctt tggagctatg gacttcaagg tgctccaaga gagcaaggct    660
```

```
gaggtgccac tggacattgt ccagagcact tgtaaatacc ctgactacct gaaaatgagt    720
gctgatgcct atggagacag tatgtggttc tacctgagga gggaacaact ttttgccaga    780
cactacttca acagggctgg caaggtggga gagaccatcc ctgctgaact ctacctgaaa    840
ggcagcaatg gcagggaacc tcctccatcc tctgtctatg tggctacacc atctggcagt    900
atgattacct ctgaggctca acttttcaac aagccatact ggctccaaag ggctcaagga    960
cacaacaatg gcatctgttg gggcaaccaa cttttgtga cagtggtgga caccaccagg    1020
agcaccaata tgaccatcag cacagccaca gaacaactta gcaaatatga tgccaggaag    1080
ataaaccaat acctgaggca tgtggaggaa tatgaactcc aatttgtgtt ccaactttgt    1140
aagattaccc tgtctgctga ggtgatggct tacctgcaca atatgaatgc caacctgttg    1200
gaggactgga acattggact gagccctcct gtggctacct ccttggagga caaatacaga    1260
tatgtgagga gcacagccat cacttgtcag agggaacaac ctccaacaga gaagcaggac    1320
ccactggcta aatacaagtt ctgggatgtg aacctccaag actccttcag cacagacctg    1380
gaccagtttc cactgggcag gaagttcctg ctccaagcag                         1420
```

```
<210> SEQ ID NO 140
<211> LENGTH: 36
<212> TYPE: DNA
<213> ORGANISM: Artificial sequence
<220> FEATURE:
<223> OTHER INFORMATION: 5610 HPV56L1 F2

<400> SEQUENCE: 140
gaagttcctg ctccaagcag gactgaaagc caagcc                             36

<210> SEQ ID NO 141
<211> LENGTH: 36
<212> TYPE: DNA
<213> ORGANISM: Artificial sequence
<220> FEATURE:
<223> OTHER INFORMATION: 5611 HPV56L1 R2

<400> SEQUENCE: 141
ctgtctagat ttacttcttc accttcttcc tcttgg                             36

<210> SEQ ID NO 142
<211> LENGTH: 116
<212> TYPE: DNA
<213> ORGANISM: Artificial sequence
<220> FEATURE:
<223> OTHER INFORMATION: 5612 HPV56L1 amplified sequence 2

<400> SEQUENCE: 142
gaagttcctg ctccaagcag gactgaaagc caagccaaaa ctgaaagggg ctgccccaac    60
cagcaccagg acctcctctg ccaagaggaa gaaggtgaag aagtaaatct agacag       116

<210> SEQ ID NO 143
<211> LENGTH: 38
<212> TYPE: PRT
<213> ORGANISM: Homo sapiens
<220> FEATURE:
<221> NAME/KEY: misc_feature
<223> OTHER INFORMATION: 5613 Amino acid sequence of HPV type 59 L1
      protein aa 471-508

<400> SEQUENCE: 143

Leu Gln Leu Gly Ala Arg Pro Lys Pro Thr Ile Gly Pro Arg Lys Arg
1               5                   10                  15
```

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 144
<211> LENGTH: 473
<212> TYPE: PRT
<213> ORGANISM: Homo sapiens
<220> FEATURE:
<221> NAME/KEY: misc_feature
<223> OTHER INFORMATION: 5801 Amino acid sequence of HPV type 58 L1
      protein aa 1-473

<400> SEQUENCE: 144

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly Asn Pro
        35                  40                  45

Tyr Phe Ser Ile Lys Ser Pro Asn Asn Asn Lys Lys Val Leu Val Pro
50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Val Ser Gly His Pro Tyr Leu Asn Lys Phe Asp
        115                 120                 125

Asp Thr Glu Thr Ser Asn Arg Tyr Pro Ala Gln Pro Gly Ser Asp Asn
130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
                165                 170                 175

Asn Asn Asn Ala Ala Ala Thr Asp Cys Pro Pro Leu Glu Leu Phe Asn
            180                 185                 190

Ser Ile Ile Glu Asp Gly Asp Met Val Asp Thr Gly Phe Gly Cys Met
        195                 200                 205

Asp Phe Gly Thr Leu Gln Ala Asn Lys Ser Asp Val Pro Ile Asp Ile
210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Lys Leu Gly Glu Ala Val Pro
            260                 265                 270

Asp Asp Leu Tyr Ile Lys Gly Ser Gly Asn Thr Ala Val Ile Gln Ser
        275                 280                 285

Ser Ala Phe Phe Pro Thr Pro Ser Gly Ser Ile Val Thr Ser Glu Ser
290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr

```
                        325                 330                 335

Thr Arg Ser Thr Asn Met Thr Leu Cys Thr Glu Val Thr Lys Glu Gly
            340                 345                 350

Thr Tyr Lys Asn Asp Asn Phe Lys Glu Tyr Val Arg His Val Glu Glu
            355                 360                 365

Tyr Asp Leu Gln Phe Val Phe Gln Leu Cys Lys Ile Thr Leu Thr Ala
    370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Ala Pro
                420                 425                 430

Pro Lys Glu Lys Glu Asp Pro Leu Asn Lys Tyr Thr Phe Trp Glu Val
                435                 440                 445

Asn Leu Lys Glu Lys Phe Ser Ala Asp Leu Asp Gln Phe Pro Leu Gly
            450                 455                 460

Arg Lys Phe Leu Leu Gln Ser Gly Leu
465                 470

<210> SEQ ID NO 145
<211> LENGTH: 26
<212> TYPE: PRT
<213> ORGANISM: Homo sapiens
<220> FEATURE:
<221> NAME/KEY: misc_feature
<223> OTHER INFORMATION: 5802 Amino acid sequence of HPV type 33 L1
      protein aa 474-499

<400> SEQUENCE: 145

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25

<210> SEQ ID NO 146
<211> LENGTH: 499
<212> TYPE: PRT
<213> ORGANISM: Artificial sequence
<220> FEATURE:
<223> OTHER INFORMATION: 5803 Amino acid sequence of chimeric HPV type
      58 L1 protein

<400> SEQUENCE: 146

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly Asn Pro
        35                  40                  45

Tyr Phe Ser Ile Lys Ser Pro Asn Asn Asn Lys Lys Val Leu Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110
```

Pro Leu Gly Val Gly Val Ser Gly His Pro Tyr Leu Asn Lys Phe Asp
            115                 120                 125

Asp Thr Glu Thr Ser Asn Arg Tyr Pro Ala Gln Pro Gly Ser Asp Asn
130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
                165                 170                 175

Asn Asn Asn Ala Ala Thr Asp Cys Pro Pro Leu Glu Leu Phe Asn
            180                 185                 190

Ser Ile Ile Glu Asp Gly Asp Met Val Asp Thr Gly Phe Gly Cys Met
        195                 200                 205

Asp Phe Gly Thr Leu Gln Ala Asn Lys Ser Asp Val Pro Ile Asp Ile
    210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Leu Arg Arg Glu Gln Met Phe
                245                 250                 255

Val Arg His Phe Phe Asn Arg Ala Gly Lys Leu Gly Glu Ala Val Pro
        260                 265                 270

Asp Asp Leu Tyr Ile Lys Gly Ser Gly Asn Thr Ala Val Ile Gln Ser
    275                 280                 285

Ser Ala Phe Phe Pro Thr Pro Ser Gly Ser Ile Val Thr Ser Glu Ser
290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Asp Thr
            325                 330                 335

Thr Arg Ser Thr Asn Met Thr Leu Cys Thr Glu Val Thr Lys Glu Gly
                340                 345                 350

Thr Tyr Lys Asn Asp Asn Phe Lys Glu Tyr Val Arg His Val Glu Glu
            355                 360                 365

Tyr Asp Leu Gln Phe Val Phe Gln Leu Cys Lys Ile Thr Leu Thr Ala
370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Ala Pro
            420                 425                 430

Pro Lys Glu Lys Glu Asp Pro Leu Asn Lys Tyr Thr Phe Trp Glu Val
        435                 440                 445

Asn Leu Lys Glu Lys Phe Ser Ala Asp Leu Asp Gln Phe Pro Leu Gly
450                 455                 460

Arg Lys Phe Leu Leu Gln Ser Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys

<210> SEQ ID NO 147
<211> LENGTH: 1501
<212> TYPE: DNA
<213> ORGANISM: Artificial sequence

```
<220> FEATURE:
<223> OTHER INFORMATION: 5804 Nucleotide sequence of chimeric HPV type
      58 L1 protein

<400> SEQUENCE: 147
atgagcgtgt ggaggcccag cgaggccacc gtgtacctgc ccccgtgcc cgtgagcaag      60 gtggtgagca ccgacgagta cgtgagcagg accagcatct actactacgc cggcagcagc    120
aggctgctgg ccgtgggcaa ccctacttc agcatcaaga ccccaacaa caacaagaag     180 gtgctggtgc ccaaggtgag cggcctgcag tacagggtgt tcagggtgag gctgcccgac    240
cccaacaagt tcggcttccc cgacaccagc ttctacaacc ccgacaccca gaggctggtg    300
tgggcctgcg tgggcctgga gatcggcagg ggccagcccc tgggcgtggg cgtgagcggc    360 caccccctacc tgaacaagtt cgacgacacc gagaccagca caggtaccc cgcccagccc    420 ggcagcgaca cagggagtg cctgagcatg gactacaagc agacccagct gtgcctgatc    480
ggctgcaagc cccccaccgg cgagcactgg ggcaagggcg tggcctgcaa caacaacgcc    540
gccgccaccg actgccccc cctggagctg ttcaacagca tcatcgagga cggcgacatg    600
gtggacaccg gcttcggctg catggacttc ggcaccctgc aggccaacaa gagcgacgtg    660
cccatcgaca tctgcaacag cacctgcaag taccccgact acctgaagat ggccagcgag    720
ccctacggcg acagcctgtt cttcttcctg aggagggagc agatgttcgt gaggcacttc    780
ttcaacaggg ccggcaagct gggcgaggcc gtgcccgacg acctgtacat caagggcagc    840
ggcaacaccg ccgtgatcca gagcagcgcc ttcttcccca ccccagcgg cagcatcgtg    900 accagcgaga gccagctgtt caacaagccc tactggctgc agagggccca gggccacaac    960
aacggcatct gctggggcaa ccagctgttc gtgaccgtgg tggacaccac caggagcacc   1020
aacatgaccc tgtgcaccga ggtgaccaag gagggcacct acaagaacga caacttcaag   1080
gagtacgtga ggcacgtgga ggagtacgac ctgcagttcg tgttccagct gtgcaagatc   1140
accctgaccg ccgagatcat gacctacatc cacaccatgg acagcaacat cctggaggac   1200
tggcagttcg gcctgacccc cccccccagc gccagcctgc aggacaccta caggttcgtg   1260
accagccagg ccatcacctg ccagaagacc gccccccca aggagaagga ggaccccctg   1320
aacaagtaca ccttctggga ggtgaacctg aaggagaagt cagcgccga cctggaccag   1380 ttccccctgg gcaggaagtt cctgctgcag agcggcctga agccaagcc aaaactgaaa   1440 agggctgccc caaccagcac caggacctcc tctgccaaga ggaagaaggt gaagaagtaa   1500
a                                                                    1501

<210> SEQ ID NO 148
<211> LENGTH: 1516
<212> TYPE: DNA
<213> ORGANISM: Artificial sequence
<220> FEATURE:
<223> OTHER INFORMATION: 5805 Synthetic HPV58 L1 gene

<400> SEQUENCE: 148
ctgggtacca tgagcgtgtg gaggcccagc gaggccaccg tgtacctgcc ccccgtgccc     60
gtgagcaagg tggtgagcac cgacgagtac gtgagcagga ccagcatcta ctactacgcc    120
ggcagcagca ggctgctggc cgtgggcaac ccctacttca gcatcaagag ccccaacaac    180
aacaagaagg tgctggtgcc caaggtgagc ggcctgcagt acagggtgtt cagggtgagg    240
ctgcccgacc ccaacaagtt cggcttcccc gacaccagct tctacaaccc cgacacccag    300
aggctggtgt gggcctgcgt gggcctggag atcggcaggg gccagcccct gggcgtgggc    360
```

| | |
|---|---|
| gtgagcggcc acccctacct gaacaagttc gacgacaccg agaccagcaa caggtacccc | 420 |
| gcccagcccg gcagcgacaa cagggagtgc ctgagcatgg actacaagca gacccagctg | 480 |
| tgcctgatcg gctgcaagcc ccccaccggc gagcactggg gcaagggcgt ggcctgcaac | 540 |
| aacaacgccc ccgccaccga ctgccccccc ctggagctgt tcaacagcat catcgaggac | 600 |
| ggcgacatgg tggacaccgg cttcggctgc atggacttcg gcaccctgca ggccaacaag | 660 |
| agcgacgtgc ccatcgacat ctgcaacagc acctgcaagt accccgacta cctgaagatg | 720 |
| gccagcgagc cctacggcga cagcctgttc ttcttcctga ggagggagca gatgttcgtg | 780 |
| aggcacttct tcaacagggc cggcaagctg ggcgaggccg tgcccgacga cctgtacatc | 840 |
| aagggcagcg gcaacaccgc cgtgatccag agcagcgcct tcttccccac ccccagcggc | 900 |
| agcatcgtga ccagcgagag ccagctgttc aacaagccct actggctgca gagggcccag | 960 |
| ggccacaaca acggcatctg ctggggcaac cagctgttcg tgaccgtggt ggacaccacc | 1020 |
| aggagccacc acatgaccct gtgcaccgag gtgaccaagg agggcaccta caagaacgac | 1080 |
| aacttcaagg agtacgtgag gcacgtggag gagtacgacc tgcagttcgt gttccagctg | 1140 |
| tgcaagatca ccctgaccgc cgagatcatg acctacatcc acaccatgga cagcaacatc | 1200 |
| ctggaggact ggcagttcgg cctgaccccc cccccagcg ccagcctgca ggacacctac | 1260 |
| aggttcgtga ccagccaggc catcacctgc cagaagaccg ccccccccaa ggagaaggag | 1320 |
| gacccctga caagtacac cttctgggag gtgaacctga aggagaagtt cagcgccgac | 1380 |
| ctggaccagt tccccctggg caggaagttc ctgctgcaga gcggcctgaa ggccaagccc | 1440 |
| aggctgaaga ggagcgcccc caccaccagg gcccccagca ccaagaggaa gaaggtgaag | 1500 |
| aagtaaactc gagctc | 1516 |

<210> SEQ ID NO 149
<211> LENGTH: 1519
<212> TYPE: DNA
<213> ORGANISM: Artificial sequence
<220> FEATURE:
<223> OTHER INFORMATION: 5806 Synthetic HPV33 L1 gene

<400> SEQUENCE: 149

| | |
|---|---|
| ctgggtacca tgagtgtgtg gagaccatct gaggctacag tctacctgcc tcctgtgcct | 60 |
| gtgagcaagg tggtgagcac agatgaatat gtgagcagga ccagcatcta ctactatgct | 120 |
| ggctccagca gactgctggc tgtgggacac ccatacttca gcatcaagaa cccaaccaat | 180 |
| gccaagaaac tgctggtgcc aaaggtgtct ggactccaat acagggtgtt cagggtgaga | 240 |
| ctgcctgacc caaacaagtt tggctttcct gacacctcct tctacaaccc tgacacccag | 300 |
| agactggtgt gggcttgtgt gggattggag attggcaggg acaaccact gggagtgggc | 360 |
| atctctggac acccactgct gaacaagttt gatgacacag agacaggcaa caaatacccc | 420 |
| ggacaacctg gagcagacaa cagggagtgt ctgagtatgg actacaagca gacccaactt | 480 |
| tgtctgctgg gctgtaagcc tccaacagga gaacactggg gcaagggagt ggcttgtacc | 540 |
| aatgctgccc ctgccaatga ctgtcctcca ttggaactga taacaccat cattgaggat | 600 |
| ggagatatgg tggacacagg cttggctgt atggacttca gaccctcca gccaacaag | 660 |
| tctgatgtgc caattgacat ctgtggcagc acttgtaaat accctgacta cctgaaaatg | 720 |
| acctctgaac catatggaga ctccctgttc ttcttcctga ggggaaca gatgtttgtg | 780 |
| agacacttct tcaacagggc tggcaccctg ggagaggctg tgcctgatga cctctacatc | 840 |

```
aagggctctg gcaccacagc cagcatccag tcctctgcct tctttccaac accatctggc    900
agtatggtga cctctgagag ccaacttttc aacaagccat actggctcca aagggctcaa    960
ggacacaaca atggcatctg ttggggcaac caggtgtttg tgacagtggt ggacaccacc   1020
aggagcacca atatgaccct gtgtaccccag gtgacctctg acagcaccta caagaatgag   1080
```

```
aacttcaagg aatacatcag gcatgtggag gaatatgacc tccaatttgt gttccaactt   1140
tgtaaggtga ccctgacagc agaggtgatg acctacatcc atgctatgaa ccctgacatc   1200
ttggaggact ggcagtttgg actgacacct cctccatctg cctccctcca agacacctac   1260
aggtttgtga ccagccaggc tatcacttgt cagaagacag tgcctccaaa ggagaaggag   1320
gacccactgg gcaaatacac cttctgggag gtggacctga agagaagtt ctctgctgac   1380 ctggaccagt ttccactggg caggaagttc ctgctccaag caggactgaa agccaagcca   1440
aaactgaaaa gggctgcccc aaccagcacc aggacctcct ctgccaagag gaagaaggtg   1500
aagaagtaaa ctcgagctc                                                1519
```

```
<210> SEQ ID NO 150
<211> LENGTH: 34
<212> TYPE: DNA
<213> ORGANISM: Artificial sequence
<220> FEATURE:
<223> OTHER INFORMATION: 5807 HPV58L1 F1

<400> SEQUENCE: 150
cttggtacca tgagcgtgtg gaggcccagc gagg                                 34

<210> SEQ ID NO 151
<211> LENGTH: 36
<212> TYPE: DNA
<213> ORGANISM: Artificial sequence
<220> FEATURE:
<223> OTHER INFORMATION: 5808 HPV58L1 R1

<400> SEQUENCE: 151
gcttggcttt caggccgctc tgcagcagga acttcc                               36

<210> SEQ ID NO 152
<211> LENGTH: 1438
<212> TYPE: DNA
<213> ORGANISM: Artificial sequence
<220> FEATURE:
<223> OTHER INFORMATION: 5809 HPV58L1 amplified sequence 1

<400> SEQUENCE: 152
cttggtacca tgagcgtgtg gaggcccagc gaggccaccg tgtacctgcc ccccgtgccc     60
gtgagcaagg tggtgagcac cgacgagtac gtgagcagga ccagcatcta ctactacgcc    120
ggcagcagca ggctgctggc cgtgggcaac ccctacttca gcatcaagag ccccaacaac    180
aacaagaagg tgctggtgcc caaggtgagc ggcctgcagt acagggtgtt cagggtgagg    240
ctgcccgacc ccaacaagtt cggcttcccc gacaccagct ctacaacccc gacacccag    300 aggctggtgt gggcctgcgt gggcctggag atcggcaggg ccagcccct gggcgtgggc    360 gtgagcggcc acccctacct gaacaagttc gacgacaccg agaccagcaa caggtacccc    420
gcccagcccg gcagcgacaa cagggagtgc ctgagcatgg actacaagca gacccagctg    480
tgcctgatcg gctgcaagcc ccccaccggc gagcactggg gcaagggcgt ggcctgcaac    540
aacaacgccg ccgccaccga ctgccccccc ctggagctgt tcaacagcat catcgaggac    600
ggcgacatgg tggacaccgg cttcggctgc atggacttcg gcaccctgca ggccaacaag    660
```

```
agcgacgtgc ccatcgacat ctgcaacagc acctgcaagt accccgacta cctgaagatg    720
gccagcgagc cctacggcga cagcctgttc ttcttcctga ggagggagca gatgttcgtg    780
aggcacttct tcaacagggc cggcaagctg ggcgaggccg tgcccgacga cctgtacatc    840
aagggcagcg gcaacaccgc cgtgatccag agcagcgcct tcttccccac ccccagcggc    900
agcatcgtga ccagcgagag ccagctgttc aacaagccct actggctgca gagggcccag    960
ggccacaaca acggcatctg ctggggcaac cagctgttcg tgaccgtggt ggacaccacc   1020
aggagcacca acatgaccct gtgcaccgag gtgaccaagg agggcaccta caagaacgac   1080
aacttcaagg agtacgtgag gcacgtggag gagtacgacc tgcagttcgt gttccagctg   1140
tgcaagatca ccctgaccgc cgagatcatg acctacatcc acaccatgga cagcaacatc   1200
ctggaggact ggcagttcgg cctgaccccc cccccagcg ccagcctgca ggacacctac   1260
aggttcgtga ccagccaggc catcacctgc cagaagaccg ccccccccaa ggagaaggag   1320
gaccccctga caagtacac cttctgggag gtgaacctga aggagaagtt cagcgccgac   1380
ctggaccagt tcccctggg caggaagttc ctgctgcaga gcggcctgaa agccaagc     1438
```

<210> SEQ ID NO 153
<211> LENGTH: 35
<212> TYPE: DNA
<213> ORGANISM: Artificial sequence
<220> FEATURE:
<223> OTHER INFORMATION: 5810 HPV58L1 F2

<400> SEQUENCE: 153

```
gagcggcctg aaagccaagc caaaactgaa aaggg                                35
```

<210> SEQ ID NO 154
<211> LENGTH: 36
<212> TYPE: DNA
<213> ORGANISM: Artificial sequence
<220> FEATURE:
<223> OTHER INFORMATION: 5811 HPV58L1 R2

<400> SEQUENCE: 154

```
ctgtctagat ttacttcttc accttcttcc tcttgg                               36
```

<210> SEQ ID NO 155
<211> LENGTH: 101
<212> TYPE: DNA
<213> ORGANISM: Artificial sequence
<220> FEATURE:
<223> OTHER INFORMATION: 5812 HPV58L1 amplified sequence 2

<400> SEQUENCE: 155

```
gagcggcctg aaagccaagc caaaactgaa aagggctgcc ccaaccagca ccaggacctc    60
ctctgccaag aggaagaagg tgaagaagta aatctagaca g                        101
```

<210> SEQ ID NO 156
<211> LENGTH: 38
<212> TYPE: PRT
<213> ORGANISM: Homo sapiens
<220> FEATURE:
<221> NAME/KEY: misc_feature
<223> OTHER INFORMATION: 5813 Amino acid sequence of HPV type 59 L1
      protein aa 471-508

<400> SEQUENCE: 156

```
Leu Gln Leu Gly Ala Arg Pro Lys Pro Thr Ile Gly Pro Arg Lys Arg
1               5                   10                  15
```

Ala Ala Pro Ala Pro Thr Ser Thr Pro Ser Pro Lys Arg Val Lys Arg
            20                  25                  30

Arg Lys Ser Ser Arg Lys
        35

<210> SEQ ID NO 157
<211> LENGTH: 4
<212> TYPE: PRT
<213> ORGANISM: Human Papillomavirus
<220> FEATURE:
<221> NAME/KEY: misc_feature
<222> LOCATION: (1)..(4)
<223> OTHER INFORMATION: Tetrapeptide in L1 protein of each HPV type

<400> SEQUENCE: 157

Arg Lys Phe Leu
1

<210> SEQ ID NO 158
<211> LENGTH: 6
<212> TYPE: PRT
<213> ORGANISM: Human Papillomavirus
<220> FEATURE:
<221> NAME/KEY: misc_feature
<222> LOCATION: (1)..(6)
<223> OTHER INFORMATION: Hexapeptide in L1 protein of each HPV type

<400> SEQUENCE: 158

Leu Gly Arg Lys Phe Leu
1               5

<210> SEQ ID NO 159
<211> LENGTH: 18
<212> TYPE: PRT
<213> ORGANISM: Human Papillomavirus
<220> FEATURE:
<221> NAME/KEY: misc_feature
<222> LOCATION: (1)..(18)
<223> OTHER INFORMATION: Epitope of the L1 protein

<400> SEQUENCE: 159

Glu Glu Tyr Asp Leu Gln Phe Ile Phe Gln Leu Cys Lys Ile Thr Leu
1               5                   10                  15

Thr Ala

<210> SEQ ID NO 160
<211> LENGTH: 21
<212> TYPE: PRT
<213> ORGANISM: Human Papillomavirus
<220> FEATURE:
<221> NAME/KEY: misc_feature
<222> LOCATION: (1)..(21)
<223> OTHER INFORMATION: Epitope of the L1 protein

<400> SEQUENCE: 160

Arg His Gly Glu Glu Tyr Asp Leu Gln Phe Ile Phe Gln Leu Cys Lys
1               5                   10                  15

Ile Thr Leu Thr Ala
            20

<210> SEQ ID NO 161
<211> LENGTH: 7
<212> TYPE: PRT
<213> ORGANISM: Human Papillomavirus
<220> FEATURE:
<221> NAME/KEY: misc_feature

```
<222> LOCATION: (1)..(7)
<223> OTHER INFORMATION: Epitope of the L1 protein

<400> SEQUENCE: 161

Leu Pro Asp Pro Asn Lys Phe
1               5

<210> SEQ ID NO 162
<211> LENGTH: 10
<212> TYPE: PRT
<213> ORGANISM: Human Papillomavirus
<220> FEATURE:
<221> NAME/KEY: misc_feature
<222> LOCATION: (1)..(10)
<223> OTHER INFORMATION: Epitope of the L1 protein

<400> SEQUENCE: 162

Pro Glu Thr Gln Arg Leu Val Trp Ala Cys
1               5                   10

<210> SEQ ID NO 163
<211> LENGTH: 8
<212> TYPE: PRT
<213> ORGANISM: Human Papillomavirus
<220> FEATURE:
<221> NAME/KEY: misc_feature
<222> LOCATION: (1)..(8)
<223> OTHER INFORMATION: Epitope of the L1 protein

<400> SEQUENCE: 163

Pro Val Pro Gly Gln Tyr Asp Ala
1               5

<210> SEQ ID NO 164
<211> LENGTH: 12
<212> TYPE: PRT
<213> ORGANISM: Human Papillomavirus
<220> FEATURE:
<221> NAME/KEY: misc_feature
<222> LOCATION: (1)..(12)
<223> OTHER INFORMATION: Epitope of the L1 protein

<400> SEQUENCE: 164

Tyr Asn Pro Glu Thr Gln Arg Leu Val Trp Ala Cys
1               5                   10

<210> SEQ ID NO 165
<211> LENGTH: 8
<212> TYPE: PRT
<213> ORGANISM: Human Papillomavirus
<220> FEATURE:
<221> NAME/KEY: misc_feature
<222> LOCATION: (1)..(8)
<223> OTHER INFORMATION: Epitope of the L1 protein

<400> SEQUENCE: 165

Asp Thr Gly Tyr Gly Ala Met Asp
1               5

<210> SEQ ID NO 166
<211> LENGTH: 10
<212> TYPE: PRT
<213> ORGANISM: Human Papillomavirus
<220> FEATURE:
<221> NAME/KEY: misc_feature
<222> LOCATION: (1)..(10)
<223> OTHER INFORMATION: Epitope of the L1 protein

<400> SEQUENCE: 166
```

```
Pro Val Pro Gly Gln Tyr Asp Ala Thr Lys
1               5                   10
```

<210> SEQ ID NO 167
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: Epitope of the L1 protein

<400> SEQUENCE: 167

```
Lys Gln Asp Ile Pro Lys Val Ser Ala Tyr Gln Tyr Arg Val Phe Arg
1               5                   10                  15

Val
```

<210> SEQ ID NO 168
<211> LENGTH: 15
<212> TYPE: PRT
<213> ORGANISM: Human Papillomavirus
<220> FEATURE:
<221> NAME/KEY: misc_feature
<222> LOCATION: (1)..(15)
<223> OTHER INFORMATION: Epitope of the L1 protein

<400> SEQUENCE: 168

```
Arg Asp Asn Val Ser Val Asp Tyr Lys Gln Thr Gln Leu Cys Ile
1               5                   10                  15
```

<210> SEQ ID NO 169
<211> LENGTH: 14
<212> TYPE: PRT
<213> ORGANISM: Human Papillomavirus
<220> FEATURE:
<221> NAME/KEY: misc_feature
<222> LOCATION: (1)..(14)
<223> OTHER INFORMATION: Epitope of the L1 protein

<400> SEQUENCE: 169

```
Tyr Ser Arg His Val Glu Glu Tyr Asp Leu Gln Phe Ile Phe
1               5                   10
```

<210> SEQ ID NO 170
<211> LENGTH: 505
<212> TYPE: PRT
<213> ORGANISM: Human Papillomavirus
<220> FEATURE:
<221> NAME/KEY: misc_feature
<222> LOCATION: (1)..(505)
<223> OTHER INFORMATION: Amino Acid Sequence of Native HPV16L1

<400> SEQUENCE: 170

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
```

```
                    85                  90                  95
Arg Leu Val Trp Ala Cys Val Gly Val Glu Val Gly Arg Gly Gln Pro
                100                 105                 110
Leu Gly Val Gly Ile Ser Gly His Pro Leu Leu Asn Lys Leu Asp Asp
            115                 120                 125
Thr Glu Asn Ala Ser Ala Tyr Ala Ala Asn Ala Gly Val Asp Asn Arg
        130                 135                 140
Glu Cys Ile Ser Met Asp Tyr Lys Gln Thr Gln Leu Cys Leu Ile Gly
145                 150                 155                 160
Cys Lys Pro Pro Ile Gly Glu His Trp Gly Lys Gly Ser Pro Cys Thr
                165                 170                 175
Asn Val Ala Val Asn Pro Gly Asp Cys Pro Pro Leu Glu Leu Ile Asn
            180                 185                 190
Thr Val Ile Gln Asp Gly Asp Met Val Asp Thr Gly Phe Gly Ala Met
        195                 200                 205
Asp Phe Thr Thr Leu Gln Ala Asn Lys Ser Glu Val Pro Leu Asp Ile
    210                 215                 220
Cys Thr Ser Ile Cys Lys Tyr Pro Asp Tyr Ile Lys Met Val Ser Glu
225                 230                 235                 240
Pro Tyr Gly Asp Ser Leu Phe Phe Tyr Leu Arg Arg Glu Gln Met Phe
                245                 250                 255
Val Arg His Leu Phe Asn Arg Ala Gly Ala Val Gly Glu Asn Val Pro
            260                 265                 270
Asp Asp Leu Tyr Ile Lys Gly Ser Gly Ser Thr Ala Asn Leu Ala Ser
        275                 280                 285
Ser Asn Tyr Phe Pro Thr Pro Ser Gly Ser Met Val Thr Ser Asp Ala
    290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
        355                 360                 365
Glu Tyr Asp Leu Gln Phe Ile Phe Gln Leu Cys Lys Ile Thr Leu Thr
    370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Gly Gly Thr Leu Glu Asp
                405                 410                 415
Thr Tyr Arg Phe Val Thr Ser Gln Ala Ile Ala Cys Gln Lys His Thr
            420                 425                 430
Pro Pro Ala Pro Lys Glu Asp Pro Leu Lys Lys Tyr Thr Phe Trp Glu
        435                 440                 445
Val Asn Leu Lys Glu Lys Phe Ser Ala Asp Leu Asp Gln Phe Pro Leu
    450                 455                 460
Gly Arg Lys Phe Leu Leu Gln Ala Gly Leu Lys Ala Lys Pro Lys Phe
465                 470                 475                 480
Thr Leu Gly Lys Arg Lys Ala Thr Pro Thr Thr Ser Ser Thr Ser Thr
                485                 490                 495
Thr Ala Lys Arg Lys Lys Arg Lys Leu
            500                 505
```

<210> SEQ ID NO 171
<211> LENGTH: 502
<212> TYPE: PRT
<213> ORGANISM: Human Papillomavirus
<220> FEATURE:
<221> NAME/KEY: misc_feature
<222> LOCATION: (1)..(502)
<223> OTHER INFORMATION: Amino Acid Sequence of Native HPV35L1

<400> SEQUENCE: 171

Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
        35                  40                  45

Tyr Tyr Ala Ile Lys Lys Gln Asp Ser Asn Lys Ile Ala Val Pro Lys
    50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ser Asn Lys Tyr Val Gly Asn Ser Gly Thr Asp Asn Arg
130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
    210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Asp Ser Thr
            340                 345                 350

```
Tyr Lys Asn Asp Asn Phe Lys Glu Tyr Leu Arg His Gly Glu Glu Tyr
            355                 360                 365

Asp Leu Gln Phe Ile Phe Gln Leu Cys Lys Ile Thr Leu Thr Ala Asp
370                 375                 380

Val Met Thr Tyr Ile His Ser Met Asn Pro Ser Ile Leu Glu Asp Trp
385                 390                 395                 400

Asn Phe Gly Leu Thr Pro Pro Ser Gly Thr Leu Glu Asp Thr Tyr
            405                 410                 415

Arg Tyr Val Thr Ser Gln Ala Val Thr Cys Gln Lys Pro Ser Ala Pro
            420                 425                 430

Lys Pro Lys Asp Asp Pro Leu Lys Asn Tyr Thr Phe Trp Glu Val Asp
            435                 440                 445

Leu Lys Glu Lys Phe Ser Ala Asp Leu Asp Gln Phe Pro Leu Gly Arg
450                 455                 460

Lys Phe Leu Leu Gln Ala Gly Leu Lys Ala Arg Pro Asn Phe Arg Leu
465                 470                 475                 480

Gly Lys Arg Ala Ala Pro Ala Ser Thr Ser Lys Lys Ser Ser Thr Lys
            485                 490                 495

Arg Arg Lys Val Lys Ser
            500

<210> SEQ ID NO 172
<211> LENGTH: 501
<212> TYPE: PRT
<213> ORGANISM: Human Papillomavirus
<220> FEATURE:
<221> NAME/KEY: misc_feature
<222> LOCATION: (1)..(501)
<223> OTHER INFORMATION: Amino Acid Sequence of Native HPV11L1

<400> SEQUENCE: 172

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
```

-continued

```
                195                 200                 205
Asp Leu Gln Thr Asn Lys Ser Asp Val Pro Leu Asp Ile Cys Gly Thr
210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
                485                 490                 495

Thr Lys Thr Lys Lys
            500
```

<210> SEQ ID NO 173
<211> LENGTH: 507
<212> TYPE: PRT
<213> ORGANISM: Human Papillomavirus
<220> FEATURE:
<221> NAME/KEY: misc_feature
<222> LOCATION: (1)..(507)
<223> OTHER INFORMATION: Amino Acid Sequence of Native HPV18L1

<400> SEQUENCE: 173

```
Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
        35                  40                  45
```

```
Tyr Phe Arg Val Pro Ala Gly Gly Asn Lys Gln Asp Ile Pro Lys
     50                  55                  60

Val Ser Ala Tyr Gln Tyr Arg Val Phe Arg Val Gln Leu Pro Asp Pro
 65              70                  75                  80

Asn Lys Phe Gly Leu Pro Asp Thr Ser Ile Tyr Asn Pro Glu Thr Gln
                 85                  90                  95

Arg Leu Val Trp Ala Cys Ala Gly Val Glu Ile Gly Arg Gly Gln Pro
                100                 105                 110

Leu Gly Val Gly Leu Ser Gly His Pro Phe Tyr Asn Lys Leu Asp Asp
            115                 120                 125

Thr Glu Ser Ser His Ala Ala Thr Ser Asn Val Ser Glu Asp Val Arg
130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
                180                 185                 190

Thr Val Leu Glu Asp Gly Asp Met Val Asp Thr Gly Tyr Gly Ala Met
            195                 200                 205

Asp Phe Ser Thr Leu Gln Asp Thr Lys Cys Glu Val Pro Leu Asp Ile
    210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
                260                 265                 270

Gln Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
                340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
                405                 410                 415

Asp Thr Tyr Arg Phe Val Gln Ser Val Ala Ile Thr Cys Gln Lys Asp
                420                 425                 430

Ala Ala Pro Ala Glu Asn Lys Asp Pro Tyr Asp Lys Leu Lys Phe Trp
            435                 440                 445

Asn Val Asp Leu Lys Glu Lys Phe Ser Leu Asp Leu Asp Gln Tyr Pro
450                 455                 460
```

-continued

```
Leu Gly Arg Lys Phe Leu Val Gln Ala Gly Leu Arg Arg Lys Pro Thr
465                 470                 475                 480

Ile Gly Pro Arg Lys Arg Ser Ala Pro Ser Ala Thr Thr Ser Ser Lys
                485                 490                 495

Pro Ala Lys Arg Val Arg Val Arg Ala Arg Lys
                500                 505

<210> SEQ ID NO 174
<211> LENGTH: 500
<212> TYPE: PRT
<213> ORGANISM: Human Papillomavirus
<220> FEATURE:
<221> NAME/KEY: misc_feature
<222> LOCATION: (1)..(500)
<223> OTHER INFORMATION: Amino Acid Sequence of Native HPV6L1

<400> SEQUENCE: 174

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
                20                  25                  30

Phe Tyr His Ala Ser Ser Ser Arg Leu Leu Ala Val Gly His Pro Tyr
            35                  40                  45

Phe Ser Ile Lys Arg Ala Asn Lys Thr Val Val Pro Lys Val Ser Gly
50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
```

```
                305                 310                 315                 320
Trp Gly Asn Gln Leu Phe Val Thr Val Asp Thr Thr Arg Ser Thr
                325                 330                 335

Asn Met Thr Leu Cys Ala Ser Val Thr Thr Ser Ser Thr Tyr Thr Asn
                340                 345                 350

Ser Asp Tyr Lys Glu Tyr Met Arg His Val Glu Glu Tyr Asp Leu Gln
                355                 360                 365

Phe Ile Phe Gln Leu Cys Ser Ile Thr Leu Ser Ala Glu Val Met Ala
                370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
                420                 425                 430

Pro Asp Pro Tyr Lys Asn Leu Ser Phe Trp Glu Val Asn Leu Lys Glu
                435                 440                 445

Lys Phe Ser Ser Glu Leu Asp Gln Tyr Pro Leu Gly Arg Lys Phe Leu
                450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
                500

<210> SEQ ID NO 175
<211> LENGTH: 503
<212> TYPE: PRT
<213> ORGANISM: Human Papillomavirus
<220> FEATURE:
<221> NAME/KEY: misc_feature
<222> LOCATION: (1)..(503)
<223> OTHER INFORMATION: Amino Acid Sequence of Native HPV52L1

<400> SEQUENCE: 175

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
                20                  25                  30

Ile Tyr Tyr Tyr Ala Gly Ser Ser Arg Leu Leu Thr Val Gly His Pro
                35                  40                  45

Tyr Phe Ser Ile Lys Asn Thr Ser Ser Gly Asn Gly Lys Lys Val Leu
    50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95

Glu Thr Gln Arg Leu Val Trp Ala Cys Thr Gly Leu Glu Ile Gly Arg
                100                 105                 110

Gly Gln Pro Leu Gly Val Gly Ile Ser Gly His Pro Leu Leu Asn Lys
                115                 120                 125

Phe Asp Asp Thr Glu Thr Ser Asn Lys Tyr Ala Gly Lys Pro Gly Ile
                130                 135                 140

Asp Asn Arg Glu Cys Leu Ser Met Asp Tyr Lys Gln Thr Gln Leu Cys
145                 150                 155                 160
```

```
Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
            180                 185                 190

Leu Ile Asn Ser Val Ile Gln Asp Gly Asp Met Val Asp Thr Gly Phe
        195                 200                 205

Gly Cys Met Asp Phe Asn Thr Leu Gln Ala Ser Lys Ser Asp Val Pro
    210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
        275                 280                 285

Ala Thr Val Gln Ser Ser Ala Phe Phe Pro Thr Pro Ser Gly Ser Met
    290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350

Val Lys Lys Glu Ser Thr Tyr Lys Asn Glu Asn Phe Lys Glu Tyr Leu
        355                 360                 365

Arg His Gly Glu Glu Phe Asp Leu Gln Phe Ile Phe Gln Leu Cys Lys
    370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445

Met Phe Trp Glu Val Asp Leu Lys Glu Lys Phe Ser Ala Asp Leu Asp
    450                 455                 460

Gln Phe Pro Leu Gly Arg Lys Phe Leu Leu Gln Ala Gly Leu Gln Ala
465                 470                 475                 480

Arg Pro Lys Leu Lys Arg Pro Ala Ser Ser Ala Pro Arg Thr Ser Thr
                485                 490                 495

Lys Lys Lys Lys Val Lys Arg
            500

<210> SEQ ID NO 176
<211> LENGTH: 498
<212> TYPE: PRT
<213> ORGANISM: Human Papillomavirus
<220> FEATURE:
<221> NAME/KEY: misc_feature
<222> LOCATION: (1)..(498)
<223> OTHER INFORMATION: Amino Acid Sequence of Native HPV58L1

<400> SEQUENCE: 176
```

```
Met Ser Val Trp Arg Pro Ser Glu Ala Thr Val Tyr Leu Pro Pro Val
 1               5                  10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly Asn Pro
            35                  40                  45

Tyr Phe Ser Ile Lys Ser Pro Asn Asn Asn Lys Lys Val Leu Val Pro
     50                  55                  60

Lys Val Ser Gly Leu Gln Tyr Arg Val Phe Arg Val Arg Leu Pro Asp
 65                  70                  75                  80

Pro Asn Lys Phe Gly Phe Pro Asp Thr Ser Phe Tyr Asn Pro Asp Thr
                 85                  90                  95

Gln Arg Leu Val Trp Ala Cys Val Gly Leu Glu Ile Gly Arg Gly Gln
                100                 105                 110

Pro Leu Gly Val Gly Val Ser Gly His Pro Tyr Leu Asn Lys Phe Asp
            115                 120                 125

Asp Thr Glu Thr Ser Asn Arg Tyr Pro Ala Gln Pro Gly Ser Asp Asn
            130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
                165                 170                 175

Asn Asn Asn Ala Ala Ala Thr Asp Cys Pro Pro Leu Glu Leu Phe Asn
            180                 185                 190

Ser Ile Ile Glu Asp Gly Asp Met Val Asp Thr Gly Phe Gly Cys Met
            195                 200                 205

Asp Phe Gly Thr Leu Gln Ala Asn Lys Ser Asp Val Pro Ile Asp Ile
        210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Lys Leu Gly Glu Ala Val Pro
            260                 265                 270

Asp Asp Leu Tyr Ile Lys Gly Ser Gly Asn Thr Ala Val Ile Gln Ser
            275                 280                 285

Ser Ala Phe Phe Pro Thr Pro Ser Gly Ser Ile Val Thr Ser Glu Ser
        290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Thr Leu Cys Thr Glu Val Thr Lys Glu Gly
            340                 345                 350

Thr Tyr Lys Asn Asp Asn Phe Lys Glu Tyr Val Arg His Val Glu Glu
            355                 360                 365

Tyr Asp Leu Gln Phe Val Phe Gln Leu Cys Lys Ile Thr Leu Thr Ala
        370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Ala Pro
```

```
                420             425             430
Pro Lys Glu Lys Glu Asp Pro Leu Asn Lys Tyr Thr Phe Trp Glu Val
            435                 440                 445

Asn Leu Lys Glu Lys Phe Ser Ala Asp Leu Asp Gln Phe Pro Leu Gly
            450                 455                 460

Arg Lys Phe Leu Leu Gln Ser Gly Leu Lys Ala Lys Pro Arg Leu Lys
465                 470                 475                 480

Arg Ser Ala Pro Thr Thr Arg Ala Pro Ser Thr Lys Arg Lys Lys Val
                485                 490                 495

Lys Lys

<210> SEQ ID NO 177
<211> LENGTH: 499
<212> TYPE: PRT
<213> ORGANISM: Human Papillomavirus
<220> FEATURE:
<221> NAME/KEY: misc_feature
<222> LOCATION: (1)..(499)
<223> OTHER INFORMATION: Amino Acid Sequence of Native HPV33L1

<400> SEQUENCE: 177

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
                20                  25                  30

Ile Tyr Tyr Tyr Ala Gly Ser Ser Arg Leu Leu Ala Val Gly His Pro
            35                  40                  45

Tyr Phe Ser Ile Lys Asn Pro Thr Asn Ala Lys Lys Leu Leu Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Ile Ser Gly His Pro Leu Leu Asn Lys Phe Asp
            115                 120                 125

Asp Thr Glu Thr Gly Asn Lys Tyr Pro Gly Gln Pro Gly Ala Asp Asn
            130                 135                 140

Arg Glu Cys Leu Ser Met Asp Tyr Lys Gln Thr Gln Leu Cys Leu Leu
145                 150                 155                 160

Gly Cys Lys Pro Pro Thr Gly Glu His Trp Gly Lys Gly Val Ala Cys
                165                 170                 175

Thr Asn Ala Ala Pro Ala Asn Asp Cys Pro Pro Leu Glu Leu Ile Asn
            180                 185                 190

Thr Ile Ile Glu Asp Gly Asp Met Val Asp Thr Gly Phe Gly Cys Met
            195                 200                 205

Asp Phe Lys Thr Leu Gln Ala Asn Lys Ser Asp Val Pro Ile Asp Ile
            210                 215                 220

Cys Gly Ser Thr Cys Lys Tyr Pro Asp Tyr Leu Lys Met Thr Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Thr Leu Gly Glu Ala Val Pro
            260                 265                 270
```

```
Asp Asp Leu Tyr Ile Lys Gly Ser Gly Thr Thr Ala Ser Ile Gln Ser
            275                 280                 285

Ser Ala Phe Phe Pro Thr Pro Ser Gly Ser Met Val Thr Ser Glu Ser
290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Val Phe Val Thr Val Val Asp Thr
            325                 330                 335

Thr Arg Ser Thr Asn Met Thr Leu Cys Thr Gln Val Thr Ser Asp Ser
            340                 345                 350

Thr Tyr Lys Asn Glu Asn Phe Lys Glu Tyr Ile Arg His Val Glu Glu
            355                 360                 365

Tyr Asp Leu Gln Phe Val Phe Gln Leu Cys Lys Val Thr Leu Thr Ala
            370                 375                 380

Glu Val Met Thr Tyr Ile His Ala Met Asn Pro Asp Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Val Pro
                420                 425                 430

Pro Lys Glu Lys Glu Asp Pro Leu Gly Lys Tyr Thr Phe Trp Glu Val
            435                 440                 445

Asp Leu Lys Glu Lys Phe Ser Ala Asp Leu Asp Gln Phe Pro Leu Gly
            450                 455                 460

Arg Lys Phe Leu Leu Gln Ala Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys

<210> SEQ ID NO 178
<211> LENGTH: 504
<212> TYPE: PRT
<213> ORGANISM: Human Papillomavirus
<220> FEATURE:
<221> NAME/KEY: misc_feature
<222> LOCATION: (1)..(504)
<223> OTHER INFORMATION: Amino Acid Sequence of Native HPV31L1

<400> SEQUENCE: 178

Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
                20                  25                  30

Ile Tyr Tyr His Ala Gly Ser Ala Arg Leu Leu Thr Val Gly His Pro
            35                  40                  45

Tyr Tyr Ser Ile Pro Lys Ser Asp Asn Pro Lys Lys Ile Val Val Pro
        50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125
```

Asp Thr Glu Asn Ser Asn Arg Tyr Ala Gly Gly Pro Gly Thr Asp Asn
130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285

Asn Ser Thr Tyr Phe Pro Thr Pro Ser Gly Ser Met Val Thr Ser Asp
290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365

Glu Glu Phe Asp Leu Gln Phe Ile Phe Gln Leu Cys Lys Ile Thr Leu
370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Ser
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
450                 455                 460

Leu Gly Arg Lys Phe Leu Leu Gln Ala Gly Tyr Arg Ala Arg Pro Lys
465                 470                 475                 480

Phe Lys Ala Gly Lys Arg Ser Ala Pro Ser Ala Ser Thr Thr Thr Pro
                485                 490                 495

Ala Lys Arg Lys Lys Thr Lys Lys
            500

<210> SEQ ID NO 179
<211> LENGTH: 504
<212> TYPE: PRT
<213> ORGANISM: Human Papillomavirus
<220> FEATURE:

<221> NAME/KEY: misc_feature
<222> LOCATION: (1)..(504)
<223> OTHER INFORMATION: Amino Acid Sequence of Native HPV51L1

<400> SEQUENCE: 179

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220

Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Val Gly Val Gly Glu Asp Ile Pro Asn
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu

```
385                 390                 395                 400
Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
                420                 425                 430

Pro Pro Gln Ala Lys Pro Asp Pro Leu Ala Lys Tyr Lys Phe Trp Asp
                435                 440                 445

Val Asp Leu Lys Glu Arg Phe Ser Leu Asp Leu Asp Gln Phe Ala Leu
450                 455                 460

Gly Arg Lys Phe Leu Leu Gln Val Gly Val Gln Arg Lys Pro Arg Pro
465                 470                 475                 480

Gly Leu Lys Arg Pro Ala Ser Ser Ala Ser Ser Ser Ser Ser Ser Ser
                485                 490                 495

Ala Lys Arg Lys Arg Val Lys Lys
                500

<210> SEQ ID NO 180
<211> LENGTH: 499
<212> TYPE: PRT
<213> ORGANISM: Human Papillomavirus
<220> FEATURE:
<221> NAME/KEY: misc_feature
<222> LOCATION: (1)..(499)
<223> OTHER INFORMATION: Amino Acid Sequence of Native HPV56L1

<400> SEQUENCE: 180

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
                20                  25                  30

Ile Phe Tyr His Ala Gly Ser Ser Arg Leu Leu Ala Val Gly His Pro
                35                  40                  45

Tyr Tyr Ser Val Thr Lys Asp Asn Thr Lys Thr Asn Ile Pro Lys Val
50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
                85                  90                  95

Leu Val Trp Ala Cys Val Gly Leu Glu Val Gly Arg Gly Gln Pro Leu
                100                 105                 110

Gly Ala Gly Leu Ser Gly His Pro Leu Phe Asn Arg Leu Asp Asp Thr
                115                 120                 125

Glu Ser Ser Asn Leu Ala Asn Asn Asn Val Ile Glu Asp Ser Arg Asp
                130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Pro Leu Ala Leu Ile Asn Thr
                180                 185                 190

Pro Ile Glu Asp Gly Asp Met Ile Asp Thr Gly Phe Gly Ala Met Asp
                195                 200                 205

Phe Lys Val Leu Gln Glu Ser Lys Ala Glu Val Pro Leu Asp Ile Val
                210                 215                 220

Gln Ser Thr Cys Lys Tyr Pro Asp Tyr Leu Lys Met Ser Ala Asp Ala
225                 230                 235                 240
```

```
Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
                260                 265                 270

Glu Leu Tyr Leu Lys Gly Ser Asn Gly Arg Glu Pro Pro Ser Ser
            275                 280                 285

Val Tyr Val Ala Thr Pro Ser Gly Ser Met Ile Thr Ser Glu Ala Gln
            290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Asp Thr Thr
                325                 330                 335

Arg Ser Thr Asn Met Thr Ile Ser Thr Ala Thr Glu Gln Leu Ser Lys
                340                 345                 350

Tyr Asp Ala Arg Lys Ile Asn Gln Tyr Leu Arg His Val Glu Glu Tyr
                355                 360                 365

Glu Leu Gln Phe Val Phe Gln Leu Cys Lys Ile Thr Leu Ser Ala Glu
            370                 375                 380

Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
                420                 425                 430

Thr Glu Lys Gln Asp Pro Leu Ala Lys Tyr Lys Phe Trp Asp Val Asn
                435                 440                 445

Leu Gln Asp Ser Phe Ser Thr Asp Leu Asp Gln Phe Pro Leu Gly Arg
            450                 455                 460

Lys Phe Leu Met Gln Leu Gly Thr Arg Ser Lys Pro Ala Val Ala Thr
465                 470                 475                 480

Ser Lys Lys Arg Ser Ala Pro Thr Ser Thr Ser Thr Pro Ala Lys Arg
                485                 490                 495

Lys Arg Arg

<210> SEQ ID NO 181
<211> LENGTH: 505
<212> TYPE: PRT
<213> ORGANISM: Human Papillomavirus
<220> FEATURE:
<221> NAME/KEY: misc_feature
<222> LOCATION: (1)..(505)
<223> OTHER INFORMATION: Amino Acid Sequence of Native HPV39L1

<400> SEQUENCE: 181

Met Ala Met Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
                20                  25                  30

Ile Tyr Tyr Tyr Ala Gly Ser Ser Arg Leu Leu Thr Val Gly His Pro
                35                  40                  45

Tyr Phe Lys Val Gly Met Asn Gly Gly Arg Lys Gln Asp Ile Pro Lys
            50                  55                  60

Val Ser Ala Tyr Gln Tyr Arg Val Phe Arg Val Thr Leu Pro Asp Pro
65              70                  75                  80

Asn Lys Phe Ser Ile Pro Asp Ala Ser Leu Tyr Asn Pro Glu Thr Gln
```

```
            85                  90                  95
Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
            115                 120                 125

Thr Glu Asn Ser Pro Phe Ser Ser Thr Asn Lys Asp Ser Arg Asp
130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
            165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
            195                 200                 205

Phe Gly Ala Leu Gln Glu Thr Lys Ser Glu Val Pro Leu Asp Ile Cys
            210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
            245                 250                 255

Arg His Phe Trp Asn Arg Gly Met Val Gly Asp Ala Ile Pro Ala
            260                 265                 270

Gln Leu Tyr Ile Lys Gly Thr Asp Ile Arg Ala Asn Pro Gly Ser Ser
            275                 280                 285

Val Tyr Cys Pro Ser Pro Ser Gly Ser Met Val Thr Ser Asp Ser Gln
            290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
            325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
            355                 360                 365

Glu Tyr Asp Leu Gln Phe Ile Phe Gln Leu Cys Thr Val Thr Leu Thr
            370                 375                 380

Thr Asp Val Met Ser Tyr Ile His Thr Met Asn Ser Ser Ile Leu Asp
385                 390                 395                 400

Asn Trp Asn Phe Ala Val Ala Pro Pro Ser Ala Ser Leu Val Asp
            405                 410                 415

Thr Tyr Arg Tyr Leu Gln Ser Ala Ala Ile Thr Cys Gln Lys Asp Ala
            420                 425                 430

Pro Ala Pro Glu Lys Lys Asp Pro Tyr Asp Gly Leu Lys Phe Trp Asn
            435                 440                 445

Val Asp Leu Arg Glu Lys Phe Ser Leu Glu Leu Asp Gln Phe Pro Leu
            450                 455                 460

Gly Arg Lys Phe Leu Leu Gln Ala Arg Val Arg Arg Pro Thr Ile
465                 470                 475                 480

Gly Pro Arg Lys Arg Pro Ala Ala Ser Thr Ser Ser Ser Ser Ala Thr
            485                 490                 495

Lys His Lys Arg Lys Arg Val Ser Lys
            500                 505
```

<210> SEQ ID NO 182
<211> LENGTH: 508
<212> TYPE: PRT
<213> ORGANISM: Human Papillomavirus
<220> FEATURE:
<221> NAME/KEY: misc_feature
<222> LOCATION: (1)..(508)
<223> OTHER INFORMATION: Amino Acid Sequence of Native HPV59L1

<400> SEQUENCE: 182

Met Ala Leu Trp Arg Ser Ser Asp Asn Lys Val Tyr Leu Pro Pro Pro
1               5                   10                  15

Ser Val Ala Lys Val Val Ser Thr Asp Glu Tyr Val Thr Arg Thr Ser
            20                  25                  30

Ile Phe Tyr His Ala Gly Ser Ser Arg Leu Leu Thr Val Gly His Pro
        35                  40                  45

Tyr Phe Lys Val Pro Lys Gly Gly Asn Gly Arg Gln Asp Val Pro Lys
    50                  55                  60

Val Ser Ala Tyr Gln Tyr Arg Val Phe Arg Val Lys Leu Pro Asp Pro
65                  70                  75                  80

Asn Lys Phe Gly Leu Pro Asp Asn Thr Val Tyr Asp Pro Asn Ser Gln
                85                  90                  95

Arg Leu Val Trp Ala Cys Val Gly Val Glu Ile Gly Arg Gly Gln Pro
            100                 105                 110

Leu Gly Val Gly Leu Ser Gly His Pro Leu Tyr Asn Lys Leu Asp Asp
        115                 120                 125

Thr Glu Asn Ser His Val Ala Ser Ala Val Asp Thr Lys Asp Thr Arg
    130                 135                 140

Asp Asn Val Ser Val Asp Tyr Lys Gln Thr Gln Leu Cys Ile Ile Gly
145                 150                 155                 160

Cys Val Pro Ala Ile Gly Glu His Trp Thr Lys Gly Thr Ala Cys Lys
                165                 170                 175

Pro Thr Thr Val Val Gln Gly Asp Cys Pro Pro Leu Glu Leu Ile Asn
            180                 185                 190

Thr Pro Ile Glu Asp Gly Asp Met Val Asp Thr Gly Tyr Gly Ala Met
        195                 200                 205

Asp Phe Lys Leu Leu Gln Asp Asn Lys Ser Glu Val Pro Leu Asp Ile
    210                 215                 220

Cys Gln Ser Ile Cys Lys Tyr Pro Asp Tyr Leu Gln Met Ser Ala Asp
225                 230                 235                 240

Ala Tyr Gly Asp Ser Met Phe Phe Cys Leu Arg Arg Glu Gln Val Phe
                245                 250                 255

Ala Arg His Phe Trp Asn Arg Ser Gly Thr Met Gly Asp Gln Leu Pro
            260                 265                 270

Glu Ser Leu Tyr Ile Lys Gly Thr Asp Ile Arg Ala Asn Pro Gly Ser
        275                 280                 285

Tyr Leu Tyr Ser Pro Ser Pro Ser Gly Ser Val Val Thr Ser Asp Ser
    290                 295                 300

Gln Leu Phe Asn Lys Pro Tyr Trp Leu His Lys Ala Gln Gly Leu Asn
305                 310                 315                 320

Asn Gly Ile Cys Trp His Asn Gln Leu Phe Leu Thr Val Val Asp Thr
                325                 330                 335

Thr Arg Ser Thr Asn Leu Ser Val Cys Ala Ser Thr Thr Ser Ser Ile
            340                 345                 350

Pro Asn Val Tyr Thr Pro Thr Ser Phe Lys Glu Tyr Ala Arg His Val
            355                 360                 365

Glu Glu Phe Asp Leu Gln Phe Ile Phe Gln Leu Cys Lys Ile Thr Leu
    370                 375                 380

Thr Thr Glu Val Met Ser Tyr Ile His Asn Met Asn Thr Thr Ile Leu
385                 390                 395                 400

Glu Asp Trp Asn Phe Gly Val Thr Pro Pro Thr Ala Ser Leu Val
                405                 410                 415

Asp Thr Tyr Arg Phe Val Gln Ser Ala Ala Val Thr Cys Gln Lys Asp
            420                 425                 430

Thr Ala Pro Pro Val Lys Gln Asp Pro Tyr Asp Lys Leu Lys Phe Trp
            435                 440                 445

Pro Val Asp Leu Lys Glu Arg Phe Ser Ala Asp Leu Asp Gln Phe Pro
        450                 455                 460

Leu Gly Arg Lys Phe Leu Leu Gln Leu Gly Ala Arg Pro Lys Pro Thr
465                 470                 475                 480

Ile Gly Pro Arg Lys Arg Ala Ala Pro Ala Pro Thr Ser Thr Pro Ser
                485                 490                 495

Pro Lys Arg Val Lys Arg Lys Ser Ser Arg Lys
            500                 505

<210> SEQ ID NO 183
<211> LENGTH: 510
<212> TYPE: PRT
<213> ORGANISM: Human Papillomavirus
<220> FEATURE:
<221> NAME/KEY: misc_feature
<222> LOCATION: (1)..(510)
<223> OTHER INFORMATION: Amino Acid Sequence of Native HPV45L1

<400> SEQUENCE: 183

Met Ala Leu Trp Arg Pro Ser Asp Ser Thr Val Tyr Leu Pro Pro Pro
1               5                   10                  15

Ser Val Ala Arg Val Val Asn Thr Asp Asp Tyr Val Ser Arg Thr Ser
            20                  25                  30

Ile Phe Tyr His Ala Gly Ser Ser Arg Leu Leu Thr Val Gly Asn Pro
        35                  40                  45

Tyr Phe Arg Val Val Pro Ser Gly Ala Gly Asn Lys Gln Ala Val Pro
    50                  55                  60

Lys Val Ser Ala Tyr Gln Tyr Arg Val Phe Arg Val Ala Leu Pro Asp
65                  70                  75                  80

Pro Asn Lys Phe Gly Leu Pro Asp Ser Thr Ile Tyr Asn Pro Glu Thr
                85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
        115                 120                 125

Asp Thr Glu Ser Ala His Ala Ala Thr Ala Val Ile Thr Gln Asp Val
    130                 135                 140

Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
                165                 170                 175

Lys Pro Ala Gln Leu Gln Pro Gly Asp Cys Pro Pro Leu Glu Leu Lys
            180                 185                 190

Asn Thr Ile Ile Glu Asp Gly Asp Met Val Asp Thr Gly Tyr Gly Ala

```
              195                 200                 205
Met Asp Phe Ser Thr Leu Gln Asp Thr Lys Cys Glu Val Pro Leu Asp
210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
        275                 280                 285

Pro Gly Ser Cys Val Tyr Ser Pro Ser Pro Ser Gly Ser Ile Thr Thr
    290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
        355                 360                 365

Arg His Val Glu Glu Tyr Asp Leu Gln Phe Ile Phe Gln Leu Cys Thr
    370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
        435                 440                 445

Lys Phe Trp Thr Val Asp Leu Lys Glu Lys Phe Ser Ser Asp Leu Asp
    450                 455                 460

Gln Tyr Pro Leu Gly Arg Lys Phe Leu Val Gln Ala Gly Leu Arg Arg
465                 470                 475                 480

Arg Pro Thr Ile Gly Pro Arg Lys Arg Pro Ala Ala Ser Thr Ser Thr
                485                 490                 495

Ala Ser Arg Pro Ala Lys Arg Val Arg Ile Arg Ser Lys Lys
            500                 505                 510

<210> SEQ ID NO 184
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV6

<400> SEQUENCE: 184

Glu Leu Asp Gln Tyr Pro Leu Gly Arg Lys Phe Leu Leu Gln Ser Gly
1               5                   10                  15

Tyr

<210> SEQ ID NO 185
<211> LENGTH: 17
```

```
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV11

<400> SEQUENCE: 185

Glu Leu Asp Gln Phe Pro Leu Gly Arg Lys Phe Leu Leu Gln Ser Gly
1               5                   10                  15

Tyr

<210> SEQ ID NO 186
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV16

<400> SEQUENCE: 186

Asp Leu Asp Gln Phe Pro Leu Gly Arg Lys Phe Leu Leu Gln Ala Gly
1               5                   10                  15

Leu

<210> SEQ ID NO 187
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV18

<400> SEQUENCE: 187

Asp Leu Asp Gln Tyr Pro Leu Gly Arg Lys Phe Leu Val Gln Ala Gly
1               5                   10                  15

Leu

<210> SEQ ID NO 188
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV31

<400> SEQUENCE: 188

Asp Leu Asp Gln Phe Pro Leu Gly Arg Lys Phe Leu Leu Gln Ala Gly
1               5                   10                  15

Tyr

<210> SEQ ID NO 189
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV35

<400> SEQUENCE: 189

Asp Leu Asp Gln Phe Pro Leu Gly Arg Lys Phe Leu Leu Gln Ala Gly
1               5                   10                  15
```

-continued

Leu

<210> SEQ ID NO 190
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV39

<400> SEQUENCE: 190

Glu Leu Asp Gln Phe Pro Leu Gly Arg Lys Phe Leu Leu Gln Ala Arg
1               5                   10                  15

Val

<210> SEQ ID NO 191
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV45

<400> SEQUENCE: 191

Asp Leu Asp Gln Tyr Pro Leu Gly Arg Lys Phe Leu Val Gln Ala Gly
1               5                   10                  15

Leu

<210> SEQ ID NO 192
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV51

<400> SEQUENCE: 192

Asp Leu Asp Gln Phe Ala Leu Gly Arg Lys Phe Leu Leu Gln Val Gly
1               5                   10                  15

Val

<210> SEQ ID NO 193
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV52

<400> SEQUENCE: 193

Asp Leu Asp Gln Phe Pro Leu Gly Arg Lys Phe Leu Leu Gln Ala Gly
1               5                   10                  15

Leu

<210> SEQ ID NO 194
<211> LENGTH: 19
<212> TYPE: PRT
<213> ORGANISM: Human Papillomavirus
<220> FEATURE:
<221> NAME/KEY: misc_feature
<222> LOCATION: (1)..(19)

<223> OTHER INFORMATION: HPV56

<400> SEQUENCE: 194

Asp Leu Asp Gln Phe Pro Leu Gly Arg Lys Phe Leu Met Gln Leu Gly
1               5                   10                  15

Thr Arg Ser

<210> SEQ ID NO 195
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV58

<400> SEQUENCE: 195

Asp Leu Asp Gln Phe Pro Leu Gly Arg Lys Phe Leu Leu Gln Ser Gly
1               5                   10                  15

Leu

<210> SEQ ID NO 196
<211> LENGTH: 43
<212> TYPE: PRT
<213> ORGANISM: Human Papillomavirus
<220> FEATURE:
<221> NAME/KEY: misc_feature
<222> LOCATION: (1)..(43)
<223> OTHER INFORMATION: HPV33

<400> SEQUENCE: 196

Asp Leu Asp Gln Phe Pro Leu Gly Arg Lys Phe Leu Leu Gln Ala Gly
1               5                   10                  15

Leu Lys Ala Lys Pro Lys Leu Lys Arg Ala Ala Pro Thr Ser Thr Arg
            20                  25                  30

Thr Ser Ser Ala Lys Arg Lys Lys Val Lys Lys
        35                  40

<210> SEQ ID NO 197
<211> LENGTH: 4
<212> TYPE: PRT
<213> ORGANISM: Human Papillomavirus
<220> FEATURE:
<221> NAME/KEY: misc_feature
<222> LOCATION: (1)..(4)
<223> OTHER INFORMATION: nuclear localization sequence

<400> SEQUENCE: 197

Lys Arg Lys Lys
1

<210> SEQ ID NO 198
<211> LENGTH: 50
<212> TYPE: PRT
<213> ORGANISM: Human Papillomavirus
<220> FEATURE:
<221> NAME/KEY: misc_feature
<222> LOCATION: (1)..(50)
<223> OTHER INFORMATION: HPV59

<400> SEQUENCE: 198

Asp Leu Asp Gln Phe Pro Leu Gly Arg Lys Phe Leu Leu Gln Leu Gly
1               5                   10                  15

Ala Arg Pro Lys Pro Thr Ile Gly Pro Arg Lys Arg Ala Ala Pro Ala
            20                  25                  30

Pro Thr Ser Thr Pro Ser Pro Lys Arg Val Lys Arg Lys Ser Ser
                35                  40                  45

Arg Lys
    50

<210> SEQ ID NO 199
<211> LENGTH: 7
<212> TYPE: PRT
<213> ORGANISM: Human Papillomavirus
<220> FEATURE:
<221> NAME/KEY: misc_feature
<222> LOCATION: (1)..(7)
<223> OTHER INFORMATION: nuclear localization sequence

<400> SEQUENCE: 199

Lys Arg Val Lys Arg Arg Lys
1               5

<210> SEQ ID NO 200
<211> LENGTH: 4
<212> TYPE: PRT
<213> ORGANISM: Human Papillomavirus
<220> FEATURE:
<221> NAME/KEY: misc_feature
<222> LOCATION: (1)..(4)
<223> OTHER INFORMATION: nuclear localization sequence

<400> SEQUENCE: 200

Lys Arg Lys Arg
1

<210> SEQ ID NO 201
<211> LENGTH: 5
<212> TYPE: PRT
<213> ORGANISM: Human Papillomavirus
<220> FEATURE:
<221> NAME/KEY: misc_feature
<222> LOCATION: (1)..(5)
<223> OTHER INFORMATION: nuclear localization sequence

<400> SEQUENCE: 201

Lys Arg Lys Arg Lys
1               5

<210> SEQ ID NO 202
<211> LENGTH: 6
<212> TYPE: PRT
<213> ORGANISM: Human Papillomavirus
<220> FEATURE:
<221> NAME/KEY: misc_feature
<222> LOCATION: (1)..(6)
<223> OTHER INFORMATION: nuclear localization sequence

<400> SEQUENCE: 202

Lys Arg Lys Lys Arg Lys
1               5